US012435318B2

(12) United States Patent
Beaudoin et al.

(10) Patent No.: US 12,435,318 B2
(45) Date of Patent: *Oct. 7, 2025

(54) REVERSE TRANSCRIPTASE MUTANTS WITH INCREASED ACTIVITY AND THERMOSTABILITY

(71) Applicant: Integrated DNA Techonolgies, Inc., Coralville, IA (US)

(72) Inventors: Sarah Franz Beaudoin, Iowa City, IA (US); Christopher Anthony Vakulskas, North Liberty, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/380,982

(22) Filed: Jul. 20, 2021

(65) Prior Publication Data

US 2023/0031558 A1 Feb. 2, 2023

Related U.S. Application Data

(60) Provisional application No. 63/054,228, filed on Jul. 20, 2020.

(51) Int. Cl.

| | |
|---|---|
| ***C12N 9/12*** | (2006.01) |
| ***C12P 19/34*** | (2006.01) |
| ***C12Q 1/686*** | (2018.01) |

(52) U.S. Cl.

CPC ............ *C12N 9/1276* (2013.01); *C12P 19/34* (2013.01); *C12Q 1/686* (2013.01)

(58) Field of Classification Search

CPC ..................................................... C12N 9/1276

See application file for complete search history.

(56) References Cited

U.S. PATENT DOCUMENTS

| | | | |
|---|---|---|---|
| 2014/0045244 | A1 | 2/2014 | Park et al. |
| 2014/0286907 | A1 | 9/2014 | Sarkis et al. |
| 2014/0363854 | A1 | 12/2014 | Smith et al. |
| 2016/0340657 | A1 | 11/2016 | Hogrefe et al. |
| 2017/0298403 | A1 | 10/2017 | Janulaitis et al. |

FOREIGN PATENT DOCUMENTS

| | | | |
|---|---|---|---|
| CN | 106 906 237 | | 6/2017 |
| KR | 20160113177 | * | 9/2016 |
| WO | WO 2007/022045 | | 2/2007 |

(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak

(74) *Attorney, Agent, or Firm* — McDonnell Boehnen Hulbert & Berghoff LLP

(57) ABSTRACT

The disclosure provides Moloney murine leukemia virus (MMLV) reverse transcriptase (RTase) mutants. The disclosure as provides suitable amino acid positions in MMLV RTase for mutagenesis and methods and kits for using MMLV RTase mutants to synthesize cDNA from RNA templates.

12 Claims, 4 Drawing Sheets

Specification includes a Sequence Listing.

(56) References Cited

FOREIGN PATENT DOCUMENTS

WO WO 2015/075842 5/2015

OTHER PUBLICATIONS

English Translation of KR 20160113177 A. retrieved on May 2, 2023.*
Fransceus. J Ind Microbiol Biotechnol. May 2017;44(4-5):687-695.*
Sanavia. Computational and Structural Biotechnology Journal, vol. 18, 2020, pp. 1968-1979.*
Crowther et al. "Structural and energetic characterization of nucleic acid binding to the fingers domain of Moloney murine leukemia virus reverse transcriptase" Proteins: Structure, Function, and Bioinformatics 57(1):15-26 (Oct. 2004).
The International Search Report for International Application No. PCT/US2021/042407; mailed Feb. 2, 2022, pp. 1-5.
Konishi et al., "Stabilization of Moloney murine leukemia virus reverse transcriptase by site-directed mutagenesis of surface residue Val433", Bioscience, Biotechnology, and Biochemistry, vol. 78, No. 1, pp. 75-78 (Jan. 2014).
Lim. Crystal structure of the moloney murine leukemia virus RNase H domain. J Viral. Sep. 2006; 80(17):8379-89.
Shinnick. Nucleotide sequence of Moloney murine leukaemia virus. Nature. Oct. 15-21, 1981; 293(5833):543-8.

* cited by examiner

REVERSE TRANSCRIPTASE MUTANTS WITH INCREASED ACTIVITY AND THERMOSTABILITY

CROSS-REFERENCE TO RELATED APPLICATIONS

This application claims benefit under 35 U.S.C. § 119(e) of U.S. Provisional Application No. 63/054,228 filed Jul. 20, 2020. The above listed application is incorporated by reference herein in its entirety for all purposes.

REFERENCE TO AN ELECTRONIC SEQUENCE LISTING

The instant application contains a Sequence Listing which has been submitted electronically as a text file in ASCII format and is hereby incorporated by reference in its entirety. The name of the ASCII text file is "20-1076-US_Sequence-Listing_ST25_FINAL.txt", was created on Jul. 19, 2021, and is 492 kilobytes in size.

FIELD OF THE DISCLOSURE

The disclosure relates to Moloney murine leukemia virus (MMLV) reverse transcriptase (RTase) mutants. The disclosure also relates to suitable amino acid positions in MMLV RTase for mutagenesis and methods for using MMLV RTase mutants to synthesize cDNA from RNA templates.

BACKGROUND

Reverse transcriptase (RTase) enzymes have revolutionized molecular biology. RTase is a critical component of the reverse transcription polymerase chain reaction (RT-PCR) allowing the production of complementary DNA (cDNA) from RNA. The cDNA produced in reverse transcription reactions can be used in a wide range of downstream applications, including quantitative PCR, gene expression analysis, isolated RNA sequencing, gene cloning, and cDNA library creation.

RTases, first derived from retroviruses, facilitate the reverse transcription of RNA into cDNA by utilizing RNA-dependent polymerase and RNase H, a non-sequence-specific endonuclease enzyme that catalyzes cleavage of RNA in an RNA/DNA duplex. This results in virus replication and integration of the viral sequence into host DNA thereby allowing for the proliferation of the virus along with host DNA. Within the laboratory setting, RTases from Moloney murine leukemia virus (MMLV), avian myeloblastosis virus (AMV), and human immunodeficiency virus type 1 (HIV-1) are the most commonly used RTase for cDNA synthesis.

RTases for research applications are often mutated multi-generational MMLV and AMV RTases that have been optimized for laboratory procedures. Mutations in the RTases alter properties of the enzymes, including thermostability, RTase activity, 5' mRNA coverage, and RNase H activity.

AMV RTases are thermostable and less sensitive to thermal degradation than MMLV RTase and are preferred for RNA having a strong secondary structure. In addition, AMV RTases are often suitable for use with RNA molecules that are five kilobases or longer because of the heat stability of AMV RTases. However, the high temperatures required to resolve strong secondary structures or long RNA strands can negatively impact RNA integrity and fidelity of transcription. AMV also possess an intrinsic RNase activity that degrades RNA in an RNA/DNA hybrid, which can result in reduced total cDNA and reduced full-length cDNA yield.

MMLV RTase is characterized by low RNase H activity and a higher fidelity as compared to AMV RTase. The reduced RNase H activity allows MMLV RTases to be used for the reverse transcription of long RNAs (>5 kb). However, the RNase H activity of MMLV RTase limits the efficiency of synthesizing long cDNA in vitro. Mutations in MMLV RTase have been introduced to reduce RNase H activity. In addition, because the optimal temperature for MMLV RTase activity is ~37° C., the enzyme lacks the ability to effectively reverse transcribe RNAs with strong secondary structures. The use of MMLV RTase at elevated temperatures can compromise cDNA length and yield as a result of lower enzyme activity. MMLV RTase mutants that substitute $Mn^{2+}$ for $Mg^{2+}$ in the reaction mixture attempt to overcome these limitations, but are characterized by inefficiency and error.

Thus, despite the unique properties of AMV and MMLV RTases, there exists a need for an RTase that combines the beneficial attributes of AMV and MMLV RTases. Consistent with this, the present application discloses MMLV RTase mutants, isolated through rational mutagenesis of MMLV RTase, that exhibit increased RTase activity and thermostability as compared to RTases, including RNase H minus constructs, that are currently available in the art.

SUMMARY

The disclosure provides Moloney murine leukemia virus (MMLV) reverse transcriptase (RTase) mutants. The disclosure also provides suitable amino acid positions in MMLV RTase for mutagenesis and methods and kits for using MMLV RTase mutants to synthesize cDNA from RNA templates.

One aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least one amino acid substitution that is: (a) an isoleucine to arginine, lysine or methionine substitution at position 61 (I61R, I61K or I61M); (b) a glutamine to arginine, lysine or isoleucine substitution at position 68 (Q68R, Q68K or Q68I); (c) a glutamine to arginine, histidine or isoleucine substitution at position 79 (Q79R, Q79H or Q79I); (d) a leucine to arginine, lysine or asparagine substitution at position 99 (L99R, L99K or L99N); (e) a glutamic acid to aspartic acid, methionine or typtophan substitution at position 282 (E282D, E282M or E282W); and/or (f) an arginine to alanine substitution at position 298 (R298A).

Another aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least two amino acid substitutions that are: (a) an isoleucine to arginine substitution at position 61 (I61R); (b) a glutamine to arginine substitution at position 68 (Q68R); (c) a glutamine to arginine substitution at position 79 (Q79R); (d) a leucine to arginine substitution at position 99 (L99R); (e) a glutamic acid to aspartic acid substitution at position 282 (E282D); and/or (f) an arginine to alanine substitution at position 298 (R298A): (a) an isoleucine to arginine substitution at position 61 and a glutamic acid to aspartic acid substitution at position 282 (I61R/E282D); (b) a leucine to arginine at substitution position 99 and a glutamic acid to aspartic acid substitution at position 282 (L99R/E282D); (c) a glutamine to arginine substitution at position 68 and a glutamic acid to aspartic acid substitution at position 282 (Q68R/E282D); (d) a glutamine to arginine substitution at position 79 and a glutamic acid to aspartic acid substitution at position 282 (Q79R/E282D); (e) a glutamic acid to aspartic acid substitution at position 282 and an arginine to alanine substitution at position 298 (E282D/R298A); (f) an isoleucine to arginine substitution at position 61 and a leucine to arginine substitution at position 99 (I61R/L99R); (g) an isoleucine to arginine substitution at position 61 and a glutamine to arginine substitution at position 68 (I61R/Q68R); (h) an isoleucine to arginine substitution at position 61 and a glutamine to arginine substitution at position 79 (I61R/Q79R); (i) an isoleucine to arginine substitution at position 61 and an arginine to alanine substitution at position 298 (I61R/R298A); (j) a glutamine to arginine substitution at position 68 and a leucine to arginine substitution at position 99 (Q68R/L99R); (k) a glutamine to arginine substitution at position 79 and a leucine to arginine substitution at position 99 (Q79R/L99R); (1) a leucine to arginine at substitution position 99 and an arginine to alanine substitution at position 298 (L99R/R298A); (m) a glutamine to arginine substitution at position 68 and a glutamine to arginine substitution at position 79 (Q68R/Q79R); (n) a glutamine to arginine substitution at position 68 and an arginine to alanine substitution at position 298 (Q68R/R298A); or (o) a glutamine to arginine substitution at position 79 and an arginine to alanine substitution at position 298 (Q79R/R298A).

Another aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least three amino acid substitutions that are: (a) a glutamine to arginine substitution at position 68 (Q68R); (b) a glutamine to arginine substitution at position 79 (Q79R); (c) a leucine to arginine substitution at position 99 (L99R); and/or (d) a glutamic acid to aspartic acid substitution at position 282 (E282D): (a) a glutamine to arginine substitution at position 68, a leucine to arginine substitution at position 99 and a glutamic acid to aspartic acid substitution at position 282 (Q68R/L99R/E282D); (b) a glutamine to arginine substitution at position 79, a leucine to arginine substitution at position 99 and a glutamic acid to aspartic acid substitution at position 282 (Q79R/L99R/E282D); (c) a glutamine to arginine substitution at position 68, a glutamine to arginine substitution at position 68 and a glutamic acid to aspartic acid substitution at position 282 (Q68R/Q79R/E282D); or (d) a glutamine to arginine substitution at position 68, a glutamine to arginine substitution at position 68 and a leucine to arginine substitution at position 99 (Q68R/Q79R/L99R).

Another aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least four amino acid substitutions that are: (a) a glutamine to arginine, lysine or isoleucine substitution at position 68 (Q68R, Q68K or Q68I); (b) a glutamine to arginine, histidine or isoleucine substitution at position 79 (Q79R, Q79H or Q79I); (c) a leucine to arginine, lysine or asparagine substitution at position 99 (L99R, L99K or L99N); (d) a glutamic acid to aspartic acid, methionine or typtophan substitution at position 282 (E282D, E282M or E282W); (a) a glutamine to arginine substitution at position 68, a glutamine to arginine substitution at position 79, a leucine to arginine substitution at position 99 and a glutamic acid to aspartic acid substitution at position 282 (Q68R/Q79R/L99R/E282D); (b) a glutamine to arginine substitution at position 68, a glutamine to arginine substitution at position 79, a leucine to lysine substitution at position 99 and a glutamic acid to aspartic acid substitution at position 282 (Q68R/Q79R/L99K/E282D); (c) a glutamine to arginine substitution at position 68, a glutamine to arginine substitution at position 79, a leucine to asparagine substitution at position 99 and a glutamic acid to aspartic acid substitution at position 282 (Q68R/Q79R/L99N/E282D); (d) a glutamine to isoleucine substitution at position 68, a glutamine to arginine substitution at position 79, a leucine to arginine substitution at position 99 and a glutamic acid to aspartic acid substitution at position 282 (Q68I/Q79R/L99R/E282D); (e) a glutamine to lysine substitution at position 68, a glutamine to arginine substitution at position 79, a leucine to arginine substitution at position 99 and a glutamic acid to aspartic acid substitution at position 282 (Q68K/Q79R/L99R/E282D); (f) a glutamine to arginine substitution at position 68, a glutamine to histidine substitution at position 79, a leucine to arginine substitution at position 99 and a glutamic acid to aspartic acid substitution at position 282 (Q68R/Q79H/L99R/E282D); (g) a glutamine to arginine substitution at position 68, a glutamine to isoleucine substitution at position 79, a leucine to arginine substitution at position 99 and a glutamic acid to aspartic acid substitution at position 282 (Q68R/Q79I/L99R/E282D); (h) a glutamine to arginine substitution at position 68, a glutamine to arginine substitution at position 79, a leucine to arginine substitution at position 99 and a glutamic acid to methionine substitution at position 282 (Q68R/Q79R/L99R/E282M); (i) a glutamine to arginine substitution at position 68, a glutamine to arginine substitution at position 79, a leucine to arginine substitution at position 99 and a glutamic acid to tryptophan substitution at position 282 (Q68R/Q79R/L99R/E282W); (j) a glutamine to isoleucine substitution at position 68, a glutamine to histidine substitution at position 79, a leucine to lysine substitution at position 99 and a glutamic acid to methionine substitution at position 282 (Q68I/Q79H/L99K/E282M);

Another aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least five amino acid substitutions that are: (a) an isoleucine to lysine or methionine substitution at position 61 (I61K or I61M); (b) a glutamine to arginine or isoleucine substitution at position 68 (Q68R or Q68I); (c) a glutamine to arginine or histidine substitution at position 79 (Q79R or Q79H); (d) a leucine to arginine or lysine substitution at position 99 (L99R or L99K); (e) a glutamic acid to aspartic acid or methionine substitution at position 282 (E282D or E282M): (a) an isoleucine to lysine substitution at position 61, a glutamine to arginine substitution at position 68, a glutamine to arginine substitution at position 79, a leucine to arginine substitution at position 99 and a glutamic acid to aspartic acid substitution at position 282 (I61K/Q68R/Q79R/L99R/E282D); (b) an isoleucine to methionine substitution at position 61, a glutamine to arginine substitution at position 68, a glutamine to arginine substitution at position 79, a leucine to arginine substitution at position 99 and a glutamic acid to aspartic acid substitution at position 282 (I61M/Q68R/Q79R/L99R/E282D); or (c) an isoleucine to methionine substitution at position 61, a glutamine to isoleucine substitution at position 68, a glutamine to histidine substitution at position 79, a leucine to lysine substitution at position 99 and a glutamic acid to methionine substitution at position 282 (I61M/Q68IR/Q79H/L99K/E282M).

Another aspect of the disclosure provides an isolated Moloney murine leukemia virus (MMLV) reverse transcriptase (RTase) mutant comprising the amino acid sequence of SEQ ID NO: 637, wherein the amino acid sequence of the MMLV RTase mutant further comprises at least five or more amino acid substitutions that are: (a) a glutamine to arginine, lysine or isoleucine substitution at position 68 (Q68R, Q68K or Q68I); (b) a glutamine to arginine, histidine or isoleucine substitution at position 79 (Q79R, Q79H or Q79I); (c) a leucine to arginine, lysine or asparagine substitution at position 99 (L99R, L99K or L99N); (d) a glutamic acid to aspartic acid, methionine or typtophan substitution at position 282 (E282D, E282M or E282W); (e) a glutamine to glutamic acid substitution at position 299; (f) threonine to glutamic acid substitution at position 332; (g) valine to arginine substitution at position 433; (h) isoleucine to glutamic acid substitution at position 593; (a) a glutamine to arginine substitution at position 68, a glutamine to arginine substitution at position 79, a leucine to arginine substitution at position 99 and a glutamic acid to aspartic acid substitution at position 282, a glutamine to glutamic acid substitution at position 299, a valine to arginine substation at position 433 and a isoleucine to glutamic acid at position 593 (Q68R/Q79R/L99R/E282D/Q299E/V433R/I593E): (b) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a valine to arginine substation at position 433 and a isoleucine to glutamic acid at position 593 (Q68R/Q79R/L82R/L99R/E282D/Q299E/V433R/I593E); (c) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a threonine to glutamic acid substitution at position 332, and a isoleucine to glutamic acid at position 593 (Q68R/Q79R/L82R/L99R/E282D/Q299E/T332E/I593E); (d) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a threonine to glutamic acid substitution at position 332, a valine to arginine substitution at position 433, and a isoleucine to glutamic acid at position 593 (Q68R/Q79R/L82R/L99R/E282D/Q299E/T332E/V433R/I593E)

Another aspect of the disclosure provides an isolated nucleic acid molecule comprising a nucleotide sequence encoding an MMLV RTase mutant of the disclosure.

Other aspects of the disclosure provide a composition or a kit comprising an MMLV RTase mutant of the disclosure.

Other aspects of the disclosure provide methods for synthesizing complementary deoxyribonucleic acid (cDNA) or methods for performing reverse transcription-polymerase chain reaction (RT-PCR) using an MMLV RTase mutant of the disclosure.

Specific embodiments of the disclosure will become evident from the following more detailed description and the claims.

DETAILED DESCRIPTION

Figure 1A:
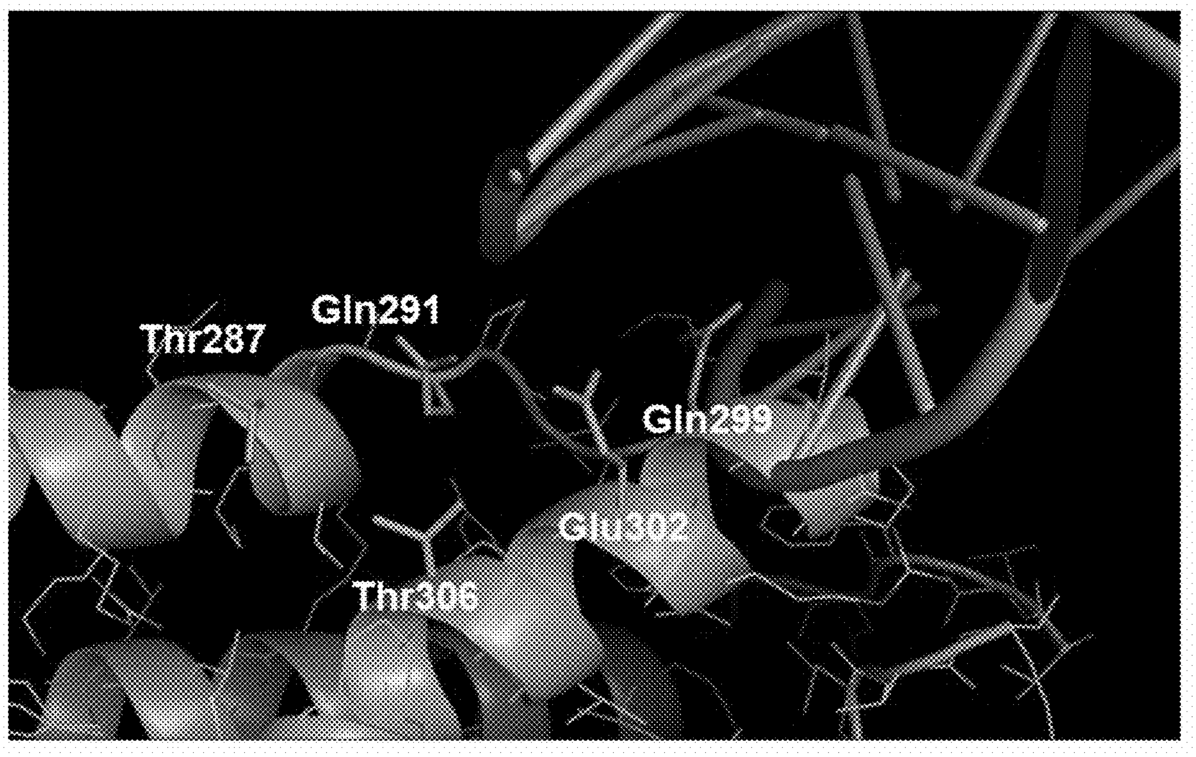
FIGS. 1A-1C are schematics showing reverse transcriptase mutagenesis selection by rational design. Amino acid positions for mutagenesis were chosen at the substrate binding site (FIGS. 1A and 1B) or near the substrate binding site (FIG. 1C).

The disclosure relates to Moloney murine leukemia virus (MMLV) reverse transcriptase (RTase) mutants. The disclosure also relates to suitable amino acid positions in MMLV RTase for mutagenesis and methods and kits for using MMLV RTase mutants to synthesize cDNA from RNA templates.

The MMLV RTase mutants of the disclosure, which have been identified and isolated, at least in part, through rational mutagenesis of a base construct of MMLV RTase, were found to have increased RTase activity and thermostability as compared to wild-type MMLV RTase and certain MMLV RTase mutants, including RNase H minus RTases, that are currently available in the art.

Reference will now be made in detail to exemplary embodiments of the claimed invention. While the claimed invention will be described in conjunction with the exemplary embodiments, it will be understood that it is not intended to limit the claimed invention to those embodiments. To the contrary, it is intended to cover alternatives, modifications, and equivalents, as may be included within the spirit and scope of the claimed invention, as defined by the appended claims.

Those of ordinary skill in the art may make modifications and variations to the embodiments described herein without departing from the spirit or scope of the claimed invention. In addition, although certain methods and materials are described herein, other methods and materials that are similar or equivalent to those described herein can also be used to practice the claimed invention.

In addition, any of the compositions or methods provided, disclosed, or described herein can be combined with one or more of any of the other compositions and methods provided, disclosed, or described herein.

1. Definitions

Unless defined otherwise, all technical and scientific terms used herein have the meaning commonly understood by a person skilled in the art to which the claimed invention belongs. The terminology used herein is for describing particular embodiments only and is not intended to be limiting of the claimed invention. All technical and scientific terms used herein have the same meaning.

The following references provide those of skill in the art with a general understanding of many of the terms used herein (unless defined otherwise herein): Singleton et al., Dictionary of Microbiology and Molecular Biology, 3rd ed.

(Wiley, 2006); Walker, The Cambridge Dictionary of Science and Technology (Cambridge University Press, 1990); Rieger et al., Glossary of Genetics: Classical and Molecular, 5th ed. (Springer Verlag, 1991); and Hale et al., Harper Collins Dictionary of Biology (HarperCollins Publishers, 1991). Generally, the procedures or methods described herein and the like are common methods used in the art. Such standard techniques can be found in reference manuals such as, for example, Green et al., Molecular Cloning: A Laboratory Manual, 4th ed. (Cold Spring Harbor Laboratory Press, 2012), and Ausubel, Current Protocols in Molecular Biology (John Wiley & Sons Inc., 2004).

The following terms may have meanings ascribed to them below, unless specified otherwise. However, it should be understood that other meanings known or understood by those having ordinary skill in the art are also possible, and within the scope of the claimed invention. All publications, patent applications, patents, and other references mentioned or discussed herein are expressly incorporated by reference in their entireties. In the case of conflict, the present specification, including definitions, will control. In addition, the materials, methods, and examples are illustrative only and not intended to be limiting.

As used herein, the singular forms “a,” “and,” and “the” include plural references, unless the context clearly dictates otherwise.

As used herein, the term “or” means, and is used interchangeably with, the term “and/or,” unless context clearly indicates otherwise.

As used herein, the term “including” means, and is used interchangeably with, the phrase “including but not limited to.”

As used herein, the term “such as” means, and is used interchangeably with, the phrase “such as, for example” or “such as but not limited.”

Unless specifically stated or obvious from context, as used herein, the term “about” is understood as within a range of normal tolerance in the art, for example, within two standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms “nucleic acid molecule” and “polynucleotide” refer to a polymer or large biomolecule comprised of nucleotides. The term “nucleic acid” includes deoxyribonucleic acid (DNA), ribonucleic acid (RNA), and analogs thereof. Non-limiting examples of nucleic acid molecules include DNA (e.g., genomic DNA, cDNA), RNA molecules (e.g., mRNA, rRNA, cRNA, tRNA), and chimeras thereof. A nucleic acid molecule can be obtained by cloning techniques or synthesized, using techniques that are known to those of skill in the art. DNA can be double-stranded or single-stranded (coding strand or non-coding strand, i.e., antisense). A nucleic acid backbone may comprise a variety of linkages known in the art, including one or more of sugar-phosphodiester linkages, peptide-nucleic acid bonds (referred to as “peptide nucleic acids” (PNA)), phosphorothioate linkages, methylphosphonate linkages, or combinations thereof. Sugar moieties of the nucleic acid may be ribose or deoxyribose, or similar compounds having known substitutions, for example, 2' methoxy substitutions (containing a 2'-O-methylribofuranosyl moiety) and/or 2' halide substitutions. Nitrogenous bases may be conventional bases (adenine (A), guanine (G), thymine (T), cytosine (C), and uracil (U)), known analogs thereof (e.g., inosine), known derivatives of purine or pyrimidine bases, or “abasic” residues in which the backbone includes no nitrogenous base for one or more residues. A nucleic acid may comprise only conventional sugars, bases, and linkages, as found in RNA and DNA, or may include both conventional components and substitutions (e.g., conventional bases linked via a methoxy backbone, or a nucleic acid including conventional bases and one or more base analogs). An “isolated nucleic acid molecule,” as is generally understood by those of skill in the art and as used herein, refers to a polymer of nucleotides, and includes but is not limited to DNA and RNA.

As used herein, the term “probe” refers to a nucleic acid oligonucleotide that hybridizes specifically to a target sequence in a nucleic acid or its complement, under conditions that promote hybridization, thereby allowing detection of the target sequence or its amplified nucleic acid. Detection may either be direct (i.e., resulting from a probe hybridizing directly to the target or amplified sequence) or indirect (i.e., resulting from a probe hybridizing to an intermediate molecular structure that links the probe to the target or amplified sequence). A probe’s “target” generally refers to a sequence within an amplified nucleic acid sequence (i.e., a subset of the amplified sequence) that hybridizes specifically to at least a portion of the probe sequence by standard hydrogen bonding or “base pairing.” Sequences that are “sufficiently complementary” allow stable hybridization of a probe sequence to a target sequence, even if the two sequences are not completely complementary. A probe may be labeled or unlabeled. A probe can be produced by molecular cloning of a specific DNA sequence or it can be synthesized. Probes for use in the methods disclosed herein can be readily designed and used by those of skill in the art.

As used herein, the term “primer” refers to a nucleic acid oligonucleotide that hybridizes specifically to a target sequence in a nucleic acid or its complement, and which is capable of priming the synthesis of a nascent nucleic acid in a template-dependent process. Primers may be provided in double-stranded or single-stranded form. Primers for use in the methods disclosed herein can be readily designed and used by those of skill in the art.

Probes or primers for use in the methods disclosed herein may be of any suitable length, depending on the particular assay format and the particular needs and targeted sequences employed. For example, the probes or primers for use in the methods disclosed herein are at least 10 nucleotides in length, or at least 15, 20, 25, 30, or more than 30 nucleotides in length, and they may be adapted to be especially suited for a chosen nucleic acid amplification system and/or hybridization system used. Longer probes and primers are also within the scope of the disclosure.

A “transcribed polynucleotide” or “nucleotide transcript” is a polynucleotide (e.g., mRNA, hnRNA, cDNA, or analog of such RNA or cDNA) that is complementary to or having a high percentage of identity (e.g., at least 80% identity) with all or a portion of a mature mRNA made by transcription of a marker of the disclosure and normal post-transcriptional processing (e.g., splicing), if any, of the RNA transcript, and reverse transcription of the RNA transcript.

As used herein, the terms "reverse transcriptase," "RTase," or "RT" refer to an enzyme that is used to generate complementary (cDNA) from an RNA template in a process known as "reverse transcription." The term reverse transcriptase, as used herein, also refers to any enzyme that exhibits reverse transcription activity. Reverse transcriptases can be derived from a variety of sources including but not limited to viruses including retroviruses and DNA polymerases exhibiting transcriptase activity. Such retroviruses include but are not limited to Moloney murine leukemia virus (MMLV), avian myeloblastosis virus (AMV), and human immunodeficiency virus (HIV).

Reverse transcriptase activity can be measured by incubating an RTase in a buffer containing an RNA template and deoxynucleotides. One of skill in the art will recognize that a wide range of conditions can be used to perform reverse transcription reactions and multiple methods exist for measuring the quantity of cDNA produced during reverse transcription.

Reverse transcriptases of the disclosure include reverse transcriptases having one or a combination of the properties described herein. Such properties include but are not limited to increased activity, enhanced DNA synthesis, enhanced stability or enhanced thermostability, reduced or eliminated RNase H activity, reduced terminal deoxynucleotidyl transferase activity, increased accuracy or increased fidelity, increased specificity, or altered half-life, for example when compared to a base construct. As used herein, the term "base construct" refers to the initial RTase from which the RTase mutants of the disclosure are prepared (e.g. for example a wild-type RTase or a modified wild-type RTase).

As used herein, the terms "accuracy" and "fidelity" are used interchangeably and refer to ability of an RTase to accurately replicate a desired template; i.e., the ability of the RTase to accurately perform cDNA synthesis in a reverse transcription reaction. The "fidelity" or "accuracy" of a reverse transcriptase can be assessed by determining the frequency of incorrect nucleotide incorporation into the synthesized cDNA molecule, which may be referred to as the enzyme's error rate. As used herein, the term "increased fidelity" refers to RTase mutants of the disclosure that exhibit an error rate lower than that of the base construct. For example, the RTase mutants as disclosed herein can exhibit an error rate that is 10%, 15%, 20%, 25%, 30%, 35%, 40%, 45%, 50%, 55%, 60%, 65%, 70%, 75%, 80%, 85%, 90%, 95%, 100%, or 200% lower than, or at least 2-fold, 3-fold, 4-fold, 5-fold, or 10-fold, or more than 10-fold lower than the error rate of the RTase base construct . . . .

As used herein, the term "specificity" refers to a decrease in mis-priming by an RTase during cDNA synthesis. An RTase mutant's specificity can be assessed by performing a reverse transcription reaction at a particular temperature, including higher temperatures, and comparing the amount of mis-priming in that reaction with the amount of mis-priming in a reaction performed with the wild-type RTase (or the RTase base construct) under identical conditions.

As used herein with respect to the RTase molecules of the disclosure, the terms "stable" and "thermostable" are used interchangeably and refer to an enzyme that is resistant to heat inactivation and remains active at temperatures in excess of 37° C. (e.g., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 70° C., or higher temperatures). For example, in one embodiment the disclosure provides an RTase mutant having activity with a longer half-life than that of the base construct RTase at an elevated temperature. Thus, RTase mutants with "enhanced thermostability" can refer to RTase mutants of the disclosure that exhibit an increase in thermostability at temperatures of about 50° C. up to about 90° C. as compared to the base construct RTase. In some embodiments, the thermostability of the RTase mutant is at least 1.5 fold or greater as compared to the thermostability of the base construct RTase. Comparisons of cDNA produced by a base construct and RTase mutant are compared using identical reaction conditions for the base construct and RTase mutant reactions. Reaction conditions can include but are not limited to salt concentration, buffer concentration, pH, divalent metal ion concentration, temperature, nucleoside triphosphate concentration, template concentration, RTase concentration, primer concentration, time, and in one-step PCR, the quantitative PCR primer and probe concentrations.

As used herein, the term "enhanced DNA synthesis" refers to an RTase enzyme that produces more DNA (e.g. cDNA) than the base RTase construct. In some embodiments, DNA synthesis can be measured by quantitative PCR at standard reaction conditions, as compared to the base construct RTase. Consistent with assessments of thermostability, quantitative comparisons are made under similar or the same reaction conditions and the amount of cDNA synthesized using the base construct RTase is compared to the amount of cDNA produced using the RTase mutant (see Tables 4, 5, 6, and 7). In some embodiments, the RTase mutant of the disclosure with enhanced DNA synthesis may produce about 5% to about 200% more cDNA than the base construct RTase. In some embodiments, the RTase mutant of the disclosure with enhanced DNA synthesis has at least 10%, 15%, 20%, 25%, 30%, 35%, 40%, 45%, 50%, 55%, 60%, 65%, 70%, 75%, 80%, 85%, 90%, 95%, 100%, or 200% more than, or at least 2-fold, 3-fold, 4-fold, 5-fold, or 10-fold, or more than 10-fold more DNA synthesis than the RTase base construct DNA synthesis.

Reverse transcriptase activity, as described herein, was evaluated in a one-step or two-step procedure. The one-step procedure combines reverse transcription and quantitative PCR in a single reaction. The method is performed by including Gene Expression Master Mix, RTase, RNA, a fluorescent probe, and primers and probes as described in Example 3. The two-step procedure comprises reverse transcription followed by quantitative PCR. In the reverse transcription step, RTase is added to a mixture containing RNA, gene specific primers, first strand synthesis buffer, and RNase. The resultant cDNA is then quantified in a second step wherein the cDNA is combined with Gene Expression Master Mix, primers and probes, and a fluorescent marker. The cDNA produced in either the one-step and two-step procedures is quantified, and the mean and standard deviation reported as shown herein in Tables 4, 5, 6, and 7.

As used herein, "RNase H activity" refers to cleavage of RNA in DNA-RNA duplexes via a hydrolytic mechanism to produce 5' phosphate terminated oligonucleotides. RNase H activity does not include degradation of single-stranded nucleic acids, duplex DNA, or double-stranded RNA. As used herein, the phrase "substantially lacks RNase H activity" means having less than 10%, 5%, 1%, 0.5%, or 0.1% of the activity of a wild type enzyme. As used herein, the phrase "lacks RNase H activity" means having undetectable RNase H activity or having less than about 1%, 0.5%, or 0.1% of the RNase H activity of a wild type enzyme.

As used herein, the term "mutation" refers to a change introduced into the nucleic acid sequence encoding a protein that changes the amino acid sequence of the protein, including but not limited to substitutions, insertions, deletions, point mutations, transpositions, inversions, frame shifts, nonsense mutations, truncations, or other forms of aberrations. A mutation may produce no discernible changes or result in a new property, function, or trait of the mutated protein. An RTase mutant of the disclosure may have one or more mutations in the nucleic acid sequence encoding the RTase mutant resulting in one or more mutations in the amino acid sequence of the RTase mutant. A mutation can result in one or more amino acids being substituted for an alternate amino acid residue, including Ala, Arg, Asn, Asp, Cys, Gln, Glu, Gly, His, Ile, Leu, Lys, Met, Phe, Pro, Ser, Thr, Trp, Tyr, and/or Val. The resulting amino acid mutations may impart altered functional and biological properties to the RTase mutant including but not limited to increased activity, enhanced DNA synthesis, enhanced stability or enhanced thermostability, reduced or eliminated RNase H activity, reduced terminal deoxynucleotidyl transferase activity, increased accuracy or increased fidelity, increased specificity, or altered half-life.

As used herein, the terms “detecting,” “detection,” “determining,” and the like refer to assays performed for identification of the quantity of cDNA synthesis as a marker of RTase activity. The amount of marker expression or activity detected in the sample can be the same as, decreased, or increased as compared to the amount of marker expression or activity detected using the RTase base construct. One of skill in the art will understand that amount of cDNA can be quantified using multiple techniques.

The term “increased,” as used herein with regard to RTase activity, refers to the level of RTase activity of an RTase mutant as compared to the RTase base construct. An RTase mutant has “increased” RTase activity if the level of its RTase activity, as measured by the quantity of cDNA synthesized or as measured by other methods known in the art, is more than the RTase base construct activity. For example, the RTase activity of the RTase mutant is increased if the RTase activity is at least 10%, 15%, 20%, 25%, 30%, 35%, 40%, 45%, 50%, 55%, 60%, 65%, 70%, 75%, 80%, 85%, 90%, 95%, or 100% more than, or at least 2-fold, 3-fold, 4-fold, 5-fold, or 10-fold, or more than 10-fold more than the RTase base construct activity.

The term “decreased,” as used herein with regard to RTase activity, refers to the level of RTase activity of an RTase mutant as compared to the RTase base construct. An RTase mutant has “decreased” RTase activity if the level of its RTase activity, as measured by the quantity of cDNA synthesized or as measured by other methods known in the art is less than the RTase base construct activity. For example, the RTase activity of the RTase mutant is decreased if the RTase activity is at least 95%, 90%, 85%, 80%, 75%, 70%, 65%, 60%, 55%, 50%, 45%, 40%, 35%, 30%, 25%, 20%, 15%, 10%, or 5% less than, or at least 2-fold, 3-fold, 4-fold, 5-fold, 10-fold, or more than 10-fold less than the RTase base construct activity.

As used herein, the term “amplification” refers to any known in vitro procedure for obtaining multiple copies of a target nucleic acid sequence or its complement or fragments thereof. In vitro amplification refers to production of an amplified nucleic acid that may contain less than the complete target region sequence or its complement. Known in vitro amplification methods include, for example, transcription-mediated amplification, replicase-mediated amplification, polymerase chain reaction (PCR) amplification, ligase chain reaction (LCR) amplification, and strand-displacement amplification (SDA, including multiple strand-displacement amplification method (MSDA)). Replicase-mediated amplification uses self-replicating RNA molecules, and a replicase such as Q-β-replicase. PCR amplification uses DNA polymerase, primers, and thermal cycling to synthesize multiple copies of the two complementary strands of DNA or cDNA. PCR involves denaturation of a double-stranded DNA molecule, followed by annealing of DNA primers directed to the sequence of interest, and amplification/extension of the newly formed DNA strand. LCR amplification uses at least four separate oligonucleotides to amplify a target and its complementary strand by using multiple cycles of hybridization, ligation, and denaturation. SDA is a method in which a primer contains a recognition site for a restriction endonuclease that permits the endonuclease to nick one strand of a hemimodified DNA duplex that includes the target sequence, followed by amplification in a series of primer extension and strand displacement steps. Other strand-displacement amplification methods known in the art (e.g., MSDA) do not require endonuclease nicking. Those of skill in the art will understand that the oligonucleotide primer sequences of the disclosure may be readily used in any in vitro amplification method based on primer extension by a polymerase. As commonly known in the art, oligonucleotides are designed to bind to a complementary sequence under selected conditions.

As used herein, “real time PCR” or “quantitative PCR” refers to a PCR method wherein the amount of product being formed can be monitored using florescent probes and quantified by tracking the fluorescent signal produced, above a threshold level. Real time PCR can be performed in a one-step reaction that includes the reverse transcription step in a simultaneous reaction (i.e., real time PCR or RT-PCR) or in a two-step reaction in which the reverse transcription step and PCR steps are performed consecutively.

As used herein, the term “complementary” refers to the broad concept of sequence complementarity between regions of two nucleic acid strands or between two regions of the same nucleic acid strand. A first region of a nucleic acid is complementary to a second region of the same or a different nucleic acid if, when the two regions are arranged in an antiparallel fashion, at least one nucleotide of the first region is capable of base pairing with a nucleotide of the second region. In some embodiments, the first region comprises a first portion and the second region comprises a second portion, whereby, when the first and second portions are arranged in an antiparallel fashion, at least about 50%, 75%, 80%, 85%, 90%, 95%, 96%, 97%, 98%, or 99% of the nucleotides of the first portion are capable of base pairing with nucleotides in the second portion. In another embodiment, all nucleotides of the first portion are capable of base pairing with nucleotides in the second portion.

Polypeptide and polynucleotide sequences may be aligned, and percentages of identical amino acids or nucleotides in a specified region may be determined against another polypeptide or polynucleotide sequence, using computer algorithms that are publicly available. The percent identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the disclosure; and then multiplying by 100 to determine the percent identity.

As used herein, the terms “sample” and “biological sample” include a specimen or culture obtained from any source. Biological samples can be obtained from cerebrospinal fluid, lacrimal fluid, blood (including any blood product, such as whole blood, plasma, serum, or specific types of cells of the blood), urine, saliva, and the like. Biological samples also include tissue samples, such as biopsy tissues or pathological tissues that have previously been fixed (e.g., formaline snap frozen, cytological processing).

2. Reverse Transcriptases

The disclosure relates to Moloney murine leukemia virus (MMLV) reverse transcriptase (RTase) mutants. The MMLV RTase mutants of the disclosure are prepared by modifying the sequence of an MMLV RTase base construct (SEQ ID NO: 637). In one embodiment, the MMLV RTase mutant of the disclosure comprises the amino acid sequence of SEQ ID NO: 637, wherein the amino acid sequence of the MMLV RTase mutant further comprises at least one amino acid substitution that is: (a) an isoleucine to arginine, lysine or methionine substitution at position 61 (I61R, I61K or I61M); (b) a glutamine to arginine, lysine or isoleucine substitution at position 68 (Q68R, Q68K or Q68I); (c) a glutamine to arginine, histidine or isoleucine substitution at position 79 (Q79R, Q79H or Q79I); (d) a leucine to arginine, lysine or asparagine substitution at position 99 (L99R, L99K or L99N); (e) a glutamic acid to aspartic acid, methionine or typtophan substitution at position 282 (E282D, E282M or E282W); and/or (f) an arginine to alanine substitution at position 298 (R298A).

In another embodiment, the MMLV RTase mutant of the disclosure comprises the amino acid sequence of SEQ ID NO: 637, wherein the amino acid sequence of the MMLV RTase mutant further comprises at least two amino acid substitutions that are: (a) an isoleucine to arginine substitution at position 61 (I61R); (b) a glutamine to arginine substitution at position 68 (Q68R); (c) a glutamine to arginine substitution at position 79 (Q79R); (d) a leucine to arginine substitution at position 99 (L99R); (e) a glutamic acid to aspartic acid substitution at position 282 (E282D); and/or (f) an arginine to alanine substitution at position 298 (R298A): (a) an isoleucine to arginine substitution at position 61 and a glutamic acid to aspartic acid substitution at position 282 (I61R/E282D); (b) a leucine to arginine at substitution position 99 and a glutamic acid to aspartic acid substitution at position 282 (L99R/E282D); (c) a glutamine to arginine substitution at position 68 and a glutamic acid to aspartic acid substitution at position 282 (Q68R/E282D); (d) a glutamine to arginine substitution at position 79 and a glutamic acid to aspartic acid substitution at position 282 (Q79R/E282D); (e) a glutamic acid to aspartic acid substitution at position 282 and an arginine to alanine substitution at position 298 (E282D/R298A); (f) an isoleucine to arginine substitution at position 61 and a leucine to arginine substitution at position 99 (I61R/L99R); (g) an isoleucine to arginine substitution at position 61 and a glutamine to arginine substitution at position 68 (I61R/Q68R); (h) an isoleucine to arginine substitution at position 61 and a glutamine to arginine substitution at position 79 (I61R/Q79R); (i) an isoleucine to arginine substitution at position 61 and an arginine to alanine substitution at position 298 (I61R/R298A); (j) a glutamine to arginine substitution at position 68 and a leucine to arginine substitution at position 99 (Q68R/L99R); (k) a glutamine to arginine substitution at position 79 and a leucine to arginine substitution at position 99 (Q79R/L99R); (1) a leucine to arginine at substitution position 99 and an arginine to alanine substitution at position 298 (L99R/R298A); (m) a glutamine to arginine substitution at position 68 and a glutamine to arginine substitution at position 79 (Q68R/Q79R); (n) a glutamine to arginine substitution at position 68 and an arginine to alanine substitution at position 298 (Q68R/R298A); or (o) a glutamine to arginine substitution at position 79 and an arginine to alanine substitution at position 298 (Q79R/R298A).

In another embodiment, the MMLV RTase mutant of the disclosure comprises the amino acid sequence of SEQ ID NO: 637, wherein the amino acid sequence of the MMLV RTase mutant further comprises at least three amino acid substitutions that are: (a) a glutamine to arginine substitution at position 68 (Q68R); (b) a glutamine to arginine substitution at position 79 (Q79R); (c) a leucine to arginine substitution at position 99 (L99R); and/or (d) a glutamic acid to aspartic acid substitution at position 282 (E282D): (a) a glutamine to arginine substitution at position 68, a leucine to arginine substitution at position 99 and a glutamic acid to aspartic acid substitution at position 282 (Q68R/L99R/E282D); (b) a glutamine to arginine substitution at position 79, a leucine to arginine substitution at position 99 and a glutamic acid to aspartic acid substitution at position 282 (Q79R/L99R/E282D); (c) a glutamine to arginine substitution at position 68, a glutamine to arginine substitution at position 68 and a glutamic acid to aspartic acid substitution at position 282 (Q68R/Q79R/E282D); or (d) a glutamine to arginine substitution at position 68, a glutamine to arginine substitution at position 68 and a leucine to arginine substitution at position 99 (Q68R/Q79R/L99R).

In another embodiment, the MMLV RTase mutant of the disclosure comprises the amino acid sequence of SEQ ID NO: 637, wherein the amino acid sequence of the MMLV RTase mutant further comprises at least four amino acid substitutions that are: (a) a glutamine to arginine, lysine or isoleucine substitution at position 68 (Q68R, Q68K or Q68I); (b) a glutamine to arginine, histidine or isoleucine substitution at position 79 (Q79R, Q79H or Q79I); (c) a leucine to arginine, lysine or asparagine substitution at position 99 (L99R, L99K or L99N); (d) a glutamic acid to aspartic acid, methionine or typtophan substitution at position 282 (E282D, E282M or E282W): (a) a glutamine to arginine substitution at position 68, a glutamine to arginine substitution at position 79, a leucine to arginine substitution at position 99 and a glutamic acid to aspartic acid substitution at position 282 (Q68R/Q79R/L99R/E282D); (b) a glutamine to arginine substitution at position 68, a glutamine to arginine substitution at position 79, a leucine to lysine substitution at position 99 and a glutamic acid to aspartic acid substitution at position 282 (Q68R/Q79R/L99K/E282D); (c) a glutamine to arginine substitution at position 68, a glutamine to arginine substitution at position 79, a leucine to asparagine substitution at position 99 and a glutamic acid to aspartic acid substitution at position 282 (Q68R/Q79R/L99N/E282D); (d) a glutamine to isoleucine substitution at position 68, a glutamine to arginine substitution at position 79, a leucine to arginine substitution at position 99 and a glutamic acid to aspartic acid substitution at position 282 (Q68I/Q79R/L99R/E282D); (e) a glutamine to lysine substitution at position 68, a glutamine to arginine substitution at position 79, a leucine to arginine substitution at position 99 and a glutamic acid to aspartic acid substitution at position 282 (Q68K/Q79R/L99R/E282D); (f) a glutamine to arginine substitution at position 68, a glutamine to histidine substitution at position 79, a leucine to arginine substitution at position 99 and a glutamic acid to aspartic acid substitution at position 282 (Q68R/Q79H/L99R/E282D); (g) a glutamine to arginine substitution at position 68, a glutamine to isoleucine substitution at position 79, a leucine to arginine substitution at position 99 and a glutamic acid to aspartic acid substitution at position 282 (Q68R/Q79I/L99R/E282D); (h) a glutamine to arginine substitution at position 68, a glutamine to arginine substitution at position 79, a leucine to arginine substitution at position 99 and a glutamic acid to methionine substitution at position 282 (Q68R/Q79R/L99R/E282M); (i) a glutamine to arginine substitution at position 68, a glutamine to arginine substitution at position 79, a leucine to arginine substitution at position 99 and a glutamic acid to tryptophan substitution at position 282 (Q68R/Q79R/L99R/E282W); or (j) a glutamine to isoleucine substitution at position 68, a glutamine to histidine substitution at position 79, a leucine to lysine substitution at position 99 and a glutamic acid to methionine substitution at position 282 (Q68I/Q79H/L99K/E282M).

In another embodiment, the MMLV RTase mutant of the disclosure comprises the amino acid sequence of SEQ ID NO: 637, wherein the amino acid sequence of the MMLV RTase mutant further comprises at least five amino acid substitutions that are: (a) an isoleucine to lysine or methionine substitution at position 61 (I61K or I61M); (b) a glutamine to arginine or isoleucine substitution at position 68 (Q68R or Q68I); (c) a glutamine to arginine or histidine substitution at position 79 (Q79R or Q79H); (d) a leucine to arginine or lysine substitution at position 99 (L99R or L99K); (e) a glutamic acid to aspartic acid or methionine substitution at position 282 (E282D or E282M): (a) an isoleucine to lysine substitution at position 61, a glutamine to arginine substitution at position 68, a glutamine to arginine substitution at position 79, a leucine to arginine substitution at position 99 and a glutamic acid to aspartic acid substitution at position 282 (I61K/Q68R/Q79R/L99R/E282D); (b) an isoleucine to methionine substitution at position 61, a glutamine to arginine substitution at position 68, a glutamine to arginine substitution at position 79, a leucine to arginine substitution at position 99 and a glutamic acid to aspartic acid substitution at position 282 (I61M/Q68R/Q79R/L99R/E282D); or (c) an isoleucine to methionine substitution at position 61, a glutamine to isoleucine substitution at position 68, a glutamine to histidine substitution at position 79, a leucine to lysine substitution at position 99 and a glutamic acid to methionine substitution at position 282 (I61M/Q68IR/Q79H/L99K/E282M).

In another embodiment, the MMLV RTase mutant of the disclosure comprises the amino acid sequence of SEQ ID NO: 637, wherein the amino acid sequence of the MMLV RTase mutant further comprises at least five or more amino acid substitutions that are: (a) a glutamine to arginine, lysine or isoleucine substitution at position 68 (Q68R, Q68K or Q68I); (b) a glutamine to arginine, histidine or isoleucine substitution at position 79 (Q79R, Q79H or Q79I); (c) a leucine to arginine, lysine or asparagine substitution at position 99 (L99R, L99K or L99N); (d) a glutamic acid to aspartic acid, methionine or typtophan substitution at position 282 (E282D, E282M or E282W); (e) a glutamine to glutamic acid substitution at position 299; (f) threonine to glutamic acid substitution at position 332; (g) valine to arginine substitution at position 433; (h) isoleucine to glutamic acid substitution at position 593; (a) a glutamine to arginine substitution at position 68, a glutamine to arginine substitution at position 79, a leucine to arginine substitution at position 99 and a glutamic acid to aspartic acid substitution at position 282, a glutamine to glutamic acid substitution at position 299, a valine to arginine substation at position 433 and a isoleucine to glutamic acid at position 593 (Q68R/Q79R/L99R/E282D/Q299E/V433R/I593E): (b) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a valine to arginine substation at position 433 and a isoleucine to glutamic acid at position 593 (Q68R/Q79R/L82R/L99R/E282D/Q299E/V433R/I593E); (c) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a threonine to glutamic acid substitution at position 332, and a isoleucine to glutamic acid at position 593 (Q68R/Q79R/L82R/L99R/E282D/Q299E/T332E/I593E); (d) a glutamine to arginine substitution at position 68, a glutamine to arginine substitution at position 79, a leucine to argine substitution at position 82, a leucine to arginine substitution at position 99 and a glutamic acid to aspartic acid substitution at position 282, a glutamine to glutamic acid substitution at position 299, a threonine to glutamic acid substitution at position 332, a valine to arginine substitution at position 433, and a isoleucine to glutamic acid at position 593 (Q68R/Q79R/L82R/L99R/E282D/Q299E/T332E/V433R/I593E)

In one embodiment the RTase mutant amino acid sequence comprises a mutant selected from Table 3, Table 8, Table 9, Table 12, or Table 33. In one aspect the RTase mutant amino acid sequence comprises a mutant selected from SEQ ID NO: 638, SEQ ID NO: 639, SEQ ID NO: 640, SEQ ID NO: 641, SEQ ID NO: 642, SEQ ID NO:643, SEQ ID NO: 644, SEQ ID NO: 645, SEQ ID NO: 646, SEQ ID NO: 647, SEQ ID NO: 648, SEQ ID NO: 649, SEQ ID NO: 650, SEQ ID NO: 651, SEQ ID NO: 652, SEQ ID NO: 653, SEQ ID NO: 654, SEQ ID NO: 655, SEQ ID NO: 656, SEQ ID NO: 657, SEQ ID NO: 658, SEQ ID NO: 659, SEQ ID NO: 660, SEQ ID NO: 661, SEQ ID NO: 662, SEQ ID NO: 663, SEQ ID NO: 664, SEQ ID NO: 665, SEQ ID NO: 666, SEQ ID NO: 667, SEQ ID NO: 668, SEQ ID NO: 669, SEQ ID NO: 679, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 679, SEQ ID NO: 670, SEQ ID NO: 671, SEQ ID NO: 672, SEQ ID NO: 673, SEQ ID NO: 674, SEQ ID NO: 675, SEQ ID NO: 676, SEQ ID NO: 677, SEQ ID NO: 678, SEQ ID NO: 679, SEQ ID NO: 680, SEQ ID NO: 681, SEQ ID NO: 682, SEQ ID NO: 683, SEQ ID NO: 684, SEQ ID NO: 685, SEQ ID NO: 686, SEQ ID NO: 687, SEQ ID NO: 688, SEQ ID NO: 689, SEQ ID NO: 690, SEQ ID NO: 691, SEQ ID NO: 692, SEQ ID NO: 693, SEQ ID NO: 694, SEQ ID NO: 695, SEQ ID NO: 696, SEQ ID NO: 697, SEQ ID NO: 698, or SEQ ID NO: 699.

In one embodiment the RTase mutant amino acid sequence comprises a C-terminal extension. In one aspect the C-terminal extension comprises a peptide sequence. In another embodiment an isolated polypeptide encodes a RTase mutant with a C-terminal extension The claimed invention is based, at least in part, on the discovery that certain single and double amino acid mutations introduced into an MMLV RTase sequence, as disclosed herein, result in an MMLV RTase with increased or enhanced thermostability and/or RTase activity. Accordingly, methods for synthesizing the MMLV RTase mutants and methods for performing reverse transcription-polymerase chain reaction (RT-PCR) are also provided herein. Further provided are kits comprising the isolated MMLV RTase single, double, triple, or more mutations.

In certain embodiments, the mutated RTase is derived from the retrovirus Moloney murine leukemia virus (MMLV). In other embodiments, a mutated RTase of the disclosure could be derived from the RTase from a retrovirus other than MMLV, such as avian myeloblastosis virus (AMV) or human immunodeficiency virus type 1 (HIV-1), by introducing the same mutations into an RTase base construct obtained from the other retrovirus.

In certain embodiments, the RTase mutants of the disclosure are obtained by genetic engineering techniques that are well known in the art. For example, site-directed and random mutagenesis can be used to generate the RTase mutants of the disclosure.

In one embodiment of the disclosure, an RTase mutant of the disclosure is part of a composition.

3. Mutagenesis

The RTase mutants of the disclosure can be prepared by standard methods disclosed herein or known in the art. In one embodiment, the nucleic acid sequence of the RTase base construct (SEQ ID NO: 637) is modified to create a nucleic acid sequence encoding an RTase mutant. One of skill in the art will recognize that colonies with the appropriate strains can be used to grow and express an RTase mutant of interest, and following cell harvest and protein isolation, the RTase mutant can be used in cDNA synthesis techniques. Non-limiting examples of mutagenesis and cDNA synthesis are described herein in Examples 1-3.

As used herein, the term "mutagenesis" refers to the introduction of a genetic change in the nucleic acid sequence of a cell, wherein the alteration is then inherited by each cell. One of skill in the art will understand that mutations in a given nucleic acid sequence can be introduced using a variety of methods. One of skill in the art will further recognize that mutagenesis methods seek to mutate a target gene or target polynucleotide. The target gene may encode any one or more desired proteins. Mutagenesis methods commonly use a synthetic oligonucleotide that carries the desired sequence modification. The mutagenic oligonucleotide is incorporated into the DNA sequence using in vitro enzymatic DNA synthesis and is propagated in a mutant or wild-type bacterium.

Site directed mutagenesis, wherein targeted mutations are introduced into one or more desired positions of a template polynucleotide, may be achieved using primer extension mutagenesis. This technique requires the use of a specific primer that contains one or more desired mutations relative to the template polynucleotide. The mutagenesis primer can be a synthetic oligonucleotide or a PCR product. The mutated primer may include one or more substitutions, deletions, additions, or combinations thereof.

Mutated reverse transcriptases may also be generated using random mutagenesis, wherein mutations are introduced into the mutagenesis primer during synthesis. Randomly mutagenized oligonucleotides may also be used as mutagenesis primers.

In another embodiment, the mutated reverse transcriptases of the disclosure can be developed using error-prone rolling circle amplification (RCA). In this technique, the fidelity of a DNA polymerase is decreased by performing the RCA in the presence of $MnCl_2$ or by decreasing the amount of input DNA.

4. cDNA Synthesis

The disclosure also relates to the activity of MMLV RTases, as measured by the quantity of cDNA produced by the MMLV RTases disclosed herein. cDNA can be prepared using one-step or two-step procedures and can be obtained from a variety of template molecules. As used herein, the term "template molecule" refers to a biological molecule that carries the genetic code for use in making a new nucleic acid strand. For example, in DNA replication, the unwound double helix and each single-stranded DNA molecule is used as a template to synthesize a complementary strand. Reverse transcription generates cDNA from RNA. One of skill in the art will understand that cDNA molecules may be prepared from a variety of nucleic acid template molecules. In one embodiment, the nucleic acid template can be single-stranded or double-stranded DNA. In one embodiment, RNA can be used in cDNA synthesis. In certain embodiments, the MMLV RTase mutants of the disclosure exhibit increased or enhanced thermostability and/or RTase activity as compared to an RTase base construct. In other embodiments, the MMLV RTase mutants of the disclosure exhibit altered half-life, reduced or eliminated RNase H activity, reduced terminal deoxynucleotidyl transferase activity, increased accuracy or fidelity, or increased specificity.

The disclosure also provides methods for synthesizing cDNA using the MMLV RTase mutants of the disclosure that have single or double amino acid mutations. The MMLV RTase mutants of the disclosure may be used in methods that produce a first strand cDNA or a first and second strand cDNA. One of skill in the art will understand that first and second strand cDNA may form a double-stranded DNA molecule, which may include a full-length cDNA sequence and cDNA libraries.

The cDNA molecules that have been reverse transcribed by the MMLV RTase mutants of the disclosure may be isolated, or the reaction mixture containing the cDNA molecules may be directly used in downstream applications or for further analysis or manipulation. Amplification methods that may be used to practice the methods of the disclosure are described herein and are well known in the art. Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as AMV RTase or MMLV RTase).

Amplification methods utilize pairs of primers that selectively hybridize to nucleic acids corresponding to a specific nucleotide sequence of interest that are contacted with the isolated nucleic acid under conditions that permit selective hybridization. Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain methods, the detection may be performed by visual means. Alternatively, the detection may involve indirect identification of the product via chemiluminescence, radioactive scintigraphy of incorporated radiolabel or fluorescent label, or even via a system using electrical or thermal impulse signals.

Methods based on ligation of two (or more) oligonucleotides in the presence of a nucleic acid having the sequence of the resulting "di-oligonucleotide," thereby amplifying the di-oligonucleotide, also may be used in the amplification step of the disclosure.

In some embodiments of the disclosure, the detection process can utilize a hybridization technique, for example, wherein a specific primer or probe is selected to anneal to a target biomarker of interest, and thereafter detection of selective hybridization is made. As commonly known in the art, the oligonucleotide probes and primers can be designed by taking into consideration the melting point of hybridization thereof with its targeted sequence.

One of skill in the art will recognize that cDNA molecules made using the MMLV RTase mutants of the disclosure can be used in a variety of additional downstream applications. For example, amplification methods may include one-step PCR, two-step PCR, real-time or quantitative PCR, hot-start PCR, nested PCR, touch down PCR, differential display PCR (DDRT-PCR), microarray technologies, inverse PCR, Rapid amplification of PCR ends (RACE or anchored PCR), multiplex PCR, and site directed PCR mutagenesis. Synthesized cDNA and cDNA libraries created with the MMLV RTase mutants of the disclosure can be used in cloning and/or sequencing for further characterization. One of skill in the art will recognize that nucleic acid amplification using cDNA prepared with the MMLV RTase mutants of the disclosure may include additional techniques not listed herein.

To enable hybridization to occur under the methods presented above, oligonucleotide primers and probes should comprise an oligonucleotide sequence that has at least 70%, 75%, 80%, 85%, 90%, 95%, 96%, 97%, 98%, 99%, or 100% identity to a portion of the sequence of interest.

5. Biological Samples

The MMLV RTase mutants and associated methods of the disclosure may be practiced with any suitable biological sample from which RNA or DNA can be isolated. In one embodiment of the disclosure, the biological sample may be a bodily fluid or tissue obtained from either a diseased or a healthy subject. In some embodiments of the disclosure, the biological sample may be a bodily fluid, including but not limited to whole blood, plasma, serum, feces, or urine. In another embodiment, the methods of the disclosure may be practiced with any suitable samples that are freshly isolated or that have been frozen or stored after having been collected from a subject, for example, with a known diagnosis, treatment, and/or outcome history. Samples may be collected by any non-invasive means, such as, for example, fine needle aspiration or needle biopsy, or alternatively, by an invasive method, including, for example, surgical biopsy. In such embodiments, RNA or DNA can be extracted from a biological sample (e.g., blood serum) before analysis. Methods of RNA and DNA extraction are well known in the art.

A number of kits for use in extracting RNA (i.e., total RNA or mRNA) from bodily fluids or tissues (e.g., blood serum) and are known in the art and commercially available. One of ordinary skill in the art can easily select an appropriate kit for a particular situation.

In certain embodiments of the disclosure, after extraction, mRNA is amplified, and transcribed into cDNA, which can then serve as template for multiple rounds of transcription by the appropriate RNA polymerase. Amplification methods that may be used to practice the methods of the disclosure are described herein and are well known in the art. Reverse transcription reactions may be carried out using non-specific primers, such as an anchored oligo-dT primer, or random sequence primers, or using a target-specific primer complementary to the RNA for each genetic probe being monitored, or using thermostable DNA polymerases, such as MMLV RTase or the MMLV RTase mutants of the disclosure.

In certain embodiments, the RNA isolated from a biological sample (e.g., after amplification and/or conversion to cDNA or cRNA) is labeled with a detectable agent before being analyzed. The role of a detectable agent is to facilitate detection of RNA or to allow visualization of hybridized nucleic acid fragments (e.g., nucleic acid fragments hybridized to genetic probes in an array-based assay). In some embodiments, the detectable agent is selected such that it generates a signal which can be measured and whose intensity is related to the amount of labeled nucleic acids present in the sample being analyzed.

Methods for labeling nucleic acid molecules are well known in the art. A review of labeling protocols and label detection techniques can be found in Kricka, *Ann. Clin. Biochem.* 39: 114-29 (2002); van Gijlswijk et al., *Expert Rev. Mol. Diagn.* 1: 81-91 (2001); and Joos et al., *J. Biotechnol.* 35: 135-53 (1994). Standard nucleic acid labeling methods include incorporation of radioactive agents; direct attachment of fluorescent dyes or of enzymes; chemical modifications of nucleic acid fragments making them detectable immunochemically or by other affinity reactions; and enzyme-mediated labeling methods, such as random priming, nick translation, PCR, and tailing with terminal transferase.

Any of a wide variety of detectable agents can be used to practice the methods of the disclosure. Suitable detectable agents include but are not limited to various ligands, radionuclides, fluorescent dyes, chemiluminescent agents, microparticles (such as, for example, quantum dots, nanocrystals, and phosphors), enzymes (such as, for example, those used in an ELISA, i.e., horseradish peroxidase, beta-galactosidase, luciferase, and alkaline phosphatase), colorimetric labels, magnetic labels, biotin, dioxigenin, or other haptens and proteins for which antisera or monoclonal antibodies are available.

6. Kits

The disclosure also provides kits for use in reverse transcription or related technologies. These kits include one or more of the following: an MMLV RTase mutant enzyme, reagents and buffers for conducting a reverse transcriptase reaction, a box, vial tubes, ampules, and the like. Kits can also include instructions for use of the kit for practicing any of the methods disclosed herein or other methods known to those of skill in the art.

EXAMPLES

The claimed invention is further illustrated by the following Examples, which should not be construed as limiting. Those of skill in the art will recognize that the claimed invention may be practiced with variations of the disclosed structures, materials, compositions, and methods, and such variations are regarded as within the scope of the claimed invention.

The RTases described herein were overexpressed in *E. coli*, purified to homogeneity, and tested for their ability to enhance RNA detection in the context of reverse transcriptase quantitative PCR (RT-qPCR).

Example 1. Preparation of Reverse Transcriptase Mutants by Site Directed Mutagenesis a. Cloning of MMLV RTase Mutants Created from Base Construct (RNase H Minus Construct)

Figure 1B:
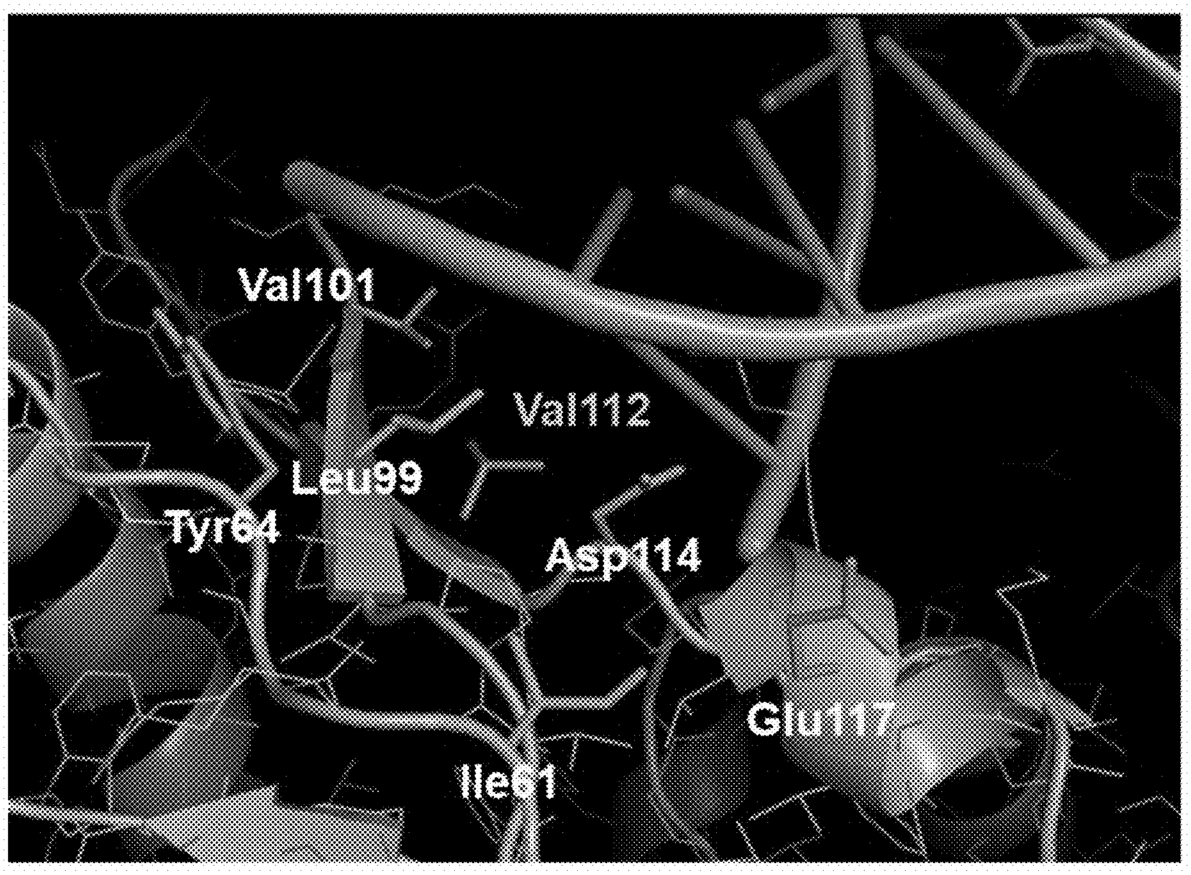
Figure 1C:
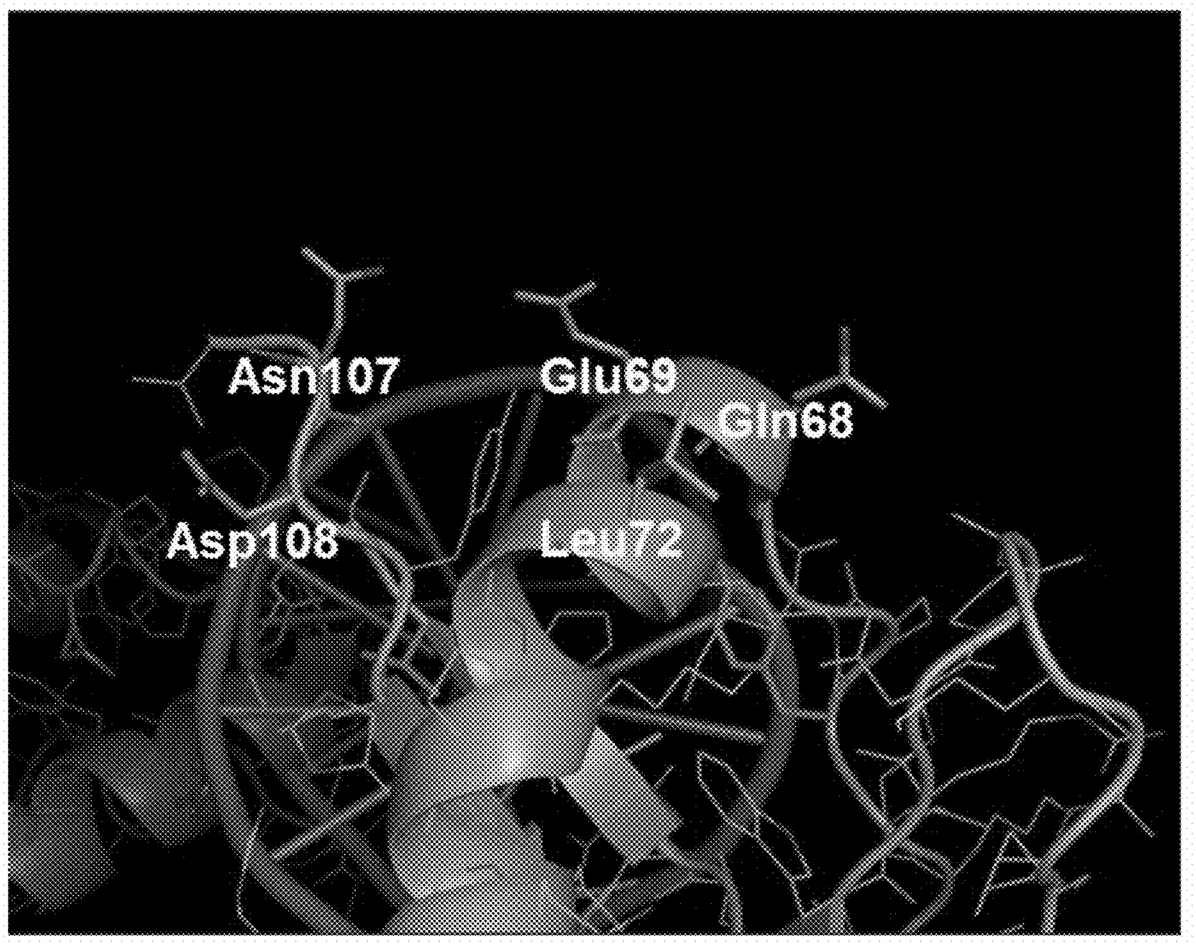

MMLV RTase mutants were prepared by first introducing three mutations (D524G, E562Q, and D583N) into the amino acid sequence of the wild-type, or naturally occurring, MMLV RTase to prepare an MMLV RTase base construct (SEQ ID NO: 637). The three mutations, which are contained in the SuperScript II RTase (Invitrogen), have been shown to reduce RNase H activity (see U.S. Pat. No. 5,405,776). The MMLV RTase base construct was optimized for *E. coli* expression and obtained as gBlocks® Gene Fragments (Integrated DNA Technologies) or by custom gene synthesis with the appropriate purification tag. Subsequent genes were amplified using standard PCR conditions and primers (see Table 1). Amplified DNA was subjected to purification using a QIAquick PCR Purification kit (Qiagen, Catalog #28104), followed by gene fragment assembly into a pET28b expression plasmid. Plasmid DNA was isolated and sequenced to verify the desired sequence following transformation into *E. coli* cells. MMLV RTase mutations were selected by rational design (FIGS. 1A-1C) and introduced by site-directed mutagenesis, using standard PCR conditions and primers (see Table 1). Resulting plasmids were transformed into *E. coli* BL21(DE3) cells for expression.

TABLE 1

Sequences of primers used for cloning of MMLV RTase base constructs and mutants into pET28b.

| SEQ ID NO: | Primer Name | Primer Sequence (5'-3') |
|---|---|---|
| 1 | pET28b 5' Reverse | GGTATATCTCCTTCTTAAAGTTAAACAAAATTATTTCTAGAGGGGAAT |
| 2 | pET28b 3' Forward | GATCCGGCTGCTAACAAAGCC |
| 3 | MMLV 5' Primer | TTTTGTTTAACTTTAAGAAGGAGATATACCATGGGCAGCAGCCATCATCATC |
| 4 | MMLV 3' Primer | GCAGCCAACTCAGCTTCCTTTCGGGCTTTGTTAAAAATGCTCGCTAGTGTAGGGAGAGC |
| 5 | MMLV K53A Top SDM | AAGCACCGTTGATCATCCCGTTAGCGGCAACGTCTACACCTGTCTCTATCAAAC |
| 6 | MMLV K53R Top SDM | AAGCACCGTTGATCATCCCGTTACGTGCAACGTCTACACCTGTCTCTATCAAAC |
| 7 | MMLV K53E Top SDM | AAGCACCGTTGATCATCCCGTTAGAAGCAACGTCTACACCTGTCTCTATCAAAC |
| 8 | MMLV T55A Top SDM | CCGTTGATCATCCCGTTAAAGGCAGCGTCTACACCTGTCTCTATCAAACAGTACCCC |
| 9 | MMLV T55R Top SDM | CCGTTGATCATCCCGTTAAAGGCACGTTCTACACCTGTCTCTATCAAACAGTACCCC |
| 10 | MMLV T55E Top SDM | CCGTTGATCATCCCGTTAAAGGCAGAATCTACACCTGTCTCTATCAAACAGTACCCC |
| 11 | MMLV T57A Top SDM | ATCATCCCGTTAAAGGCAACGTCTGCGCCTGTCTCTATCAAACAGTACCCCATGAG |
| 12 | MMLV T57R Top SDM | ATCATCCCGTTAAAGGCAACGTCTCGTCCTGTCTCTATCAAACAGTACCCCATGAG |
| 13 | MMLV T57E Top SDM | ATCATCCCGTTAAAGGCAACGTCTGAACCTGTCTCTATCAAACAGTACCCCATGAG |
| 14 | MMLV V59A Top SDM | CCGTTAAAGGCAACGTCTACACCTGCGTCTATCAAACAGTACCCCATGAGTCAAGAGG |
| 15 | MMLV V59R Top SDM | CCGTTAAAGGCAACGTCTACACCTCGTTCTATCAAACAGTACCCCATGAGTCAAGAGG |
| 16 | MMLV V59E Top SDM | CCGTTAAAGGCAACGTCTACACCTGAATCTATCAAACAGTACCCCATGAGTCAAGAGG |
| 17 | MMLV I61A Top SDM | TAAAGGCAACGTCTACACCTGTCTCTGCGAAACAGTACCCCATGAGTCAAGAGG |
| 18 | MMLV I61R Top SDM | TAAAGGCAACGTCTACACCTGTCTCTCGTAAACAGTACCCCATGAGTCAAGAGG |
| 19 | MMLV I61E Top SDM | TAAAGGCAACGTCTACACCTGTCTCTGAAAAACAGTACCCCATGAGTCAAGAGG |
| 20 | MMLV K62A Top SDM | GGCAACGTCTACACCTGTCTCTATCGCGCAGTACCCCATGAGTCAAGAGGC |
| 21 | MMLV K62R Top SDM | GGCAACGTCTACACCTGTCTCTATCCGTCAGTACCCCATGAGTCAAGAGGC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 22 | MMLV K62E Top SDM | GGCAACGTCTACACCTGTCTCTATCGAACAGTACC CCATGAGTCAAGAGGC |
| 23 | MMLV Q68A Top SDM | CTGTCTCTATCAAACAGTACCCCATGAGTGCGGAG GCCCGCCTGGG |
| 24 | MMLV Q68R Top SDM | CTGTCTCTATCAAACAGTACCCCATGAGTCGTGAG GCCCGCCTGGG |
| 25 | MMLV Q68E Top SDM | CTGTCTCTATCAAACAGTACCCCATGAGTGAAGAG GCCCGCCTGGG |
| 26 | MMLV K75A Top SDM | GGCCCGCCTGGGGATTGCGCCACATATTCAGCGCT TGCTGGACCA |
| 27 | MMLV K75R Top SDM | GGCCCGCCTGGGGATTCGTCCACATATTCAGCGCT TGCTGGACCA |
| 28 | MMLV K75E Top SDM | GGCCCGCCTGGGGATTGAACCACATATTCAGCGCT TGCTGGACCA |
| 29 | MMLV Q79A Top SDM | CGCCTGGGGATTAAGCCACATATTGCGCGCTTGCT GGACCAGGGG |
| 30 | MMLV Q79R Top SDM | CGCCTGGGGATTAAGCCACATATTCGTCGCTTGCT GGACCAGGGG |
| 31 | MMLV Q79E Top SDM | CGCCTGGGGATTAAGCCACATATTGAACGCTTGCT GGACCAGGGG |
| 32 | MMLV L99A Top SDM | CCGTGGAACACCCCCCTTGCGCCCGTGAAAAAGCC AGGTACAAAC |
| 33 | MMLV L99R Top SDM | CCGTGGAACACCCCCCTTCGTCCCGTGAAAAAGCC AGGTACAAAC |
| 34 | MMLV L99E Top SDM | CCGTGGAACACCCCCCTTGAACCCGTGAAAAAGCC AGGTACAAAC |
| 35 | MMLV V101A Top SDM | CACCCCCCTTCTGCCCGCGAAAAAGCCAGGTACAA ACGATTATCGTCC |
| 36 | MMLV V101R Top SDM | CACCCCCCTTCTGCCCCGTAAAAAGCCAGGTACAA ACGATTATCGTCC |
| 37 | MMLV V101E Top SDM | CACCCCCCTTCTGCCCGAAAAAAAGCCAGGTACAA ACGATTATCGTCC |
| 38 | MMLV K102A Top SDM | CCCCCTTCTGCCCGTGGCGAAGCCAGGTACAAACG ATTATCGTCC |
| 39 | MMLV K102R Top SDM | CCCCCTTCTGCCCGTGCGTAAGCCAGGTACAAACG ATTATCGTCC |
| 40 | MMLV K102E Top SDM | CCCCCTTCTGCCCGTGGAAAAGCCAGGTACAAACG ATTATCGTCC |
| 41 | MMLV K103A Top SDM | CCCCCTTCTGCCCGTGAAAGCGCCAGGTACAAACG ATTATCGTCCAGTT |
| 42 | MMLV K103R Top SDM | CCCCCTTCTGCCCGTGAAACGTCCAGGTACAAACG ATTATCGTCCAGTT |
| 43 | MMLV K103E Top SDM | CCCCCTTCTGCCCGTGAAAGAACCAGGTACAAACG ATTATCGTCCAGTT |
| 44 | MMLV T106A Top SDM | GCCCGTGAAAAAGCCAGGTGCGAACGATTATCGTC CAGTTCAAGATCTTCG |
| 45 | MMLV T106R Top SDM | GCCCGTGAAAAAGCCAGGTCGTAACGATTATCGTC CAGTTCAAGATCTTCG |
| 46 | MMLV T106E Top SDM | GCCCGTGAAAAAGCCAGGTGAAAACGATTATCGTC CAGTTCAAGATCTTCG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 47 | MMLV N107A Top SDM | CCCGTGAAAAAGCCAGGTACAGCGGATTATCGTCC AGTTCAAGATCTTCGCG |
| 48 | MMLV N107R Top SDM | CCCGTGAAAAAGCCAGGTACACGTGATTATCGTCC AGTTCAAGATCTTCGCG |
| 49 | MMLV N107E Top SDM | CCCGTGAAAAAGCCAGGTACAGAAGATTATCGTCC AGTTCAAGATCTTCGCG |
| 50 | MMLV Y109A Top SDM | CGTGAAAAAGCCAGGTACAAACGATGCGCGTCCAG TTCAAGATCTTCGCG |
| 51 | MMLV Y109R Top SDM | CGTGAAAAAGCCAGGTACAAACGATCGTCGTCCAG TTCAAGATCTTCGCG |
| 52 | MMLV Y109E Top SDM | CGTGAAAAAGCCAGGTACAAACGATGAACGTCCAG TTCAAGATCTTCGCG |
| 53 | MMLV R110A Top SDM | CGTGAAAAAGCCAGGTACAAACGATTATGCGCCAG TTCAAGATCTTCGCGAGG |
| 54 | MMLV R110K Top SDM | CGTGAAAAAGCCAGGTACAAACGATTATAAACCAG TTCAAGATCTTCGCGAGG |
| 55 | MMLV R110E Top SDM | CGTGAAAAAGCCAGGTACAAACGATTATGAACCAG TTCAAGATCTTCGCGAGG |
| 56 | MMLV V112A Top SDM | GCCAGGTACAAACGATTATCGTCCAGCGCAAGATC TTCGCGAGGTCAACAAAC |
| 57 | MMLV V112R Top SDM | GCCAGGTACAAACGATTATCGTCCACGTCAAGATC TTCGCGAGGTCAACAAAC |
| 58 | MMLV V112E Top SDM | GCCAGGTACAAACGATTATCGTCCAGAACAAGATC TTCGCGAGGTCAACAAAC |
| 59 | MMLV K120A Top SDM | AGTTCAAGATCTTCGCGAGGTCAACGCGCGCGTAG AAGACATCCATCCGAC |
| 60 | MMLV K120R Top SDM | AGTTCAAGATCTTCGCGAGGTCAACCGTCGCGTAG AAGACATCCATCCGAC |
| 61 | MMLV K120E Top SDM | AGTTCAAGATCTTCGCGAGGTCAACGAACGCGTAG AAGACATCCATCCGAC |
| 62 | MMLV E123A Top SDM | GCGAGGTCAACAAACGCGTAGCGGACATCCATCCG ACTGTACCTAATCC |
| 63 | MMLV E123R Top SDM | GCGAGGTCAACAAACGCGTACGTGACATCCATCCG ACTGTACCTAATCC |
| 64 | MMLV E123D Top SDM | GCGAGGTCAACAAACGCGTAGATGACATCCATCCG ACTGTACCTAATCC |
| 65 | MMLV T128V Top SDM | ACGCGTAGAAGACATCCATCCGGTGGTACCTAATC CTTATAATCTGTTATCAGGCCTGC |
| 66 | MMLV T128R Top SDM | ACGCGTAGAAGACATCCATCCGCGTGTACCTAATC CTTATAATCTGTTATCAGGCCTGC |
| 67 | MMLV T128E Top SDM | ACGCGTAGAAGACATCCATCCGGAAGTACCTAATC CTTATAATCTGTTATCAGGCCTGC |
| 68 | MMLV K193A Top SDM | CGTCTGCCCCAGGGCTTTGCGAACAGCCCCACATT GTTCGATGAA |
| 69 | MMLV K193R Top SDM | CGTCTGCCCCAGGGCTTTCGTAACAGCCCCACATT GTTCGATGAA |
| 70 | MMLV K193E Top SDM | CGTCTGCCCCAGGGCTTTGAAAACAGCCCCACATT GTTCGATGAA |
| 71 | MMLV E282A Top SDM | AGAAGGTCAACGTTGGCTGACTGCGGCGCGTAAGG AGACCGTAATG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 72 | MMLV E282R Top SDM | AGAAGGTCAACGTTGGCTGACTCGTGCGCGTAAGG AGACCGTAATG |
| 73 | MMLV E282D Top SDM | AGAAGGTCAACGTTGGCTGACTGATGCGCGTAAGG AGACCGTAATG |
| 74 | MMLV A283V Top SDM | GAAGGTCAACGTTGGCTGACTGAAGTGCGTAAGGA GACCGTAATGGGGC |
| 75 | MMLV A283R Top SDM | GAAGGTCAACGTTGGCTGACTGAACGTCGTAAGGA GACCGTAATGGGGC |
| 76 | MMLV A283E Top SDM | GAAGGTCAACGTTGGCTGACTGAAGAACGTAAGGA GACCGTAATGGGGC |
| 77 | MMLV Q291A Top SDM | GCGTAAGGAGACCGTAATGGGGGCGCCTACGCCTA AGACGCCACG |
| 78 | MMLV Q291R Top SDM | GCGTAAGGAGACCGTAATGGGGCGTCCTACGCCTA AGACGCCACG |
| 79 | MMLV Q291E Top SDM | GCGTAAGGAGACCGTAATGGGGGAACCTACGCCTA AGACGCCACG |
| 80 | MMLV T293A Top SDM | GAGACCGTAATGGGGCAGCCTGCGCCTAAGACGCC ACGCCAGTTG |
| 81 | MMLV T293R Top SDM | GAGACCGTAATGGGGCAGCCTCGTCCTAAGACGCC ACGCCAGTTG |
| 82 | MMLV T293E Top SDM | GAGACCGTAATGGGGCAGCCTGAACCTAAGACGCC ACGCCAGTTG |
| 83 | MMLV K295A Top SDM | GTAATGGGGCAGCCTACGCCTGCGACGCCACGCCA GTTGCGTGAA |
| 84 | MMLV K295R Top SDM | GTAATGGGGCAGCCTACGCCTCGTACGCCACGCCA GTTGCGTGAA |
| 85 | MMLV K295E Top SDM | GTAATGGGGCAGCCTACGCCTGAAACGCCACGCCA GTTGCGTGAA |
| 86 | MMLV T296A Top SDM | TGGGGCAGCCTACGCCTAAGGCGCCACGCCAGTTG CGTGAATTTT |
| 87 | MMLV T296R Top SDM | TGGGGCAGCCTACGCCTAAGCGTCCACGCCAGTTG CGTGAATTTT |
| 88 | MMLV T296E Top SDM | TGGGGCAGCCTACGCCTAAGGAACCACGCCAGTTG CGTGAATTTT |
| 89 | MMLV R298A Top SDM | GCCTACGCCTAAGACGCCAGCGCAGTTGCGTGAAT TTTTGGGCACAG |
| 90 | MMLV R298K Top SDM | GCCTACGCCTAAGACGCCAAAACAGTTGCGTGAAT TTTTGGGCACAG |
| 91 | MMLV R298E Top SDM | GCCTACGCCTAAGACGCCAGAACAGTTGCGTGAAT TTTTGGGCACAG |
| 92 | MMLV R301A Top SDM | CCTAAGACGCCACGCCAGTTGGCGGAATTTTTGGG CACAGCGGGA |
| 93 | MMLV R301K Top SDM | CCTAAGACGCCACGCCAGTTGAAAGAATTTTTGGG CACAGCGGGA |
| 94 | MMLV R301E Top SDM | CCTAAGACGCCACGCCAGTTGGAAGAATTTTTGGG CACAGCGGGA |
| 95 | MMLV K329A Top SDM | GCACCCCTGTACCCCTTAACAGCGACAGGGACGCT TTTCAACTGG |
| 96 | MMLV K329R Top SDM | GCACCCCTGTACCCCTTAACACGTACAGGGACGCT TTTCAACTGG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 97 | MMLV K329E Top SDM | GCACCCCTGTACCCCTTAACAGAAACAGGGACGCT TTTCAACTGG |
| 98 | MMLV K53A Btm SDM | GTTTGATAGAGACAGGTGTAGACGTTGCCGCTAAC GGGATGATCAACGGTGCTT |
| 99 | MMLV K53R Btm SDM | GTTTGATAGAGACAGGTGTAGACGTTGCACGTAAC GGGATGATCAACGGTGCTT |
| 100 | MMLV K53E Btm SDM | GTTTGATAGAGACAGGTGTAGACGTTGCTTCTAAC GGGATGATCAACGGTGCTT |
| 101 | MMLV T55A Btm SDM | GGGGTACTGTTTGATAGAGACAGGTGTAGACGCTG CCTTTAACGGGATGATCAACGG |
| 102 | MMLV T55R Btm SDM | GGGGTACTGTTTGATAGAGACAGGTGTAGAACGTG CCTTTAACGGGATGATCAACGG |
| 103 | MMLV T55E Btm SDM | GGGGTACTGTTTGATAGAGACAGGTGTAGATTCTG CCTTTAACGGGATGATCAACGG |
| 104 | MMLV T57A Btm SDM | CTCATGGGGTACTGTTTGATAGAGACAGGCGCAGA CGTTGCCTTTAACGGGATGAT |
| 105 | MMLV T57R Btm SDM | CTCATGGGGTACTGTTTGATAGAGACAGGACGAGA CGTTGCCTTTAACGGGATGAT |
| 106 | MMLV T57E Btm SDM | CTCATGGGGTACTGTTTGATAGAGACAGGTTCAGA CGTTGCCTTTAACGGGATGAT |
| 107 | MMLV V59A Btm SDM | CCTCTTGACTCATGGGGTACTGTTTGATAGACGCA GGTGTAGACGTTGCCTTTAACGG |
| 108 | MMLV V59R Btm SDM | CCTCTTGACTCATGGGGTACTGTTTGATAGAACGA GGTGTAGACGTTGCCTTTAACGG |
| 109 | MMLV V59E Btm SDM | CCTCTTGACTCATGGGGTACTGTTTGATAGATTCA GGTGTAGACGTTGCCTTTAACGG |
| 110 | MMLV I61A Btm SDM | CCTCTTGACTCATGGGGTACTGTTTCGCAGAGACA GGTGTAGACGTTGCCTTTA |
| 111 | MMLV I61R Btm SDM | CCTCTTGACTCATGGGGTACTGTTTACGAGAGACA GGTGTAGACGTTGCCTTTA |
| 112 | MMLV I61E Btm SDM | CCTCTTGACTCATGGGGTACTGTTTTTCAGAGACA GGTGTAGACGTTGCCTTTA |
| 113 | MMLV K62A Btm SDM | GCCTCTTGACTCATGGGGTACTGCGCGATAGAGAC AGGTGTAGACGTTGCC |
| 114 | MMLV K62R Btm SDM | GCCTCTTGACTCATGGGGTACTGACGGATAGAGAC AGGTGTAGACGTTGCC |
| 115 | MMLV K62E Btm SDM | GCCTCTTGACTCATGGGGTACTGTTCGATAGAGAC AGGTGTAGACGTTGCC |
| 116 | MMLV Q68A Btm SDM | CTGTCTCTATCAAACAGTACCCCATGAGTGCGGAG GCCCGCCTGGG |
| 117 | MMLV Q68R Btm SDM | CTGTCTCTATCAAACAGTACCCCATGAGTCGTGAG GCCCGCCTGGG |
| 118 | MMLV Q68E Btm SDM | CTGTCTCTATCAAACAGTACCCCATGAGTGAAGAG GCCCGCCTGGG |
| 119 | MMLV K75A Btm SDM | TGGTCCAGCAAGCGCTGAATATGTGGCGCAATCCC CAGGCGGGCC |
| 120 | MMLV K75R Btm SDM | TGGTCCAGCAAGCGCTGAATATGTGGACGAATCCC CAGGCGGGCC |
| 121 | MMLV K75E Btm SDM | TGGTCCAGCAAGCGCTGAATATGTGGTTCAATCCC CAGGCGGGCC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 122 | MMLV Q79A Btm SDM | CCCCTGGTCCAGCAAGCGCGCAATATGTGGCTTAA TCCCCAGGCG |
| 123 | MMLV Q79R Btm SDM | CCCCTGGTCCAGCAAGCGACGAATATGTGGCTTAA TCCCCAGGCG |
| 124 | MMLV Q79E Btm SDM | CCCCTGGTCCAGCAAGCGTTCAATATGTGGCTTAA TCCCCAGGCG |
| 125 | MMLV L99A Btm SDM | GTTTGTACCTGGCTTTTTCACGGGCGCAAGGGGGG TGTTCCACGG |
| 126 | MMLV L99R Btm SDM | GTTTGTACCTGGCTTTTTCACGGGACGAAGGGGGG TGTTCCACGG |
| 127 | MMLV L99E Btm SDM | GTTTGTACCTGGCTTTTTCACGGGTTCAAGGGGGG TGTTCCACGG |
| 128 | MMLV V101A Btm SDM | GGACGATAATCGTTTGTACCTGGCTTTTTCGCGGG CAGAAGGGGGGTG |
| 129 | MMLV V101R Btm SDM | GGACGATAATCGTTTGTACCTGGCTTTTTACGGGG CAGAAGGGGGGTG |
| 130 | MMLV V101E Btm SDM | GGACGATAATCGTTTGTACCTGGCTTTTTTTCGGG CAGAAGGGGGGTG |
| 131 | MMLV K102A Btm SDM | GGACGATAATCGTTTGTACCTGGCTTCGCCACGGG CAGAAGGGGG |
| 132 | MMLV K102R Btm SDM | GGACGATAATCGTTTGTACCTGGCTTACGCACGGG CAGAAGGGGG |
| 133 | MMLV K102E Btm SDM | GGACGATAATCGTTTGTACCTGGCTTTTCCACGGG CAGAAGGGGG |
| 134 | MMLV K103A Btm SDM | AACTGGACGATAATCGTTTGTACCTGGCGCTTTCA CGGGCAGAAGGGGG |
| 135 | MMLV K103R Btm SDM | AACTGGACGATAATCGTTTGTACCTGGACGTTTCA CGGGCAGAAGGGGG |
| 136 | MMLV K103E Btm SDM | AACTGGACGATAATCGTTTGTACCTGGTTCTTTCA CGGGCAGAAGGGGG |
| 137 | MMLV T106A Btm SDM | CGAAGATCTTGAACTGGACGATAATCGTTCGCACC TGGCTTTTTCACGGGC |
| 138 | MMLV T106R Btm SDM | CGAAGATCTTGAACTGGACGATAATCGTTACGACC TGGCTTTTTCACGGGC |
| 139 | MMLV T106E Btm SDM | CGAAGATCTTGAACTGGACGATAATCGTTTTCACC TGGCTTTTTCACGGGC |
| 140 | MMLV N107A Btm SDM | CGCGAAGATCTTGAACTGGACGATAATCCGCTGTA CCTGGCTTTTTCACGGG |
| 141 | MMLV N107R Btm SDM | CGCGAAGATCTTGAACTGGACGATAATCACGTGTA CCTGGCTTTTTCACGGG |
| 142 | MMLV N107E Btm SDM | CGCGAAGATCTTGAACTGGACGATAATCTTCTGTA CCTGGCTTTTTCACGGG |
| 143 | MMLV Y109A Btm SDM | CGCGAAGATCTTGAACTGGACGCGCATCGTTTGTA CCTGGCTTTTTCACG |
| 144 | MMLV Y109R Btm SDM | CGCGAAGATCTTGAACTGGACGACGATCGTTTGTA CCTGGCTTTTTCACG |
| 145 | MMLV Y109E Btm SDM | CGCGAAGATCTTGAACTGGACGTTCATCGTTTGTA CCTGGCTTTTTCACG |
| 146 | MMLV R110A Btm SDM | CCTCGCGAAGATCTTGAACTGGCGCATAATCGTTT GTACCTGGCTTTTTCACG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 147 | MMLV R110K Btm SDM | CCTCGCGAAGATCTTGAACTGGTTTATAATCGTTT GTACCTGGCTTTTTCACG |
| 148 | MMLV R110E Btm SDM | CCTCGCGAAGATCTTGAACTGGTTCATAATCGTTT GTACCTGGCTTTTTCACG |
| 149 | MMLV V112A Btm SDM | GTTTGTTGACCTCGCGAAGATCTTGCGCTGGACGA TAATCGTTTGTACCTGGC |
| 150 | MMLV V112R Btm SDM | GTTTGTTGACCTCGCGAAGATCTTGACGTGGACGA TAATCGTTTGTACCTGGC |
| 151 | MMLV V112E Btm SDM | GTTTGTTGACCTCGCGAAGATCTTGTTCTGGACGA TAATCGTTTGTACCTGGC |
| 152 | MMLV K120A Btm SDM | GTCGGATGGATGTCTTCTACGCGCGCGTTGACCTC GCGAAGATCTTGAACT |
| 153 | MMLV K120R Btm SDM | GTCGGATGGATGTCTTCTACGCGACGGTTGACCTC GCGAAGATCTTGAACT |
| 154 | MMLV K120E Btm SDM | GTCGGATGGATGTCTTCTACGCGTTCGTTGACCTC GCGAAGATCTTGAACT |
| 155 | MMLV E123A Btm SDM | GGATTAGGTACAGTCGGATGGATGTCCGCTACGCG TTTGTTGACCTCGC |
| 156 | MMLV E123R Btm SDM | GGATTAGGTACAGTCGGATGGATGTCACGTACGCG TTTGTTGACCTCGC |
| 157 | MMLV E123D Btm SDM | GGATTAGGTACAGTCGGATGGATGTCATCTACGCG TTTGTTGACCTCGC |
| 158 | MMLV T128V Btm SDM | GCAGGCCTGATAACAGATTATAAGGATTAGGTACC ACCGGATGGATGTCTTCTACGCGT |
| 159 | MMLV T128R Btm SDM | GCAGGCCTGATAACAGATTATAAGGATTAGGTACA CGCGGATGGATGTCTTCTACGCGT |
| 160 | MMLV T128E Btm SDM | GCAGGCCTGATAACAGATTATAAGGATTAGGTACT TCCGGATGGATGTCTTCTACGCGT |
| 161 | MMLV K193A Btm SDM | TTCATCGAACAATGTGGGGCTGTTCGCAAAGCCCT GGGGCAGACG |
| 162 | MMLV K193R Btm SDM | TTCATCGAACAATGTGGGGCTGTTACGAAAGCCCT GGGGCAGACG |
| 163 | MMLV K193E Btm SDM | TTCATCGAACAATGTGGGGCTGTTTTCAAAGCCCT GGGGCAGACG |
| 164 | MMLV E282A Btm SDM | CATTACGGTCTCCTTACGCGCCGCAGTCAGCCAAC GTTGACCTTCT |
| 165 | MMLV E282R Btm SDM | CATTACGGTCTCCTTACGCGCACGAGTCAGCCAAC GTTGACCTTCT |
| 166 | MMLV E282D Btm SDM | CATTACGGTCTCCTTACGCGCATCAGTCAGCCAAC GTTGACCTTCT |
| 167 | MMLV A283V Btm SDM | GCCCCATTACGGTCTCCTTACGCACTTCAGTCAGC CAACGTTGACCTTC |
| 168 | MMLV A283R Btm SDM | GCCCCATTACGGTCTCCTTACGACGTTCAGTCAGC CAACGTTGACCTTC |
| 169 | MMLV A283E Btm SDM | GCCCCATTACGGTCTCCTTACGTTCTTCAGTCAGC CAACGTTGACCTTC |
| 170 | MMLV Q291A Btm SDM | CGTGGCGTCTTAGGCGTAGGCGCCCCCATTACGGT CTCCTTACGC |
| 171 | MMLV Q291R Btm SDM | CGTGGCGTCTTAGGCGTAGGACGCCCCATTACGGT CTCCTTACGC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 172 | MMLV Q291E Btm SDM | CGTGGCGTCTTAGGCGTAGGTTCCCCCATTACGGT CTCCTTACGC |
| 173 | MMLV T293A Btm SDM | CAACTGGCGTGGCGTCTTAGGCGCAGGCTGCCCCA TTACGGTCTC |
| 174 | MMLV T293R Btm SDM | CAACTGGCGTGGCGTCTTAGGACGAGGCTGCCCCA TTACGGTCTC |
| 175 | MMLV T293E Btm SDM | CAACTGGCGTGGCGTCTTAGGTTCAGGCTGCCCCA TTACGGTCTC |
| 176 | MMLV K295A Btm SDM | TTCACGCAACTGGCGTGGCGTCGCAGGCGTAGGCT GCCCCATTAC |
| 177 | MMLV K295R Btm SDM | TTCACGCAACTGGCGTGGCGTACGAGGCGTAGGCT GCCCCATTAC |
| 178 | MMLV K295E Btm SDM | TTCACGCAACTGGCGTGGCGTTTCAGGCGTAGGCT GCCCCATTAC |
| 179 | MMLV T296A Btm SDM | AAAATTCACGCAACTGGCGTGGCGCCTTAGGCGTA GGCTGCCCCA |
| 180 | MMLV T296R Btm SDM | AAAATTCACGCAACTGGCGTGGACGCTTAGGCGTA GGCTGCCCCA |
| 181 | MMLV T296E Btm SDM | AAAATTCACGCAACTGGCGTGGTTCCTTAGGCGTA GGCTGCCCCA |
| 182 | MMLV R298A Btm SDM | CTGTGCCCAAAAATTCACGCAACTGCGCTGGCGTC TTAGGCGTAGGC |
| 183 | MMLV R298K Btm SDM | CTGTGCCCAAAAATTCACGCAACTGTTTTGGCGTC TTAGGCGTAGGC |
| 184 | MMLV R298E Btm SDM | CTGTGCCCAAAAATTCACGCAACTGTTCTGGCGTC TTAGGCGTAGGC |
| 185 | MMLV R301A Btm SDM | TCCCGCTGTGCCCAAAAATTCCGCCAACTGGCGTG GCGTCTTAGG |
| 186 | MMLV R301K Btm SDM | TCCCGCTGTGCCCAAAAATTCTTTCAACTGGCGTG GCGTCTTAGG |
| 187 | MMLV R301E Btm SDM | TCCCGCTGTGCCCAAAAATTCTTCCAACTGGCGTG GCGTCTTAGG |
| 188 | MMLV K329A Btm SDM | CCAGTTGAAAAGCGTCCCTGTCGCTGTTAAGGGGT ACAGGGGTGC |
| 189 | MMLV K329R Btm SDM | CCAGTTGAAAAGCGTCCCTGTACGTGTTAAGGGGT ACAGGGGTGC |
| 190 | MMLV K329E Btm SDM | CCAGTTGAAAAGCGTCCCTGTTTCTGTTAAGGGGT ACAGGGGTGC |
| 191 | MMLV I61G Top SDM | TAAAGGCAACGTCTACACCTGTCTCTGGCAAACAG TACCCCATGAGTCAAGAGG |
| 192 | MMLV I61G Btm SDM | CCTCTTGACTCATGGGGTACTGTTTGCCAGAGACA GGTGTAGACGTTGCCTTTA |
| 193 | MMLV I61L Top SDM | TAAAGGCAACGTCTACACCTGTCTCTCTGAAACAG TACCCCATGAGTCAAGAGG |
| 194 | MMLV I61L Btm SDM | CCTCTTGACTCATGGGGTACTGTTTCAGAGAGACA GGTGTAGACGTTGCCTTTA |
| 195 | MMLV I61V Top SDM | TAAAGGCAACGTCTACACCTGTCTCTGTGAAACAG TACCCCATGAGTCAAGAGG |
| 196 | MMLV I61V Btm SDM | CCTCTTGACTCATGGGGTACTGTTTCACAGAGACA GGTGTAGACGTTGCCTTTA |

TABLE 1-continued

Sequences of primers used for cloning of MMLV RTase base constructs and mutants into pET28b.

| SEQ ID NO: | Primer Name | Primer Sequence (5'-3') |
|---|---|---|
| 197 | MMLV I61P Top SDM | TAAAGGCAACGTCTACACCTGTCTCTCCGAAACAG TACCCCATGAGTCAAGAGG |
| 198 | MMLV I61P Btm SDM | CCTCTTGACTCATGGGGTACTGTTTCGGAGAGACA GGTGTAGACGTTGCCTTTA |
| 199 | MMLV I61M Top SDM | TAAAGGCAACGTCTACACCTGTCTCTATGAAACAG TACCCCATGAGTCAAGAGG |
| 200 | MMLV I61M Btm SDM | CCTCTTGACTCATGGGGTACTGTTTCATAGAGACA GGTGTAGACGTTGCCTTTA |
| 201 | MMLV I61S Top SDM | TAAAGGCAACGTCTACACCTGTCTCTAGCAAACAG TACCCCATGAGTCAAGAGG |
| 202 | MMLV I61S Btm SDM | CCTCTTGACTCATGGGGTACTGTTTGCTAGAGACA GGTGTAGACGTTGCCTTTA |
| 203 | MMLV I61T Top SDM | TAAAGGCAACGTCTACACCTGTCTCTACCAAACAG TACCCCATGAGTCAAGAGG |
| 204 | MMLV I61T Btm SDM | CCTCTTGACTCATGGGGTACTGTTTGGTAGAGACA GGTGTAGACGTTGCCTTTA |
| 205 | MMLV I61C Top SDM | TAAAGGCAACGTCTACACCTGTCTCTTGCAAACAG TACCCCATGAGTCAAGAGG |
| 206 | MMLV I61C Btm SDM | CCTCTTGACTCATGGGGTACTGTTTGCAAGAGACA GGTGTAGACGTTGCCTTTA |
| 207 | MMLV I61F Top SDM | TAAAGGCAACGTCTACACCTGTCTCTTTTAAACAG TACCCCATGAGTCAAGAGG |
| 208 | MMLV I61F Btm SDM | CCTCTTGACTCATGGGGTACTGTTTAAAAGAGACA GGTGTAGACGTTGCCTTTA |
| 209 | MMLV I61Y Top SDM | TAAAGGCAACGTCTACACCTGTCTCTTATAAACAG TACCCCATGAGTCAAGAGG |
| 210 | MMLV I61Y Btm SDM | CCTCTTGACTCATGGGGTACTGTTTATAAGAGACA GGTGTAGACGTTGCCTTTA |
| 211 | MMLV I61H Top SDM | TAAAGGCAACGTCTACACCTGTCTCTCATAAACAG TACCCCATGAGTCAAGAGG |
| 212 | MMLV I61H Btm SDM | CCTCTTGACTCATGGGGTACTGTTTATGAGAGACA GGTGTAGACGTTGCCTTTA |
| 213 | MMLV I61W Top SDM | TAAAGGCAACGTCTACACCTGTCTCTTGGAAACAG TACCCCATGAGTCAAGAGG |
| 214 | MMLV I61W Btm SDM | CCTCTTGACTCATGGGGTACTGTTTCCAAGAGACA GGTGTAGACGTTGCCTTTA |
| 215 | MMLV I61D Top SDM | TAAAGGCAACGTCTACACCTGTCTCTGATAAACAG TACCCCATGAGTCAAGAGG |
| 216 | MMLV I61D Btm SDM | CCTCTTGACTCATGGGGTACTGTTTATCAGAGACA GGTGTAGACGTTGCCTTTA |
| 217 | MMLV I61N Top SDM | TAAAGGCAACGTCTACACCTGTCTCTAACAAACAG TACCCCATGAGTCAAGAGG |
| 218 | MMLV I61N Btm SDM | CCTCTTGACTCATGGGGTACTGTTTGTTAGAGACA GGTGTAGACGTTGCCTTTA |
| 219 | MMLV I61Q Top SDM | TAAAGGCAACGTCTACACCTGTCTCTCAGAAACAG TACCCCATGAGTCAAGAGG |
| 220 | MMLV I61Q Btm SDM | CCTCTTGACTCATGGGGTACTGTTTCTGAGAGACA GGTGTAGACGTTGCCTTTA |
| 221 | MMLV I61K Top SDM | TAAAGGCAACGTCTACACCTGTCTCTAAAAAACAG TACCCCATGAGTCAAGAGG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 222 | MMLV I61K Btm SDM | CCTCTTGACTCATGGGGTACTGTTTTTAGAGACA GGTGTAGACGTTGCCTTTA |
| 223 | MMLV Q68G Top SDM | CTGTCTCTATCAAACAGTACCCCATGAGTGGCGAG GCCCGCCTGGG |
| 224 | MMLV Q68G Btm SDM | CCCAGGCGGGCCTCGCCACTCATGGGGTACTGTTT GATAGAGACAG |
| 225 | MMLV Q68L Top SDM | CTGTCTCTATCAAACAGTACCCCATGAGTCTGGAG GCCCGCCTGGG |
| 226 | MMLV Q68L Btm SDM | CCCAGGCGGGCCTCCAGACTCATGGGGTACTGTTT GATAGAGACAG |
| 227 | MMLV Q68I Top SDM | CTGTCTCTATCAAACAGTACCCCATGAGTATTGAG GCCCGCCTGGG |
| 228 | MMLV Q68I Btm SDM | CCCAGGCGGGCCTCAATACTCATGGGGTACTGTTT GATAGAGACAG |
| 229 | MMLV Q68V Top SDM | CTGTCTCTATCAAACAGTACCCCATGAGTGTGGAG GCCCGCCTGGG |
| 230 | MMLV Q68V Btm SDM | CCCAGGCGGGCCTCCACACTCATGGGGTACTGTTT GATAGAGACAG |
| 231 | MMLV Q68P Top SDM | CTGTCTCTATCAAACAGTACCCCATGAGTCCGGAG GCCCGCCTGGG |
| 232 | MMLV Q68P Btm SDM | CCCAGGCGGGCCTCCGGACTCATGGGGTACTGTTT GATAGAGACAG |
| 233 | MMLV Q68M Top SDM | CTGTCTCTATCAAACAGTACCCCATGAGTATGGAG GCCCGCCTGGG |
| 234 | MMLV Q68M Btm SDM | CCCAGGCGGGCCTCCATACTCATGGGGTACTGTTT GATAGAGACAG |
| 235 | MMLV Q68S Top SDM | CTGTCTCTATCAAACAGTACCCCATGAGTAGCGAG GCCCGCCTGGG |
| 236 | MMLV Q68S Btm SDM | CCCAGGCGGGCCTCGCTACTCATGGGGTACTGTTT GATAGAGACAG |
| 237 | MMLV Q68T Top SDM | CTGTCTCTATCAAACAGTACCCCATGAGTACCGAG GCCCGCCTGGG |
| 238 | MMLV Q68T Btm SDM | CCCAGGCGGGCCTCGGTACTCATGGGGTACTGTTT GATAGAGACAG |
| 239 | MMLV Q68C Top SDM | CTGTCTCTATCAAACAGTACCCCATGAGTTGCGAG GCCCGCCTGGG |
| 240 | MMLV Q68C Btm SDM | CCCAGGCGGGCCTCGCAACTCATGGGGTACTGTTT GATAGAGACAG |
| 241 | MMLV Q68F Top SDM | CTGTCTCTATCAAACAGTACCCCATGAGTTTTGAG GCCCGCCTGGG |
| 242 | MMLV Q68F Btm SDM | CCCAGGCGGGCCTCAAAACTCATGGGGTACTGTTT GATAGAGACAG |
| 243 | MMLV Q68Y Top SDM | CTGTCTCTATCAAACAGTACCCCATGAGTTATGAG GCCCGCCTGGG |
| 244 | MMLV Q68Y Btm SDM | CCCAGGCGGGCCTCATAACTCATGGGGTACTGTTT GATAGAGACAG |
| 245 | MMLV Q68H Top SDM | CTGTCTCTATCAAACAGTACCCCATGAGTCATGAG GCCCGCCTGGG |
| 246 | MMLV Q68H Btm SDM | CCCAGGCGGGCCTCATGACTCATGGGGTACTGTTT GATAGAGACAG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 247 | MMLV Q68W Top SDM | CTGTCTCTATCAAACAGTACCCCATGAGTTGGGAG GCCCGCCTGGG |
| 248 | MMLV Q68W Btm SDM | CCCAGGCGGGCCTCCCAACTCATGGGGTACTGTTT GATAGAGACAG |
| 249 | MMLV Q68D Top SDM | CTGTCTCTATCAAACAGTACCCCATGAGTGATGAG GCCCGCCTGGG |
| 250 | MMLV Q68D Btm SDM | CCCAGGCGGGCCTCATCACTCATGGGGTACTGTTT GATAGAGACAG |
| 251 | MMLV Q68N Top SDM | CTGTCTCTATCAAACAGTACCCCATGAGTAACGAG GCCCGCCTGGG |
| 252 | MMLV Q68N Btm SDM | CCCAGGCGGGCCTCGTTACTCATGGGGTACTGTTT GATAGAGACAG |
| 253 | MMLV Q68K Top SDM | CTGTCTCTATCAAACAGTACCCCATGAGTAAAGAG GCCCGCCTGGG |
| 254 | MMLV Q68K Btm SDM | CCCAGGCGGGCCTCTTTACTCATGGGGTACTGTTT GATAGAGACAG |
| 255 | MMLV Q79G Top SDM | CGCCTGGGGATTAAGCCACATATTGGCCGCTTGCT GGACCAGGGG |
| 256 | MMLV Q79G Btm SDM | CCCCTGGTCCAGCAAGCGGCCAATATGTGGCTTAA TCCCCAGGCG |
| 257 | MMLV Q79L Top SDM | CGCCTGGGGATTAAGCCACATATTCTGCGCTTGCT GGACCAGGGG |
| 258 | MMLV Q79L Btm SDM | CCCCTGGTCCAGCAAGCGCAGAATATGTGGCTTAA TCCCCAGGCG |
| 259 | MMLV Q79I Top SDM | CGCCTGGGGATTAAGCCACATATTATTCGCTTGCT GGACCAGGGG |
| 260 | MMLV Q79I Btm SDM | CCCCTGGTCCAGCAAGCGAATAATATGTGGCTTAA TCCCCAGGCG |
| 261 | MMLV Q79V Top SDM | CGCCTGGGGATTAAGCCACATATTGTGCGCTTGCT GGACCAGGGG |
| 262 | MMLV Q79V Btm SDM | CCCCTGGTCCAGCAAGCGCACAATATGTGGCTTAA TCCCCAGGCG |
| 263 | MMLV Q79P Top SDM | CGCCTGGGGATTAAGCCACATATTCCGCGCTTGCT GGACCAGGGG |
| 264 | MMLV Q79P Btm SDM | CCCCTGGTCCAGCAAGCGCGGAATATGTGGCTTAA TCCCCAGGCG |
| 265 | MMLV Q79M Top SDM | CGCCTGGGGATTAAGCCACATATTATGCGCTTGCT GGACCAGGGG |
| 266 | MMLV Q79M Btm SDM | CCCCTGGTCCAGCAAGCGCATAATATGTGGCTTAA TCCCCAGGCG |
| 267 | MMLV Q79S Top SDM | CGCCTGGGGATTAAGCCACATATTAGCCGCTTGCT GGACCAGGGG |
| 268 | MMLV Q79S Btm SDM | CCCCTGGTCCAGCAAGCGGCTAATATGTGGCTTAA TCCCCAGGCG |
| 269 | MMLV Q79T Top SDM | CGCCTGGGGATTAAGCCACATATTACCCGCTTGCT GGACCAGGGG |
| 270 | MMLV Q79T Btm SDM | CCCCTGGTCCAGCAAGCGGGTAATATGTGGCTTAA TCCCCAGGCG |
| 271 | MMLV Q79C Top SDM | CGCCTGGGGATTAAGCCACATATTTGCCGCTTGCT GGACCAGGGG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 272 | MMLV Q79C Btm SDM | CCCCTGGTCCAGCAAGCGGCAAATATGTGGCTTAA TCCCCAGGCG |
| 273 | MMLV Q79F Top SDM | CGCCTGGGGATTAAGCCACATATTTTTCGCTTGCT GGACCAGGGG |
| 274 | MMLV Q79F Btm SDM | CCCCTGGTCCAGCAAGCGAAAAATATGTGGCTTAA TCCCCAGGCG |
| 275 | MMLV Q79Y Top SDM | CGCCTGGGGATTAAGCCACATATTTATCGCTTGCT GGACCAGGGG |
| 276 | MMLV Q79Y Btm SDM | CCCCTGGTCCAGCAAGCGATAAATATGTGGCTTAA TCCCCAGGCG |
| 277 | MMLV Q79H Top SDM | CGCCTGGGGATTAAGCCACATATTCATCGCTTGCT GGACCAGGGG |
| 278 | MMLV Q79H Btm SDM | CCCCTGGTCCAGCAAGCGATGAATATGTGGCTTAA TCCCCAGGCG |
| 279 | MMLV Q79W Top SDM | CGCCTGGGGATTAAGCCACATATTTGGCGCTTGCT GGACCAGGGG |
| 280 | MMLV Q79W Btm SDM | CCCCTGGTCCAGCAAGCGCCAAATATGTGGCTTAA TCCCCAGGCG |
| 281 | MMLV Q79D Top SDM | CGCCTGGGGATTAAGCCACATATTGATCGCTTGCT GGACCAGGGG |
| 282 | MMLV Q79D Btm SDM | CCCCTGGTCCAGCAAGCGATCAATATGTGGCTTAA TCCCCAGGCG |
| 283 | MMLV Q79N Top SDM | CGCCTGGGGATTAAGCCACATATTAACCGCTTGCT GGACCAGGGG |
| 284 | MMLV Q79N Btm SDM | CCCCTGGTCCAGCAAGCGGTTAATATGTGGCTTAA TCCCCAGGCG |
| 285 | MMLV Q79K Top SDM | CGCCTGGGGATTAAGCCACATATTAAACGCTTGCT GGACCAGGGG |
| 286 | MMLV Q79K Btm SDM | CCCCTGGTCCAGCAAGCGTTTAATATGTGGCTTAA TCCCCAGGCG |
| 287 | MMLV L99G Top SDM | CCGTGGAACACCCCCCTTGGCCCCGTGAAAAAGCC AGGTACAAAC |
| 288 | MMLV L99G Btm SDM | GTTTGTACCTGGCTTTTTCACGGGGCCAAGGGGGG TGTTCCACGG |
| 289 | MMLV L99I Top SDM | CCGTGGAACACCCCCCTTATTCCCGTGAAAAAGCC AGGTACAAAC |
| 290 | MMLV L99I Btm SDM | GTTTGTACCTGGCTTTTTCACGGGAATAAGGGGGG TGTTCCACGG |
| 291 | MMLV L99V Top SDM | CCGTGGAACACCCCCCTTGTGCCCGTGAAAAAGCC AGGTACAAAC |
| 292 | MMLV L99V Btm SDM | GTTTGTACCTGGCTTTTTCACGGGCACAAGGGGGG TGTTCCACGG |
| 293 | MMLV L99P Top SDM | CCGTGGAACACCCCCCTTCCGCCCGTGAAAAAGCC AGGTACAAAC |
| 294 | MMLV L99P Btm SDM | GTTTGTACCTGGCTTTTTCACGGGCGGAAGGGGGG TGTTCCACGG |
| 295 | MMLV L99M Top SDM | CCGTGGAACACCCCCCTTATGCCCGTGAAAAAGCC AGGTACAAAC |
| 296 | MMLV L99M Btm SDM | GTTTGTACCTGGCTTTTTCACGGGCATAAGGGGGG TGTTCCACGG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 297 | MMLV L99S Top SDM | CCGTGGAACACCCCCCTTAGCCCCGTGAAAAAGCC AGGTACAAAC |
| 298 | MMLV L99S Btm SDM | GTTTGTACCTGGCTTTTTCACGGGGCTAAGGGGGG TGTTCCACGG |
| 299 | MMLV L99T Top SDM | CCGTGGAACACCCCCCTTACCCCCGTGAAAAAGCC AGGTACAAAC |
| 300 | MMLV L99T Btm SDM | GTTTGTACCTGGCTTTTTCACGGGGGTAAGGGGGG TGTTCCACGG |
| 301 | MMLV L99C Top SDM | CCGTGGAACACCCCCCTTTGCCCCGTGAAAAAGCC AGGTACAAAC |
| 302 | MMLV L99C Btm SDM | GTTTGTACCTGGCTTTTTCACGGGGCAAAGGGGGG TGTTCCACGG |
| 303 | MMLV L99F Top SDM | CCGTGGAACACCCCCCTTTTTCCCGTGAAAAAGCC AGGTACAAAC |
| 304 | MMLV L99F Btm SDM | GTTTGTACCTGGCTTTTTCACGGGAAAAAGGGGGG TGTTCCACGG |
| 305 | MMLV L99Y Top SDM | CCGTGGAACACCCCCCTTTATCCCGTGAAAAAGCC AGGTACAAAC |
| 306 | MMLV L99Y Btm SDM | GTTTGTACCTGGCTTTTTCACGGGATAAAGGGGGG TGTTCCACGG |
| 307 | MMLV L99H Top SDM | CCGTGGAACACCCCCCTTCATCCCGTGAAAAAGCC AGGTACAAAC |
| 308 | MMLV L99H Btm SDM | GTTTGTACCTGGCTTTTTCACGGGATGAAGGGGGG TGTTCCACGG |
| 309 | MMLV L99W Top SDM | CCGTGGAACACCCCCCTTTGGCCCGTGAAAAAGCC AGGTACAAAC |
| 310 | MMLV L99W Btm SDM | GTTTGTACCTGGCTTTTTCACGGGCCAAAGGGGGG TGTTCCACGG |
| 311 | MMLV L99D Top SDM | CCGTGGAACACCCCCCTTGATCCCGTGAAAAAGCC AGGTACAAAC |
| 312 | MMLV L99D Btm SDM | GTTTGTACCTGGCTTTTTCACGGGATCAAGGGGGG TGTTCCACGG |
| 313 | MMLV L99N Top SDM | CCGTGGAACACCCCCCTTAACCCCGTGAAAAAGCC AGGTACAAAC |
| 314 | MMLV L99N Btm SDM | GTTTGTACCTGGCTTTTTCACGGGGTTAAGGGGGG TGTTCCACGG |
| 315 | MMLV L99Q Top SDM | CCGTGGAACACCCCCCTTCAGCCCGTGAAAAAGCC AGGTACAAAC |
| 316 | MMLV L99Q Btm SDM | GTTTGTACCTGGCTTTTTCACGGGCTGAAGGGGGG TGTTCCACGG |
| 317 | MMLV L99K Top SDM | CCGTGGAACACCCCCCTTAAACCCGTGAAAAAGCC AGGTACAAAC |
| 318 | MMLV L99K Btm SDM | GTTTGTACCTGGCTTTTTCACGGGTTTAAGGGGGG TGTTCCACGG |
| 319 | MMLV E282G Top SDM | AGAAGGTCAACGTTGGCTGACTGGCGCGCGTAAGG AGACCGTAATG |
| 320 | MMLV E282G Btm SDM | CATTACGGTCTCCTTACGCGCGCCAGTCAGCCAAC GTTGACCTTCT |
| 321 | MMLV E282L Top SDM | AGAAGGTCAACGTTGGCTGACTCTGGCGCGTAAGG AGACCGTAATG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 322 | MMLV E282L Btm SDM | CATTACGGTCTCCTTACGCGCCAGAGTCAGCCAAC GTTGACCTTCT |
| 323 | MMLV E2821 Top SDM | AGAAGGTCAACGTTGGCTGACTATTGCGCGTAAGG AGACCGTAATG |
| 324 | MMLV E2821 Btm SDM | CATTACGGTCTCCTTACGCGCAATAGTCAGCCAAC GTTGACCTTCT |
| 325 | MMLV E282V Top SDM | AGAAGGTCAACGTTGGCTGACTGTGGCGCGTAAGG AGACCGTAATG |
| 326 | MMLV E282V Btm SDM | CATTACGGTCTCCTTACGCGCCACAGTCAGCCAAC GTTGACCTTCT |
| 327 | MMLV E282P Top SDM | AGAAGGTCAACGTTGGCTGACTCCGGCGCGTAAGG AGACCGTAATG |
| 328 | MMLV E282P Btm SDM | CATTACGGTCTCCTTACGCGCCGGAGTCAGCCAAC GTTGACCTTCT |
| 329 | MMLV E282M Top SDM | AGAAGGTCAACGTTGGCTGACTATGGCGCGTAAGG AGACCGTAATG |
| 330 | MMLV E282M Btm SDM | CATTACGGTCTCCTTACGCGCCATAGTCAGCCAAC GTTGACCTTCT |
| 331 | MMLV E282S Top SDM | AGAAGGTCAACGTTGGCTGACTAGCGCGCGTAAGG AGACCGTAATG |
| 332 | MMLV E282S Btm SDM | CATTACGGTCTCCTTACGCGCGCTAGTCAGCCAAC GTTGACCTTCT |
| 333 | MMLV E282T Top SDM | AGAAGGTCAACGTTGGCTGACTACCGCGCGTAAGG AGACCGTAATG |
| 334 | MMLV E282T Btm SDM | CATTACGGTCTCCTTACGCGCGGTAGTCAGCCAAC GTTGACCTTCT |
| 335 | MMLV E282C Top SDM | AGAAGGTCAACGTTGGCTGACTTGCGCGCGTAAGG AGACCGTAATG |
| 336 | MMLV E282C Btm SDM | CATTACGGTCTCCTTACGCGCGCAAGTCAGCCAAC GTTGACCTTCT |
| 337 | MMLV E282F Top SDM | AGAAGGTCAACGTTGGCTGACTTTTGCGCGTAAGG AGACCGTAATG |
| 338 | MMLV E282F Btm SDM | CATTACGGTCTCCTTACGCGCAAAAGTCAGCCAAC GTTGACCTTCT |
| 339 | MMLV E282Y Top SDM | AGAAGGTCAACGTTGGCTGACTTATGCGCGTAAGG AGACCGTAATG |
| 340 | MMLV E282Y Btm SDM | CATTACGGTCTCCTTACGCGCATAAGTCAGCCAAC GTTGACCTTCT |
| 341 | MMLV E282H Top SDM | AGAAGGTCAACGTTGGCTGACTCATGCGCGTAAGG AGACCGTAATG |
| 342 | MMLV E282H Btm SDM | CATTACGGTCTCCTTACGCGCATGAGTCAGCCAAC GTTGACCTTCT |
| 343 | MMLV E282W Top SDM | AGAAGGTCAACGTTGGCTGACTTGGGCGCGTAAGG AGACCGTAATG |
| 344 | MMLV E282W Btm SDM | CATTACGGTCTCCTTACGCGCCCAAGTCAGCCAAC GTTGACCTTCT |
| 345 | MMLV E282N Top SDM | AGAAGGTCAACGTTGGCTGACTAACGCGCGTAAGG AGACCGTAATG |
| 346 | MMLV E282N Btm SDM | CATTACGGTCTCCTTACGCGCGTTAGTCAGCCAAC GTTGACCTTCT |

TABLE 1-continued

Sequences of primers used for cloning of MMLV RTase base constructs and mutants into pET28b.

| SEQ ID NO: | Primer Name | Primer Sequence (5'-3') |
|---|---|---|
| 347 | MMLV E282Q Top SDM | AGAAGGTCAACGTTGGCTGACTCAGGCGCGTAAGG AGACCGTAATG |
| 348 | MMLV E282Q Btm SDM | CATTACGGTCTCCTTACGCGCCTGAGTCAGCCAAC GTTGACCTTCT |
| 349 | MMLV E282K Top SDM | AGAAGGTCAACGTTGGCTGACTAAAGCGCGTAAGG AGACCGTAATG |
| 350 | MMLV E282K Btm SDM | CATTACGGTCTCCTTACGCGCTTTAGTCAGCCAAC GTTGACCTTCT |
| 351 | MMLV R298G Top SDM | GCCTACGCCTAAGACGCCAGGCCAGTTGCGTGAAT TTTTGGGCACAG |
| 352 | MMLV R298G Btm SDM | CTGTGCCCAAAAATTCACGCAACTGGCCTGGCGTC TTAGGCGTAGGC |
| 353 | MMLV R298L Top SDM | GCCTACGCCTAAGACGCCACTGCAGTTGCGTGAAT TTTTGGGCACAG |
| 354 | MMLV R298L Btm SDM | CTGTGCCCAAAAATTCACGCAACTGCAGTGGCGTC TTAGGCGTAGGC |
| 355 | MMLV R298I Top SDM | GCCTACGCCTAAGACGCCAATTCAGTTGCGTGAAT TTTTGGGCACAG |
| 356 | MMLV R298I Btm SDM | CTGTGCCCAAAAATTCACGCAACTGAATTGGCGTC TTAGGCGTAGGC |
| 357 | MMLV R298V Top SDM | GCCTACGCCTAAGACGCCAGTGCAGTTGCGTGAAT TTTTGGGCACAG |
| 358 | MMLV R298V Btm SDM | CTGTGCCCAAAAATTCACGCAACTGCACTGGCGTC TTAGGCGTAGGC |
| 359 | MMLV R298P Top SDM | GCCTACGCCTAAGACGCCACCGCAGTTGCGTGAAT TTTTGGGCACAG |
| 360 | MMLV R298P Btm SDM | CTGTGCCCAAAAATTCACGCAACTGCGGTGGCGTC TTAGGCGTAGGC |
| 361 | MMLV R298M Top SDM | GCCTACGCCTAAGACGCCAATGCAGTTGCGTGAAT TTTTGGGCACAG |
| 362 | MMLV R298M Btm SDM | CTGTGCCCAAAAATTCACGCAACTGCATTGGCGTC TTAGGCGTAGGC |
| 363 | MMLV R298S Top SDM | GCCTACGCCTAAGACGCCAAGCCAGTTGCGTGAAT TTTTGGGCACAG |
| 364 | MMLV R298S Btm SDM | CTGTGCCCAAAAATTCACGCAACTGGCTTGGCGTC TTAGGCGTAGGC |
| 365 | MMLV R298T Top SDM | GCCTACGCCTAAGACGCCAACCCAGTTGCGTGAAT TTTTGGGCACAG |
| 366 | MMLV R298T Btm SDM | CTGTGCCCAAAAATTCACGCAACTGGGTTGGCGTC TTAGGCGTAGGC |
| 367 | MMLV R298C Top SDM | GCCTACGCCTAAGACGCCATGCCAGTTGCGTGAAT TTTTGGGCACAG |
| 368 | MMLV R298C Btm SDM | CTGTGCCCAAAAATTCACGCAACTGGCATGGCGTC TTAGGCGTAGGC |
| 369 | MMLV R298F Top SDM | GCCTACGCCTAAGACGCCATTTCAGTTGCGTGAAT TTTTGGGCACAG |
| 370 | MMLV R298F Btm SDM | CTGTGCCCAAAAATTCACGCAACTGAAATGGCGTC TTAGGCGTAGGC |
| 371 | MMLV R298Y Top SDM | GCCTACGCCTAAGACGCCATATCAGTTGCGTGAAT TTTTGGGCACAG |

TABLE 1-continued

Sequences of primers used for cloning of MMLV RTase base constructs and mutants into pET28b.

| SEQ ID NO: | Primer Name | Primer Sequence (5'-3') |
|---|---|---|
| 372 | MMLV R298Y Btm SDM | CTGTGCCCAAAAATTCACGCAACTGATATGGCGTC TTAGGCGTAGGC |
| 373 | MMLV R298H Top SDM | GCCTACGCCTAAGACGCCACATCAGTTGCGTGAAT TTTTGGGCACAG |
| 374 | MMLV R298H Btm SDM | CTGTGCCCAAAAATTCACGCAACTGATGTGGCGTC TTAGGCGTAGGC |
| 375 | MMLV R298W Top SDM | GCCTACGCCTAAGACGCCATGGCAGTTGCGTGAAT TTTTGGGCACAG |
| 376 | MMLV R298W Btm SDM | CTGTGCCCAAAAATTCACGCAACTGCCATGGCGTC TTAGGCGTAGGC |
| 377 | MMLV R298D Top SDM | GCCTACGCCTAAGACGCCAGATCAGTTGCGTGAAT TTTTGGGCACAG |
| 378 | MMLV R298D Btm SDM | CTGTGCCCAAAAATTCACGCAACTGATCTGGCGTC TTAGGCGTAGGC |
| 379 | MMLV R298N Top SDM | GCCTACGCCTAAGACGCCAAACCAGTTGCGTGAAT TTTTGGGCACAG |
| 380 | MMLV R298N Btm SDM | CTGTGCCCAAAAATTCACGCAACTGGTTTGGCGTC TTAGGCGTAGGC |
| 381 | MMLV R298Q Top SDM | GCCTACGCCTAAGACGCCACAGCAGTTGCGTGAAT TTTTGGGCACAG |
| 382 | MMLV R298Q Btm SDM | CTGTGCCCAAAAATTCACGCAACTGCTGTGGCGTC TTAGGCGTAGGC |
| 383 | MMLV I61R/Q68R Top SDM | AGGCAACGTCTACACCTGTCTCTCGTAAACAGTAC CCCATGAGTCGTGAGGCCCGCCTGGGG |
| 384 | MMLV I61R/Q68R Btm SDM | CCCCAGGCGGGCCTCACGACTCATGGGGTACTGTT TACGAGAGACAGGTGTAGACGTTGCCT |
| 385 | MMLV I61K/Q68R Top SDM | AGGCAACGTCTACACCTGTCTCTAAAAAACAGTAC CCCATGAGTCGTGAGG |
| 386 | MMLV I61K/Q68R Btm SDM | CCTCACGACTCATGGGGTACTGTTTTTTAGAGACA GGTGTAGACGTTGCCT |
| 387 | MMLV I61M/Q68R Top SDM | AGGCAACGTCTACACCTGTCTCTATGAAACAGTAC CCCATGAGTCGTGAGG |
| 388 | MMLV I61M/Q68R Btm SDM | CCTCACGACTCATGGGGTACTGTTTCATAGAGACA GGTGTAGACGTTGCCT |
| 389 | MMLV I61M/Q681 Top SDM | AGGCAACGTCTACACCTGTCTCTATGAAACAGTAC CCCATGAGTATTGAGGCC |
| 390 | MMLV I61M/Q681 Btm SDM | GGCCTCAATACTCATGGGGTACTGTTTCATAGAGA CAGGTGTAGACGTTGCCT |
| 393 | MMLV 5' Primer | CCGCCTGGGGTCTCTATCAAACAGTACCCCATGGC GCAAGAGGC |
| 394 | MMLV 3' Primer | CCGCCTGGGGTCTCTATCAAACAGTACCCCATGCG TCAAGAGGC |
| 395 | MMLV G73A Top SDM | CATGAGTCAAGAGGCCCGCGAGGGGATTAAGCCAC ATATTCAGCG |
| 396 | MMLV G73R Top SDM | GAGTCAAGAGGCCCGCCTGGCGATTAAGCCACATA TTCAGCGCTTGC |
| 397 | MMLV G73E Top SDM | GAGTCAAGAGGCCCGCCTGCGTATTAAGCCACATA TTCAGCGCTTGC |
| 398 | MMLV P76A Top SDM | GAGTCAAGAGGCCCGCCTGGAGATTAAGCCACATA TTCAGCGCTTGC |
| 399 | MMLV P76R Top SDM | GGCCCGCCTGGGGATTAAGGCGCATATTCAGCGCT TGCTGGACC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 400 | MMLV P76E Top SDM | GGCCCGCCTGGGGATTAAGCGTCATATTCAGCGCT TGCTGGACC |
| 401 | MMLV I177A Top SDM | GGCCCGCCTGGGGATTAAGGAGCATATTCAGCGCT TGCTGGACC |
| 402 | MMLV I177R Top SDM | CCGCCTGGGGATTAAGCCAGCGATTCAGCGCTTGC TGGACCAG |
| 403 | MMLV I177E Top SDM | CCGCCTGGGGATTAAGCCACGTATTCAGCGCTTGC TGGACCAG |
| 404 | MMLV L82A Top SDM | CCGCCTGGGGATTAAGCCAGAGATTCAGCGCTTGC TGGACCAG |
| 405 | MMLV L82R Top SDM | GATTAAGCCACATATTCAGCGCTTGGCGGACCAGG GGATCTTGGTCC |
| 406 | MMLV L82E Top SDM | GATTAAGCCACATATTCAGCGCTTGCGTGACCAGG GGATCTTGGTCC |
| 407 | MMLV D83A Top SDM | GATTAAGCCACATATTCAGCGCTTGGAGGACCAGG GGATCTTGGTCC |
| 408 | MMLV D83R Top SDM | GCCACATATTCAGCGCTTGCTGGCGCAGGGGATCT TGGTCCCATG |
| 409 | MMLV D83E Top SDM | GCCACATATTCAGCGCTTGCTGCGTCAGGGGATCT TGGTCCCATG |
| 410 | MMLV I125A Top SDM | GCCACATATTCAGCGCTTGCTGGAGCAGGGGATCT TGGTCCCATG |
| 411 | MMLV I125R Top SDM | AGGTCAACAAACGCGTAGAAGACGCGCATCCGACT GTACCTAATCCTTATAAT |
| 412 | MMLV I125E Top SDM | AGGTCAACAAACGCGTAGAAGACCGTCATCCGACT GTACCTAATCCTTATAAT |
| 413 | MMLV V129A Top SDM | AGGTCAACAAACGCGTAGAAGACGAGCATCCGACT GTACCTAATCCTTATAAT |
| 414 | MMLV V129R Top SDM | GCGTAGAAGACATCCATCCGACTGCGCCTAATCCT TATAATCTGTTATCAGGC |
| 415 | MMLV V129E Top SDM | GCGTAGAAGACATCCATCCGACTCGTCCTAATCCT TATAATCTGTTATCAGGC |
| 416 | MMLV L198A Top SDM | GCGTAGAAGACATCCATCCGACTGAGCCTAATCCT TATAATCTGTTATCAGGC |
| 417 | MMLV L198R Top SDM | AGGGCTTTAAAAACAGCCCCACAGCGTTCGATGAA GCACTTCACCGTGA |
| 418 | MMLV L198E Top SDM | AGGGCTTTAAAAACAGCCCCACACGTTTCGATGAA GCACTTCACCGTGA |
| 419 | MMLV E201A Top SDM | AGGGCTTTAAAAACAGCCCCACAGAGTTCGATGAA GCACTTCACCGTGA |
| 420 | MMLV E201R Top SDM | TTTAAAAACAGCCCCACATTGTTCGATGCGGCACT TCACCGTGACTTAGCAG |
| 421 | MMLV E201D Top SDM | TTTAAAAACAGCCCCACATTGTTCGATCGTGCACT TCACCGTGACTTAGCAG |
| 422 | MMLV R205A Top SDM | TTTAAAAACAGCCCCACATTGTTCGATGATGCACT TCACCGTGACTTAGCAG |
| 423 | MMLV R205K Top SDM | CACATTGTTCGATGAAGCACTTCACGCGGACTTAG CAGACTTCCGTATCCA |
| 424 | MMLV R205E Top SDM | CACATTGTTCGATGAAGCACTTCACAAAGACTTAG CAGACTTCCGTATCCA |

TABLE 1-continued

Sequences of primers used for cloning of MMLV RTase base constructs and mutants into pET28b.

| SEQ ID NO: | Primer Name | Primer Sequence (5'-3') |
|---|---|---|
| 425 | MMLV D209A Top SDM | GATGAAGCACTTCACCGTGACTTAGAGGACTTCCG TATCCAACACCCAG |
| 426 | MMLV D209R Top SDM | AAGCACTTCACCGTGACTTAGCAGCGTTCCGTATC CAACACCCAGACTT |
| 427 | MMLV D209E Top SDM | AAGCACTTCACCGTGACTTAGCACGTTTCCGTATC CAACACCCAGACTT |
| 428 | MMLV F210A Top SDM | AAGCACTTCACCGTGACTTAGCAGAGTTCCGTATC CAACACCCAGACTT |
| 429 | MMLV F210R Top SDM | CACTTCACCGTGACTTAGCAGACGCGCGTATCCAA CACCCAGACTTAATTC |
| 430 | MMLV F210E Top SDM | CACTTCACCGTGACTTAGCAGACCGTCGTATCCAA CACCCAGACTTAATTC |
| 431 | MMLV R211A Top SDM | CACTTCACCGTGACTTAGCAGACGAGCGTATCCAA CACCCAGACTTAATTC |
| 432 | MMLV R211K Top SDM | TTCACCGTGACTTAGCAGACTTCGCGATCCAACAC CCAGACTTAATTCTGTTA |
| 433 | MMLV R211E Top SDM | TTCACCGTGACTTAGCAGACTTCAAAATCCAACAC CCAGACTTAATTCTGTTA |
| 434 | MMLV I212A Top SDM | TTCACCGTGACTTAGCAGACTTCGAGATCCAACAC CCAGACTTAATTCTGTTA |
| 435 | MMLV I212R Top SDM | CCGTGACTTAGCAGACTTCCGTGCGCAACACCCAG ACTTAATTCTGTTACAG |
| 436 | MMLV I212E Top SDM | CCGTGACTTAGCAGACTTCCGTCGTCAACACCCAG ACTTAATTCTGTTACAG |
| 437 | MMLV Q213A Top SDM | CCGTGACTTAGCAGACTTCCGTGAGCAACACCCAG ACTTAATTCTGTTACAG |
| 438 | MMLV Q213R Top SDM | GTGACTTAGCAGACTTCCGTATCGCGCACCCAGAC TTAATTCTGTTACAGTAT |
| 439 | MMLV Q213E Top SDM | GTGACTTAGCAGACTTCCGTATCCGTCACCCAGAC TTAATTCTGTTACAGTAT |
| 440 | MMLV K348A Top SDM | GTGACTTAGCAGACTTCCGTATCGAGCACCCAGAC TTAATTCTGTTACAGTAT |
| 441 | MMLV K348R Top SDM | AGCAAAAGGCGTATCAGGAGATCGCGCAAGCTTTG TTGACCGCACCC |
| 442 | MMLV K348E Top SDM | AGCAAAAGGCGTATCAGGAGATCCGTCAAGCTTTG TTGACCGCACCC |
| 443 | MMLV L352A Top SDM | AGCAAAAGGCGTATCAGGAGATCGAGCAAGCTTTG TTGACCGCACCC |
| 444 | MMLV L352R Top SDM | CGTATCAGGAGATCAAACAAGCTTTGGCGACCGCA CCCGCGTTGGG |
| 445 | MMLV L352E Top SDM | CGTATCAGGAGATCAAACAAGCTTTGCGTACCGCA CCCGCGTTGGG |
| 446 | MMLV K285A Top SDM | CGTATCAGGAGATCAAACAAGCTTTGGAGACCGCA CCCGCGTTGGG |
| 447 | MMLV K285R Top SDM | GTTGGCTGACTGAAGCGCGTGCGGAGACCGTAATG GGGCAGC |
| 448 | MMLV K285E Top SDM | GTTGGCTGACTGAAGCGCGTCGTGAGACCGTAATG GGGCAGC |
| 449 | MMLV Q299A Top SDM | GTTGGCTGACTGAAGCGCGTGAGGAGACCGTAATG GGGCAGC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 450 | MMLV Q299R Top SDM | TACGCCTAAGACGCCACGCGCGTTGCGTGAATTTT TGGGCACAGC |
| 451 | MMLV Q299E Top SDM | TACGCCTAAGACGCCACGCCGTTTGCGTGAATTTT TGGGCACAGC |
| 452 | MMLV G308A Top SDM | TACGCCTAAGACGCCACGCGAGTTGCGTGAATTTT TGGGCACAGC |
| 453 | MMLV G308R Top SDM | GCGTGAATTTTTGGGCACAGCGGCGTTCTGTCGTT TATGGATTCCTGGG |
| 454 | MMLV G308E Top SDM | GCGTGAATTTTTGGGCACAGCGCGTTTCTGTCGTT TATGGATTCCTGGG |
| 455 | MMLV R311A Top SDM | GCGTGAATTTTTGGGCACAGCGGAGTTCTGTCGTT TATGGATTCCTGGG |
| 456 | MMLV R311K Top SDM | GGGCACAGCGGGATTCTGTGCGTTATGGATTCCTG GGTTCGCTGA |
| 457 | MMLV R311E Top SDM | GGGCACAGCGGGATTCTGTAAATTATGGATTCCTG GGTTCGCTGA |
| 458 | MMLV Y271A Top SDM | GGGCACAGCGGGATTCTGTGAGTTATGGATTCCTG GGTTCGCTGA |
| 459 | MMLV Y271R Top SDM | GTCAAAAACAGGTAAAGTACCTTGGGGCGTTGCTG AAAGAAGGTCAACGTTGG |
| 460 | MMLV Y271E Top SDM | GTCAAAAACAGGTAAAGTACCTTGGGCGTTTGCTG AAAGAAGGTCAACGTTGG |
| 461 | MMLV L280A Top SDM | GTCAAAAACAGGTAAAGTACCTTGGGGAGTTGCTG AAAGAAGGTCAACGTTGG |
| 462 | MMLV L280R Top SDM | TGCTGAAAGAAGGTCAACGTTGGGCGACTGAAGCG CGTAAGGAGACC |
| 463 | MMLV L280E Top SDM | TGCTGAAAGAAGGTCAACGTTGGCGTACTGAAGCG CGTAAGGAGACC |
| 464 | MMLV L357A Top SDM | TGCTGAAAGAAGGTCAACGTTGGGAGACTGAAGCG CGTAAGGAGACC |
| 465 | MMLV L357R Top SDM | TTTGTTGACCGCACCCGCGGCGGGTCTTCCGGATT TAACCAAGCC |
| 466 | MMLV L357E Top SDM | TTTGTTGACCGCACCCGCGCGTGGTCTTCCGGATT TAACCAAGCC |
| 467 | MMLV T328A Top SDM | TTTGTTGACCGCACCCGCGGAGGGTCTTCCGGATT TAACCAAGCC |
| 468 | MMLV T328R Top SDM | CTGCACCCCTGTACCCCTTAGCGAAAACAGGGACG CTTTTCAACTGG |
| 469 | MMLV T328E Top SDM | CTGCACCCCTGTACCCCTTACGTAAAACAGGGACG CTTTTCAACTGG |
| 470 | MMLV G331A Top SDM | CTGCACCCCTGTACCCCTTAGAGAAAACAGGGACG CTTTTCAACTGG |
| 471 | MMLV G331R Top SDM | CCCCTGTACCCCTTAACAAAAACAGCGACGCTTTT CAACTGGGGGCC |
| 472 | MMLV G331E Top SDM | CCCCTGTACCCCTTAACAAAAACACGTACGCTTTT CAACTGGGGGCC |
| 473 | MMLV T332A Top SDM | CCCCTGTACCCCTTAACAAAAACAGAGACGCTTTT CAACTGGGGGCC |
| 474 | MMLV T332R Top SDM | CTGTACCCCTTAACAAAAACAGGGGCGCTTTTCAA CTGGGGGCCAGAC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 475 | MMLV T332E Top SDM | CTGTACCCCTTAACAAAAACAGGGCGTCTTTTCAA CTGGGGGCCAGAC |
| 476 | MMLV N335A Top SDM | CTGTACCCCTTAACAAAAACAGGGGAGCTTTTCAA CTGGGGGCCAGAC |
| 477 | MMLV N335R Top SDM | CCTTAACAAAAACAGGGACGCTTTTCGCGTGGGGG CCAGACCAGCAAA |
| 478 | MMLV N335E Top SDM | CCTTAACAAAAACAGGGACGCTTTTCCGTTGGGGG CCAGACCAGCAAA |
| 479 | MMLV E367A Top SDM | CTTCCGGATTTAACCAAGCCCTTTGCGCTGTTCGT TGATGAAAAACAGGGATAT |
| 480 | MMLV E367R Top SDM | CTTCCGGATTTAACCAAGCCCTTTCGTCTGTTCGT TGATGAAAAACAGGGATAT |
| 481 | MMLV E367D Top SDM | CTTCCGGATTTAACCAAGCCCTTTGATCTGTTCGT TGATGAAAAACAGGGATAT |
| 482 | MMLV F369A Top SDM | GATTTAACCAAGCCCTTTGAGCTGGCGGTTGATGA AAAACAGGGATATGCAAAAG |
| 483 | MMLV F369R Top SDM | GATTTAACCAAGCCCTTTGAGCTGCGTGTTGATGA AAAACAGGGATATGCAAAAG |
| 484 | MMLV F369E Top SDM | GATTTAACCAAGCCCTTTGAGCTGGAGGTTGATGA AAAACAGGGATATGCAAAAG |
| 485 | MMLV R389A Top SDM | CCCAAAAGTTAGGCCCGTGGGCGCGCCCTGTTGCT TACTTGAGTAA |
| 486 | MMLV R389K Top SDM | CCCAAAAGTTAGGCCCGTGGAAACGCCCTGTTGCT TACTTGAGTAA |
| 487 | MMLV R389E Top SDM | CCCAAAAGTTAGGCCCGTGGGAGCGCCCTGTTGCT TACTTGAGTAA |
| 488 | MMLV V433A Top SDM | AGTTGACGATGGGTCAACCCTTAGCGATCTTGGCT CCACATGCTGTAGA |
| 489 | MMLV V433R Top SDM | AGTTGACGATGGGTCAACCCTTACGTATCTTGGCT CCACATGCTGTAGA |
| 490 | MMLV V433E Top SDM | AGTTGACGATGGGTCAACCCTTAGAGATCTTGGCT CCACATGCTGTAGA |
| 491 | MMLV V476A Top SDM | GGATCGTGTACAATTTGGACCAGTTGCGGCTTTGA ATCCAGCTACTTTGCTTC |
| 492 | MMLV V476R Top SDM | GGATCGTGTACAATTTGGACCAGTTCGTGCTTTGA ATCCAGCTACTTTGCTTC |
| 493 | MMLV V476E Top SDM | GGATCGTGTACAATTTGGACCAGTTGAGGCTTTGA ATCCAGCTACTTTGCTTC |
| 494 | MMLV I593A Top SDM | CGTTATGCTTTTGCAACAGCGCATGCGCATGGCGA AATTTACCGCCGC |
| 495 | MMLV I593R Top SDM | CGTTATGCTTTTGCAACAGCGCATCGTCATGGCGA AATTTACCGCCGC |
| 496 | MMLV I593E Top SDM | CGTTATGCTTTTGCAACAGCGCATGAGCATGGCGA AATTTACCGCCGC |
| 497 | MMLV E596A Top SDM | GCAACAGCGCATATCCATGGCGCGATTTACCGCCG CCGTGGTC |
| 498 | MMLV E596R Top SDM | GCAACAGCGCATATCCATGGCCGTATTTACCGCCG CCGTGGTC |
| 499 | MMLV E596D Top SDM | GCAACAGCGCATATCCATGGCGATATTTACCGCCG CCGTGGTC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 500 | MMLV I597A Top SDM | CAACAGCGCATATCCATGGCGAAGCGTACCGCCGC CGTGGTCTG |
| 501 | MMLV I597R Top SDM | CAACAGCGCATATCCATGGCGAACGTTACCGCCGC CGTGGTCTG |
| 502 | MMLV I597E Top SDM | CAACAGCGCATATCCATGGCGAAGAGTACCGCCGC CGTGGTCTG |
| 503 | MMLV R650A Top SDM | AGCGGAGGCTCGTGGAAACGCGATGGCGGACCAAG CTGCCC |
| 504 | MMLV R650K Top SDM | AGCGGAGGCTCGTGGAAACAAAATGGCGGACCAAG CTGCCC |
| 505 | MMLV R650E Top SDM | AGCGGAGGCTCGTGGAAACGAGATGGCGGACCAAG CTGCCC |
| 506 | MMLV Q654A Top SDM | GTGGAAACCGTATGGCGGACGCGGCTGCCCGTAAG GCGGC |
| 507 | MMLV Q654R Top SDM | GTGGAAACCGTATGGCGGACCGTGCTGCCCGTAAG GCGGC |
| 508 | MMLV Q654E Top SDM | GTGGAAACCGTATGGCGGACGAGGCTGCCCGTAAG GCGGC |
| 509 | MMLV R657A Top SDM | TATGGCGGACCAAGCTGCCGCGAAGGCGGCGATCA CAGAGAC |
| 510 | MMLV R657K Top SDM | TATGGCGGACCAAGCTGCCAAAAAGGCGGCGATCA CAGAGAC |
| 511 | MMLV R657E Top SDM | TATGGCGGACCAAGCTGCCGAGAAGGCGGCGATCA CAGAGAC |
| 512 | MMLV G73A Btm SDM | GCAAGCGCTGAATATGTGGCTTAATCGCCAGGCGG GCCTCTTGACTC |
| 513 | MMLV G73R Btm SDM | GCAAGCGCTGAATATGTGGCTTAATACGCAGGCGG GCCTCTTGACTC |
| 514 | MMLV G73E Btm SDM | GCAAGCGCTGAATATGTGGCTTAATCTCCAGGCGG GCCTCTTGACTC |
| 515 | MMLV P76A Btm SDM | GGTCCAGCAAGCGCTGAATATGCGCCTTAATCCCC AGGCGGGCC |
| 516 | MMLV P76R Btm SDM | GGTCCAGCAAGCGCTGAATATGACGCTTAATCCCC AGGCGGGCC |
| 517 | MMLV P76E Btm SDM | GGTCCAGCAAGCGCTGAATATGCTCCTTAATCCCC AGGCGGGCC |
| 518 | MMLV I177A Btm SDM | CTGGTCCAGCAAGCGCTGAATCGCTGGCTTAATCC CCAGGCGG |
| 519 | MMLV H77R Btm SDM | CTGGTCCAGCAAGCGCTGAATACGTGGCTTAATCC CCAGGCGG |
| 520 | MMLV I177E Btm SDM | CTGGTCCAGCAAGCGCTGAATCTCTGGCTTAATCC CCAGGCGG |
| 521 | MMLV L82A Btm SDM | GGACCAAGATCCCCTGGTCCGCCAAGCGCTGAATA TGTGGCTTAATC |
| 522 | MMLV L82R Btm SDM | GGACCAAGATCCCCTGGTCACGCAAGCGCTGAATA TGTGGCTTAATC |
| 523 | MMLV L82E Btm SDM | GGACCAAGATCCCCTGGTCCTCCAAGCGCTGAATA TGTGGCTTAATC |
| 524 | MMLV D83A Btm SDM | CATGGGACCAAGATCCCCTGCGCCAGCAAGCGCTG AATATGTGGC |

TABLE 1-continued

| Sequences of primers used for cloning of MMLV RTase base constructs and mutants into pET28b. | | |
|---|---|---|
| SEQ ID NO: | Primer Name | Primer Sequence (5'-3') |
| 525 | MMLV D83R Btm SDM | CATGGGACCAAGATCCCCTGACGCAGCAAGCGCTG AATATGTGGC |
| 526 | MMLV D83E Btm SDM | CATGGGACCAAGATCCCCTGCTCCAGCAAGCGCTG AATATGTGGC |
| 527 | MMLV I125A Btm SDM | ATTATAAGGATTAGGTACAGTCGGATGCGCGTCTT CTACGCGTTTGTTGACCT |
| 528 | MMLV I125R Btm SDM | ATTATAAGGATTAGGTACAGTCGGATGACGGTCTT CTACGCGTTTGTTGACCT |
| 529 | MMLV I125E Btm SDM | ATTATAAGGATTAGGTACAGTCGGATGCTCGTCTT CTACGCGTTTGTTGACCT |
| 530 | MMLV V129A Btm SDM | GCCTGATAACAGATTATAAGGATTAGGCGCAGTCG GATGGATGTCTTCTACGC |
| 531 | MMLV V129R Btm SDM | GCCTGATAACAGATTATAAGGATTAGGACGAGTCG GATGGATGTCTTCTACGC |
| 532 | MMLV V129E Btm SDM | GCCTGATAACAGATTATAAGGATTAGGCTCAGTCG GATGGATGTCTTCTACGC |
| 533 | MMLV L198A Btm SDM | TCACGGTGAAGTGCTTCATCGAACGCTGTGGGGCT GTTTTTAAAGCCCT |
| 534 | MMLV L198R Btm SDM | TCACGGTGAAGTGCTTCATCGAAACGTGTGGGGCT GTTTTTAAAGCCCT |
| 535 | MMLV L198E Btm SDM | TCACGGTGAAGTGCTTCATCGAACTCTGTGGGGCT GTTTTTAAAGCCCT |
| 536 | MMLV E201A Btm SDM | CTGCTAAGTCACGGTGAAGTGCCGCATCGAACAAT GTGGGGCTGTTTTTAAA |
| 537 | MMLV E201R Btm SDM | CTGCTAAGTCACGGTGAAGTGCACGATCGAACAAT GTGGGGCTGTTTTTAAA |
| 538 | MMLV E201D Btm SDM | CTGCTAAGTCACGGTGAAGTGCATCATCGAACAAT GTGGGGCTGTTTTTAAA |
| 539 | MMLV R205A Btm SDM | TGGATACGGAAGTCTGCTAAGTCCGCGTGAAGTGC TTCATCGAACAATGTG |
| 540 | MMLV R205K Btm SDM | TGGATACGGAAGTCTGCTAAGTCTTTGTGAAGTGC TTCATCGAACAATGTG |
| 541 | MMLV R205E Btm SDM | TGGATACGGAAGTCTGCTAAGTCCTCGTGAAGTGC TTCATCGAACAATGTG |
| 542 | MMLV D209A Btm SDM | AAGTCTGGGTGTTGGATACGGAACGCTGCTAAGTC ACGGTGAAGTGCTT |
| 543 | MMLV D209R Btm SDM | AAGTCTGGGTGTTGGATACGGAAACGTGCTAAGTC ACGGTGAAGTGCTT |
| 544 | MMLV D209E Btm SDM | AAGTCTGGGTGTTGGATACGGAACTCTGCTAAGTC ACGGTGAAGTGCTT |
| 545 | MMLV F210A Btm SDM | GAATTAAGTCTGGGTGTTGGATACGCGCGTCTGCT AAGTCACGGTGAAGTG |
| 546 | MMLV F210R Btm SDM | GAATTAAGTCTGGGTGTTGGATACGACGGTCTGCT AAGTCACGGTGAAGTG |
| 547 | MMLV F210E Btm SDM | GAATTAAGTCTGGGTGTTGGATACGCTCGTCTGCT AAGTCACGGTGAAGTG |
| 548 | MMLV R211A Btm SDM | TAACAGAATTAAGTCTGGGTGTTGGATCGCGAAGT CTGCTAAGTCACGGTGAA |
| 549 | MMLV R211K Btm SDM | TAACAGAATTAAGTCTGGGTGTTGGATTTTGAAGT CTGCTAAGTCACGGTGAA |

TABLE 1-continued

Sequences of primers used for cloning of MMLV RTase base constructs and mutants into pET28b.

| SEQ ID NO: | Primer Name | Primer Sequence (5'-3') |
|---|---|---|
| 550 | MMLV R211E Btm SDM | TAACAGAATTAAGTCTGGGTGTTGGATCTCGAAGT CTGCTAAGTCACGGTGAA |
| 551 | MMLV I212A Btm SDM | CTGTAACAGAATTAAGTCTGGGTGTTGCGCACGGA AGTCTGCTAAGTCACGG |
| 552 | MMLV I212R Btm SDM | CTGTAACAGAATTAAGTCTGGGTGTTGACGACGGA AGTCTGCTAAGTCACGG |
| 553 | MMLV I212E Btm SDM | CTGTAACAGAATTAAGTCTGGGTGTTGCTCACGGA AGTCTGCTAAGTCACGG |
| 554 | MMLV Q213A Btm SDM | ATACTGTAACAGAATTAAGTCTGGGTGCGCGATAC GGAAGTCTGCTAAGTCAC |
| 555 | MMLV Q213R Btm SDM | ATACTGTAACAGAATTAAGTCTGGGTGACGGATAC GGAAGTCTGCTAAGTCAC |
| 556 | MMLV Q213E Btm SDM | ATACTGTAACAGAATTAAGTCTGGGTGCTCGATAC GGAAGTCTGCTAAGTCAC |
| 557 | MMLV K348A Btm SDM | GGGTGCGGTCAACAAAGCTTGCGCGATCTCCTGAT ACGCCTTTTGCT |
| 558 | MMLV K348R Btm SDM | GGGTGCGGTCAACAAAGCTTGACGGATCTCCTGAT ACGCCTTTTGCT |
| 559 | MMLV K348E Btm SDM | GGGTGCGGTCAACAAAGCTTGCTCGATCTCCTGAT ACGCCTTTTGCT |
| 560 | MMLV L352A Btm SDM | CCCAACGCGGGTGCGGTCGCCAAAGCTTGTTTGAT CTCCTGATACG |
| 561 | MMLV L352R Btm SDM | CCCAACGCGGGTGCGGTACGCAAAGCTTGTTTGAT CTCCTGATACG |
| 562 | MMLV L352E Btm SDM | CCCAACGCGGGTGCGGTCTCCAAAGCTTGTTTGAT CTCCTGATACG |
| 563 | MMLV K285A Btm SDM | GCTGCCCCATTACGGTCTCCGCACGCGCTTCAGTC AGCCAAC |
| 564 | MMLV K285R Btm SDM | GCTGCCCCATTACGGTCTCACGACGCGCTTCAGTC AGCCAAC |
| 565 | MMLV K285E Btm SDM | GCTGCCCCATTACGGTCTCCTCACGCGCTTCAGTC AGCCAAC |
| 566 | MMLV Q299A Btm SDM | GCTGTGCCCAAAAATTCACGCAACGCGCGTGGCGT CTTAGGCGTA |
| 567 | MMLV Q299R Btm SDM | GCTGTGCCCAAAAATTCACGCAAACGGCGTGGCGT CTTAGGCGTA |
| 568 | MMLV Q299E Btm SDM | GCTGTGCCCAAAAATTCACGCAACTCGCGTGGCGT CTTAGGCGTA |
| 569 | MMLV G308A Btm SDM | CCCAGGAATCCATAAACGACAGAACGCCGCTGTGC CCAAAAATTCACGC |
| 570 | MMLV G308R Btm SDM | CCCAGGAATCCATAAACGACAGAAACGCGCTGTGC CCAAAAATTCACGC |
| 571 | MMLV G308E Btm SDM | CCCAGGAATCCATAAACGACAGAACTCCGCTGTGC CCAAAAATTCACGC |
| 572 | MMLV R311A Btm SDM | TCAGCGAACCCAGGAATCCATAACGCACAGAATCC CGCTGTGCCC |
| 573 | MMLV R311K Btm SDM | TCAGCGAACCCAGGAATCCATAATTTACAGAATCC CGCTGTGCCC |
| 574 | MMLV R311E Btm SDM | TCAGCGAACCCAGGAATCCATAACTCACAGAATCC CGCTGTGCCC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 575 | MMLV Y271A Btm SDM | CCAACGTTGACCTTCTTTCAGCAACGCCCCAAGGT ACTTTACCTGTTTTTGAC |
| 576 | MMLV Y271R Btm SDM | CCAACGTTGACCTTCTTTCAGCAAACGCCCAAGGT ACTTTACCTGTTTTTGAC |
| 577 | MMLV Y271E Btm SDM | CCAACGTTGACCTTCTTTCAGCAACTCCCCAAGGT ACTTTACCTGTTTTTGAC |
| 578 | MMLV L280A Btm SDM | GGTCTCCTTACGCGCTTCAGTCGCCCAACGTTGAC CTTCTTTCAGCA |
| 579 | MMLV L280R Btm SDM | GGTCTCCTTACGCGCTTCAGTACGCCAACGTTGAC CTTCTTTCAGCA |
| 580 | MMLV L280E Btm SDM | GGTCTCCTTACGCGCTTCAGTCTCCCAACGTTGAC CTTCTTTCAGCA |
| 581 | MMLV L357A Btm SDM | GGCTTGGTTAAATCCGGAAGACCCGCCGCGGGTGC GGTCAACAAA |
| 582 | MMLV L357R Btm SDM | GGCTTGGTTAAATCCGGAAGACCACGCGCGGGTGC GGTCAACAAA |
| 583 | MMLV L357E Btm SDM | GGCTTGGTTAAATCCGGAAGACCCTCCGCGGGTGC GGTCAACAAA |
| 584 | MMLV T328A Btm SDM | CCAGTTGAAAAGCGTCCCTGTTTTCGCTAAGGGGT ACAGGGGTGCAG |
| 585 | MMLV T328R Btm SDM | CCAGTTGAAAAGCGTCCCTGTTTTACGTAAGGGGT ACAGGGGTGCAG |
| 586 | MMLV T328E Btm SDM | CCAGTTGAAAAGCGTCCCTGTTTTCTCTAAGGGGT ACAGGGGTGCAG |
| 587 | MMLV G331A Btm SDM | GGCCCCCAGTTGAAAAGCGTCGCTGTTTTTGTTAA GGGGTACAGGGG |
| 588 | MMLV G331R Btm SDM | GGCCCCCAGTTGAAAAGCGTACGTGTTTTTGTTAA GGGGTACAGGGG |
| 589 | MMLV G331E Btm SDM | GGCCCCCAGTTGAAAAGCGTCTCTGTTTTTGTTAA GGGGTACAGGGG |
| 590 | MMLV T332A Btm SDM | GTCTGGCCCCCAGTTGAAAAGCGCCCCTGTTTTTG TTAAGGGGTACAG |
| 591 | MMLV T332R Btm SDM | GTCTGGCCCCCAGTTGAAAAGACGCCCTGTTTTTG TTAAGGGGTACAG |
| 592 | MMLV T332E Btm SDM | GTCTGGCCCCCAGTTGAAAAGCTCCCCTGTTTTTG TTAAGGGGTACAG |
| 593 | MMLV N335A Btm SDM | TTTGCTGGTCTGGCCCCCACGCGAAAAGCGTCCCT GTTTTTGTTAAGG |
| 594 | MMLV N335R Btm SDM | TTTGCTGGTCTGGCCCCCAACGGAAAAGCGTCCCT GTTTTTGTTAAGG |
| 595 | MMLV N335E Btm SDM | TTTGCTGGTCTGGCCCCCACTCGAAAAGCGTCCCT GTTTTTGTTAAGG |
| 596 | MMLV E367A Btm SDM | ATATCCCTGTTTTTCATCAACGAACAGCGCAAAGG GCTTGGTTAAATCCGGAAG |
| 597 | MMLV E367R Btm SDM | ATATCCCTGTTTTTCATCAACGAACAGACGAAAGG GCTTGGTTAAATCCGGAAG |
| 598 | MMLV E367D Btm SDM | ATATCCCTGTTTTTCATCAACGAACAGATCAAAGG GCTTGGTTAAATCCGGAAG |
| 599 | MMLV F369A Btm SDM | CTTTTGCATATCCCTGTTTTTCATCAACCGCCAGC TCAAAGGGCTTGGTTAAATC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 600 | MMLV F369R Btm SDM | CTTTTGCATATCCCTGTTTTTCATCAACACGCAGC TCAAAGGGCTTGGTTAAATC |
| 601 | MMLV F369E Btm SDM | CTTTTGCATATCCCTGTTTTTCATCAACCTCCAGC TCAAAGGGCTTGGTTAAATC |
| 602 | MMLV R389A Btm SDM | TTACTCAAGTAAGCAACAGGGCGCGCCCACGGGCC TAACTTTTGGG |
| 603 | MMLV R389K Btm SDM | TTACTCAAGTAAGCAACAGGGCGTTTCCACGGGCC TAACTTTTGGG |
| 604 | MMLV R389E Btm SDM | TTACTCAAGTAAGCAACAGGGCGCTCCCACGGGCC TAACTTTTGGG |
| 605 | MMLV V433A Btm SDM | TCTACAGCATGTGGAGCCAAGATCGCTAAGGGTTG ACCCATCGTCAACT |
| 606 | MMLV V433R Btm SDM | TCTACAGCATGTGGAGCCAAGATACGTAAGGGTTG ACCCATCGTCAACT |
| 607 | MMLV V433E Btm SDM | TCTACAGCATGTGGAGCCAAGATCTCTAAGGGTTG ACCCATCGTCAACT |
| 608 | MMLV V476A Btm SDM | GAAGCAAAGTAGCTGGATTCAAAGCCGCAACTGGT CCAAATTGTACACGATCC |
| 609 | MMLV V476R Btm SDM | GAAGCAAAGTAGCTGGATTCAAAGCACGAACTGGT CCAAATTGTACACGATCC |
| 610 | MMLV V476E Btm SDM | GAAGCAAAGTAGCTGGATTCAAAGCCTCAACTGGT CCAAATTGTACACGATCC |
| 611 | MMLV I593A Btm SDM | GCGGCGGTAAATTTCGCCATGCGCATGCGCTGTTG CAAAAGCATAACG |
| 612 | MMLV I593R Btm SDM | GCGGCGGTAAATTTCGCCATGACGATGCGCTGTTG CAAAAGCATAACG |
| 613 | MMLV I593E Btm SDM | GCGGCGGTAAATTTCGCCATGCTCATGCGCTGTTG CAAAAGCATAACG |
| 614 | MMLV E596A Btm SDM | GACCACGGCGGCGGTAAATCGCGCCATGGATATGC GCTGTTGC |
| 615 | MMLV E596R Btm SDM | GACCACGGCGGCGGTAAATACGGCCATGGATATGC GCTGTTGC |
| 616 | MMLV E596D Btm SDM | GACCACGGCGGCGGTAAATATCGCCATGGATATGC GCTGTTGC |
| 617 | MMLV I597A Btm SDM | CAGACCACGGCGGCGGTACGCTTCGCCATGGATAT GCGCTGTTG |
| 618 | MMLV I597R Btm SDM | CAGACCACGGCGGCGGTAACGTTCGCCATGGATAT GCGCTGTTG |
| 619 | MMLV I597E Btm SDM | CAGACCACGGCGGCGGTACTCTTCGCCATGGATAT GCGCTGTTG |
| 620 | MMLV R650A Btm SDM | GGGCAGCTTGGTCCGCCATCGCGTTTCCACGAGCC TCCGCT |
| 621 | MMLV R650K Btm SDM | GGGCAGCTTGGTCCGCCATTTTGTTTCCACGAGCC TCCGCT |
| 622 | MMLV R650E Btm SDM | GGGCAGCTTGGTCCGCCATCTCGTTTCCACGAGCC TCCGCT |
| 623 | MMLV Q654A Btm SDM | GCCGCCTTACGGGCAGCCGCGTCCGCCATACGGTT TCCAC |
| 624 | MMLV Q654R Btm SDM | GCCGCCTTACGGGCAGCACGGTCCGCCATACGGTT TCCAC |

TABLE 1-continued

Sequences of primers used for cloning of MMLV RTase base constructs and mutants into pET28b.

| SEQ ID NO: | Primer Name | Primer Sequence (5'-3') |
|---|---|---|
| 625 | MMLV Q654E Btm SDM | GCCGCCTTACGGGCAGCCTCGTCCGCCATACGGTTTCCAC |
| 626 | MMLV R657A Btm SDM | GTCTCTGTGATCGCCGCCTTCGCGGCAGCTTGGTCCGCCATA |
| 627 | MMLV R657K Btm SDM | GTCTCTGTGATCGCCGCCTTTTTGGCAGCTTGGTCCGCCATA |
| 628 | MMLV R657E Btm SDM | GTCTCTGTGATCGCCGCCTTCTCGGCAGCTTGGTCCGCCATA |
| 629 | MMLV L280R Top SDM V2 | ATTTGCTGAAAGAAGGTCAACGTTGGCGTACTGATGCGCGTAAGGAGACC |
| 630 | MMLV L280R Btm SDM V2 | GGTCTCCTTACGCGCATCAGTACGCCAACGTTGACCTTCTTTCAGCAAAT |
| 631 | MMLV L82R Top SDM V2 | GGGATTAAGCCACATATTCGTCGCTTGCGTGACCAGGGGATCTTGGTCCC |
| 632 | MMLV L82R Btm SDM V2 | GGGACCAAGATCCCCTGGTCACGCAAGCGACGAATATGTGGCTTAATCCC |

Figure 2:
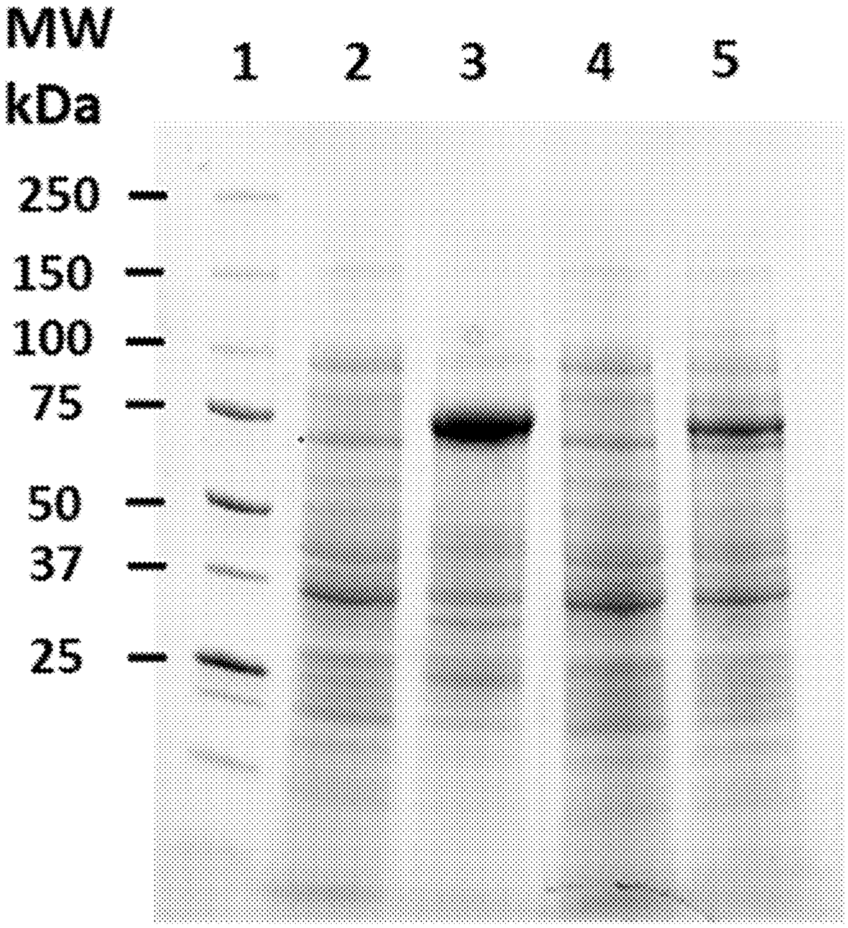
FIG. 2 shows Western blot analysis of test induction results in in BL21(DE3) cells for MMLV RT in TB medium. Lane 1—Precision Plus Protein Unstained Standards (Bio Rad, Cat #161-0363), Lane 2—Time=0 hour, Lane 3—Time=3 hours after induction at 37° C., Lane 4—Time=0 hour, Lane 5—Time=21 hours after induction at 18° C.

Example 2: Preparation of Reverse Transcriptase Mutants for Screening Increased Activity and Thermostability a. Overexpression of MMLV RTase and Mutant Variants A test induction was used to determine optimum growing conditions. A colony, with the appropriate strain, was used to inoculate Terrific Broth (TB) media (50 mL) with kanamycin (0.05 mg/mL) and grown at 37° C. until an OD of approximately 0.9 was reached. The 50 mL culture was divided in half to accommodate two induction temperatures. IPTG (1M; 12.5 μL) was used to induce protein expression, followed by growth at two induction temperatures for 21 hours. Aliquots (normalized to an OD of 1.25) were taken at 3 and 21 hours, cells were harvested at 13,000×g for one minute, and harvested cells were stored at −20° C. Cells were resuspended in 1×SDS-PAGE running buffer (270 μL) and 5×SDS-PAGE loading dye (70 μL). Samples were boiled for 5 minutes, sonicated, and loaded (15 μL) onto a 4-20% Mini-PROTEAN® TGX Stain-Free™ Protein Gel (Bio Rad, Cat #4568094). SDS-PAGE images are shown in FIG. 2.

b. Expression and Purification of MMLV RTase and Mutant Variants

A colony with the appropriate strain was used to inoculate TB media (1 mL, in a 96-well deep well plate) with kanamycin (0.05 mg/mL) and grown at 37° C. until an OD of approximately 0.9 was achieved followed by cooling of the plate on ice for 5 minutes. Protein expression was induced by the addition of 100 mM IPTG (5 μL), followed by growth at 18° C. for 21 hours. Cells were harvested by spinning samples at 4,700×g for 10 minutes.

Cell pellets were re-suspended in a lysis buffer (50 mM $NaPO_4$, pH 7.8, 5% glycerol, 300 mM NaCl, and 10 mM imidazole) and lysed by the addition of 1× BugBuster® (Millipore Sigma, Cat #70921) and incubation on an end-over-end mixer for 15 minutes at room temperature. Cell debris was removed by centrifuging the lysate at 16,000×g for 20 minutes at 4° C.

Cleared lysates were applied to a HisPur™ Ni-NTA spin plate (ThermoFisher, Cat #88230). Resin was equilibrated with Screening His-Bind buffer (50 mM $NaPO_4$, pH 7.8, 5% glycerol, 300 mM NaCl, and 10 mM imidazole) and samples loaded. Samples were washed three times with Screening His-Wash buffer (50 mM NaPO4, pH 7.8, 5% glycerol, 300 mM NaCl, and 25 mM imidazole) and eluted using Screening His-Elution buffer (50 mM $NaPO_4$, pH 7.8, 5% glycerol, 300 mM NaCl, and 250 mM imidazole). Purified proteins were normalized to a set concentration (100 nM) for testing purposes.

Example 3: Evaluation of Reverse Transcriptase Mutants a. Evaluation of Ability of RTase Mutants to Synthesize DNA The ability of mutant RTase to synthesize cDNA from purified total RNA (DNased, isolated from HeLa cells) was compared to an MMLV RTase base construct (RNase H minus construct). Mutant MMLV RTases were tested in two formats: (1) standard two-step cDNA synthesis with gene specific primers, followed by qPCR, and (2) one-step addition of the RTase in Integrated DNA Technologies PrimeTime® Gene Expression Master Mix (GEM).

b. Standard Two-Step Procedure

RTases (2 μL, 100 nM) were added to a reaction mixture containing RNA (50 ng), dNTPs (100 μM), gene specific primer set (500 nM; see Table 2), first strand synthesis buffer (1×, 50 mM Tris-HCl, pH 8.3, 75 mM KCl, 3 mM $MgCl_2$, 10 mM DTT), and SuperaseIN (0.17 U/μL) in a 50 μL volume. The reaction was allowed to proceed at 50° C. for 15 minutes, followed by incubation at 80° C. for 10 minutes.

cDNA synthesized by RTase mutants was quantified by qPCR amplification using an assay that identified the SFRS9 gene in human cells. The assay master mix composition included GEM (1×), ROX (50 nM), SFRS9 primer set (500 nM; see Table 2), and SFRS9 probe (250 nM; see Table 2). Assay master mix and synthesized cDNA were mixed at a 4:1 ratio for a final volume of 20 μL. The reaction was run on qPCR (QuantStudio) for 40 cycles under the following cycle conditions: 95° C. hold for 3 minutes, 95° C. for 15 seconds, and 60° C. for one minute.

TABLE 2

Sequences of primers and probes used for qPCR assays.

| SEQ ID NO: | Primer Name | Primer Sequence (5'-3') |
|---|---|---|
| 633 | Hs SFRS9 Forward Primer | GTCGAGTATCTCAGAAAAGAAGACA |
| 634 | Hs SFRS9 Reverse Primer | CTCGGATGTAGGAAGTTTCACC |
| 635 | Hs SFRS9 Probe - SUN | /5SUN/ATGCCCTGC/ZEN/GTAAACTGGATGACA/3IABkFQ/ |

c. One-Step Procedure in GEM

RTases (1 μL, 100 nM) were added to a reaction mixture containing RNA (10 ng), GEM (1×), ROX (50 nM), SFRS9 primer set (500 nM; see Table 2), and SFRS9 probe (250 nM; see Table 2) in a final volume of 20 μL. The reaction was run on a qPCR machine (QuantStudio) for 40 cycles using the following cycle conditions: 60° C. hold for 15 minutes, 95° C. hold for 3 minutes, 95° C. for 15 seconds, and 60° C. for one minute.

d. MMLV RTase Base Construct and Single Mutant Variants

As described in Example 1, MMLV RTase single mutant variants were prepared by introducing selected mutations into the MMLV RTase base construct by site-directed mutagenesis, using standard PCR conditions and primers. The sequences of the MMLV RTase base construct and single mutant variants are shown in Table 3. One of skill in the art will understand that the MMLV RTase amino acid sequence set forth in SEQ ID NO: 637 is a truncated form of the full-length amino acid sequence of wild-type, or naturally occurring, MMLV RTase. In addition, a person having ordinary skill in the art will understand that a methionine residue is required to recombinantly produce the MMLV RTase base construct and mutants of the disclosure, and as such, that the MMLV RTase sequences disclosed herein (see, e.g., Tables 3, 8 and 9) include a methionine residue at the N-terminal end of the amino acid sequence. However, with respect to the present disclosure and for the purpose of identifying and numbering residues in the MMLV RTase amino acid sequence where mutations have been introduced, this methionine residue is considered to be amino acid residue 0 (i.e., is not counted) and the second amino acid residue (e.g., threonine in the MMLV RTase base construct set forth in SEQ ID NO: 637) is considered to be amino acid residue 1.

TABLE 3

Sequences of MMLV RTase base construct and single mutant MMLV RTase constructs.

| SEQ ID NO: | Construct | Construct Sequence (DNA: 5'-3' or AA) |
|---|---|---|
| 636 | MMLV RTase | ATGACTTTAAATATTGAGGATGAGCATCGTTTA<br>CATGAGACATCAAAAGAACCCGACGTGAGCTTA<br>GGGTCAACGTGGCTTTCTGACTTCCCCCAGGCG<br>TGGGCGGAGACTGGCGGAATGGGGTTAGCTGTC<br>CGCCAAGCACCGTTGATCATCCCGTTAAAGGCA<br>ACGTCTACACCTGTCTCTATCAAACAGTACCCC<br>ATGAGTCAAGAGGCCCGCCTGGGGATTAAGCCA<br>CATATTCAGCGCTTGCTGGACCAGGGGATCTTG<br>GTCCCATGTCAATCTCCGTGGAACACCCCCCTT<br>CTGCCCGTGAAAAAGCCAGGTACAAACGATTAT<br>CGTCCAGTTCAAGATCTTCGCGAGGTCAACAAA<br>CGCGTAGAAGACATCCATCCGACTGTACCTAAT<br>CCTTATAATCTGTTATCAGGCCTGCCCCCATCG<br>CACCAATGGTATACAGTATTAGACTTGAAAGAC<br>GCGTTCTTTTGCCTGCGTCTGCACCCAACGTCT<br>CAGCCGCTGTTTGCGTTCGAATGGCGTGATCCT<br>GAAATGGGAATTTCGGGTCAGTTAACCTGGACT<br>CGTCTGCCCCAGGGCTTTAAAAACAGCCCCACA<br>TTGTTCGATGAAGCACTTCACCGTGACTTAGCA<br>GACTTCCGTATCCAACACCCAGACTTAATTCTG<br>TTACAGTATGTTGACGACCTTTTGTTGGCGGCA<br>ACGTCTGAACTTGACTGTCAGCAAGGCACACGC<br>GCGTTATTACAAACGTTAGGTAACTTAGGATAT<br>CGTGCGTCCGCGAAAAAGGCGCAAATTTGTCAA<br>AAACAGGTAAAGTACCTTGGGTATTTGCTGAAA<br>GAAGGTCAACGTTGGCTGACTGAAGCGCGTAAG<br>GAGACCGTAATGGGGCAGCCTACGCCTAAGACG<br>CCACGCCAGTTGCGTGAATTTTTGGGCACAGCG<br>GGATTCTGTCGTTTATGGATTCCTGGGTTCGCT<br>GAAATGGCTGCACCCCTGTACCCCTTAACAAAA<br>ACAGGGACGCTTTTCAACTGGGGGCCAGACCAG<br>CAAAAGGCGTATCAGGAGATCAAACAAGCTTTG<br>TTGACCGCACCCGCGTTGGGTCTTCCGGATTTA<br>ACCAAGCCCTTTGAGCTGTTCGTTGATGAAAAA<br>CAGGGATATGCAAAAGGAGTATTAACCCAAAAG<br>TTAGGCCCGTGGCGTCGCCCTGTTGCTTACTTG<br>AGTAAAAAATTGGATCCTGTCGCAGCAGGATGG<br>CCACCGTGCTTGCGTATGGTCGCGGCAATTGCC<br>GTTTTGACAAAGGATGCAGGTAAGTTGACGATG<br>GGTCAACCCTTAGTAATCTTGGCTCCACATGCT |

TABLE 3-continued

Sequences of MMLV RTase base construct and single mutant MMLV RTase constructs.

| SEQ ID NO: | Construct | Construct Sequence (DNA: 5'-3' or AA) |
|---|---|---|
| | | GTAGAAGCGTTAGTAAAGCAGCCCCCAGACCGC<br>TGGCTTTCTAATGCGCGCATGACCCACTATCAG<br>GCGCTTCTGCTTGATACGGATCGTGTACAATTT<br>GGACCAGTTGTAGCTTTGAATCCAGCTACTTTG<br>CTTCCCCTTCCAGAAGAAGGACTTCAGCACAAT<br>TGTTTAGATATTCTGGCCGAGGCACATGGGACG<br>CGCCCTGATTTGACGGATCAGCCACTGCCTGAT<br>GCCGACCATACATGGTATACTGGCGGCAGTAGT<br>CTTCTTCAAGAGGGGCAACGCAAGGCGGGAGCA<br>GCCGTCACTACGGAGACCGAAGTTATCTGGGCC<br>AAAGCGTTACCCGCGGGAACATCCGCGCAACGT<br>GCACAGTTAATCGCTCTGACACAGGCCCTGAAG<br>ATGGCAGAGGGCAAAAAGTTGAATGTCTACACC<br>AACTCACGTTATGCTTTTGCAACAGCGCATATC<br>CATGGCGAAATTTACCGCCGCCGTGGTCTGCTG<br>ACTAGTGAGGGTAAGGAAATTAAAAATAAAGAT<br>GAGATTCTTGCGTTGTTAAAAGCTTTATTCTTA<br>CCAAAACGCCTTTCGATCATTCATTGCCCGGGG<br>CATCAAAAGGGTCACTCAGCGGAGGCTCGTGGA<br>AACCGTATGGCGGACCAAGCTGCCCGTAAGGCG<br>GCGATCACAGAGACCCCGGATACATCAACGCTG<br>TTGATCGAAAACAGCTCTCCCTACACTAGCGAG<br>CATTTTTAA |
| 637 | MMLV RTase | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKI<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 638 | MMLV RTase with I61R mutation | MTLNIEDEHRLHETSKEPDVSLGSTWLSDFPQA<br>WAETGGMGLAVRQAPLIIPLKATSTPVSRKQYP<br>MSQEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 639 | MMLV RTase with Q68R mutation | MTLNIEDEHRLHETSKEPDVSLGSTWLSDFPQA<br>WAETGGMGLAVRQAPLIIPLKATSTPVSIKQYP<br>MSREARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA |

TABLE 3-continued

Sequences of MMLV RTase base construct and single mutant MMLV RTase constructs.

| SEQ ID NO: | Construct | Construct Sequence (DNA: 5'-3' or AA) |
|---|---|---|
| | | TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 640 | MMLV RTase with Q79R mutation | MTLNIEDEHRLHETSKEPDVSLGSTWLSDFPQA WAETGGMGLAVRQAPLIIPLKATSTPVSIKQYP MSQEARLGIKPHIRRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 641 | MMLV RTase with L99R mutation | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPR LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 642 | MMLV RTase with E282D mutation | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS |

TABLE 3-continued

| Sequences of MMLV RTase base construct and single mutant MMLV RTase constructs. | | |
|---|---|---|
| SEQ ID NO: | Construct | Construct Sequence (DNA: 5'-3' or AA) |
| | | LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 643 | MMLV RTase with R298A mutation | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |

e. Experimental Results

The two-step and one-step reactions for MMLV RTase base construct and MMLV RTase single mutant variants were analyzed and reported by copy number output based on a standard curve (see Tables 4 and 5). Six single mutant MMLV RTase variants were found to exhibit an increase in the overall activity and thermostability as compared to the MMLV RTase base construct. The six single mutant MMLV RTase variants were as follows: I61R, Q68R, Q79R, L99R, E282D, and R298A.

TABLE 4

Two-step cDNA synthesis by MMLV RT single mutants. Data was generated via qPCR human normalizer assay and translated by copy number.

| MMLV RT Variant | Quantity Mean | Quantity Standard Deviation |
|---|---|---|
| MMLV-II | 21,046.784 | 954.827 |
| MMLV-II A283V | 280.423 | 50.910 |
| MMLV-II A283R | 10,390.819 | 340.236 |
| MMLV-II A283E | 7,378.705 | 122.716 |
| MMLV-II E123A | 15,059.791 | 556.095 |
| MMLV-II E123R | 19,043.292 | 415.522 |
| MMLV-II E123D | 3,619.959 | 243.766 |
| MMLV-II E282A | 19,939.551 | 1,645.246 |
| MMLV-II E282R | 15,588.940 | 546.467 |
| MMLV-II E282D | 24,282.327 | 2,259.264 |
| MMLV-II I61A | 648.252 | 45.640 |
| MMLV-II I61R | 26,280.811 | 549.417 |
| MMLV-II I61E | 10,966.741 | 469.747 |
| MMLV-II K102A | 98.438 | 12.778 |
| MMLV-II K102R | 780.114 | 90.331 |
| MMLV-II K102E | 1,674.854 | 157.485 |
| MMLV-II K103A | 359.984 | 67.322 |
| MMLV-II K103R | 206.765 | 20.758 |
| MMLV-II K103E | 200.883 | 16.719 |
| MMLV-II K120A | 217.787 | 72.696 |
| MMLV-II K120R | 3,619.338 | 100.478 |
| MMLV-II K120E | 2,230.375 | 210.050 |
| MMLV-II K193A | 2,736.271 | 162.383 |

TABLE 4-continued

Two-step cDNA synthesis by MMLV RT single mutants. Data was generated via qPCR human normalizer assay and translated by copy number.

| MMLV RT Variant | Quantity Mean | Quantity Standard Deviation |
|---|---|---|
| MMLV-II K193R | 11,496.935 | 193.681 |
| MMLV-II K193E | 325.109 | 50.932 |
| MMLV-II K295A | 8,101.927 | 348.373 |
| MMLV-II K295R | 6,879.112 | 131.993 |
| MMLV-II K295E | 9,673.612 | 351.106 |
| MMLV-II K329A | 3,199.167 | 212.003 |
| MMLV-II K329R | 10,387.670 | 330.429 |
| MMLV-II K329E | 18,306.813 | 1,167.600 |
| MMLV-II K53A | 474.465 | 62.390 |
| MMLV-II K53R | 369.020 | 49.436 |
| MMLV-II K53E | 5,308.165 | 104.585 |
| MMLV-II K62A | 2,102.396 | 64.197 |
| MMLV-II K62R | 4,920.330 | 251.414 |
| MMLV-II K62E | 71.723 | 11.419 |
| MMLV-II K75A | 76.659 | 24.657 |
| MMLV-II K75R | 2,842.314 | 77.212 |
| MMLV-II K75E | 1,697.887 | 158.946 |
| MMLV-II L99A | 1,576.246 | 213.455 |
| MMLV-II L99R | 37,070.048 | 1,531.910 |
| MMLV-II L99E | 195.448 | 22.530 |
| MMLV-II N107A | 3,354.325 | 176.385 |
| MMLV-II N107R | 41.532 | 24.527 |
| MMLV-II N107E | 8,523.285 | 353.411 |
| MMLV-II Q291A | 14,093.444 | 576.318 |
| MMLV-II Q291R | 15,736.443 | 566.630 |
| MMLV-II Q291E | 1,480.309 | 93.187 |
| MMLV-II Q68A | n.d. | n.d. |
| MMLV-II Q68R | 20,158.035 | 722.022 |
| MMLV-II Q68E | 2,263.714 | 150.236 |
| MMLV-II Q79A | 2,317.484 | 43.518 |
| MMLV-II Q79R | 37,480.443 | 1,268.309 |
| MMLV-II Q79E | 489.184 | 39.449 |
| MMLV-II R110A | 1,815.710 | 7.917 |
| MMLV-II R110K | 502.172 | 38.619 |
| MMLV-II R110E | 383.331 | 38.162 |
| MMLV-II R298A | 44,477.013 | 3,036.502 |

TABLE 4-continued

Two-step cDNA synthesis by MMLV RT single mutants. Data was generated via qPCR human normalizer assay and translated by copy number.

| MMLV RT Variant | Quantity Mean | Quantity Standard Deviation |
|---|---|---|
| MMLV-II R298K | 14,925.202 | 186.581 |
| MMLV-II R298E | 1,150.932 | 56.107 |
| MMLV-II R301A | 2,745.075 | 82.646 |
| MMLV-II R301K | 12,813.899 | 568.898 |
| MMLV-II R301E | 1,583.826 | 198.913 |
| MMLV-II T106A | 16,641.642 | 179.631 |
| MMLV-II T106R | 2,248.217 | 71.295 |
| MMLV-II T106E | 10,302.113 | 250.531 |
| MMLV-II T128V | 7,034.032 | 351.446 |
| MMLV-II T128R | 3,465.069 | 143.456 |
| MMLV-II T128E | 10,709.019 | 110.124 |
| MMLV-II T293A | 4,612.880 | 167.335 |
| MMLV-II T293R | 13,753.879 | 319.851 |
| MMLV-II T293E | 12,893.457 | 223.100 |
| MMLV-II T296A | 2,192.531 | 76.071 |
| MMLV-II T296R | 893.449 | 51.913 |
| MMLV-II T296E | 473.936 | 102.414 |
| MMLV-II T55A | 5,774.471 | 223.173 |
| MMLV-II T55R | 3,284.089 | 314.651 |
| MMLV-II T55E | 6,143.058 | 429.507 |
| MMLV-II T57A | 6,129.791 | 285.070 |
| MMLV-II T57R | 888.244 | 11.952 |
| MMLV-II T57E | 1,487.448 | 71.681 |
| MMLV-II V101A | 552.130 | 98.391 |
| MMLV-II V101R | 4,754.017 | 107.434 |
| MMLV-II V101E | 1,388.699 | 87.091 |
| MMLV-II V112A | 2,085.594 | 72.265 |
| MMLV-II V112R | 377.194 | 41.722 |
| MMLV-II V112E | 210.825 | 17.715 |
| MMLV-II V59A | 628.779 | 15.216 |
| MMLV-II V59R | 6,662.173 | 210.234 |
| MMLV-II V59E | 3,249.465 | 79.848 |
| MMLV-II Y109A | 101.656 | 6.717 |
| MMLV-II Y109R | 349.373 | 27.171 |
| MMLV-II Y109E | 1,029.589 | 45.189 |
| MMLV-IV | 71,572.714 | 4,656.679 |

TABLE 5

One-step cDNA synthesis by MMLV RT single mutants. Data was generated via qPCR human normalizer assay and data is translated by copy number.

| MMLV RT Variant | Quantity Mean | Quantity Standard Deviation |
|---|---|---|
| MMLV-II | 20,638.973 | 614.785 |
| MMLV-II A283V | 8,802.753 | 220.902 |
| MMLV-II A283R | 14,379.575 | 337.562 |
| MMLV-II A283E | 16,396.614 | 203.476 |
| MMLV-II E123A | 17,975.218 | 259.986 |
| MMLV-II E123R | 20,652.508 | 515.600 |
| MMLV-II E123D | 14,452.672 | 242.000 |
| MMLV-II E282A | 19,017.751 | 827.419 |
| MMLV-II E282R | 17,180.421 | 204.739 |
| MMLV-II E282D | 20,735.271 | 420.881 |
| MMLV-II I61A | 7,450.147 | 348.788 |
| MMLV-II I61R | 25,123.507 | 2,977.836 |
| MMLV-II I61E | 17,441.860 | 1,662.749 |
| MMLV-II K102A | 9,342.754 | 120.846 |
| MMLV-II K102R | 10,563.589 | 255.139 |
| MMLV-II K102E | 13,925.008 | 307.601 |
| MMLV-II K103A | 9,429.555 | 437.351 |
| MMLV-II K103R | 9,009.846 | 155.888 |
| MMLV-II K103E | 7,985.278 | 189.792 |
| MMLV-II K120A | 8,593.433 | 438.722 |
| MMLV-II K120R | 12,558.793 | 407.946 |
| MMLV-II K120E | 12,268.574 | 303.495 |
| MMLV-II K193A | 12,977.263 | 537.992 |
| MMLV-II K193R | 13,446.766 | 2,337.906 |
| MMLV-II K193E | 8,536.558 | 182.514 |
| MMLV-II K295A | 13,506.491 | 1,613.467 |

TABLE 5-continued

One-step cDNA synthesis by MMLV RT single mutants. Data was generated via qPCR human normalizer assay and data is translated by copy number.

| MMLV RT Variant | Quantity Mean | Quantity Standard Deviation |
|---|---|---|
| MMLV-II K295R | 13,944.407 | 1,839.608 |
| MMLV-II K295E | 15,021.823 | 650.111 |
| MMLV-II K329A | 13,284.541 | 246.298 |
| MMLV-II K329R | 15,935.899 | 970.971 |
| MMLV-II K329E | 20,628.859 | 884.254 |
| MMLV-II K53A | 10,868.676 | 161.435 |
| MMLV-II K53R | 9,908.252 | 632.663 |
| MMLV-II K53E | 20,666.775 | 518.895 |
| MMLV-II K62A | 9,454.043 | 732.242 |
| MMLV-II K62R | 14,532.171 | 63.450 |
| MMLV-II K62E | 8,341.361 | 436.076 |
| MMLV-II K75A | 9,084.502 | 113.100 |
| MMLV-II K75R | 13,106.462 | 331.663 |
| MMLV-II K75E | 11,191.849 | 565.160 |
| MMLV-II L99A | 12,876.076 | 49.507 |
| MMLV-II L99R | 27,167.197 | 142.371 |
| MMLV-II L99E | 6,534.199 | 2,730.598 |
| MMLV-II N107A | 13,563.421 | 349.378 |
| MMLV-II N107R | 8,654.167 | 497.167 |
| MMLV-II N107E | 16,675.075 | 172.596 |
| MMLV-II Q291A | 20,957.729 | 150.006 |
| MMLV-II Q291R | 17,980.723 | 346.436 |
| MMLV-II Q291E | 11,025.722 | 407.116 |
| MMLV-II Q68A | n.d. | n.d. |
| MMLV-II Q68R | 24,925.791 | 937.265 |
| MMLV-II Q68E | 12,844.484 | 165.039 |
| MMLV-II Q79A | 12,038.975 | 482.596 |
| MMLV-II Q79R | 28,458.521 | 296.595 |
| MMLV-II Q79E | 10,358.863 | 309.043 |
| MMLV-II R110A | 11,517.764 | 562.094 |
| MMLV-II R110K | 8,112.167 | 76.742 |
| MMLV-II R110E | 8,809.423 | 290.785 |
| MMLV-II R298A | 27,817.905 | 172.690 |
| MMLV-II R298K | 18,222.660 | 825.743 |
| MMLV-II R298E | 10,783.790 | 783.279 |
| MMLV-II R301A | 11,344.854 | 63.499 |
| MMLV-II R301K | 17,584.850 | 445.587 |
| MMLV-II R301E | 10,146.906 | 1,879.902 |
| MMLV-II T106A | 17,717.520 | 215.965 |
| MMLV-II T106R | 11,680.187 | 148.213 |
| MMLV-II T106E | 21,203.557 | 366.469 |
| MMLV-II T128V | 14,384.970 | 355.754 |
| MMLV-II T128R | 12,938.223 | 464.841 |
| MMLV-II T128E | 14,781.394 | 1,930.931 |
| MMLV-II T293A | 15,658.189 | 347.640 |
| MMLV-II T293R | 19,976.165 | 253.604 |
| MMLV-II T293E | 17,580.335 | 404.397 |
| MMLV-II T296A | 10,312.142 | 159.775 |
| MMLV-II T296R | 8,482.071 | 92.806 |
| MMLV-II T296E | 7,687.972 | 112.884 |
| MMLV-II T55A | 18,073.262 | 618.174 |
| MMLV-II T55R | 11,546.179 | 138.906 |
| MMLV-II T55E | 12,299.658 | 815.911 |
| MMLV-II T57A | 14,700.042 | 2,916.521 |
| MMLV-II T57R | 11,195.901 | 145.433 |
| MMLV-II T57E | 11,958.503 | 605.445 |
| MMLV-II V101A | 10,697.751 | 269.696 |
| MMLV-II VI01R | 8,934.765 | 53.924 |
| MMLV-II V101E | 11,295.874 | 296.506 |
| MMLV-II V112A | 12,854.738 | 356.724 |
| MMLV-II V112R | 6,331.802 | 303.453 |
| MMLV-II V112E | 7,643.184 | 448.446 |
| MMLV-II V59A | 9,520.143 | 339.954 |
| MMLV-II V59R | 18,523.053 | 499.377 |
| MMLV-II V59E | 16,029.631 | 137.454 |
| MMLV-II Y109A | 8,421.361 | 185.196 |
| MMLV-II Y109R | 8,581.961 | 129.732 |
| MMLV-II Y109E | 10,216.473 | 416.388 |
| MMLV-IV | 65,726.159 | 1,811.314 |

Example 4: Extension of Reverse Transcriptase Single Mutants

The amino acid positions that enclosed the MMLV RTase single mutants identified in Example 3 were further evaluated to include all possible amino acid substitutions at that position. The single mutants were cloned, overexpressed, and purified as described in Examples 1 and 2, and evaluated as described in Example 3. The two-step and one-step reactions for MMLV RTase base construct and MMLV RTase double mutant variants were analyzed and reported by copy number output based on a standard curve (see Tables 6 and 7). Ten single mutant MMLV RTase variants (see Table 8) were found to exhibit an increase in the overall activity and thermostability as compared to the MMLV RTase base construct. The ten single mutant MMLV RTase variants were as follows: I61K, I61M, Q68I, Q68K, Q79H, Q79I, L99K, L99N, E282M and E282W.

TABLE 6

Two-step cDNA synthesis by MMLV RT single mutants. Data was generated via qPCR human normalizer assay and translated by copy number.

| MMLV RT Variant | Quantity Mean | Quantity Standard Deviation |
|---|---|---|
| MMLV-II | 1,484.121 | 125.278 |
| MMLV-II E282C | 749.332 | 37.947 |
| MMLV-II E282F | 968.042 | 28.112 |
| MMLV-II E282G | 841.839 | 30.618 |
| MMLV-II E282H | 936.562 | 64.904 |
| MMLV-II E282I | 1,418.551 | 8.682 |
| MMLV-II E282K | 2,399.973 | 50.862 |
| MMLV-II E282L | 1,778.903 | 134.133 |
| MMLV-II E282M | 2,115.328 | 125.477 |
| MMLV-II E282N | 1,175.130 | 79.221 |
| MMLV-II E282P | 1,529.331 | 61.525 |
| MMLV-II E282Q | 1,856.418 | 24.118 |
| MMLV-II E282S | 673.670 | 44.770 |
| MMLV-II E282T | 994.318 | 24.066 |
| MMLV-II E282V | 748.877 | 29.053 |
| MMLV-II E282W | 2,469.404 | 141.080 |
| MMLV-II E282Y | 1,360.706 | 338.309 |
| MMLV-II I61C | 283.240 | 11.244 |
| MMLV-II I61D | 349.008 | 10.979 |
| MMLV-II I61F | 784.163 | 22.643 |
| MMLV-II I61G | 395.348 | 21.967 |
| MMLV-II I61H | 736.015 | 30.271 |
| MMLV-II I61K | 4,479.606 | 62.627 |
| MMLV-II I61L | 1,106.547 | 38.553 |
| MMLV-II I61M | 4,198.088 | 93.025 |
| MMLV-II I61N | 709.752 | 29.312 |
| MMLV-II I61P | 32.935 | 16.814 |
| MMLV-II I61Q | 1,311.695 | 145.810 |
| MMLV-II I61S | 797.783 | 50.626 |
| MMLV-II I61T | 628.173 | 33.371 |
| MMLV-II I61V | 1,439.915 | 27.490 |
| MMLV-II I61W | 442.039 | 29.310 |
| MMLV-II I61Y | 534.249 | 26.831 |
| MMLV-II L99C | 3,109.142 | 80.016 |
| MMLV-II L99D | 83.653 | 3.432 |
| MMLV-II L99F | 2,811.513 | 79.584 |
| MMLV-II L99G | 908.041 | 16.157 |
| MMLV-II L99H | 4,881.196 | 390.497 |
| MMLV-II L99I | 910.072 | 71.671 |
| MMLV-II L99K | 6,410.818 | 127.262 |
| MMLV-II L99M | 976.548 | 65.154 |
| MMLV-II L99N | 4,974.458 | 162.464 |
| MMLV-II L99P | 6.416 | 1.820 |
| MMLV-II L99Q | 3,908.473 | 337.167 |
| MMLV-II L99S | 3,793.955 | 86.959 |
| MMLV-II L99T | 4,189.211 | 27.640 |
| MMLV-II L99V | 964.081 | 48.105 |
| MMLV-II L99W | 1,614.660 | 40.442 |
| MMLV-II L99Y | 2,123.406 | 181.945 |
| MMLV-II Q68A | 1,184.702 | 7.676 |

TABLE 6-continued

Two-step cDNA synthesis by MMLV RT single mutants. Data was generated via qPCR human normalizer assay and translated by copy number.

| MMLV RT Variant | Quantity Mean | Quantity Standard Deviation |
|---|---|---|
| MMLV-II Q68C | 2,038.167 | 36.463 |
| MMLV-II Q68D | 1,613.880 | 77.796 |
| MMLV-II Q68F | 1,805.647 | 62.456 |
| MMLV-II Q68G | 2,262.873 | 69.688 |
| MMLV-II Q68H | 106.421 | 9.860 |
| MMLV-II Q68I | 2,675.446 | 73.874 |
| MMLV-II Q68K | 1,042.979 | 70.081 |
| MMLV-II Q68L | 1,070.742 | 57.215 |
| MMLV-II Q68M | 1,342.806 | 58.349 |
| MMLV-II Q68N | 1,993.946 | 65.808 |
| MMLV-II Q68P | 2,025.753 | 25.540 |
| MMLV-II Q68S | 1,895.984 | 26.959 |
| MMLV-II Q68T | 431.442 | 22.751 |
| MMLV-II Q68V | 1,534.710 | 110.794 |
| MMLV-II Q68W | 1,790.706 | 124.583 |
| MMLV-II Q79C | 2,477.812 | 107.510 |
| MMLV-II Q79D | 627.902 | 11.073 |
| MMLV-II Q79F | 1,786.571 | 126.904 |
| MMLV-II Q79G | 2,702.985 | 83.998 |
| MMLV-II Q79H | 2,851.710 | 57.501 |
| MMLV-II Q79I | 2,967.710 | 57.440 |
| MMLV-II Q79K | 1,346.751 | 64.513 |
| MMLV-II Q79L | 2,214.615 | 67.622 |
| MMLV-II Q79M | 1,847.181 | 31.384 |
| MMLV-II Q79N | 1,365.563 | 54.775 |
| MMLV-II Q79P | 674.074 | 42.100 |
| MMLV-II Q79S | 2,199.353 | 52.958 |
| MMLV-II Q79T | 1,523.163 | 77.025 |
| MMLV-II Q79V | 1,704.661 | 77.643 |
| MMLV-II Q79W | 2,186.489 | 31.470 |
| MMLV-II Q79Y | 2,326.023 | 123.508 |
| MMLV-II R298C | 79.970 | 9.815 |
| MMLV-II R298D | 0.000 | 0.000 |
| MMLV-II R298F | 84.760 | 9.362 |
| MMLV-II R298G | 357.027 | 15.726 |
| MMLV-II R298H | 269.257 | 20.814 |
| MMLV-II R298I | 130.983 | 5.364 |
| MMLV-II R298L | 199.612 | 5.843 |
| MMLV-II R298M | 172.013 | 18.710 |
| MMLV-II R298N | 199.678 | 2.660 |
| MMLV-II R298P | 122.098 | 5.900 |
| MMLV-II R298Q | 118.092 | 40.694 |
| MMLV-II R298S | 406.112 | 7.695 |
| MMLV-II R298T | 618.616 | 20.023 |
| MMLV-II R298V | 136.498 | 13.297 |
| MMLV-II R298W | 68.096 | 7.016 |
| MMLV-II R298Y | 162.713 | 7.854 |
| MMLV-IV | 6,830.294 | 376.878 |

TABLE 7

One-step cDNA synthesis by MMLV RT single mutants. Data was generated via qPCR human normalizer assay and data is translated by copy number.

| MMLV RT Variant | Quantity Mean | Quantity Standard Deviation |
|---|---|---|
| MMLV-II | 408.018 | 8.693 |
| MMLV-II E282C | 175.083 | 7.005 |
| MMLV-II E282F | 1,043.025 | 16.137 |
| MMLV-II E282G | 635.037 | 13.293 |
| MMLV-II E282H | 656.956 | 10.018 |
| MMLV-II E282I | 1,033.125 | 44.996 |
| MMLV-II E282K | 751.309 | 17.611 |
| MMLV-II E282L | 1,072.350 | 80.365 |
| MMLV-II E282M | 1,318.072 | 51.735 |
| MMLV-II E282N | 539.305 | 10.767 |
| MMLV-II E282P | 725.869 | 92.685 |
| MMLV-II E282Q | 626.674 | 12.129 |
| MMLV-II E282S | 354.956 | 34.850 |
| MMLV-II E282T | 485.477 | 45.783 |

TABLE 7-continued

One-step cDNA synthesis by MMLV RT single mutants. Data was generated via qPCR human normalizer assay and data is translated by copy number.

| MMLV RT Variant | Quantity Mean | Quantity Standard Deviation |
|---|---|---|
| MMLV-II E282V | 594.047 | 27.898 |
| MMLV-II E282W | 913.290 | 61.145 |
| MMLV-II E282Y | 759.920 | 34.784 |
| MMLV-II I61C | 219.438 | 18.403 |
| MMLV-II I61D | 347.020 | 13.303 |
| MMLV-II I61F | 428.623 | 25.316 |
| MMLV-II I61G | 389.503 | 21.764 |
| MMLV-II I61H | 514.330 | 18.416 |
| MMLV-II I61K | 2,343.894 | 67.214 |
| MMLV-II I61L | 621.572 | 14.892 |
| MMLV-II I61M | 2,536.807 | 150.371 |
| MMLV-II I61N | 538.519 | 20.736 |
| MMLV-II I61P | 61.683 | 18.802 |
| MMLV-II I61Q | 701.471 | 32.487 |
| MMLV-II I61S | 611.977 | 30.430 |
| MMLV-II I61T | 534.254 | 31.643 |
| MMLV-II I61V | 881.608 | 20.662 |
| MMLV-II I61W | 428.440 | 17.964 |
| MMLV-II I61Y | 347.930 | 4.412 |
| MMLV-II L99C | 2,390.104 | 35.867 |
| MMLV-II L99D | 185.044 | 6.975 |
| MMLV-II L99F | 1,577.767 | 7.757 |
| MMLV-II L99G | 987.225 | 9.718 |
| MMLV-II L99H | 3,886.372 | 111.670 |
| MMLV-II L99I | 613.648 | 46.303 |
| MMLV-II L99K | 7,597.650 | 321.753 |
| MMLV-II L99M | 934.817 | 52.006 |
| MMLV-II L99N | 4,689.222 | 160.641 |
| MMLV-II L99P | 18.537 | 1.131 |
| MMLV-II L99Q | 2,394.744 | 64.077 |
| MMLV-II L99S | 3,293.831 | 111.802 |
| MMLV-II L99T | 3,505.113 | 101.670 |
| MMLV-II L99V | 677.756 | 49.356 |
| MMLV-II L99W | 839.088 | 50.301 |
| MMLV-II L99Y | 1,127.536 | 19.074 |
| MMLV-II Q68A | 827.617 | 30.689 |
| MMLV-II Q68C | 1,110.680 | 45.944 |
| MMLV-II Q68D | 1,045.802 | 25.488 |
| MMLV-II Q68F | 1,210.166 | 120.899 |
| MMLV-II Q68G | 907.279 | 30.688 |
| MMLV-II Q68H | 150.384 | 6.867 |
| MMLV-II Q68I | 1,550.372 | 76.712 |
| MMLV-II Q68K | 1,712.176 | 47.342 |
| MMLV-II Q68L | 651.039 | 51.426 |
| MMLV-II Q68M | 1,395.463 | 34.805 |
| MMLV-II Q68N | 1,241.364 | 25.780 |
| MMLV-II Q68P | 1,249.444 | 13.709 |
| MMLV-II Q68S | 1,125.260 | 21.324 |
| MMLV-II Q68T | 792.901 | 31.513 |
| MMLV-II Q68V | 1,026.654 | 24.972 |
| MMLV-II Q68W | 1,594.175 | 101.221 |
| MMLV-II Q79C | 1,948.151 | 87.341 |
| MMLV-II Q79D | 458.131 | 10.763 |
| MMLV-II Q79F | 1,623.675 | 50.723 |
| MMLV-II Q79G | 1,885.097 | 20.190 |
| MMLV-II Q79H | 2,508.763 | 149.926 |
| MMLV-II Q79I | 2,329.030 | 76.545 |
| MMLV-II Q79K | 1,861.302 | 24.320 |
| MMLV-II Q79L | 1,496.247 | 30.399 |
| MMLV-II Q79M | 1,496.469 | 38.178 |
| MMLV-II Q79N | 995.813 | 42.279 |
| MMLV-II Q79P | 526.914 | 23.216 |
| MMLV-II Q79S | 1,685.124 | 42.694 |
| MMLV-II Q79T | 966.505 | 8.377 |
| MMLV-II Q79V | 1,218.191 | 21.512 |
| MMLV-II Q79W | 1,962.326 | 37.135 |
| MMLV-II Q79Y | 2,218.504 | 56.938 |
| MMLV-II R298C | 45.500 | 1.456 |
| MMLV-II R298D | 0.000 | 0.000 |
| MMLV-II R298F | 104.825 | 5.133 |
| MMLV-II R298G | 323.542 | 14.052 |
| MMLV-II R298H | 253.202 | 47.711 |
| MMLV-II R298I | 205.982 | 8.304 |
| MMLV-II R298L | 213.674 | 15.199 |
| MMLV-II R298M | 176.347 | 12.484 |
| MMLV-II R298N | 142.969 | 39.198 |
| MMLV-II R298P | 188.995 | 3.689 |
| MMLV-II R298Q | 95.525 | 44.292 |
| MMLV-II R298S | 307.614 | 9.962 |
| MMLV-II R298T | 487.828 | 3.480 |
| MMLV-II R298V | 255.828 | 12.902 |
| MMLV-II R298W | 37.872 | 8.482 |
| MMLV-II R298Y | 153.333 | 25.137 |
| MMLV-IV | 19,407.721 | 466.310 |

TABLE 8

Sequences of single mutant MMLV RTase variants.

| SEQ ID NO: | Construct | Construct Sequence (AA) |
|---|---|---|
| 644 | MMLV RTase with I61K mutation | MTLNIEDEHRLHETSKEPDVSLGSTWLSDFPQA WAETGGMGLAVRQAPLIIPLKATSTPVSKKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |

TABLE 8-continued

Sequences of single mutant MMLV RTase variants.

| SEQ ID NO: | Construct | Construct Sequence (AA) |
|---|---|---|
| 645 | MMLV RTase with I61M mutation | MTLNIEDEHRLHETSKEPDVSLGSTWLSDFPQA<br>WAETGGMGLAVRQAPLIIPLKATSTPVSMKQYP<br>MSQEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 646 | MMLV RTase with Q681 mutation | MTLNIEDEHRLHETSKEPDVSLGSTWLSDFPQA<br>WAETGGMGLAVRQAPLIIPLKATSTPVSIKQYP<br>MSIEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 647 | MMLV RTase with Q68K mutation | MTLNIEDEHRLHETSKEPDVSLGSTWLSDFPQA<br>WAETGGMGLAVRQAPLIIPLKATSTPVSIKQYP<br>MSKEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 648 | MMLV RTase with Q79H mutation | MTLNIEDEHRLHETSKEPDVSLGSTWLSDFPQA<br>WAETGGMGLAVRQAPLIIPLKATSTPVSIKQYP<br>MSQEARLGIKPHIHRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK |

TABLE 8-continued

Sequences of single mutant MMLV RTase variants.

| SEQ ID NO: | Construct | Construct Sequence (AA) |
|---|---|---|
| | | TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 649 | MMLV RTase with Q791 mutation | MTLNIEDEHRLHETSKEPDVSLGSTWLSDFPQA<br>WAETGGMGLAVRQAPLIIPLKATSTPVSIKQYP<br>MSQEARLGIKPHIIRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 650 | MMLV RTase with L99K mutation | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPL<br>KPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 651 | MMLV RTase with L99N mutation | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPL<br>NPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTEARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI |

TABLE 8-continued

Sequences of single mutant MMLV RTase variants.

| SEQ ID NO: | Construct | Construct Sequence (AA) |
|---|---|---|
| | | HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 652 | MMLV RTase with E282M mutation | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTMARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 653 | MMLV RTase with E282W mutation | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTWARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |

Example 5: Stacking of Reverse Transcriptase Mutants with Enhanced Activity a. MMLV RTase Double Mutants The MMLV RTase single mutants identified in Example 3 were stacked to further improve the ability of MMLV RTase to synthesize cDNA from purified total RNA (DNased, isolated from HeLa cells) as compared to the MMLV RTase base construct (RNase H minus construct). Fifteen MMLV RTase double mutant variants (see Table 9) were cloned, overexpressed, and purified as described in Examples 1 and 2, and evaluated as described in Example 3. The two-step and one-step reactions for MMLV RTase base construct and MMLV RTase double mutant variants were analyzed and reported by copy number output based on a standard curve (see Tables 10 and 11).

Four of the fifteen MMLV RTase double mutant variants were found to exhibit increased overall activity and thermostability as compared to the other MMLV RTase double mutant variants, and almost all of the MMLV RTase double mutant variants exhibited increased overall activity and thermostability as compared to the MMLV RTase base construct. The four MMLV RTase double mutant variants that were found to exhibit the highest overall activity were E282D/L99R L99R/068R L99R/079R and 068R/079R.

TABLE 9

Sequences of double mutant MMLV RTase variants.

| SEQ ID NO: | Construct | Construct Sequence (AA) |
|---|---|---|
| 654 | MMLV RTase with I61R/E282D mutations | MTLNIEDEHRLHETSKEPDVSLGSTWLSDFPQA<br>WAETGGMGLAVRQAPLIIPLKATSTPVSRKQYP<br>MSQEARLGIKPHIQRLLDQGILVPCQSPWNTPL |

TABLE 9-continued

Sequences of double mutant MMLV RTase variants.

| SEQ ID NO: | Construct | Construct Sequence (AA) |
|---|---|---|
| | | LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 655 | MMLV RTase with L99R/E282D mutations | MTLNIEDEHRLHETSKEPDVSLGSTWLSDFPQA<br>WAETGGMGLAVRQAPLIIPLKATSTPVSIKQYP<br>MSQEARLGIKPHIQRLLDQGILVPCQSPWNTPR<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 656 | MMLV RTase with Q68R/E282D mutations | MTLNIEDEHRLHETSKEPDVSLGSTWLSDFPQA<br>WAETGGMGLAVRQAPLIIPLKATSTPVSIKQYP<br>MSREARLGIKPHIQRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 657 | MMLV RTase with Q79R/E282D mutations | MTLNIEDEHRLHETSKEPDVSLGSTWLSDFPQA<br>WAETGGMGLAVRQAPLIIPLKATSTPVSIKQYP<br>MSQEARLGIKPHIRRLLDQGILVPCQSPWNTPL<br>LPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM |

TABLE 9-continued

Sequences of double mutant MMLV RTase variants.

| SEQ ID NO: | Construct | Construct Sequence (AA) |
|---|---|---|
| | | GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 658 | MMLV RTase with E282D/R298A mutations | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 659 | MMLV RTase with I61R/L99R mutations | MTLNIEDEHRLHETSKEPDVSLGSTWLSDFPQA WAETGGMGLAVRQAPLIIPLKATSTPVSRKQYP MSQEARLGIKPHIQRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 660 | MMLV RTase with I61R/Q68R mutations | MTLNIEDEHRLHETSKEPDVSLGSTWLSDFPQA WAETGGMGLAVRQAPLIIPLKATSTPVSRKQYP MSREARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEH |

TABLE 9-continued

Sequences of double mutant MMLV RTase variants.

| SEQ ID NO: | Construct | Construct Sequence (AA) |
|---|---|---|
| 661 | MMLV RTase with I61R/Q79R mutations | MTLNIEDEHRLHETSKEPDVSLGSTWLSDFPQA WAETGGMGLAVRQAPLIIPLKATSTPVSRKQYP MSQEARLGIKPHIRRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 662 | MMLV RTase with I61R/R298A mutations | MTLNIEDEHRLHETSKEPDVSLGSTWLSDFPQA WAETGGMGLAVRQAPLIIPLKATSTPVSRKQYP MSQEARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 663 | MMLV RTase with Q68R/L99R mutations | MTLNIEDEHRLHETSKEPDVSLGSTWLSDFPQA WAETGGMGLAVRQAPLIIPLKATSTPVSIKQYP MSREARLGIKPHIQRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 664 | MMLV RTase with Q79R/L99R mutations | MTLNIEDEHRLHETSKEPDVSLGSTWLSDFPQA WAETGGMGLAVRQAPLIIPLKATSTPVSIKQYP MSQEARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT |

TABLE 9-continued

Sequences of double mutant MMLV RTase variants.

| SEQ ID NO: | Construct | Construct Sequence (AA) |
|---|---|---|
| | | PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 665 | MMLV RTase with L99R/R298A mutations | MTLNIEDEHRLHETSKEPDVSLGSTWLSDFPQA WAETGGMGLAVRQAPLIIPLKATSTPVSIKQYP MSQEARLGIKPHIQRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 666 | MMLV RTase with Q68R/Q79R mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 667 | MMLV RTase with Q68R/R298A mutations | MTLNIEDEHRLHETSKEPDVSLGSTWLSDFPQA WAETGGMGLAVRQAPLIIPLKATSTPVSIKQYP MSREARLGIKPHIQRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL |

TABLE 9-continued

| Sequences of double mutant MMLV RTase variants. | | |
|---|---|---|
| SEQ ID NO: | Construct | Construct Sequence (AA) |
| | | PKRLSIIHCPGHQKGHSAEARGNRMADQAARKA AITETPDTSTLLIENSSPYTSEHF |
| 668 | MMLV RTase with Q79R/R298A mutations | MTLNIEDEHRLHETSKEPDVSLGSTWLSDFPQA WAETGGMGLAVRQAPLIIPLKATSTPVSIKQYP MSQEARLGIKPHIRRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PAQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |

TABLE 10

| Two-Step cDNA synthesis by MMLV RT double mutants. Data was generated via qPCR human normalizer assay and data is translated by copy number. | | |
|---|---|---|
| MMLV RT Variant | Quantity Mean | Quantity Standard Deviation |
| MMLV-II | 1,773.623 | 5.057 |
| MMLV-II E282D/I61R | 4,810.277 | 143.422 |
| MMLV-II E282D/L99R | 7,266.281 | 50.730 |
| MMLV-II E282D/Q68R | 5,186.392 | 69.563 |
| MMLV-II E282D/Q79R | 4,311.403 | 95.402 |
| MMLV-II E282D/R298A | 1,366.524 | 16.429 |
| MMLV-II I61R/L99R | 6,061.812 | 174.619 |
| MMLV-II I61R/Q68R | 5,899.316 | 39.879 |
| MMLV-II I61R/Q79R | 5,257.089 | 98.378 |
| MMLV-II I61R/R298A | 2,661.223 | 68.948 |
| MMLV-II L99R/Q68R | 7,750.519 | 94.408 |
| MMLV-II L99R/Q79R | 7,455.203 | 124.095 |
| MMLV-II L99R/R298A | 5,351.021 | 179.558 |
| MMLV-II Q68R/Q79R | 7,178.681 | 86.595 |
| MMLV-II Q68R/R298A | 4,524.340 | 84.703 |
| MMLV-II Q79R/R298A | 3,739.608 | 58.621 |
| MMLV-IV | 8,258.715 | 79.458 |

TABLE 11

| One-Step cDNA synthesis by MMLV RT double mutants. Data was generated via qPCR human normalizer assay and data is translated by cony number. | | |
|---|---|---|
| MMLV-RT Variant | Quantity Mean | Quantity Standard Deviation |
| MMLV-II | 859.127 | 24.795 |
| MMLV-II E282D/I61R | 2,948.906 | 49.177 |
| MMLV-II E282D/L99R | 4,814.957 | 239.110 |
| MMLV-II E282D/Q68R | 3,709.046 | 131.434 |
| MMLV-II E282D/Q79R | 3,694.187 | 98.772 |
| MMLV-II E282D/R298A | 794.643 | 39.913 |
| MMLV-II I61R/L99R | 3,443.713 | 180.210 |
| MMLV-II I61R/Q68R | 3,525.138 | 112.288 |
| MMLV-II I61R/Q79R | 3,125.990 | 120.996 |
| MMLV-II I61R/R298A | 2,006.208 | 83.559 |
| MMLV-II L99R/Q68R | 6,755.852 | 102.788 |
| MMLV-II L99R/Q79R | 6,709.502 | 35.997 |
| MMLV-II L99R/R298A | 2,128.451 | 55.565 |
| MMLV-II Q68R/Q79R | 6,343.821 | 140.779 |
| MMLV-II Q68R/R298A | 2,406.470 | 74.117 |
| MMLV-II Q79R/R298A | 2,301.759 | 22.849 |
| MMLV-IV | 15,411.857 | 333.388 |

b. Cloning of MMLV RTase Triple and More Mutants

Following the double mutant variants, MMLV RTase single mutants were stacked further to improve the ability of MMLV RTase to synthesize cDNA from purified total RNA (DNased, isolated from HeLa cells) as compared to the MMLV RTase base construct (RNase H minus construct). Seventeen MMLV RTase triple or more mutant variants (see Table 12) were cloned as described in Example 1.

TABLE 12

| Sequences of triple or more mutant MMLV RTase variants. | | |
|---|---|---|
| SEQ ID NO: | Construct | Construct Sequence (AA) |
| 669 | MMLV RTase with Q68R/L99R/E282D mutations | MTLNIEDEHRLHETSKEPDVSLGSTWLSDFPQA WAETGGMGLAVRQAPLIIPLKATSTPVSIKQYP MSREARLGIKPHIQRLLDQGILVPCQSPWNTPL RPVKKPGTNDYRPVQDLREVNKRVEDIHPTVPN PYNLLSGLPPSHQWYTVLDLKDAFFCLRLHPTS |

TABLE 12-continued

Sequences of triple or more mutant MMLV RTase variants.

| SEQ ID NO: | Construct | Construct Sequence (AA) |
|---|---|---|
| | | QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 670 | MMLV RTase with Q79R/L99R/E282D mutations | MTLNIEDEHRLHETSKEPDVSLGSTWLSDFPQA WAETGGMGLAVRQAPLIIPLKATSTPVSIKQYP MSQEARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 671 | MMLV RTase with Q68R/Q79R/E282D mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL LPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 672 | MMLV RTase with Q68R/Q79R/L99R mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTEARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN |

TABLE 12-continued

| SEQ ID NO: | Construct | Construct Sequence (AA) |
|---|---|---|
| Sequences of triple or more mutant MMLV RTase variants. | | |
| | | CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 673 | MMLV RTase with Q68R/Q79R/L99R/E282D mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 674 | MMLV RTase with Q68R/Q79R/L99K/E282D mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL KPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 675 | MMLV RTase with Q68R/Q79R/L99N/E282D mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL NPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 676 | MMLV RTase with Q68I/Q79R/L99R/E282D mutations | MTLNIEDEHRLHETSKEPDVSLGSTWLSDFPQA WAETGGMGLAVRQAPLIIPLKATSTPVSIKQYP MSIEARLGIKPHIRRLLDQGILVPCQSPWNTPL |

TABLE 12-continued

Sequences of triple or more mutant MMLV RTase variants.

| SEQ ID NO: | Construct | Construct Sequence (AA) |
|---|---|---|
| | | RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 677 | MMLV RTase with Q68K/Q79R/L99R/E282D mutations | MTLNIEDEHRLHETSKEPDVSLGSTWLSDFPQA<br>WAETGGMGLAVRQAPLIIPLKATSTPVSIKQYP<br>MSKEARLGIKPHIRRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 678 | MMLV RTase with Q68R/Q79H/L99R/E282D mutations | MTLNIEDEHRLHETSKEPDVSLGSTWLSDFPQA<br>WAETGGMGLAVRQAPLIIPLKATSTPVSIKQYP<br>MSREARLGIKPHIHRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 679 | MMLV RTase with Q68R/Q79I/L99R/E282D mutations | MTLNIEDEHRLHETSKEPDVSLGSTWLSDFPQA<br>WAETGGMGLAVRQAPLIIPLKATSTPVSIKQYP<br>MSREARLGIKPHIIRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM |

TABLE 12-continued

Sequences of triple or more mutant MMLV RTase variants.

| SEQ ID NO: | Construct | Construct Sequence (AA) |
|---|---|---|
| | | GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 680 | MMLV RTase with Q68R/Q79R/L99R/E282M mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTMARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 681 | MMLV RTase with Q68R/Q79R/L99R/E282W mutations | MTLNIEDEHRLHETSKEPDVSLGSTWLSDFPQA WAETGGMGLAVRQAPLIIPLKATSTPVSIKQYP MSREARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTWARKETVMGQPTPKT PRQLREFLGTAGFCRLWPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |
| 682 | MMLV RTase with I61K/Q68R/Q79R/L99R/ E282D mutations | MTLNIEDEHRLHETSKEPDVSLGSTWLSDFPQA WAETGGMGLAVRQAPLIIPLKATSTPVSKKQYP MSREARLGIKPHIRRLLDQGILVPCQSPWNTPL RPVKKPGTNDYRPVQDLREVNKRVEDIHPTVPN PYNLLSGLPPSHQWYTVLDLKDAFFCLRLHPTS QPLFAFEWRDPEMGISGQLTWTRLPQGFKNSPT LFDEALHRDLADFRIQHPDLILLQYVDDLLLAA TSELDCQQGTRALLQTLGNLGYRASAKKAQICQ KQVKYLGYLLKEGQRWLTDARKETVMGQPTPKT PRQLREFLGTAGFCRLWIPGFAEMAAPLYPLTK TGTLFNWGPDQQKAYQEIKQALLTAPALGLPDL TKPFELFVDEKQGYAKGVLTQKLGPWRRPVAYL SKKLDPVAAGWPPCLRMVAAIAVLTKDAGKLTM GQPLVILAPHAVEALVKQPPDRWLSNARMTHYQ ALLLDTDRVQFGPVVALNPATLLPLPEEGLQHN CLDILAEAHGTRPDLTDQPLPDADHTWYTGGSS LLQEGQRKAGAAVTTETEVIWAKALPAGTSAQR AQLIALTQALKMAEGKKLNVYTNSRYAFATAHI HGEIYRRRGLLTSEGKEIKNKDEILALLKALFL PKRLSIIHCPGHQKGHSAEARGNRMADQAARKA AITETPDTSTLLIENSSPYTSEHF |

TABLE 12-continued

| Sequences of triple or more mutant MMLV RTase variants. | | |
|---|---|---|
| SEQ ID NO: | Construct | Construct Sequence (AA) |
| 683 | MMLV RTase with I61M/Q68R/Q79R/L99R/ E282D mutations | MTLNIEDEHRLHETSKEPDVSLGSTWLSDFPQA<br>WAETGGMGLAVRQAPLIIPLKATSTPVSMKQYP<br>MSREARLGIKPHIRRLLDQGILVPCQSPWNTPL<br>RPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTDARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 684 | MMLV RTase with Q68I/Q79H/L99K/E282M mutations | MTLNIEDEHRLHETSKEPDVSLGSTWLSDFPQA<br>WAETGGMGLAVRQAPLIIPLKATSTPVSIKQYP<br>MSIEARLGIKPHIHRLLDQGILVPCQSPWNTPL<br>KPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTMARKETVMGQPTPKT<br>PRQLREFLGTAGFCRLWIPGFAEMAAPLYPLTK<br>TGTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |
| 685 | MMLV RTase with 161M/Q68I/Q79H/L99K/ E282M mutations | MTLNIEDEHRLHETSKEPDVSLGSTWLSDFPQA<br>WAETGGMGLAVRQAPLIIPLKATSTPVSMKQYP<br>MSIEARLGIKPHIHRLLDQGILVPCQSPWNTPL<br>KPVKKPGTNDYRPVQDLREVNKRVEDIHPTVPN<br>PYNLLSGLPPSHQWYTVLDLKDAFFCLRLHPTS<br>QPLFAFEWRDPEMGISGQLTWTRLPQGFKNSPT<br>LFDEALHRDLADFRIQHPDLILLQYVDDLLLAA<br>TSELDCQQGTRALLQTLGNLGYRASAKKAQICQ<br>KQVKYLGYLLKEGQRWLTMARKETVMGQPTPKT<br>PRQLREFLGTAGFCRLWIPGFAEMAAPLYPLTK<br>TTLFNWGPDQQKAYQEIKQALLTAPALGLPDL<br>TKPFELFVDEKQGYAKGVLTQKLGPWRRPVAYL<br>SKKLDPVAAGWPPCLRMVAAIAVLTKDAGKLTM<br>GQPLVILAPHAVEALVKQPPDRWLSNARMTHYQ<br>ALLLDTDRVQFGPVVALNPATLLPLPEEGLQHN<br>CLDILAEAHGTRPDLTDQPLPDADHTWYTGGSS<br>LLQEGQRKAGAAVTTETEVIWAKALPAGTSAQR<br>AQLIALTQALKMAEGKKLNVYTNSRYAFATAHI<br>HGEIYRRRGLLTSEGKEIKNKDEILALLKALFL<br>PKRLSIIHCPGHQKGHSAEARGNRMADQAARKA<br>AITETPDTSTLLIENSSPYTSEHF |

c. Expression and Purification of MMLV RTase and Mutant Variants

A colony with the appropriate strain was used to inoculate TB media (200 mL) with kanamycin (0.05 mg/mL) and grown at 37° C. until an OD of approximately 0.9 was achieved followed by cooling of the flask for 30 minutes at 4° C. Protein expression was induced by the addition of 1 M IPTG (100 μL), followed by growth at 18° C. for 21 hours. Cells were harvested by spinning samples at 4,700×g for 10 minutes.

Cell pellets were re-suspended in a lysis buffer (50 mM $NaPO_4$, pH 7.8, 5% glycerol, 300 mM NaCl, 10 mM imidazole, 5 mM DTT, 0.01% n-ocyl-β-D-glucopyranoside, DNaseI, 10 mM CaCl2, lysozyme (1 mg/mL), and protease inhibitor). The sample was lysed on an Avestin Emulsiflex C3 pre-chilled to 4° C. at 15-20 kpsi with three passes. Cell debris was removed by centrifuging the lysate at 16,000×g for 30 minutes at 4° C.

Cleared lysates were applied to a HisTrap HP column (Cytiva Life Sciences, Cat #17524701). The resin was equilibrated with MMLV His-Bind buffer (50 mM NaPO4, pH 7.8, 5% glycerol, 0.3 M NaCl, 10 mM imidazole, 1 mM DTT and 0.01% IGEPAL-CA), followed by sample loading. The samples were washed with MMLV His-Bind buffer, followed by a 25% B wash (B=MMLV His Elution buffer=50 mM NaPO4, pH 7.8, 5% glycerol, 0.3 M NaCl, 250 mM imidazole, 1 mM DTT and 0.01% IGEPAL-CA). The sample was eluted with 100% B for 10 CVs in 45 mL fractions.

Purified proteins were applied to a HiTrap Heparin HP column (Cytiva Life Sciences, Cat #17040601). The resin was equilibrated with MMLV Heparin-Bind buffer (50 mM Tris HCl pH 8.5, 75 mM NaCl, 1 mM DTT, 5% glycerol and 0.01% IGEPAL-CA), followed by sample loading. The sample was washed with MLV Heparin Bind buffer, followed by a 25% B wash (B=MLV Heparin Elution Buffer). The sample was eluted with 60% B for 10 CVs in 45 mL fractions.

Purified proteins were applied to a Bio-Scale™ Mini CHT™ Cartridge (Bio-Rad Laboratories, Cat #7324322). The resin was washed with 1 M NaOH, followed by equilibration with MMLV Heparin-Bind buffer and sample loading. The sample was washed with MLV Heparin Elution buffer, followed by MMLV Heparin Bind buffer. The sample was linearly eluted to 100% B2 (B2=MMLV HA Elution Buffer=250 mM KPO4 pH 7.5, 1 mM DTT, 5% glycerol and 0.01% IGEPAL-CA) for 15 CVs in 5 mL fractions.

Fractions containing purified protein were pooled and dialyzed in MMLV Storage Buffer (50 mM Tris-HCl (pH 7.5), 100 mM NaCl, 1 mM DTT, 50% (v/v) glycerol).

d. Evaluation of Ability of Purified WLV RTase Mutant Variants to Synthesize DNA by Gene Specific Priming MMLV RTase base construct and MMLV RTase mutant variants evaluated as described in Example 3. Temperatures were adjusted for both two-step and one-step reactions to 55 and 60° C., respectively. The two-step and one-step reactions for MMLV RTase base construct and MMLV RTase mutant variants were analyzed and reported by Ct output from the qPCR (see Tables 13 and 14).

Six of the seventeen MMLV RTase triple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The six MMLV RTase mutant variants that were found to exhibit the highest overall activity were Q68R/L99R, Q68R/Q79R/L99R, Q68R/Q79R/L99R/E282D, Q68R/Q79R/L99K/E282D, Q68R/Q79R/L99R/E282W, I61M/Q68R/Q79R/L99R/E282D and Q68I/Q79H/L99K/E282M.

TABLE 13

Two-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II | 0.625 | 25.520 | 0.047 |
| MMLV-II L99R/E282D | 0.625 | 24.332 | 0.060 |
| MMLV-II Q68R/L99R | 0.625 | 22.207 | 0.097 |
| MMLV-II Q79R/L99R | 0.625 | 23.789 | 0.012 |
| MMLV-II Q68R/Q79R | 0.625 | 23.629 | 0.038 |
| MMLV-II Q68R/L99R/E282D | 0.625 | 22.855 | 0.079 |
| MMLV-II Q79R/L99R/E282D | 0.625 | 23.095 | 0.035 |
| MMLV-II Q68R/Q79R/E282D | 0.625 | 22.526 | 0.027 |
| MMLV-II Q68R/Q79R/L99R | 0.625 | 22.099 | 0.018 |
| MMLV-II Q68R/Q79R/L99R/E282D | 0.625 | 21.056 | 0.023 |
| MMLV-II Q68R/Q79R/L99K/E282D | 0.625 | 21.833 | 0.031 |
| MMLV-II Q68R/Q79R/L99N/E282D | 0.625 | 23.607 | 0.031 |
| MMLV-II Q68I/Q79R/L99R/E282D | 0.625 | 23.858 | 0.029 |
| MMLV-II Q68K/Q79R/L99R/E282D | 0.625 | 22.615 | 0.054 |
| MMLV-II Q68R/Q79H/L99R/E282D | 0.625 | 28.866 | 0.008 |
| MMLV-II Q68R/Q79I/L99R/E282D | 0.625 | 23.283 | 0.085 |
| MMLV-II Q68R/Q79R/L99R/E282M | 0.625 | 25.073 | 0.097 |
| MMLV-II Q68R/Q79R/L99R/E282W | 0.625 | 22.331 | 0.048 |
| MMLV-II I61K/Q68R/Q79R/L99R/E282D | 0.625 | 23.271 | 0.065 |
| MMLV-II I61M/Q68R/Q79R/L99R/E282D | 0.625 | 22.133 | 0.018 |
| MMLV-II Q68I/Q79H/L99K/E282M | 0.625 | 23.344 | 0.037 |
| MMLV-II I61M/Q68I/Q79H/L99K/E282M | 0.625 | 25.255 | 0.058 |
| MMLV-II | 2.5 | 22.154 | 0.052 |
| MMLV-II L99R/E282D | 2.5 | 21.501 | 0.054 |
| MMLV-II Q68R/L99R | 2.5 | 21.151 | 0.048 |
| MMLV-II Q79R/L99R | 2.5 | 21.229 | 0.163 |
| MMLV-II Q68R/Q79R | 2.5 | 21.228 | 0.054 |
| MMLV-II Q68R/L99R/E282D | 2.5 | 21.126 | 0.030 |
| MMLV-II Q79R/L99R/E282D | 2.5 | 21.418 | 0.033 |
| MMLV-II Q68R/Q79R/E282D | 2.5 | 21.011 | 0.052 |
| MMLV-II Q68R/Q79R/L99R | 2.5 | 20.953 | 0.041 |
| MMLV-II Q68R/Q79R/L99R/E282D | 2.5 | 21.113 | 0.108 |
| MMLV-II Q68R/Q79R/L99K/E282D | 2.5 | 20.906 | 0.081 |
| MMLV-II Q68R/Q79R/L99N/E282D | 2.5 | 21.196 | 0.029 |
| MMLV-II Q68I/Q79R/L99R/E282D | 2.5 | 21.369 | 0.009 |
| MMLV-II Q68K/Q79R/L99R/E282D | 2.5 | 20.960 | 0.030 |
| MMLV-II Q68R/Q79H/L99R/E282D | 2.5 | 26.167 | 0.038 |
| MMLV-II Q68R/Q79I/L99R/E282D | 2.5 | 21.012 | 0.056 |
| MMLV-II Q68R/Q79R/L99R/E282M | 2.5 | 21.277 | 0.036 |
| MMLV-II Q68R/Q79R/L99R/E282W | 2.5 | 20.944 | 0.020 |
| MMLV-II I61K/Q68R/Q79R/L99R/E282D | 2.5 | 21.320 | 0.009 |
| MMLV-II I61M/Q68R/Q79R/L99R/E282D | 2.5 | 21.095 | 0.013 |
| MMLV-II Q68I/Q79H/L99K/E282M | 2.5 | 21.329 | 0.047 |
| MMLV-II I61M/Q68I/Q79H/L99K/E282M | 2.5 | 22.159 | 0.031 |
| MMLV-II | 10 | 21.575 | 0.101 |
| MMLV-II L99R/E282D | 10 | 21.546 | 0.041 |
| MMLV-II Q68R/L99R | 10 | 21.343 | 0.021 |

TABLE 13-continued

Two-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II Q79R/L99R | 10 | 21.387 | 0.016 |
| MMLV-II Q68R/Q79R | 10 | 21.147 | 0.032 |
| MMLV-II Q68R/L99R/E282D | 10 | 21.265 | 0.076 |
| MMLV-II Q79R/L99R/E282D | 10 | 21.250 | 0.036 |
| MMLV-II Q68R/Q79R/E282D | 10 | 21.135 | 0.015 |
| MMLV-II Q68R/Q79R/L99R | 10 | 21.051 | 0.036 |
| MMLV-II Q68R/Q79R/L99R/E282D | 10 | 21.159 | 0.065 |
| MMLV-II Q68R/Q79R/L99K/E282D | 10 | 21.056 | 0.032 |
| MMLV-II Q68R/Q79R/L99N/E282D | 10 | 21.180 | 0.052 |
| MMLV-II Q68I/Q79R/L99R/E282D | 10 | 21.068 | 0.069 |
| MMLV-II Q68K/Q79R/L99R/E282D | 10 | 21.065 | 0.053 |
| MMLV-II Q68R/Q79H/L99R/E282D | 10 | 21.683 | 0.075 |
| MMLV-II Q68R/Q79I/L99R/E282D | 10 | 21.152 | 0.064 |
| MMLV-II Q68R/Q79R/L99R/E282M | 10 | 21.029 | 0.055 |
| MMLV-II Q68R/Q79R/L99R/E282W | 10 | 21.214 | 0.052 |
| MMLV-II I61K/Q68R/Q79R/L99R/E282D | 10 | 21.391 | 0.051 |
| MMLV-II I61M/Q68R/Q79R/L99R/E282D | 10 | 21.307 | 0.038 |
| MMLV-II Q68I/Q79H/L99K/E282M | 10 | 21.583 | 0.019 |
| MMLV-II I61M/Q68I/Q79H/L99K/E282M | 10 | 21.759 | 0.029 |

TABLE 14

One-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II | 0.625 | 22.153 | 0.122 |
| MMLV-II L99R/E282D | 0.625 | 21.713 | 0.111 |
| MMLV-II Q68R/L99R | 0.625 | 21.334 | 0.167 |
| MMLV-II Q79R/L99R | 0.625 | 21.398 | 0.069 |
| MMLV-II Q68R/Q79R | 0.625 | 21.546 | 0.096 |
| MMLV-II Q68R/L99R/E282D | 0.625 | 21.112 | 0.149 |
| MMLV-II Q79R/L99R/E282D | 0.625 | 21.260 | 0.104 |
| MMLV-II Q68R/Q79R/E282D | 0.625 | 21.014 | 0.102 |
| MMLV-II Q68R/Q79R/L99R | 0.625 | 20.338 | 0.042 |
| MMLV-II Q68R/Q79R/L99R/E282D | 0.625 | 19.537 | 0.120 |
| MMLV-II Q68R/Q79R/L99K/E282D | 0.625 | 20.516 | 0.131 |
| MMLV-II Q68R/Q79R/L99N/E282D | 0.625 | 20.960 | 0.023 |
| MMLV-II Q68I/Q79R/L99R/E282D | 0.625 | 21.325 | 0.088 |
| MMLV-II Q68K/Q79R/L99R/E282D | 0.625 | 20.602 | 0.038 |
| MMLV-II Q68R/Q79H/L99R/E282D | 0.625 | 23.889 | 0.042 |
| MMLV-II Q68R/Q79I/L99R/E282D | 0.625 | 21.375 | 0.035 |
| MMLV-II Q68R/Q79R/L99R/E282M | 0.625 | 21.805 | 0.054 |
| MMLV-II Q68R/Q79R/L99R/E282W | 0.625 | 20.229 | 0.085 |

TABLE 14-continued

One-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II I61K/Q68R/Q79R/L99R/E282D | 0.625 | 20.972 | 0.037 |
| MMLV-II I61M/Q68R/Q79R/L99R/E282D | 0.625 | 20.225 | 0.042 |
| MMLV-II Q68I/Q79H/L99K/E282M | 0.625 | 20.578 | 0.061 |
| MMLV-II I61M/Q68I/Q79H/L99K/E282M | 0.625 | 21.107 | 0.101 |
| MMLV-II | 2.5 | 20.874 | 0.042 |
| MMLV-II L99R/E282D | 2.5 | 19.679 | 0.047 |
| MMLV-II Q68R/L99R | 2.5 | 19.152 | 0.024 |
| MMLV-II Q79R/L99R | 2.5 | 19.202 | 0.091 |
| MMLV-II Q68R/Q79R | 2.5 | 19.506 | 0.010 |
| MMLV-II Q68R/L99R/E282D | 2.5 | 19.142 | 0.060 |
| MMLV-II Q79R/L99R/E282D | 2.5 | 19.301 | 0.004 |
| MMLV-II Q68R/Q79R/E282D | 2.5 | 19.023 | 0.041 |
| MMLV-II Q68R/Q79R/L99R | 2.5 | 18.312 | 0.041 |
| MMLV-II Q68R/Q79R/L99R/E282D | 2.5 | 17.867 | 0.099 |
| MMLV-II Q68R/Q79R/L99K/E282D | 2.5 | 18.591 | 0.036 |
| MMLV-II Q68R/Q79R/L99N/E282D | 2.5 | 19.123 | 0.097 |
| MMLV-II Q68I/Q79R/L99R/E282D | 2.5 | 19.553 | 0.076 |
| MMLV-II Q68K/Q79R/L99R/E282D | 2.5 | 18.771 | 0.113 |
| MMLV-II Q68R/Q79H/L99R/E282D | 2.5 | 21.911 | 0.048 |
| MMLV-II Q68R/Q79I/L99R/E282D | 2.5 | 19.298 | 0.146 |
| MMLV-II Q68R/Q79R/L99R/E282M | 2.5 | 19.621 | 0.027 |
| MMLV-II Q68R/Q79R/L99R/E282W | 2.5 | 18.219 | 0.103 |
| MMLV-II I61K/Q68R/Q79R/L99R/E282D | 2.5 | 18.846 | 0.056 |
| MMLV-II I61M/Q68R/Q79R/L99R/E282D | 2.5 | 18.500 | 0.042 |
| MMLV-II Q68I/Q79H/L99K/E282M | 2.5 | 18.752 | 0.148 |
| MMLV-II I61M/Q68I/Q79H/L99K/E282M | 2.5 | 19.445 | 0.098 |
| MMLV-II | 10 | 18.239 | 0.025 |
| MMLV-II L99R/E282D | 10 | 17.293 | 0.021 |
| MMLV-II Q68R/L99R | 10 | 17.144 | 0.032 |
| MMLV-II Q79R/L99R | 10 | 17.324 | 0.016 |
| MMLV-II Q68R/Q79R | 10 | 17.123 | 0.072 |
| MMLV-II Q68R/L99R/E282D | 10 | 17.082 | 0.088 |
| MMLV-II Q79R/L99R/E282D | 10 | 17.353 | 0.068 |
| MMLV-II Q68R/Q79R/E282D | 10 | 17.111 | 0.036 |
| MMLV-II Q68R/Q79R/L99R | 10 | 16.562 | 0.101 |
| MMLV-II Q68R/Q79R/L99R/E282D | 10 | 16.492 | 0.066 |
| MMLV-II Q68R/Q79R/L99K/E282D | 10 | 17.027 | 0.054 |
| MMLV-II Q68R/Q79R/L99N/E282D | 10 | 17.335 | 0.080 |
| MMLV-II Q68I/Q79R/L99R/E282D | 10 | 17.726 | 0.055 |
| MMLV-II Q68K/Q79R/L99R/E282D | 10 | 17.144 | 0.140 |
| MMLV-II Q68R/Q79H/L99R/E282D | 10 | 19.772 | 0.064 |
| MMLV-II Q68R/Q79I/L99R/E282D | 10 | 17.424 | 0.020 |
| MMLV-II Q68R/Q79R/L99R/E282M | 10 | 17.624 | 0.014 |
| MMLV-II Q68R/Q79R/L99R/E282W | 10 | 16.629 | 0.080 |
| MMLV-II I61K/Q68R/Q79R/L99R/E282D | 10 | 16.903 | 0.022 |

TABLE 14-continued

One-Step cDNA synthesis by MMLV RT triple and more mutants. Data was generated via qPCR human normalizer assay and data is reported by Ct value.

| MMLV RT Variant | Concentration of RTase (nM) | Ct Mean | Ct Standard Deviation |
|---|---|---|---|
| MMLV-II I61M/Q68R/Q79R/L99R/E282D | 10 | 16.803 | 0.028 |
| MMLV-II Q6I/Q79H/L99K/E282M | 10 | 16.894 | 0.056 |
| MMLV-II I61M/Q68I/Q79H/L99K/E282M | 10 | 17.509 | 0.058 |

e. Evaluation of Ability of Purified MMLV RTase Mutant Variants to Synthesize DNA by Oligo-dT or Random Priming MMLV RTase base construct and MMLV RTase mutant variants evaluated as described in Example 3. Oligo-dT or random hexamer priming conditions were adjusted for the two-step reactions and RTase concentration was normalized to 31 nM. The two-step reactions for MMLV RTase base construct and MMLV RTase mutant variants were analyzed and reported by Ct output from the qPCR (see Tables 15 and 16).

Nine of the seventeen MMLV RTase triple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The nine MMLV RTase mutant variants that were found to exhibit the highest overall activity were Q79R/L99R/E282D, Q68R/Q79R/L99R, Q68R/Q79R/L99R/E282D, Q68R/Q79R/L99K/E282D, Q68R/Q79R/L99N/E282D, Q68K/Q79R/L99R/E282D, Q68R/Q79R/L99R/E282M, I61K/Q68R/Q79R/L99R/E282D and I61M/Q68R/Q79R/L99R/E282D.

TABLE 15

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 42 | 25.165 | 0.057 |
| MMLV-II L99R/E282D | 42 | 25.287 | 0.062 |
| MMLV-II Q68R/L99R | 42 | 25.026 | 0.035 |
| MMLV-II Q79R/L99R | 42 | 24.932 | 0.032 |
| MMLV-II Q68R/Q79R | 42 | 25.002 | 0.076 |
| MMLV-II Q68R/L99R/E282D | 42 | 24.964 | 0.068 |
| MMLV-II Q79R/L99R/E282D | 42 | 24.822 | 0.106 |
| MMLV-II Q68R/Q79R/E282D | 42 | 24.905 | 0.134 |
| MMLV-II Q68R/Q79R/L99R | 42 | 24.673 | 0.131 |
| MMLV-II Q68R/Q79R/L99R/E282D | 42 | 24.523 | 0.111 |
| MMLV-II Q68R/Q79R/L99K/E282D | 42 | 24.677 | 0.076 |
| MMLV-II Q68R/Q79R/L99N/E282D | 42 | 24.635 | 0.087 |
| MMLV-II Q68I/Q79R/L99R/E282D | 42 | 25.010 | 0.074 |
| MMLV-II Q68K/Q79R/L99R/E282D | 42 | 24.676 | 0.066 |
| MMLV-II Q68R/Q79H/L99R/E282D | 42 | 28.929 | 0.021 |
| MMLV-II Q68R/Q79I/L99R/E282D | 42 | 24.932 | 0.039 |

TABLE 15-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99R/E282M | 42 | 24.900 | 0.113 |
| MMLV-II Q68R/Q79R/L99R/E282W | 42 | 24.967 | 0.091 |
| MMLV-II I61K/Q68R/Q79R/L99R/E282D | 42 | 24.597 | 0.076 |
| MMLV-II I61M/Q68R/Q79R/L99R/E282D | 42 | 24.833 | 0.007 |
| MMLV-II Q68I/Q79H/L99K/E282M | 42 | 25.440 | 0.048 |
| MMLV-II I61M/Q68I/Q79H/L99K/E282M | 42 | 25.679 | 0.050 |
| MMLV-II | 55 | 34.223 | 0.406 |
| MMLV-II L99R/E282D | 55 | 34.732 | 3.729 |
| MMLV-II Q68R/L99R | 55 | 31.509 | 0.169 |
| MMLV-II Q79R/L99R | 55 | 31.831 | 0.019 |
| MMLV-II Q68R/Q79R | 55 | 32.633 | 1.094 |
| MMLV-II Q68R/L99R/E282D | 55 | 32.089 | 0.075 |
| MMLV-II Q79R/L99R/E282D | 55 | 32.134 | 0.081 |
| MMLV-II Q68R/Q79R/E282D | 55 | 34.639 | 3.791 |
| MMLV-II Q68R/Q79R/L99R | 55 | 29.559 | 0.029 |
| MMLV-II Q68R/Q79R/L99R/E282D | 55 | 28.013 | 0.136 |
| MMLV-II Q68R/Q79R/L99K/E282D | 55 | 29.712 | 0.090 |
| MMLV-II Q68R/Q79R/L99N/E282D | 55 | 30.442 | 0.224 |
| MMLV-II Q68I/Q79R/L99R/E282D | 55 | 32.857 | 0.378 |
| MMLV-II Q68K/Q79R/L99R/E282D | 55 | 31.186 | 0.630 |
| MMLV-II Q68R/Q79H/L99R/E282D | 55 | 37.338 | 1.882 |
| MMLV-II Q68R/Q79I/L99R/E282D | 55 | 31.830 | 0.120 |
| MMLV-II Q68R/Q79R/L99R/E282M | 55 | 31.682 | 0.181 |
| MMLV-II Q68R/Q79R/L99R/E282W | 55 | 32.256 | 0.228 |
| MMLV-II I61K/Q68R/Q79R/L99R/E282D | 55 | 30.362 | 0.129 |
| MMLV-II I61M/Q68R/Q79R/L99R/E282D | 55 | 31.473 | 0.070 |
| MMLV-II Q68I/Q79H/L99K/E282M | 55 | 32.892 | 0.286 |
| MMLV-II I61M/Q68I/Q79H/L99K/E282M | 55 | 33.872 | 0.131 |

TABLE 16

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 42 | 24.675 | 0.054 |
| MMLV-II L99R/E282D | 42 | 24.864 | 0.043 |
| MMLV-II Q68R/L99R | 42 | 24.577 | 0.066 |
| MMLV-II Q79R/L99R | 42 | 24.630 | 0.103 |
| MMLV-II Q68R/Q79R | 42 | 24.496 | 0.050 |
| MMLV-II Q68R/L99R/E282D | 42 | 24.549 | 0.059 |
| MMLV-II Q79R/L99R/E282D | 42 | 24.625 | 0.013 |
| MMLV-II Q68R/Q79R/E282D | 42 | 24.623 | 0.083 |
| MMLV-II Q68R/Q79R/L99R | 42 | 24.494 | 0.070 |
| MMLV-II Q68R/Q79R/L99R/E282D | 42 | 24.422 | 0.035 |
| MMLV-II Q68R/Q79R/L99K/E282D | 42 | 24.517 | 0.066 |

TABLE 16-continued

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99N/E282D | 42 | 24.324 | 0.059 |
| MMLV-II Q68I/Q79R/L99R/E282D | 42 | 24.488 | 0.070 |
| MMLV-II Q68K/Q79R/L99R/E282D | 42 | 24.501 | 0.041 |
| MMLV-II Q68R/Q79H/L99R/E282D | 42 | 26.574 | 0.029 |
| MMLV-II Q68R/Q79I/L99R/E282D | 42 | 24.496 | 0.055 |
| MMLV-II Q68R/Q79R/L99R/E282M | 42 | 24.382 | 0.043 |
| MMLV-II Q68R/Q79R/L99R/E282W | 42 | 24.617 | 0.109 |
| MMLV-II I61K/Q68R/Q79R/L99R/E282D | 42 | 24.391 | 0.045 |
| MMLV-II I61M/Q68R/Q79R/L99R/E282D | 42 | 24.426 | 0.028 |
| MMLV-II Q68I/Q79H/L99K/E282M | 42 | 24.660 | 0.027 |
| MMLV-II I61M/Q68I/Q79H/L99K/E282M | 42 | 24.949 | 0.052 |
| MMLV-II | 55 | 32.082 | 0.095 |
| MMLV-II L99R/E282D | 55 | 31.612 | 0.190 |
| MMLV-II Q68R/L99R | 55 | 30.349 | 0.041 |
| MMLV-II Q79R/L99R | 55 | 30.494 | 0.094 |
| MMLV-II Q68R/Q79R | 55 | 29.735 | 0.153 |
| MMLV-II Q68R/L99R/E282D | 55 | 30.724 | 0.045 |
| MMLV-II Q79R/L99R/E282D | 55 | 30.774 | 0.152 |
| MMLV-II Q68R/Q79R/E282D | 55 | 30.232 | 0.079 |
| MMLV-II Q68R/Q79R/L99R | 55 | 28.270 | 0.340 |
| MMLV-II Q68R/Q79R/L99R/E282D | 55 | 26.673 | 0.143 |
| MMLV-II Q68R/Q79R/L99K/E282D | 55 | 28.258 | 0.018 |
| MMLV-II Q68R/Q79R/L99N/E282D | 55 | 28.973 | 0.116 |
| MMLV-II Q68I/Q79R/L99R/E282D | 55 | 31.617 | 0.071 |
| MMLV-II Q68K/Q79R/L99R/E282D | 55 | 28.994 | 0.110 |
| MMLV-II Q68R/Q79H/L99R/E282D | 55 | 35.664 | 0.695 |
| MMLV-II Q68R/Q79I/L99R/E282D | 55 | 30.265 | 0.116 |
| MMLV-II Q68R/Q79R/L99R/E282M | 55 | 29.765 | 0.059 |
| MMLV-II Q68R/Q79R/L99R/E282W | 55 | 30.535 | 0.424 |
| MMLV-II I61K/Q68R/Q79R/L99R/E282D | 55 | 28.878 | 0.038 |
| MMLV-II I61M/Q68R/Q79R/L99R/E282D | 55 | 29.778 | 0.081 |
| MMLV-II Q68I/Q79H/L99K/E282M | 55 | 31.836 | 0.222 |
| MMLV-II I61M/Q68I/Q79H/L99K/E282M | 55 | 31.984 | 0.223 |

f. Evaluation of Ability of Purified MMLV RTase Mutant Variants to Synthesize DNA Over a Wide Range of Temperatures MMLV RTase base construct and MMLV RTase mutant variants evaluated as described in Example 3. Oligo-dT or random hexamer priming conditions and reaction temperatures were adjusted for the two-step reactions and RTase concentration was normalized to 31 nM. The two-step reactions for MMLV RTase base construct and MMLV RTase mutant variants were analyzed and reported by Ct output from the qPCR (see Tables 17 and 18).

Six of the nine MMLV RTase triple or more mutant variants were found to exhibit high overall activity as compared to the other MMLV RTase stacked mutant variants over a wide range of temperatures, spanning from 37.0 to 65° C., regardless of which priming method used. All of the MMLV RTase stacked mutant variants exhibited increased overall activity and thermostability as compared to the MMLV RTase base construct. The six MMLV RTase mutant variants that were found to exhibit the highest overall activity at a wide range of temperatures were Q68R/Q79R/L99R, Q68R/Q79R/L99R/E282D, Q68R/Q79R/L99K/E282D, Q68R/Q79R/L99N/E282D, I61K/Q68R/Q79R/L99R/E282D and I61M/Q68R/Q79R/L99R/E282D.

TABLE 17

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 37.0 | 26.593 | 0.020 |
| MMLV-II Q79R/L99R/E282D | 37.0 | 25.713 | 0.024 |
| MMLV-II Q68R/Q79R/L99R | 37.0 | 25.164 | 0.059 |
| MMLV-II Q68R/Q79R/L99R/E282D | 37.0 | 25.163 | 0.035 |
| MMLV-II Q68R/Q79R/L99K/E282D | 37.0 | 25.135 | 0.078 |
| MMLV-II Q68R/Q79R/L99N/E282D | 37.0 | 25.693 | 0.048 |
| MMLV-II Q68K/Q79R/L99R/E282D | 37.0 | 25.491 | 0.062 |
| MMLV-II Q68R/Q79R/L99R/E282M | 37.0 | 25.450 | 0.083 |
| MMLV-II I61K/Q68R/Q79R/L99R/E282D | 37.0 | 25.094 | 0.071 |
| MMLV-II I61M/Q68R/Q79R/L99R/E282D | 37.0 | 25.356 | 0.034 |
| MMLV-II | 37.8 | 26.623 | 0.062 |
| MMLV-II Q79R/L99R/E282D | 37.8 | 25.516 | 0.078 |
| MMLV-II Q68R/Q79R/L99R | 37.8 | 25.251 | 0.094 |
| MMLV-II Q68R/Q79R/L99R/E282D | 37.8 | 24.987 | 0.050 |
| MMLV-II Q68R/Q79R/L99K/E282D | 37.8 | 25.093 | 0.084 |
| MMLV-II Q68R/Q79R/L99N/E282D | 37.8 | 25.273 | 0.095 |
| MMLV-II Q68K/Q79R/L99R/E282D | 37.8 | 25.310 | 0.079 |
| MMLV-II Q68R/Q79R/L99R/E282M | 37.8 | 25.545 | 0.044 |
| MMLV-II I61K/Q68R/Q79R/L99R/E282D | 37.8 | 25.144 | 0.196 |
| MMLV-II I61M/Q68R/Q79R/L99R/E282D | 37.8 | 25.302 | 0.035 |
| MMLV-II | 39.5 | 26.430 | 0.074 |
| MMLV-II Q79R/L99R/E282D | 39.5 | 25.067 | 0.026 |
| MMLV-II Q68R/Q79R/L99R | 39.5 | 25.138 | 0.050 |
| MMLV-II Q68R/Q79R/L99R/E282D | 39.5 | 24.788 | 0.022 |
| MMLV-II Q68R/Q79R/L99K/E282D | 39.5 | 24.842 | 0.071 |
| MMLV-II Q68R/Q79R/L99N/E282D | 39.5 | 24.892 | 0.042 |
| MMLV-II Q68K/Q79R/L99R/E282D | 39.5 | 25.047 | 0.038 |
| MMLV-II Q68R/Q79R/L99R/E282M | 39.5 | 25.249 | 0.081 |
| MMLV-II I61K/Q68R/Q79R/L99R/E282D | 39.5 | 24.845 | 0.130 |
| MMLV-II I61M/Q68R/Q79R/L99R/E282D | 39.5 | 25.130 | 0.072 |
| MMLV-II | 42.0 | 25.485 | 0.052 |
| MMLV-II Q79R/L99R/E282D | 42.0 | 24.941 | 0.024 |
| MMLV-II Q68R/Q79R/L99R | 42.0 | 24.848 | 0.101 |
| MMLV-II Q68R/Q79R/L99R/E282D | 42.0 | 24.802 | 0.009 |
| MMLV-II Q68R/Q79R/L99K/E282D | 42.0 | 24.805 | 0.008 |

TABLE 17-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99N/E282D | 42.0 | 24.744 | 0.076 |
| MMLV-II Q68K/Q79R/L99R/E282D | 42.0 | 24.893 | 0.073 |
| MMLV-II Q68R/Q79R/L99R/E282M | 42.0 | 24.968 | 0.031 |
| MMLV-II I61K/Q68R/Q79R/L99R/E282D | 42.0 | 24.933 | 0.088 |
| MMLV-II I61M/Q68R/Q79R/L99R/E282D | 42.0 | 24.821 | 0.045 |
| MMLV-II | 45.2 | 25.776 | 0.028 |
| MMLV-II Q79R/L99R/E282D | 45.2 | 24.902 | 0.034 |
| MMLV-II Q68R/Q79R/L99R | 45.2 | 24.792 | 0.055 |
| MMLV-II Q68R/Q79R/L99R/E282D | 45.2 | 24.705 | 0.092 |
| MMLV-II Q68R/Q79R/L99K/E282D | 45.2 | 24.791 | 0.009 |
| MMLV-II Q68R/Q79R/L99N/E282D | 45.2 | 24.890 | 0.071 |
| MMLV-II Q68K/Q79R/L99R/E282D | 45.2 | 25.420 | 0.101 |
| MMLV-II Q68R/Q79R/L99R/E282M | 45.2 | 25.196 | 0.086 |
| MMLV-II I61K/Q68R/Q79R/L99R/E282D | 45.2 | 24.823 | 0.079 |
| MMLV-II I61M/Q68R/Q79R/L99R/E282D | 45.2 | 24.720 | 0.006 |
| MMLV-II | 47.8 | 27.932 | 0.049 |
| MMLV-II Q79R/L99R/E282D | 47.8 | 24.858 | 0.063 |
| MMLV-II Q68R/Q79R/L99R | 47.8 | 24.685 | 0.095 |
| MMLV-II Q68R/Q79R/L99R/E282D | 47.8 | 24.689 | 0.067 |
| MMLV-II Q68R/Q79R/L99K/E282D | 47.8 | 24.620 | 0.072 |
| MMLV-II Q68R/Q79R/L99N/E282D | 47.8 | 24.780 | 0.039 |
| MMLV-II Q68K/Q79R/L99R/E282D | 47.8 | 24.855 | 0.018 |
| MMLV-II Q68R/Q79R/L99R/E282M | 47.8 | 24.961 | 0.040 |
| MMLV-II I61K/Q68R/Q79R/L99R/E282D | 47.8 | 24.681 | 0.076 |
| MMLV-II I61M/Q68R/Q79R/L99R/E282D | 47.8 | 24.759 | 0.055 |
| MMLV-II | 49.2 | 30.393 | 0.118 |
| MMLV-II Q79R/L99R/E282D | 49.2 | 24.974 | 0.090 |
| MMLV-II Q68R/Q79R/L99R | 49.2 | 24.794 | 0.056 |
| MMLV-II Q68R/Q79R/L99R/E282D | 49.2 | 24.720 | 0.100 |
| MMLV-II Q68R/Q79R/L99K/E282D | 49.2 | 25.007 | 0.096 |
| MMLV-II Q68R/Q79R/L99N/E282D | 49.2 | 25.304 | 0.147 |
| MMLV-II Q68K/Q79R/L99R/E282D | 49.2 | 25.273 | 0.066 |
| MMLV-II Q68R/Q79R/L99R/E282M | 49.2 | 25.560 | 0.019 |
| MMLV-II I61K/Q68R/Q79R/L99R/E282D | 49.2 | 24.719 | 0.177 |
| MMLV-II I61M/Q68R/Q79R/L99R/E282D | 49.2 | 25.123 | 0.034 |
| MMLV-II | 50.0 | 30.870 | 0.210 |
| MMLV-II Q79R/L99R/E282D | 50.0 | 26.677 | 0.090 |
| MMLV-II Q68R/Q79R/L99R | 50.0 | 25.381 | 0.049 |
| MMLV-II Q68R/Q79R/L99R/E282D | 50.0 | 24.820 | 0.064 |
| MMLV-II Q68R/Q79R/L99K/E282D | 50.0 | 25.348 | 0.098 |
| MMLV-II Q68R/Q79R/L99N/E282D | 50.0 | 25.287 | 0.064 |
| MMLV-II Q68K/Q79R/L99R/E282D | 50.0 | 25.208 | 0.085 |
| MMLV-II Q68R/Q79R/L99R/E282M | 50.0 | 25.790 | 0.051 |
| MMLV-II I61K/Q68R/Q79R/L99R/E282D | 50.0 | 24.840 | 0.071 |
| MMLV-II I61M/Q68R/Q79R/L99R/E282D | 50.0 | 25.317 | 0.042 |
| MMLV-II | 51.0 | 27.914 | 0.002 |
| MMLV-II Q79R/L99R/E282D | 51.0 | 25.561 | 0.069 |
| MMLV-II Q68R/Q79R/L99R | 51.0 | 25.225 | 0.069 |
| MMLV-II Q68R/Q79R/L99R/E282D | 51.0 | 24.726 | 0.034 |
| MMLV-II Q68R/Q79R/L99K/E282D | 51.0 | 25.324 | 0.071 |
| MMLV-II Q68R/Q79R/L99N/E282D | 51.0 | 25.157 | 0.062 |
| MMLV-II Q68K/Q79R/L99R/E282D | 51.0 | 25.275 | 0.039 |
| MMLV-II Q68R/Q79R/L99R/E282M | 51.0 | 25.938 | 0.095 |
| MMLV-II I61K/Q68R/Q79R/L99R/E282D | 51.0 | 25.821 | 0.072 |
| MMLV-II I61M/Q68R/Q79R/L99R/E282D | 51.0 | 25.053 | 0.044 |
| MMLV-II | 51.9 | 28.602 | 0.059 |
| MMLV-II Q79R/L99R/E282D | 51.9 | 25.975 | 0.024 |
| MMLV-II Q68R/Q79R/L99R | 51.9 | 25.256 | 0.075 |
| MMLV-II Q68R/Q79R/L99R/E282D | 51.9 | 24.903 | 0.050 |
| MMLV-II Q68R/Q79R/L99K/E282D | 51.9 | 25.163 | 0.169 |
| MMLV-II Q68R/Q79R/L99N/E282D | 51.9 | 25.272 | 0.011 |
| MMLV-II Q68K/Q79R/L99R/E282D | 51.9 | 25.491 | 0.075 |
| MMLV-II Q68R/Q79R/L99R/E282M | 51.9 | 25.878 | 0.038 |
| MMLV-II I61K/Q68R/Q79R/L99R/E282D | 51.9 | 26.071 | 0.044 |
| MMLV-II I61M/Q68R/Q79R/L99R/E282D | 51.9 | 25.419 | 0.067 |
| MMLV-II | 53.8 | 26.412 | 0.082 |
| MMLV-II Q79R/L99R/E282D | 53.8 | 25.558 | 0.063 |
| MMLV-II Q68R/Q79R/L99R | 53.8 | 24.969 | 0.065 |
| MMLV-II Q68R/Q79R/L99R/E282D | 53.8 | 25.356 | 0.063 |
| MMLV-II Q68R/Q79R/L99K/E282D | 53.8 | 25.460 | 0.056 |
| MMLV-II Q68R/Q79R/L99N/E282D | 53.8 | 25.769 | 0.118 |
| MMLV-II Q68K/Q79R/L99R/E282D | 53.8 | 26.251 | 0.103 |
| MMLV-II Q68R/Q79R/L99R/E282M | 53.8 | 26.310 | 0.174 |
| MMLV-II I61K/Q68R/Q79R/L99R/E282D | 53.8 | 25.701 | 0.106 |
| MMLV-II I61M/Q68R/Q79R/L99R/E282D | 53.8 | 26.412 | 0.082 |
| MMLV-II | 56.5 | 29.343 | 0.085 |
| MMLV-II Q79R/L99R/E282D | 56.5 | 26.885 | 0.083 |
| MMLV-II Q68R/Q79R/L99R | 56.5 | 25.736 | 0.015 |
| MMLV-II Q68R/Q79R/L99R/E282D | 56.5 | 25.223 | 0.016 |
| MMLV-II Q68R/Q79R/L99K/E282D | 56.5 | 25.900 | 0.039 |
| MMLV-II Q68R/Q79R/L99N/E282D | 56.5 | 25.930 | 0.031 |
| MMLV-II Q68K/Q79R/L99R/E282D | 56.5 | 25.869 | 0.204 |
| MMLV-II Q68R/Q79R/L99R/E282M | 56.5 | 26.622 | 0.067 |
| MMLV-II I61K/Q68R/Q79R/L99R/E282D | 56.5 | 25.817 | 0.089 |

TABLE 17-continued

Two-Step cDNA synthesis by MMLV RT triple and more mutants by Oligo-dT priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II I61M/Q68R/Q79R/L99R/E282D | 56.5 | 26.290 | 0.009 |
| MMLV-II | 59.9 | 29.693 | 0.047 |
| MMLV-II Q79R/L99R/E282D | 59.9 | 27.820 | 0.014 |
| MMLV-II Q68R/Q79R/L99R | 59.9 | 26.069 | 0.057 |
| MMLV-II Q68R/Q79R/L99R/E282D | 59.9 | 25.374 | 0.061 |
| MMLV-II Q68R/Q79R/L99K/E282D | 59.9 | 26.066 | 0.053 |
| MMLV-II Q68R/Q79R/L99N/E282D | 59.9 | 25.873 | 0.018 |
| MMLV-II Q68K/Q79R/L99R/E282D | 59.9 | 26.278 | 0.073 |
| MMLV-II Q68R/Q79R/L99R/E282M | 59.9 | 27.068 | 0.075 |
| MMLV-II I61K/Q68R/Q79R/L99R/E282D | 59.9 | 26.863 | 0.025 |
| MMLV-II I61M/Q68R/Q79R/L99R/E282D | 59.9 | 26.176 | 0.072 |
| MMLV-II | 62.6 | 29.731 | 0.092 |
| MMLV-II Q79R/L99R/E282D | 62.6 | 27.161 | 0.035 |
| MMLV-II Q68R/Q79R/L99R | 62.6 | 25.929 | 0.026 |
| MMLV-II Q68R/Q79R/L99R/E282D | 62.6 | 25.303 | 0.074 |
| MMLV-II Q68R/Q79R/L99K/E282D | 62.6 | 25.907 | 0.003 |
| MMLV-II Q68R/Q79R/L99N/E282D | 62.6 | 26.145 | 0.053 |
| MMLV-II Q68K/Q79R/L99R/E282D | 62.6 | 26.181 | 0.056 |
| MMLV-II Q68R/Q79R/L99R/E282M | 62.6 | 27.134 | 0.015 |
| MMLV-II I61K/Q68R/Q79R/L99R/E282D | 62.6 | 26.025 | 0.178 |
| MMLV-II I61M/Q68R/Q79R/L99R/E282D | 62.6 | 26.304 | 0.041 |
| MMLV-II | 64.2 | 26.809 | 0.080 |
| MMLV-II Q79R/L99R/E282D | 64.2 | 27.325 | 0.038 |
| MMLV-II Q68R/Q79R/L99R | 64.2 | 26.131 | 0.018 |
| MMLV-II Q68R/Q79R/L99R/E282D | 64.2 | 25.542 | 0.135 |
| MMLV-II Q68R/Q79R/L99K/E282D | 64.2 | 26.408 | 0.093 |
| MMLV-II Q68R/Q79R/L99N/E282D | 64.2 | 26.734 | 0.040 |
| MMLV-II Q68K/Q79R/L99R/E282D | 64.2 | 30.589 | 0.128 |
| MMLV-II Q68R/Q79R/L99R/E282M | 64.2 | 26.262 | 0.090 |
| MMLV-II I61K/Q68R/Q79R/L99R/E282D | 64.2 | 27.594 | 0.118 |
| MMLV-II I61M/Q68R/Q79R/L99R/E282D | 64.2 | 27.062 | 0.051 |
| MMLV-II | 65.0 | 30.277 | 0.050 |
| MMLV-II Q79R/L99R/E282D | 65.0 | 27.119 | 0.065 |
| MMLV-II Q68R/Q79R/L99R | 65.0 | 26.078 | 0.025 |
| MMLV-II Q68R/Q79R/L99R/E282D | 65.0 | 25.583 | 0.068 |
| MMLV-II Q68R/Q79R/L99K/E282D | 65.0 | 25.906 | 0.080 |
| MMLV-II Q68R/Q79R/L99N/E282D | 65.0 | 26.943 | 0.058 |
| MMLV-II Q68K/Q79R/L99R/E282D | 65.0 | 26.413 | 0.067 |
| MMLV-II Q68R/Q79R/L99R/E282M | 65.0 | 28.233 | 0.075 |
| MMLV-II I61K/Q68R/Q79R/L99R/E282D | 65.0 | 25.778 | 0.129 |
| MMLV-II I61M/Q68R/Q79R/L99R/E282D | 65.0 | 27.345 | 0.015 |

TABLE 18

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II | 37.0 | 25.827 | 0.120 |
| MMLV-II Q79R/L99R/E282D | 37.0 | 25.616 | 0.094 |
| MMLV-II Q68R/Q79R/L99R | 37.0 | 24.747 | 0.041 |
| MMLV-II Q68R/Q79R/L99R/E282D | 37.0 | 24.595 | 0.034 |
| MMLV-II Q68R/Q79R/L99K/E282D | 37.0 | 24.917 | 0.078 |
| MMLV-II Q68R/Q79R/L99N/E282D | 37.0 | 24.817 | 0.024 |
| MMLV-II Q68K/Q79R/L99R/E282D | 37.0 | 24.757 | 0.032 |
| MMLV-II Q68R/Q79R/L99R/E282M | 37.0 | 24.754 | 0.062 |
| MMLV-II I61K/Q68R/Q79R/L99R/E282D | 37.0 | 24.883 | 0.106 |
| MMLV-II I61M/Q68R/Q79R/L99R/E282D | 37.0 | 24.776 | 0.028 |
| MMLV-II | 37.8 | 25.609 | 0.038 |
| MMLV-II Q79R/L99R/E282D | 37.8 | 25.300 | 0.061 |
| MMLV-II Q68R/Q79R/L99R | 37.8 | 24.822 | 0.037 |
| MMLV-II Q68R/Q79R/L99R/E282D | 37.8 | 24.690 | 0.044 |
| MMLV-II Q68R/Q79R/L99K/E282D | 37.8 | 24.884 | 0.033 |
| MMLV-II Q68R/Q79R/L99N/E282D | 37.8 | 24.665 | 0.022 |
| MMLV-II Q68K/Q79R/L99R/E282D | 37.8 | 24.846 | 0.021 |
| MMLV-II Q68R/Q79R/L99R/E282M | 37.8 | 24.882 | 0.043 |
| MMLV-II I61K/Q68R/Q79R/L99R/E282D | 37.8 | 24.846 | 0.059 |
| MMLV-II I61M/Q68R/Q79R/L99R/E282D | 37.8 | 24.723 | 0.023 |
| MMLV-II | 39.5 | 25.455 | 0.020 |
| MMLV-II Q79R/L99R/E282D | 39.5 | 24.790 | 0.109 |
| MMLV-II Q68R/Q79R/L99R | 39.5 | 24.712 | 0.050 |
| MMLV-II Q68R/Q79R/L99R/E282D | 39.5 | 24.543 | 0.005 |
| MMLV-II Q68R/Q79R/L99K/E282D | 39.5 | 24.714 | 0.035 |
| MMLV-II Q68R/Q79R/L99N/E282D | 39.5 | 24.520 | 0.084 |
| MMLV-II Q68K/Q79R/L99R/E282D | 39.5 | 24.752 | 0.047 |
| MMLV-II Q68R/Q79R/L99R/E282M | 39.5 | 24.850 | 0.054 |
| MMLV-II I61K/Q68R/Q79R/L99R/E282D | 39.5 | 24.698 | 0.059 |
| MMLV-II I61M/Q68R/Q79R/L99R/E282D | 39.5 | 24.682 | 0.024 |
| MMLV-II | 42.0 | 25.136 | 0.034 |
| MMLV-II Q79R/L99R/E282D | 42.0 | 24.760 | 0.052 |
| MMLV-II Q68R/Q79R/L99R | 42.0 | 24.637 | 0.037 |
| MMLV-II Q68R/Q79R/L99R/E282D | 42.0 | 24.449 | 0.008 |
| MMLV-II Q68R/Q79R/L99K/E282D | 42.0 | 24.650 | 0.068 |
| MMLV-II Q68R/Q79R/L99N/E282D | 42.0 | 24.477 | 0.055 |
| MMLV-II Q68K/Q79R/L99R/E282D | 42.0 | 24.624 | 0.029 |
| MMLV-II Q68R/Q79R/L99R/E282M | 42.0 | 24.627 | 0.044 |
| MMLV-II I61K/Q68R/Q79R/L99R/E282D | 42.0 | 24.718 | 0.083 |
| MMLV-II I61M/Q68R/Q79R/L99R/E282D | 42.0 | 24.532 | 0.021 |
| MMLV-II | 45.2 | 25.079 | 0.017 |
| MMLV-II Q79R/L99R/E282D | 45.2 | 24.624 | 0.026 |
| MMLV-II Q68R/Q79R/L99R | 45.2 | 24.525 | 0.021 |
| MMLV-II Q68R/Q79R/L99R/E282D | 45.2 | 24.430 | 0.014 |

TABLE 18-continued

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68R/Q79R/L99K/E282D | 45.2 | 24.525 | 0.037 |
| MMLV-II Q68R/Q79R/L99N/E282D | 45.2 | 34.853 | 0.705 |
| MMLV-II Q68K/Q79R/L99R/E282D | 45.2 | 24.653 | 0.055 |
| MMLV-II Q68R/Q79R/L99R/E282M | 45.2 | 24.552 | 0.060 |
| MMLV-II I61K/Q68R/Q79R/L99R/E282D | 45.2 | 24.595 | 0.027 |
| MMLV-II I61M/Q68R/Q79R/L99R/E282D | 45.2 | 24.493 | 0.016 |
| MMLV-II | 47.8 | 25.346 | 0.007 |
| MMLV-II Q79R/L99R/E282D | 47.8 | 24.521 | 0.097 |
| MMLV-II Q68R/Q79R/L99R | 47.8 | 24.605 | 0.018 |
| MMLV-II Q68R/Q79R/L99R/E282D | 47.8 | 24.333 | 0.107 |
| MMLV-II Q68R/Q79R/L99K/E282D | 47.8 | 24.516 | 0.043 |
| MMLV-II Q68R/Q79R/L99N/E282D | 47.8 | 24.527 | 0.026 |
| MMLV-II Q68K/Q79R/L99R/E282D | 47.8 | 24.539 | 0.064 |
| MMLV-II Q68R/Q79R/L99R/E282M | 47.8 | 24.631 | 0.019 |
| MMLV-II I61K/Q68R/Q79R/L99R/E282D | 47.8 | 24.227 | 0.260 |
| MMLV-II I61M/Q68R/Q79R/L99R/E282D | 47.8 | 24.441 | 0.030 |
| MMLV-II | 49.2 | 25.791 | 0.064 |
| MMLV-II Q79R/L99R/E282D | 49.2 | 24.700 | 0.033 |
| MMLV-II Q68R/Q79R/L99R | 49.2 | 24.658 | 0.008 |
| MMLV-II Q68R/Q79R/L99R/E282D | 49.2 | 24.471 | 0.069 |
| MMLV-II Q68R/Q79R/L99K/E282D | 49.2 | 24.590 | 0.024 |
| MMLV-II Q68R/Q79R/L99N/E282D | 49.2 | 24.482 | 0.099 |
| MMLV-II Q68K/Q79R/L99R/E282D | 49.2 | 24.549 | 0.028 |
| MMLV-II Q68R/Q79R/L99R/E282M | 49.2 | 24.753 | 0.030 |
| MMLV-II I61K/Q68R/Q79R/L99R/E282D | 49.2 | 24.499 | 0.157 |
| MMLV-II I61M/Q68R/Q79R/L99R/E282D | 49.2 | 24.559 | 0.033 |
| MMLV-II | 50.0 | 26.267 | 0.025 |
| MMLV-II Q79R/L99R/E282D | 50.0 | 24.729 | 0.047 |
| MMLV-II Q68R/Q79R/L99R | 50.0 | 24.462 | 0.040 |
| MMLV-II Q68R/Q79R/L99R/E282D | 50.0 | 24.412 | 0.035 |
| MMLV-II Q68R/Q79R/L99K/E282D | 50.0 | 24.438 | 0.090 |
| MMLV-II Q68R/Q79R/L99N/E282D | 50.0 | 24.509 | 0.050 |
| MMLV-II Q68K/Q79R/L99R/E282D | 50.0 | 24.405 | 0.059 |
| MMLV-II Q68R/Q79R/L99R/E282M | 50.0 | 24.547 | 0.041 |
| MMLV-II I61K/Q68R/Q79R/L99R/E282D | 50.0 | 24.504 | 0.005 |
| MMLV-II I61M/Q68R/Q79R/L99R/E282D | 50.0 | 24.481 | 0.009 |
| MMLV-II | 51.0 | 27.277 | 0.058 |
| MMLV-II Q79R/L99R/E282D | 51.0 | 25.694 | 0.104 |
| MMLV-II Q68R/Q79R/L99R | 51.0 | 24.579 | 0.037 |
| MMLV-II Q68R/Q79R/L99R/E282D | 51.0 | 24.364 | 0.019 |
| MMLV-II Q68R/Q79R/L99K/E282D | 51.0 | 24.849 | 0.041 |
| MMLV-II Q68R/Q79R/L99N/E282D | 51.0 | 24.899 | 0.121 |

TABLE 18-continued

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II Q68K/Q79R/L99R/E282D | 51.0 | 24.980 | 0.048 |
| MMLV-II Q68R/Q79R/L99R/E282M | 51.0 | 25.292 | 0.065 |
| MMLV-II I61K/Q68R/Q79R/L99R/E282D | 51.0 | 25.147 | 0.100 |
| MMLV-II I61M/Q68R/Q79R/L99R/E282D | 51.0 | 25.034 | 0.075 |
| MMLV-II | 51.9 | 28.797 | 0.055 |
| MMLV-II Q79R/L99R/E282D | 51.9 | 26.585 | 0.011 |
| MMLV-II Q68R/Q79R/L99R | 51.9 | 25.021 | 0.036 |
| MMLV-II Q68R/Q79R/L99R/E282D | 51.9 | 24.763 | 0.028 |
| MMLV-II Q68R/Q79R/L99K/E282D | 51.9 | 25.392 | 0.012 |
| MMLV-II Q68R/Q79R/L99N/E282D | 51.9 | 25.543 | 0.087 |
| MMLV-II Q68K/Q79R/L99R/E282D | 51.9 | 25.549 | 0.058 |
| MMLV-II Q68R/Q79R/L99R/E282M | 51.9 | 26.025 | 0.065 |
| MMLV-II I61K/Q68R/Q79R/L99R/E282D | 51.9 | 26.087 | 0.024 |
| MMLV-II I61M/Q68R/Q79R/L99R/E282D | 51.9 | 25.756 | 0.054 |
| MMLV-II | 53.8 | 30.985 | 0.073 |
| MMLV-II Q79R/L99R/E282D | 53.8 | 29.356 | 0.044 |
| MMLV-II Q68R/Q79R/L99R | 53.8 | 26.370 | 0.041 |
| MMLV-II Q68R/Q79R/L99R/E282D | 53.8 | 25.580 | 0.049 |
| MMLV-II Q68R/Q79R/L99K/E282D | 53.8 | 26.682 | 0.029 |
| MMLV-II Q68R/Q79R/L99N/E282D | 53.8 | 26.438 | 0.031 |
| MMLV-II Q68K/Q79R/L99R/E282D | 53.8 | 27.024 | 0.042 |
| MMLV-II Q68R/Q79R/L99R/E282M | 53.8 | 28.314 | 0.051 |
| MMLV-II I61K/Q68R/Q79R/L99R/E282D | 53.8 | 27.489 | 0.025 |
| MMLV-II I61M/Q68R/Q79R/L99R/E282D | 53.8 | 27.871 | 0.118 |
| MMLV-II | 56.5 | 33.313 | 0.164 |
| MMLV-II Q79R/L99R/E282D | 56.5 | 32.626 | 0.113 |
| MMLV-II Q68R/Q79R/L99R | 56.5 | 30.047 | 0.089 |
| MMLV-II Q68R/Q79R/L99R/E282D | 56.5 | 29.183 | 0.155 |
| MMLV-II Q68R/Q79R/L99K/E282D | 56.5 | 30.750 | 0.051 |
| MMLV-II Q68R/Q79R/L99N/E282D | 56.5 | 30.403 | 0.095 |
| MMLV-II Q68K/Q79R/L99R/E282D | 56.5 | 31.707 | 0.111 |
| MMLV-II Q68R/Q79R/L99R/E282M | 56.5 | 31.878 | 0.093 |
| MMLV-II I61K/Q68R/Q79R/L99R/E282D | 56.5 | 32.235 | 0.291 |
| MMLV-II I61M/Q68R/Q79R/L99R/E282D | 56.5 | 32.395 | 0.105 |
| MMLV-II | 59.9 | 34.408 | 0.498 |
| MMLV-II Q79R/L99R/E282D | 59.9 | 36.798 | 2.131 |
| MMLV-II Q68R/Q79R/L99R | 59.9 | 33.997 | 0.035 |
| MMLV-II Q68R/Q79R/L99R/E282D | 59.9 | 32.009 | 0.051 |
| MMLV-II Q68R/Q79R/L99K/E282D | 59.9 | 33.685 | 0.317 |
| MMLV-II Q68R/Q79R/L99N/E282D | 59.9 | 33.083 | 0.163 |
| MMLV-II Q68K/Q79R/L99R/E282D | 59.9 | 34.160 | 0.066 |
| MMLV-II Q68R/Q79R/L99R/E282M | 59.9 | 33.650 | 0.161 |

TABLE 18-continued

Two-Step cDNA synthesis by MMLV RT triple and more mutants by random hexamer priming. Data was generated via qPCR human normalizer assay and data is reported by Ct value.

| MMLV RT Variant | Temperature of Reaction (° C.) | Ct Mean | Ct Standard Deviation |
|---|---|---|---|
| MMLV-II I61K/Q68R/Q79R/L99R/E282D | 59.9 | 33.341 | 0.096 |
| MMLV-II I61M/Q68R/Q79R/L99R/E282D | 59.9 | 34.439 | 0.222 |
| MMLV-II | 62.6 | 35.163 | 0.447 |
| MMLV-II Q79R/L99R/E282D | 62.6 | 37.138 | 1.603 |
| MMLV-II Q68R/Q79R/L99R | 62.6 | 34.108 | 0.604 |
| MMLV-II Q68R/Q79R/L99R/E282D | 62.6 | 32.539 | 0.060 |
| MMLV-II Q68R/Q79R/L99K/E282D | 62.6 | 34.175 | 0.421 |
| MMLV-II Q68R/Q79R/L99N/E282D | 62.6 | 33.726 | 0.622 |
| MMLV-II Q68K/Q79R/L99R/E282D | 62.6 | 34.376 | 0.408 |
| MMLV-II Q68R/Q79R/L99R/E282M | 62.6 | 33.792 | 0.231 |
| MMLV-II I61K/Q68R/Q79R/L99R/E282D | 62.6 | 33.768 | 0.387 |
| MMLV-II I61M/Q68R/Q79R/L99R/E282D | 62.6 | 34.428 | 0.085 |
| MMLV-II | 64.2 | 37.284 | 0.764 |
| MMLV-II Q79R/L99R/E282D | 64.2 | 36.661 | 0.192 |
| MMLV-II Q68R/Q79R/L99R | 64.2 | 34.463 | 0.213 |
| MMLV-II Q68R/Q79R/L99R/E282D | 64.2 | 32.992 | 0.023 |
| MMLV-II Q68R/Q79R/L99K/E282D | 64.2 | 34.805 | 0.472 |
| MMLV-II Q68R/Q79R/L99N/E282D | 64.2 | 34.060 | 0.043 |
| MMLV-II Q68K/Q79R/L99R/E282D | 64.2 | 34.508 | 0.302 |
| MMLV-II Q68R/Q79R/L99R/E282M | 64.2 | 34.481 | 0.078 |
| MMLV-II I61K/Q68R/Q79R/L99R/E282D | 64.2 | 34.231 | 0.253 |
| MMLV-II I61M/Q68R/Q79R/L99R/E282D | 64.2 | 35.049 | 0.885 |
| MMLV-II | 65.0 | 35.809 | 0.511 |
| MMLV-II Q79R/L99R/E282D | 65.0 | 35.932 | 0.372 |
| MMLV-II Q68R/Q79R/L99R | 65.0 | 34.979 | 0.856 |
| MMLV-II Q68R/Q79R/L99R/E282D | 65.0 | 33.293 | 0.319 |
| MMLV-II Q68R/Q79R/L99K/E282D | 65.0 | 34.974 | 0.536 |
| MMLV-II Q68R/Q79R/L99N/E282D | 65.0 | 34.862 | 0.268 |
| MMLV-II Q68K/Q79R/L99R/E282D | 65.0 | 34.363 | 0.201 |
| MMLV-II Q68R/Q79R/L99R/E282M | 65.0 | 34.687 | 0.666 |
| MMLV-II I61K/Q68R/Q79R/L99R/E282D | 65.0 | 34.246 | 0.563 |
| MMLV-II I61M/Q68R/Q79R/L99R/E282D | 65.0 | 34.872 | 0.467 |

Example 6: Reverse Transcriptase Mutant Evaluation by Oligo dT or Random Priming This example demonstrates the procedure used to evaluate each mutant RTase's ability to synthesize cDNA from purified total RNA (DNased, isolated from HeLa cells) compared to the base construct of MMLV RTase. The mutant MMLV RTases were tested by two priming conditions: Oligo dT only and random hexamer priming using a standard two-step cDNA synthesis as described in Example 5. The reactions were analyzed and reported by Ct value (Tables 19 and 20). Four mutant variants of MMLV RTase showed an increase in the overall activity using oligo dT priming compared to the base construct, Q299E, T332E and V433R. Eight mutant variants of MMLV RTase showed an increase in the overall activity using random priming compared to the base construct, P76R, L82R, I125R, Y271A, L280A, L280R, T328R and V433R.

TABLE 19

Two-Step cDNA Synthesis by MMLV-RT single mutants using oligo dT priming. The data was generated via qPCR human normalizer assay and data is reported by Ct value.

| MMLV-RT Variant | Ct Mean | Ct Standard Deviation |
|---|---|---|
| MMLV-II | 40.000 | 0.000 |
| MMLV-II D209A | 40.000 | 0.000 |
| MMLV-II D209E | 40.000 | 0.000 |
| MMLV-II D209R | 40.000 | 0.000 |
| MMLV-II D83 A | 40.000 | 0.000 |
| MMLV-II D83E | 40.000 | 0.000 |
| MMLV-II D83R | 40.000 | 0.000 |
| MMLV-II E201A | 40.000 | 0.000 |
| MMLV-II E201D | 40.000 | 0.000 |
| MMLV-II E201R | 40.000 | 0.000 |
| MMLV-II E367A | 40.000 | 0.000 |
| MMLV-II E367D | 40.000 | 0.000 |
| MMLV-II E367R | 40.000 | 0.000 |
| MMLV-II E596A | 40.000 | 0.000 |
| MMLV-II E596D | 40.000 | 0.000 |
| MMLV-II E596R | 40.000 | 0.000 |
| MMLV-II F210A | 40.000 | 0.000 |
| MMLV-II F210E | 40.000 | 0.000 |
| MMLV-II F210R | 40.000 | 0.000 |
| MMLV-II F369A | 40.000 | 0.000 |
| MMLV-II F369E | 40.000 | 0.000 |
| MMLV-II F369R | 40.000 | 0.000 |
| MMLV-II G308A | 40.000 | 0.000 |
| MMLV-II G308E | 40.000 | 0.000 |
| MMLV-II G308R | 40.000 | 0.000 |
| MMLV-II G331A | 40.000 | 0.000 |
| MMLV-II G331E | 40.000 | 0.000 |
| MMLV-II G331R | 40.000 | 0.000 |
| MMLV-II G73A | 40.000 | 0.000 |
| MMLV-II G73E | 40.000 | 0.000 |
| MMLV-II G73R | 40.000 | 0.000 |
| MMLV-II H77A | 40.000 | 0.000 |
| MMLV-II H77E | 40.000 | 0.000 |
| MMLV-II H77R | 40.000 | 0.000 |
| MMLV-II I125A | 40.000 | 0.000 |
| MMLV-II I125E | 40.000 | 0.000 |
| MMLV-II I125R | 40.000 | 0.000 |
| MMLV-II I212A | 40.000 | 0.000 |
| MMLV-II I212E | 40.000 | 0.000 |
| MMLV-II I212R | 40.000 | 0.000 |
| MMLV-II I593A | 40.000 | 0.000 |
| MMLV-II I593E | 40.000 | 0.000 |
| MMLV-II I593R | 40.000 | 0.000 |
| MMLV-II I597A | 40.000 | 0.000 |
| MMLV-II I597E | 40.000 | 0.000 |
| MMLV-II I597R | 40.000 | 0.000 |
| MMLV-II K285A | 40.000 | 0.000 |
| MMLV-II K285E | 40.000 | 0.000 |
| MMLV-II K285R | 40.000 | 0.000 |
| MMLV-II K348A | 40.000 | 0.000 |
| MMLV-II K348E | 40.000 | 0.000 |
| MMLV-II K348R | 40.000 | 0.000 |
| MMLV-II L198A | 40.000 | 0.000 |
| MMLV-II L198E | 40.000 | 0.000 |
| MMLV-II L198R | 40.000 | 0.000 |
| MMLV-II L280A | 40.000 | 0.000 |
| MMLV-II L280E | 40.000 | 0.000 |
| MMLV-II L280R | 40.000 | 0.000 |
| MMLV-II L352A | 40.000 | 0.000 |
| MMLV-II L352E | 40.000 | 0.000 |
| MMLV-II L352R | 40.000 | 0.000 |
| MMLV-II L357A | 40.000 | 0.000 |
| MMLV-II L357E | 40.000 | 0.000 |
| MMLV-II L357R | 40.000 | 0.000 |
| MMLV-II L82A | 40.000 | 0.000 |
| MMLV-II L82E | 40.000 | 0.000 |

TABLE 19-continued

Two-Step cDNA Synthesis by MMLV-RT single mutants using oligo dT priming. The data was generated via qPCR human normalizer assay and data is reported by Ct value.

| MMLV-RT Variant | Ct Mean | Ct Standard Deviation |
|---|---|---|
| MMLV-II L82R | 40.000 | 0.000 |
| MMLV-II N335A | 39.787 | 0.302 |
| MMLV-II N335E | 40.000 | 0.000 |
| MMLV-II N335R | 40.000 | 0.000 |
| MMLV-II P76A | 40.000 | 0.000 |
| MMLV-II P76E | 40.000 | 0.000 |
| MMLV-II P76R | 40.000 | 0.000 |
| MMLV-II Q213A | 40.000 | 0.000 |
| MMLV-II Q213E | 40.000 | 0.000 |
| MMLV-II Q213R | 40.000 | 0.000 |
| MMLV-II Q299A | 40.000 | 0.000 |
| MMLV-II Q299E | 37.177 | 3.993 |
| MMLV-II Q299R | 40.000 | 0.000 |
| MMLV-II Q654A | 40.000 | 0.000 |
| MMLV-II Q654E | 40.000 | 0.000 |
| MMLV-II Q654R | 40.000 | 0.000 |
| MMLV-II R205A | 40.000 | 0.000 |
| MMLV-II R205E | 39.947 | 0.075 |
| MMLV-II R205K | 40.000 | 0.000 |
| MMLV-II R211A | 40.000 | 0.000 |
| MMLV-II R211E | 40.000 | 0.000 |
| MMLV-II R211K | 40.000 | 0.000 |
| MMLV-II R311A | 40.000 | 0.000 |
| MMLV-II R311E | 40.000 | 0.000 |
| MMLV-II R311K | 40.000 | 0.000 |
| MMLV-II R389A | 40.000 | 0.000 |
| MMLV-II R389E | 40.000 | 0.000 |
| MMLV-II R389K | 40.000 | 0.000 |
| MMLV-II R650A | 40.000 | 0.000 |
| MMLV-II R650E | 40.000 | 0.000 |
| MMLV-II R650K | 40.000 | 0.000 |
| MMLV-II R657A | 40.000 | 0.000 |
| MMLV-II R657E | 39.965 | 0.050 |
| MMLV-II R657K | 40.000 | 0.000 |
| MMLV-II S67A | 40.000 | 0.000 |
| MMLV-II S67E | 40.000 | 0.000 |
| MMLV-II S67R | 36.816 | 0.703 |
| MMLV-II T328A | 40.000 | 0.000 |
| MMLV-II T328E | 40.000 | 0.000 |
| MMLV-II T328R | 40.000 | 0.000 |
| MMLV-II T332A | 39.750 | 0.354 |
| MMLV-II T332E | 38.461 | 2.177 |
| MMLV-II T332R | 40.000 | 0.000 |
| MMLV-II V129A | 40.000 | 0.000 |
| MMLV-II V129E | 40.000 | 0.000 |
| MMLV-II V129R | 40.000 | 0.000 |
| MMLV-II V433A | 40.000 | 0.000 |
| MMLV-II V433E | 40.000 | 0.000 |
| MMLV-II V433R | 38.884 | 0.806 |
| MMLV-II V476A | 40.000 | 0.000 |
| MMLV-II V476E | 40.000 | 0.000 |
| MMLV-II V476R | 40.000 | 0.000 |
| MMLV-II Y271A | 40.000 | 0.000 |
| MMLV-II Y271E | 40.000 | 0.000 |
| MMLV-II Y271R | 40.000 | 0.000 |
| MMLV-IV | 31.467 | 0.190 |

TABLE 20

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II | 40.000 | 0.000 |
| MMLV-II D209A | 40.000 | 0.000 |
| MMLV-II D209E | 40.000 | 0.000 |
| MMLV-II D209R | 40.000 | 0.000 |

TABLE 20-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II D83A | 40.000 | 0.000 |
| MMLV-II D83E | 40.000 | 0.000 |
| MMLV-II D83R | 40.000 | 0.000 |
| MMLV-II E201A | 40.000 | 0.000 |
| MMLV-II E201D | 40.000 | 0.000 |
| MMLV-II E201R | 40.000 | 0.000 |
| MMLV-II E367A | 40.000 | 0.000 |
| MMLV-II E367D | 40.000 | 0.000 |
| MMLV-II E367R | 40.000 | 0.000 |
| MMLV-II E596A | 40.000 | 0.000 |
| MMLV-II E596D | 40.000 | 0.000 |
| MMLV-II E596R | 40.000 | 0.000 |
| MMLV-II F210A | 40.000 | 0.000 |
| MMLV-II F210E | 40.000 | 0.000 |
| MMLV-II F210R | 40.000 | 0.000 |
| MMLV-II F369A | 40.000 | 0.000 |
| MMLV-II F369E | 40.000 | 0.000 |
| MMLV-II F369R | 40.000 | 0.000 |
| MMLV-II G308A | 40.000 | 0.000 |
| MMLV-II G308E | 40.000 | 0.000 |
| MMLV-II G308R | 40.000 | 0.000 |
| MMLV-II G331A | 40.000 | 0.000 |
| MMLV-II G331E | 40.000 | 0.000 |
| MMLV-II G331R | 40.000 | 0.000 |
| MMLV-II G73A | 40.000 | 0.000 |
| MMLV-II G73E | 40.000 | 0.000 |
| MMLV-II G73R | 40.000 | 0.000 |
| MMLV-II H77A | 39.708 | 0.412 |
| MMLV-II H77E | 40.000 | 0.000 |
| MMLV-II H77R | 40.000 | 0.000 |
| MMLV-II I125A | 40.000 | 0.000 |
| MMLV-II I125E | 40.000 | 0.000 |
| MMLV-II I125R | 39.449 | 0.779 |
| MMLV-II I212A | 40.000 | 0.000 |
| MMLV-II I212E | 40.000 | 0.000 |
| MMLV-II I212R | 40.000 | 0.000 |
| MMLV-II I593A | 40.000 | 0.000 |
| MMLV-II I593E | 40.000 | 0.000 |
| MMLV-II I593R | 40.000 | 0.000 |
| MMLV-II I597A | 40.000 | 0.000 |
| MMLV-II I597E | 40.000 | 0.000 |
| MMLV-II I597R | 40.000 | 0.000 |
| MMLV-II K285A | 40.000 | 0.000 |
| MMLV-II K285E | 40.000 | 0.000 |
| MMLV-II K285R | 39.783 | 0.308 |
| MMLV-II K348A | 40.000 | 0.000 |
| MMLV-II K348E | 40.000 | 0.000 |
| MMLV-II K348R | 40.000 | 0.000 |
| MMLV-II L198A | 40.000 | 0.000 |
| MMLV-II L198E | 40.000 | 0.000 |
| MMLV-II L198R | 40.000 | 0.000 |
| MMLV-II L280A | 39.503 | 0.703 |
| MMLV-II L280E | 40.000 | 0.000 |
| MMLV-II L280R | 38.762 | 1.751 |
| MMLV-II L352A | 39.778 | 0.313 |
| MMLV-II L352E | 40.000 | 0.000 |
| MMLV-II L352R | 40.000 | 0.000 |
| MMLV-II L357A | 40.000 | 0.000 |
| MMLV-II L357E | 40.000 | 0.000 |
| MMLV-II L357R | 40.000 | 0.000 |
| MMLV-II L82A | 40.000 | 0.000 |
| MMLV-II L82E | 39.673 | 0.462 |
| MMLV-II L82R | 38.926 | 1.518 |
| MMLV-II N335A | 39.876 | 0.175 |
| MMLV-II N335E | 40.000 | 0.000 |
| MMLV-II N335R | 39.861 | 0.196 |
| MMLV-II P76A | 40.000 | 0.000 |
| MMLV-II P76E | 40.000 | 0.000 |
| MMLV-II P76R | 39.535 | 0.658 |
| MMLV-II Q213A | 40.000 | 0.000 |
| MMLV-II Q213E | 40.000 | 0.000 |
| MMLV-II Q213R | 40.000 | 0.000 |
| MMLV-II Q299A | 40.000 | 0.000 |

TABLE 20-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II Q299E | 40.000 | 0.000 |
| MMLV-II Q299R | 40.000 | 0.000 |
| MMLV-II Q654A | 40.000 | 0.000 |
| MMLV-II Q654E | 40.000 | 0.000 |
| MMLV-II Q654R | 40.000 | 0.000 |
| MMLV-II R205A | 39.811 | 0.267 |
| MMLV-II R205E | 40.000 | 0.000 |
| MMLV-II R205K | 40.000 | 0.000 |
| MMLV-II R211A | 40.000 | 0.000 |
| MMLV-II R211E | 40.000 | 0.000 |
| MMLV-II R211K | 40.000 | 0.000 |
| MMLV-II R311A | 40.000 | 0.000 |
| MMLV-II R311E | 40.000 | 0.000 |
| MMLV-II R311K | 40.000 | 0.000 |
| MMLV-II R389A | 40.000 | 0.000 |
| MMLV-II R389E | 40.000 | 0.000 |
| MMLV-II R389K | 40.000 | 0.000 |
| MMLV-II R650A | 40.000 | 0.000 |
| MMLV-II R650E | 40.000 | 0.000 |
| MMLV-II R650K | 40.000 | 0.000 |
| MMLV-II R657A | 40.000 | 0.000 |
| MMLV-II R657E | 40.000 | 0.000 |
| MMLV-II R657K | 40.000 | 0.000 |
| MMLV-II S67A | 40.000 | 0.000 |
| MMLV-II S67E | 39.435 | 0.800 |
| MMLV-II S67R | 38.209 | 0.977 |
| MMLV-II T328A | 40.000 | 0.000 |
| MMLV-II T328E | 40.000 | 0.000 |
| MMLV-II T328R | 39.478 | 0.739 |
| MMLV-II T332A | 40.000 | 0.000 |
| MMLV-II T332E | 40.000 | 0.000 |
| MMLV-II T332R | 40.000 | 0.000 |
| MMLV-II V129A | 40.000 | 0.000 |
| MMLV-II V129E | 40.000 | 0.000 |
| MMLV-II V129R | 40.000 | 0.000 |
| MMLV-II V433A | 40.000 | 0.000 |
| MMLV-II V433E | 40.000 | 0.000 |
| MMLV-II V433R | 38.071 | 1.452 |
| MMLV-II V476A | 40.000 | 0.000 |
| MMLV-II V476E | 40.000 | 0.000 |
| MMLV-II V476R | 40.000 | 0.000 |
| MMLV-II Y271A | 39.466 | 0.755 |
| MMLV-II Y271E | 40.000 | 0.000 |
| MMLV-II Y271R | 40.000 | 0.000 |
| MMLV-IV | 31.850 | 0.183 |

Example 7. Reverse Transcriptase Mutant Evaluation by Gene Specific Priming

This example demonstrates the procedure used to evaluate each mutant RTase's ability to synthesize cDNA from purified RNA ultramers (Integrated DNA Technologies) compared to the base construct of MMLV RTase. The mutant MMLV RTases were tested by a one-step addition of the RTase in GEM as described in Example 5. The reactions were analyzed and reported by Ct value (Table 21). Twelve mutant variants of MMLV RTase showed an increase in the overall activity compared to the base construct, H77A, D83E, D83R, Y271E, Q299E, G308E, F396A, V433R, I593E, I597A and I597R.

TABLE 21

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II | 29.065 | 0.277 |
| MMLV-II D209A | 29.583 | 0.166 |
| MMLV-II D209E | 28.900 | 0.088 |
| MMLV-II D209R | 29.266 | 0.068 |
| MMLV-II D83 A | 29.588 | 0.082 |
| MMLV-II D83E | 28.499 | 0.087 |
| MMLV-II D83R | 28.724 | 0.087 |
| MMLV-II E201A | 30.692 | 0.173 |
| MMLV-II E201D | 29.130 | 0.157 |
| MMLV-II E201R | 29.333 | 0.141 |
| MMLV-II E367A | 31.153 | 0.021 |
| MMLV-II E367D | 31.070 | 0.187 |
| MMLV-II E367R | 34.221 | 0.475 |
| MMLV-II E596A | 29.150 | 0.121 |
| MMLV-II E596D | 30.494 | 0.081 |
| MMLV-II E596R | 31.787 | 0.227 |
| MMLV-II F210A | 33.639 | 0.196 |
| MMLV-II F210E | 34.982 | 0.065 |
| MMLV-II F210R | 37.201 | 1.986 |
| MMLV-II F369A | 29.055 | 0.063 |
| MMLV-II F369E | 36.856 | 0.508 |
| MMLV-II F369R | 36.149 | 0.308 |
| MMLV-II G308A | 30.226 | 0.170 |
| MMLV-II G308E | 28.772 | 0.121 |
| MMLV-II G308R | 40.000 | 0.000 |
| MMLV-II G331A | 30.412 | 0.137 |
| MMLV-II G331E | 31.321 | 0.160 |
| MMLV-II G331R | 31.340 | 0.020 |
| MMLV-II G73A | 30.741 | 0.125 |
| MMLV-II G73E | 34.319 | 0.369 |
| MMLV-II G73R | 29.721 | 0.061 |
| MMLV-II H77A | 28.581 | 0.070 |
| MMLV-II H77E | 29.475 | 0.107 |
| MMLV-II H77R | 29.726 | 0.120 |
| MMLV-II I125A | 29.812 | 0.043 |
| MMLV-II I125E | 30.712 | 0.147 |
| MMLV-II I125R | 30.324 | 0.012 |
| MMLV-II I212A | 29.586 | 0.086 |
| MMLV-II I212E | 29.459 | 0.073 |
| MMLV-II I212R | 29.037 | 0.092 |
| MMLV-II I593A | 30.560 | 0.101 |
| MMLV-II I593E | 27.779 | 0.056 |
| MMLV-II I593R | 29.268 | 0.012 |
| MMLV-II I597A | 28.983 | 0.024 |
| MMLV-II I597E | 29.583 | 0.143 |
| MMLV-II I597R | 28.671 | 0.103 |
| MMLV-II K285A | 32.375 | 0.158 |
| MMLV-II K285E | 37.065 | 0.044 |
| MMLV-II K285R | 30.564 | 0.075 |
| MMLV-II K348A | 34.241 | 0.516 |
| MMLV-II K348E | 34.533 | 0.432 |
| MMLV-II K348R | 29.703 | 0.225 |
| MMLV-II L198A | 31.900 | 0.054 |
| MMLV-II L198E | 34.193 | 0.167 |
| MMLV-II L198R | 30.819 | 0.077 |
| MMLV-II L280A | 35.724 | 0.175 |
| MMLV-II L280E | 40.000 | 0.000 |
| MMLV-II L280R | 40.000 | 0.000 |
| MMLV-II L352A | 28.936 | 0.043 |
| MMLV-II L352E | 30.177 | 0.059 |
| MMLV-II L352R | 29.371 | 0.063 |
| MMLV-II L357A | 38.802 | 1.694 |
| MMLV-II L357E | 40.000 | 0.000 |
| MMLV-II L357R | 40.000 | 0.000 |
| MMLV-II L82A | 31.245 | 0.035 |
| MMLV-II L82E | 31.384 | 0.122 |
| MMLV-II L82R | 29.682 | 0.116 |
| MMLV-II N335A | 29.668 | 0.086 |
| MMLV-II N335E | 29.113 | 0.058 |
| MMLV-II N335R | 32.323 | 5.429 |
| MMLV-II P76A | 29.463 | 0.123 |
| MMLV-II P76E | 30.030 | 0.163 |
| MMLV-II P76R | 29.443 | 0.028 |

TABLE 21-continued

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II Q213A | 29.833 | 0.223 |
| MMLV-II Q213E | 29.677 | 0.196 |
| MMLV-II Q213R | 29.704 | 0.053 |
| MMLV-II Q299A | 31.314 | 0.200 |
| MMLV-II Q299E | 28.652 | 0.149 |
| MMLV-II Q299R | 31.711 | 0.062 |
| MMLV-II Q654A | 29.415 | 0.117 |
| MMLV-II Q654E | 30.523 | 0.057 |
| MMLV-II Q654R | 29.523 | 0.052 |
| MMLV-II R205A | 29.140 | 0.138 |
| MMLV-II R205E | 29.356 | 0.179 |
| MMLV-II R205K | 29.162 | 0.206 |
| MMLV-II R211A | 29.491 | 0.025 |
| MMLV-II R211E | 30.049 | 0.205 |
| MMLV-II R211K | 30.196 | 0.147 |
| MMLV-II R311A | 31.237 | 0.425 |
| MMLV-II R311E | 40.000 | 0.000 |
| MMLV-II R311K | 29.857 | 0.091 |
| MMLV-II R389A | 32.173 | 0.151 |
| MMLV-II R389E | 32.717 | 0.105 |
| MMLV-II R389K | 31.944 | 0.166 |
| MMLV-II R650A | 29.734 | 0.060 |
| MMLV-II R650E | 31.012 | 0.074 |
| MMLV-II R650K | 29.404 | 0.094 |
| MMLV-II R657A | 31.470 | 0.133 |
| MMLV-II R657E | 32.785 | 0.145 |
| MMLV-II R657K | 29.468 | 0.274 |
| MMLV-II S67A | 29.268 | 0.090 |
| MMLV-II S67E | 30.157 | 0.254 |
| MMLV-II S67R | 27.274 | 0.054 |
| MMLV-II T328A | 40.000 | 0.000 |
| MMLV-II T328E | 37.699 | 1.627 |
| MMLV-II T328R | 37.169 | 0.848 |
| MMLV-II T332A | 29.219 | 0.075 |
| MMLV-II T332E | 29.714 | 0.057 |
| MMLV-II T332R | 30.462 | 0.130 |
| MMLV-II V129A | 29.305 | 0.077 |
| MMLV-II V129E | 31.188 | 0.181 |
| MMLV-II V129R | 30.383 | 0.081 |
| MMLV-II V433A | 30.483 | 0.059 |
| MMLV-II V433E | 30.106 | 0.144 |
| MMLV-II V433R | 29.297 | 0.457 |
| MMLV-II V476A | 31.295 | 0.244 |
| MMLV-II V476E | 34.664 | 0.364 |
| MMLV-II V476R | 31.223 | 0.166 |
| MMLV-II Y271A | 30.854 | 0.086 |
| MMLV-II Y271E | 28.620 | 0.068 |
| MMLV-II Y271R | 33.280 | 0.258 |
| MMLV-IV | 26.368 | 0.057 |

Example 8. Further Stacking of Reverse Transcriptase Mutants with Enhanced Activity This example demonstrates the procedure used to stack the enhanced mutants found in Examples 6-7 to further improve the MMLV RTase's ability to synthesize cDNA from purified total RNA (DNased, isolated from HeLa cells) compared to the base construct and previously found mutant MMLV RTase containing the following mutations: Q68R/Q79R/L99R/E282D. The stacked mutant MMLV RTases were cloned, overexpressed and purified as described in Examples 1-2 and tested as described in Examples 6-7. Both the two- and one-step reactions were analyzed and reported by Ct value (Table 22-24). Six of the eight stacked mutant variants of MMLV RTase increased the overall activity and thermostability compared to the base construct, Q68R/Q79R/L99R/E282D/V433R, Q68R/Q79R/L99R/E282D/I593E, Q68R/Q79R/L99R/E282D/Q299E, Q68R/Q79R/L99R/E282D/T332E, Q68R/L82R/L99R/E282D and Q68R/Q79R/L82R/L99R/E282D. Subsequentially, four of those six stacked mutant variants of MMLV RTase increased the overall activity and thermostability compared to the previously identified mutant RTase (Q68R/Q79R/L99R/E282D), Q68R/Q79R/L99R/E282D/I593E, Q68R/Q79R/L99R/E282D/Q299E, Q68R/L82R/L99R/E282D and Q68R/Q79R/L82R/L99R/E282D.

Following these stacked mutant variants, MMLV RTase mutations were stacked further to improve the ability of MMLV RTase to synthesize cDNA from purified total RNA (DNased, isolated from HeLa cells) as compared to the MMLV RTase base construct (RNase H minus construct). Eight MMLV RTase sextuple or more mutant variants were cloned as described in Example 1 and overexpressed and purified as in Example 5.

MMLV RTase base construct and MMLV RTase mutant variants evaluated as described in Example 3. Temperatures were adjusted for both two-step and one-step reactions to 42/55 and 50/60° C., respectively. The two-step first strand synthesis buffer was modified from 50 mM Tris-hydrochloride, pH 8.3, 75 mM potassium chloride, 3 mM magnesium chloride and 10 mM DTT to 50 mM potassium acetate, 20 mM Tris-acetate, pH 7.0, 10 mM magnesium acetate, 100 μg/ml bovine serum albumin and 10 mM DTT. The two-step and one-step reactions for MMLV RTase base construct and MMLV RTase mutant variants were analyzed and reported by Ct output from the qPCR (Tables 22-24).

Four of the eleven MMLV RTase sextuple or more mutant variants were found to exhibit increased overall activity and thermostability as compared to the other MMLV RTase stacked mutant variants, and almost all of the MMLV RTase stacked mutant variants exhibited increased overall activity and thermostability as compared to the MMLV RTase base construct. The four MMLV RTase mutant variants that were found to exhibit the highest overall activity were Q68R/Q79R/L99R/E282D/Q299E/V433R/I593E, Q68R/Q79R/L82R/L99R/E282D/Q299E/V433R/I593E, Q68R/Q79R/L82R/L99R/E282D/Q299E/T332E/I593E and Q68R/Q79R/L82R/L99R/E282D/Q299E/T332E/V433R/I593E.

TABLE 22

Two-Step cDNA Synthesis by MMLV-RT stacked mutants using oligo dT priming. The data was generated via qPCR human normalizer assay and data is reported by Ct value.

| MMLV-RT Variant | Ct Mean | Ct Standard Deviation |
|---|---|---|
| MMLV-II | 37.388 | 0.396 |
| MMLV-II Q68R/Q79R/L99R/E282D/V433R | 29.215 | 0.113 |
| MMLV-II Q68R/Q79R/L99R/E282D/I593E | 33.563 | 0.118 |
| MMLV-II Q68R/Q79R/L99R/E282D/Q299E | 31.902 | 0.169 |
| MMLV-II Q68R/Q79R/L99R/E282D/T332E | 33.988 | 0.108 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 39.259 | 1.047 |
| MMLV-II Q68R/Q79R/L82R/L99R/E282D | 30.623 | 0.076 |
| MMLV-IV | 25.880 | 0.023 |

TABLE 23

Two-Step cDNA Synthesis by MMLV-RT stacked mutants using random priming. The data was generated via qPCR human normalizer assay and data is reported by Ct value.

| MMLV-RT Variant | Ct Mean | Ct Standard Deviation |
|---|---|---|
| MMLV-II | 36.638 | 1.014 |
| MMLV-II Q68R/Q79R/L99R/E282D/V433R | 40.000 | 0.000 |
| MMLV-II Q68R/Q79R/L99R/E282D/I593E | 32.331 | 0.111 |
| MMLV-II Q68R/Q79R/L99R/E282D/Q299E | 30.430 | 0.154 |
| MMLV-II Q68R/Q79R/L99R/E282D/T332E | 33.720 | 0.266 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 35.325 | 0.422 |
| MMLV-II Q68R/Q79R/L82R/L99R/E282D | 31.928 | 0.177 |
| MMLV-IV | 25.840 | 0.049 |

TABLE 24

One-Step cDNA Synthesis by MMLV-RT stacked mutants by gene specific priming. The data was generated via qPCR human normalizer assay and data is reported by Ct value.

| MMLV-RT Variant | Ct Mean | Ct Standard Deviation |
|---|---|---|
| MMLV-II | 33.027 | 0.048 |
| MMLV-II Q68R/Q79R/L99R/E282D/V433R | 29.937 | 0.040 |
| MMLV-II Q68R/Q79R/L99R/E282D/I593E | 28.724 | 0.081 |
| MMLV-II Q68R/Q79R/L99R/E282D/Q299E | 29.341 | 0.022 |
| MMLV-II Q68R/Q79R/L99R/E282D/T332E | 30.330 | 0.036 |
| MMLV-II Q68R/Q79R/L99R/L280R | 40.000 | 0.000 |
| MMLV-II Q68R/Q79R/L99R/L280R/E282D | 40.000 | 0.000 |
| MMLV-II Q68R/L82R/L99R/E282D | 30.559 | 0.045 |
| MMLV-II Q68R/Q79R/L82R/L99R/E282D | 30.097 | 0.033 |
| MMLV-IV | 28.975 | 0.012 |

a. Evaluation of Ability of Purified MMLV RTase Mutant Variants to Synthesize DNA Over a Wide Range of Temperatures MMLV RTase base construct MMLV RTase mutant variants evaluated as described in Example 5. Oligo-dT or random hexamer priming conditions and reaction temperatures were adjusted for the two-step reactions and RTase concentration was normalized to 31 nM. The two-step reactions for MMLV RTase base construct and MMLV RTase mutant variants were analyzed and reported by Ct output from the qPCR (see tables 25 and 26)

Five MMLV RTase mutants were found to exhibit high overall activity as compared to the MMLV RTase base construct over a wide range of temperatures, spanning from 37.0 to 51° C., regardless of which priming method used. All of the MMLV RTase stacked mutant variants exhibited increased overall activity and thermostability as compared to the MMLV RTase base construct. The five MMLV RTas mutant variants that were found to exhibit the highest overall activity at a wide range of temperatures were Q68R/Q79R/L99R/E282D, Q68R/Q79R/L99R/E282D/Q299E/V433R/I593E, Q68R/Q79R/L82R/L99R/E282D/Q299E/V433R/I593E, Q68R/Q79R/L82R/L99R/E282D/Q299E/T332E/I593E and Q68R/Q79R/L82R/L99R/E282D/Q299E/T332E/V433R/I593E

TABLE 25

Two-Step cDNA synthesis by MMLV RT quadruple and more mutants by Oligo-dT priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II | 37.0 | 26.340 | 0.033 |
| MMLV-II | 37.8 | 26.130 | 0.061 |
| MMLV-II | 39.5 | 25.830 | 0.014 |
| MMLV-II | 42.0 | 25.753 | 0.041 |
| MMLV-II | 45.2 | 25.632 | 0.077 |
| MMLV-II | 47.8 | 25.935 | 0.026 |
| MMLV-II | 49.2 | 26.478 | 0.042 |
| MMLV-II | 50.0 | 29.461 | 0.120 |
| MMLV-II | 51.0 | 29.430 | 0.098 |
| MMLV-II | 51.9 | 31.123 | 0.066 |
| MMLV-II | 53.8 | 33.632 | 0.073 |
| MMLV-II | 56.5 | 36.499 | 0.385 |
| MMLV-II | 59.9 | 37.158 | 0.427 |
| MMLV-II | 62.6 | 37.464 | 0.440 |
| MMLV-II | 64.2 | 37.082 | 0.022 |
| MMLV-II | 65.0 | 37.518 | 0.370 |
| MMLV-II Q68R/Q79R/L99R/E282D | 37.0 | 25.688 | 0.031 |
| MMLV-II Q68R/Q79R/L99R/E282D | 37.8 | 25.734 | 0.032 |
| MMLV-II Q68R/Q79R/L99R/E282D | 39.5 | 25.613 | 0.040 |
| MMLV-II Q68R/Q79R/L99R/E282D | 42.0 | 25.528 | 0.032 |
| MMLV-II Q68R/Q79R/L99R/E282D | 45.2 | 25.525 | 0.029 |
| MMLV-II Q68R/Q79R/L99R/E282D | 47.8 | 25.471 | 0.105 |
| MMLV-II Q68R/Q79R/L99R/E282D | 49.2 | 25.491 | 0.047 |
| MMLV-II Q68R/Q79R/L99R/E282D | 50.0 | 25.608 | 0.061 |
| MMLV-II Q68R/Q79R/L99R/E282D | 51.0 | 25.679 | 0.006 |
| MMLV-II Q68R/Q79R/L99R/E282D | 51.9 | 25.969 | 0.032 |
| MMLV-II Q68R/Q79R/L99R/E282D | 53.8 | 27.251 | 0.053 |
| MMLV-II Q68R/Q79R/L99R/E282D | 56.5 | 33.619 | 0.195 |
| MMLV-II Q68R/Q79R/L99R/E282D | 59.9 | 36.635 | 0.059 |
| MMLV-II Q68R/Q79R/L99R/E282D | 62.6 | 36.929 | 0.500 |

TABLE 25-continued

Two-Step cDNA synthesis by MMLV RT quadruple and more mutants by Oligo-dT priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L99R/E282D | 64.2 | 37.515 | 0.478 |
| MMLV-II Q68R/Q79R/L99R/E282D | 65.0 | 37.107 | 0.285 |
| MMLV-II Q68R/Q79R/L99R/E282D/I593E | 37.0 | 26.133 | 0.054 |
| MMLV-II Q68R/Q79R/L99R/E282D/I593E | 37.8 | 26.029 | 0.012 |
| MMLV-II Q68R/Q79R/L99R/E282D/I593E | 39.5 | 25.850 | 0.047 |
| MMLV-II Q68R/Q79R/L99R/E282D/I593E | 42.0 | 25.793 | 0.012 |
| MMLV-II Q68R/Q79R/L99R/E282D/I593E | 45.2 | 25.614 | 0.018 |
| MMLV-II Q68R/Q79R/L99R/E282D/I593E | 47.8 | 25.658 | 0.005 |
| MMLV-II Q68R/Q79R/L99R/E282D/I593E | 49.2 | 25.663 | 0.024 |
| MMLV-II Q68R/Q79R/L99R/E282D/I593E | 50.0 | 25.791 | 0.041 |
| MMLV-II Q68R/Q79R/L99R/E282D/I593E | 51.0 | 25.877 | 0.067 |
| MMLV-II Q68R/Q79R/L99R/E282D/I593E | 51.9 | 26.602 | 0.038 |
| MMLV-II Q68R/Q79R/L99R/E282D/I593E | 53.8 | 29.535 | 0.086 |
| MMLV-II Q68R/Q79R/L99R/E282D/I593E | 56.5 | 35.912 | 0.439 |
| MMLV-II Q68R/Q79R/L99R/E282D/I593E | 59.9 | 37.158 | 0.566 |
| MMLV-II Q68R/Q79R/L99R/E282D/I593E | 62.6 | 37.187 | 0.158 |
| MMLV-II Q68R/Q79R/L99R/E282D/I593E | 64.2 | 37.958 | 0.236 |
| MMLV-II Q68R/Q79R/L99R/E282D/I593E | 65.0 | 36.861 | 0.416 |
| MMLV-II Q68R/Q79R/L99R/E282D/Q299E | 37.0 | 26.106 | 0.070 |
| MMLV-II Q68R/Q79R/L99R/E282D/Q299E | 37.8 | 26.024 | 0.092 |
| MMLV-II Q68R/Q79R/L99R/E282D/Q299E | 39.5 | 25.830 | 0.122 |
| MMLV-II Q68R/Q79R/L99R/E282D/Q299E | 42.0 | 25.788 | 0.025 |
| MMLV-II Q68R/Q79R/L99R/E282D/Q299E | 45.2 | 25.634 | 0.022 |
| MMLV-II Q68R/Q79R/L99R/E282D/Q299E | 47.8 | 25.681 | 0.016 |
| MMLV-II Q68R/Q79R/L99R/E282D/Q299E | 49.2 | 25.684 | 0.029 |
| MMLV-II Q68R/Q79R/L99R/E282D/Q299E | 50.0 | 25.743 | 0.096 |
| MMLV-II Q68R/Q79R/L99R/E282D/Q299E | 51.0 | 25.870 | 0.003 |
| MMLV-II Q68R/Q79R/L99R/E282D/Q299E | 51.9 | 26.301 | 0.033 |
| MMLV-II Q68R/Q79R/L99R/E282D/Q299E | 53.8 | 28.283 | 0.036 |
| MMLV-II Q68R/Q79R/L99R/E282D/Q299E | 56.5 | 34.732 | 0.445 |
| MMLV-II Q68R/Q79R/L99R/E282D/Q299E | 59.9 | 36.947 | 0.407 |
| MMLV-II Q68R/Q79R/L99R/E282D/Q299E | 62.6 | 37.140 | 0.280 |
| MMLV-II Q68R/Q79R/L99R/E282D/Q299E | 64.2 | 37.403 | 0.205 |
| MMLV-II Q68R/Q79R/L99R/E282D/Q299E | 65.0 | 37.347 | 0.438 |
| MMLV-II Q68R/Q79R/L82R/L99R/E282D | 37.0 | 25.961 | 0.170 |
| MMLV-II Q68R/Q79R/L82R/L99R/E282D | 37.8 | 26.065 | 0.085 |
| MMLV-II Q68R/Q79R/L82R/L99R/E282D | 39.5 | 25.909 | 0.028 |
| MMLV-II Q68R/Q79R/L82R/L99R/E282D | 42.0 | 25.802 | 0.055 |
| MMLV-II Q68R/Q79R/L82R/L99R/E282D | 45.2 | 25.632 | 0.087 |
| MMLV-II Q68R/Q79R/L82R/L99R/E282D | 47.8 | 25.728 | 0.065 |
| MMLV-II Q68R/Q79R/L82R/L99R/E282D | 49.2 | 25.612 | 0.165 |
| MMLV-II Q68R/Q79R/L82R/L99R/E282D | 50.0 | 25.795 | 0.038 |
| MMLV-II Q68R/Q79R/L82R/L99R/E282D | 51.0 | 25.830 | 0.009 |
| MMLV-II Q68R/Q79R/L82R/L99R/E282D | 51.9 | 26.477 | 0.037 |
| MMLV-II Q68R/Q79R/L82R/L99R/E282D | 53.8 | 28.496 | 0.040 |
| MMLV-II Q68R/Q79R/L82R/L99R/E282D | 56.5 | 34.329 | 0.177 |
| MMLV-II Q68R/Q79R/L82R/L99R/E282D | 59.9 | 36.564 | 0.315 |
| MMLV-II Q68R/Q79R/L82R/L99R/E282D | 62.6 | 37.152 | 0.322 |
| MMLV-II Q68R/Q79R/L82R/L99R/E282D | 64.2 | 37.340 | 0.585 |
| MMLV-II Q68R/Q79R/L82R/L99R/E282D | 65.0 | 38.351 | 1.016 |
| MMLV-II Q68R/Q79R/L99R/E282D/Q299E/V433R/I593E | 37.0 | 25.853 | 0.057 |
| MMLV-II Q68R/Q79R/L99R/E282D/Q299E/V433R/I593E | 37.8 | 25.898 | 0.016 |
| MMLV-II Q68R/Q79R/L99R/E282D/Q299E/V433R/I593E | 39.5 | 25.716 | 0.093 |
| MMLV-II Q68R/Q79R/L99R/E282D/Q299E/V433R/I593E | 42.0 | 25.669 | 0.064 |
| MMLV-II Q68R/Q79R/L99R/E282D/Q299E/V433R/I593E | 45.2 | 25.643 | 0.056 |
| MMLV-II Q68R/Q79R/L99R/E282D/Q299E/V433R/I593E | 47.8 | 25.680 | 0.016 |
| MMLV-II Q68R/Q79R/L99R/E282D/Q299E/V433R/I593E | 49.2 | 25.663 | 0.057 |
| MMLV-II Q68R/Q79R/L99R/E282D/Q299E/V433R/I593E | 50.0 | 25.708 | 0.045 |
| MMLV-II Q68R/Q79R/L99R/E282D/Q299E/V433R/I593E | 51.0 | 25.557 | 0.025 |
| MMLV-II Q68R/Q79R/L99R/E282D/Q299E/V433R/I593E | 51.9 | 26.015 | 0.125 |
| MMLV-II Q68R/Q79R/L99R/E282D/Q299E/V433R/I593E | 53.8 | 27.812 | 0.048 |

TABLE 25-continued

Two-Step cDNA synthesis by MMLV RT quadruple and more mutants by Oligo-dT priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L99R/E282D/Q299E/V433R/I593E | 56.5 | 34.073 | 0.217 |
| MMLV-II Q68R/Q79R/L99R/E282D/Q299E/V433R/I593E | 59.9 | 36.512 | 0.168 |
| MMLV-II Q68R/Q79R/L99R/E282D/Q299E/V433R/I593E | 62.6 | 37.182 | 0.167 |
| MMLV-II Q68R/Q79R/L99R/E282D/Q299E/V433R/I593E | 64.2 | 37.239 | 0.291 |
| MMLV-II Q68R/Q79R/L99R/E282D/Q299E/V433R/I593E | 65.0 | 36.573 | 0.232 |
| MMLV-II Q68R/Q79R/L82R/L99R/E282D/Q299E/V433R/I593E | 37.0 | 25.789 | 0.075 |
| MMLV-II Q68R/Q79R/L82R/L99R/E282D/Q299E/V433R/I593E | 37.8 | 25.784 | 0.103 |
| MMLV-II Q68R/Q79R/L82R/L99R/E282D/Q299E/V433R/I593E | 39.5 | 25.714 | 0.025 |
| MMLV-II Q68R/Q79R/L82R/L99R/E282D/Q299E/V433R/I593E | 42.0 | 25.713 | 0.027 |
| MMLV-II Q68R/Q79R/L82R/L99R/E282D/Q299E/V433R/I593E | 45.2 | 25.690 | 0.030 |
| MMLV-II Q68R/Q79R/L82R/L99R/E282D/Q299E/V433R/I593E | 47.8 | 25.662 | 0.026 |
| MMLV-II Q68R/Q79R/L82R/L99R/E282D/Q299E/V433R/I593E | 49.2 | 25.713 | 0.021 |
| MMLV-II Q68R/Q79R/L82R/L99R/E282D/Q299E/V433R/I593E | 50.0 | 25.551 | 0.092 |
| MMLV-II Q68R/Q79R/L82R/L99R/E282D/Q299E/V433R/I593E | 51.0 | 25.561 | 0.107 |
| MMLV-II Q68R/Q79R/L82R/L99R/E282D/Q299E/V433R/I593E | 51.9 | 25.975 | 0.125 |
| MMLV-II Q68R/Q79R/L82R/L99R/E282D/Q299E/V433R/I593E | 53.8 | 27.556 | 0.023 |
| MMLV-II Q68R/Q79R/L82R/L99R/E282D/Q299E/V433R/I593E | 56.5 | 33.934 | 0.249 |
| MMLV-II Q68R/Q79R/L82R/L99R/E282D/Q299E/V433R/I593E | 59.9 | 36.473 | 0.285 |
| MMLV-II Q68R/Q79R/L82R/L99R/E282D/Q299E/V433R/I593E | 62.6 | 37.411 | 0.377 |
| MMLV-II Q68R/Q79R/L82R/L99R/E282D/Q299E/V433R/I593E | 64.2 | 37.656 | 0.478 |
| MMLV-II Q68R/Q79R/L82R/L99R/E282D/Q299E/V433R/I593E | 65.0 | 37.950 | 1.451 |
| MMLV-II Q68R/Q79R/L82R/L99R/E282D/Q299E/T332E/I593E | 37.0 | 25.788 | 0.028 |
| MMLV-II Q68R/Q79R/L82R/L99R/E282D/Q299E/T332E/I593E | 37.8 | 25.680 | 0.229 |
| MMLV-II Q68R/Q79R/L82R/L99R/E282D/Q299E/T332E/I593E | 39.5 | 25.794 | 0.051 |
| MMLV-II Q68R/Q79R/L82R/L99R/E282D/Q299E/T332E/I593E | 42.0 | 25.415 | 0.270 |
| MMLV-II Q68R/Q79R/L82R/L99R/E282D/Q299E/T332E/I593E | 45.2 | 25.631 | 0.047 |
| MMLV-II Q68R/Q79R/L82R/L99R/E282D/Q299E/T332E/I593E | 47.8 | 25.672 | 0.027 |
| MMLV-II Q68R/Q79R/L82R/L99R/E282D/Q299E/T332E/I593E | 49.2 | 25.792 | 0.045 |
| MMLV-II Q68R/Q79R/L82R/L99R/E282D/Q299E/T332E/I593E | 50.0 | 25.759 | 0.022 |
| MMLV-II Q68R/Q79R/L82R/L99R/E282D/Q299E/T332E/I593E | 51.0 | 25.852 | 0.015 |
| MMLV-II Q68R/Q79R/L82R/L99R/E282D/Q299E/T332E/I593E | 51.9 | 26.425 | 0.033 |
| MMLV-II Q68R/Q79R/L82R/L99R/E282D/Q299E/T332E/I593E | 53.8 | 29.964 | 0.023 |
| MMLV-II Q68R/Q79R/L82R/L99R/E282D/Q299E/T332E/I593E | 56.5 | 36.532 | 0.113 |
| MMLV-II Q68R/Q79R/L82R/L99R/E282D/Q299E/T332E/I593E | 59.9 | 38.246 | 0.608 |
| MMLV-II Q68R/Q79R/L82R/L99R/E282D/Q299E/T332E/I593E | 62.6 | 37.333 | 0.446 |
| MMLV-II Q68R/Q79R/L82R/L99R/E282D/Q299E/T332E/I593E | 64.2 | 37.223 | 0.212 |

TABLE 25-continued

Two-Step cDNA synthesis by MMLV RT quadruple and more mutants by Oligo-dT priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/I593E | 65.0 | 36.930 | 0.527 |
| MMLV-II Q68R/Q79R/L82R/L99R/E282D/Q299E/T332E/V433R/I593E | 37.0 | 25.863 | 0.014 |
| MMLV-II Q68R/Q79R/L82R/L99R/E282D/Q299E/T332E/V433R/I593E | 37.8 | 25.649 | 0.036 |
| MMLV-II Q68R/Q79R/L82R/L99R/E282D/Q299E/T332E/V433R/I593E | 39.5 | 25.573 | 0.057 |
| MMLV-II Q68R/Q79R/L82R/L99R/E282D/Q299E/T332E/V433R/I593E | 42.0 | 25.453 | 0.023 |
| MMLV-II Q68R/Q79R/L82R/L99R/E282D/Q299E/T332E/V433R/I593E | 45.2 | 25.447 | 0.083 |
| MMLV-II Q68R/Q79R/L82R/L99R/E282D/Q299E/T332E/V433R/I593E | 47.8 | 25.413 | 0.061 |
| MMLV-II Q68R/Q79R/L82R/L99R/E282D/Q299E/T332E/V433R/I593E | 49.2 | 25.542 | 0.035 |
| MMLV-II Q68R/Q79R/L82R/L99R/E282D/Q299E/T332E/V433R/I593E | 50.0 | 25.567 | 0.060 |
| MMLV-II Q68R/Q79R/L82R/L99R/E282D/Q299E/T332E/V433R/I593E | 51.0 | 25.741 | 0.093 |
| MMLV-II Q68R/Q79R/L82R/L99R/E282D/Q299E/T332E/V433R/I593E | 51.9 | 26.231 | 0.225 |
| MMLV-II Q68R/Q79R/L82R/L99R/E282D/Q299E/T332E/V433R/I593E | 53.8 | 28.556 | 0.142 |
| MMLV-II Q68R/Q79R/L82R/L99R/E282D/Q299E/T332E/V433R/I593E | 56.5 | 35.202 | 0.208 |
| MMLV-II Q68R/Q79R/L82R/L99R/E282D/Q299E/T332E/V433R/I593E | 59.9 | 36.991 | 0.419 |
| MMLV-II Q68R/Q79R/L82R/L99R/E282D/Q299E/T332E/V433R/I593E | 62.6 | 37.168 | 0.463 |
| MMLV-II Q68R/Q79R/L82R/L99R/E282D/Q299E/T332E/V433R/I593E | 64.2 | 37.670 | 0.410 |
| MMLV-II Q68R/Q79R/L82R/L99R/E282D/Q299E/T332E/V433R/I593E | 65.0 | 37.680 | 0.273 |

TABLE 26

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II | 37.0 | 26.365 | 0.066 |
| MMLV-II | 37.8 | 26.390 | 0.006 |
| MMLV-II | 39.5 | 25.939 | 0.016 |
| MMLV-II | 42.0 | 25.798 | 0.029 |
| MMLV-II | 45.2 | 25.849 | 0.064 |
| MMLV-II | 47.8 | 26.647 | 0.050 |
| MMLV-II | 49.2 | 28.326 | 0.028 |
| MMLV-II | 50.0 | 29.340 | 0.010 |
| MMLV-II | 51.0 | 30.684 | 0.099 |

TABLE 26-continued

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II | 51.9 | 32.462 | 0.163 |
| MMLV-II | 53.8 | 33.855 | 0.307 |
| MMLV-II | 56.5 | 35.376 | 0.461 |
| MMLV-II | 59.9 | 36.098 | 0.481 |
| MMLV-II | 62.6 | 36.391 | 0.367 |
| MMLV-II | 64.2 | 36.442 | 0.547 |
| MMLV-II | 65.0 | 35.871 | 0.301 |
| MMLV-II Q68R/Q79R/L99R/E282D | 37.0 | 25.699 | 0.009 |
| MMLV-II Q68R/Q79R/L99R/E282D | 37.8 | 25.674 | 0.038 |
| MMLV-II Q68R/Q79R/L99R/E282D | 39.5 | 25.594 | 0.029 |
| MMLV-II Q68R/Q79R/L99R/E282D | 42.0 | 25.496 | 0.016 |
| MMLV-II Q68R/Q79R/L99R/E282D | 45.2 | 25.431 | 0.011 |
| MMLV-II Q68R/Q79R/L99R/E282D | 47.8 | 25.420 | 0.036 |
| MMLV-II Q68R/Q79R/L99R/E282D | 49.2 | 25.481 | 0.023 |
| MMLV-II Q68R/Q79R/L99R/E282D | 50.0 | 25.646 | 0.035 |
| MMLV-II Q68R/Q79R/L99R/E282D | 51.0 | 25.979 | 0.012 |
| MMLV-II Q68R/Q79R/L99R/E282D | 51.9 | 26.591 | 0.053 |
| MMLV-II Q68R/Q79R/L99R/E282D | 53.8 | 28.345 | 0.091 |
| MMLV-II Q68R/Q79R/L99R/E282D | 56.5 | 32.976 | 0.109 |
| MMLV-II Q68R/Q79R/L99R/E282D | 59.9 | 34.407 | 0.158 |
| MMLV-II Q68R/Q79R/L99R/E282D | 62.6 | 35.130 | 0.014 |
| MMLV-II Q68R/Q79R/L99R/E282D | 64.2 | 34.866 | 0.258 |
| MMLV-II Q68R/Q79R/L99R/E282D | 65.0 | 35.317 | 0.299 |
| MMLV-II Q68R/Q79R/L99R/E282D/I593E | 37.0 | 26.079 | 0.036 |
| MMLV-II Q68R/Q79R/L99R/E282D/I593E | 37.8 | 25.951 | 0.015 |
| MMLV-II Q68R/Q79R/L99R/E282D/I593E | 39.5 | 25.801 | 0.055 |
| MMLV-II Q68R/Q79R/L99R/E282D/I593E | 42.0 | 25.602 | 0.087 |
| MMLV-II Q68R/Q79R/L99R/E282D/I593E | 45.2 | 25.424 | 0.038 |
| MMLV-II Q68R/Q79R/L99R/E282D/I593E | 47.8 | 25.520 | 0.011 |
| MMLV-II Q68R/Q79R/L99R/E282D/I593E | 49.2 | 25.674 | 0.046 |
| MMLV-II Q68R/Q79R/L99R/E282D/I593E | 50.0 | 25.922 | 0.015 |
| MMLV-II Q68R/Q79R/L99R/E282D/I593E | 51.0 | 26.351 | 0.014 |
| MMLV-II Q68R/Q79R/L99R/E282D/I593E | 51.9 | 27.411 | 0.092 |
| MMLV-II Q68R/Q79R/L99R/E282D/I593E | 53.8 | 30.482 | 0.048 |
| MMLV-II Q68R/Q79R/L99R/E282D/I593E | 56.5 | 33.914 | 0.075 |
| MMLV-II Q68R/Q79R/L99R/E282D/I593E | 59.9 | 35.443 | 0.191 |
| MMLV-II Q68R/Q79R/L99R/E282D/I593E | 62.6 | 35.872 | 0.445 |
| MMLV-II Q68R/Q79R/L99R/E282D/I593E | 64.2 | 36.107 | 0.011 |
| MMLV-II Q68R/Q79R/L99R/E282D/I593E | 65.0 | 35.715 | 0.299 |
| MMLV-II Q68R/Q79R/L99R/E282D/Q299E | 37.0 | 25.955 | 0.040 |
| MMLV-II Q68R/Q79R/L99R/E282D/Q299E | 37.8 | 25.934 | 0.023 |
| MMLV-II Q68R/Q79R/L99R/E282D/Q299E | 39.5 | 25.669 | 0.035 |
| MMLV-II Q68R/Q79R/L99R/E282D/Q299E | 42.0 | 25.523 | 0.016 |
| MMLV-II Q68R/Q79R/L99R/E282D/Q299E | 45.2 | 25.532 | 0.054 |
| MMLV-II Q68R/Q79R/L99R/E282D/Q299E | 47.8 | 25.550 | 0.021 |
| MMLV-II Q68R/Q79R/L99R/E282D/Q299E | 49.2 | 25.620 | 0.030 |
| MMLV-II Q68R/Q79R/L99R/E282D/Q299E | 50.0 | 25.711 | 0.035 |
| MMLV-II Q68R/Q79R/L99R/E282D/Q299E | 51.0 | 26.215 | 0.056 |
| MMLV-II Q68R/Q79R/L99R/E282D/Q299E | 51.9 | 26.969 | 0.013 |
| MMLV-II Q68R/Q79R/L99R/E282D/Q299E | 53.8 | 29.622 | 0.060 |
| MMLV-II Q68R/Q79R/L99R/E282D/Q299E | 56.5 | 33.679 | 0.234 |
| MMLV-II Q68R/Q79R/L99R/E282D/Q299E | 59.9 | 35.253 | 0.144 |
| MMLV-II Q68R/Q79R/L99R/E282D/Q299E | 62.6 | 35.408 | 0.441 |
| MMLV-II Q68R/Q79R/L99R/E282D/Q299E | 64.2 | 35.586 | 0.139 |
| MMLV-II Q68R/Q79R/L99R/E282D/Q299E | 65.0 | 36.076 | 0.700 |
| MMLV-II Q68R/Q79R/L82R/L99R/E282D | 37.0 | 25.884 | 0.012 |
| MMLV-II Q68R/Q79R/L82R/L99R/E282D | 37.8 | 25.833 | 0.009 |
| MMLV-II Q68R/Q79R/L82R/L99R/E282D | 39.5 | 25.684 | 0.077 |
| MMLV-II Q68R/Q79R/L82R/L99R/E282D | 42.0 | 25.553 | 0.026 |
| MMLV-II Q68R/Q79R/L82R/L99R/E282D | 45.2 | 25.471 | 0.043 |
| MMLV-II Q68R/Q79R/L82R/L99R/E282D | 47.8 | 25.491 | 0.085 |
| MMLV-II Q68R/Q79R/L82R/L99R/E282D | 49.2 | 25.646 | 0.014 |
| MMLV-II Q68R/Q79R/L82R/L99R/E282D | 50.0 | 25.765 | 0.039 |
| MMLV-II Q68R/Q79R/L82R/L99R/E282D | 51.0 | 26.365 | 0.044 |
| MMLV-II Q68R/Q79R/L82R/L99R/E282D | 51.9 | 27.170 | 0.071 |
| MMLV-II Q68R/Q79R/L82R/L99R/E282D | 53.8 | 29.662 | 0.048 |
| MMLV-II Q68R/Q79R/L82R/L99R/E282D | 56.5 | 33.853 | 0.162 |
| MMLV-II Q68R/Q79R/L82R/L99R/E282D | 59.9 | 34.899 | 0.325 |
| MMLV-II Q68R/Q79R/L82R/L99R/E282D | 62.6 | 35.557 | 0.145 |
| MMLV-II Q68R/Q79R/L82R/L99R/E282D | 64.2 | 35.360 | 0.222 |

TABLE 26-continued

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D | 65.0 | 35.614 | 0.403 |
| MMLV-II Q68R/Q79R/L99R/E282D/Q299E/V433R/I593E | 37.0 | 25.706 | 0.031 |
| MMLV-II Q68R/Q79R/L99R/E282D/Q299E/V433R/I593E | 37.8 | 25.757 | 0.101 |
| MMLV-II Q68R/Q79R/L99R/E282D/Q299E/V433R/I593E | 39.5 | 25.435 | 0.036 |
| MMLV-II Q68R/Q79R/L99R/E282D/Q299E/V433R/I593E | 42.0 | 25.417 | 0.025 |
| MMLV-II Q68R/Q79R/L99R/E282D/Q299E/V433R/I593E | 45.2 | 25.425 | 0.023 |
| MMLV-II Q68R/Q79R/L99R/E282D/Q299E/V433R/I593E | 47.8 | 25.401 | 0.049 |
| MMLV-II Q68R/Q79R/L99R/E282D/Q299E/V433R/I593E | 49.2 | 25.467 | 0.009 |
| MMLV-II Q68R/Q79R/L99R/E282D/Q299E/V433R/I593E | 50.0 | 25.516 | 0.056 |
| MMLV-II Q68R/Q79R/L99R/E282D/Q299E/V433R/I593E | 51.0 | 25.880 | 0.039 |
| MMLV-II Q68R/Q79R/L99R/E282D/Q299E/V433R/I593E | 51.9 | 26.348 | 0.064 |
| MMLV-II Q68R/Q79R/L99R/E282D/Q299E/V433R/I593E | 53.8 | 28.506 | 0.018 |
| MMLV-II Q68R/Q79R/L99R/E282D/Q299E/V433R/I593E | 56.5 | 32.812 | 0.242 |
| MMLV-II Q68R/Q79R/L99R/E282D/Q299E/V433R/I593E | 59.9 | 34.123 | 0.163 |
| MMLV-II Q68R/Q79R/L99R/E282D/Q299E/V433R/I593E | 62.6 | 35.108 | 0.027 |
| MMLV-II Q68R/Q79R/L99R/E282D/Q299E/V433R/I593E | 64.2 | 34.796 | 0.171 |
| MMLV-II Q68R/Q79R/L99R/E282D/Q299E/V433R/I593E | 65.0 | 34.999 | 0.064 |
| MMLV-II Q68R/Q79R/L82R/L99R/E282D/Q299E/V433R/I593E | 37.0 | 25.711 | 0.080 |
| MMLV-II Q68R/Q79R/L82R/L99R/E282D/Q299E/V433R/I593E | 37.8 | 25.916 | 0.224 |
| MMLV-II Q68R/Q79R/L82R/L99R/E282D/Q299E/V433R/I593E | 39.5 | 25.665 | 0.052 |
| MMLV-II Q68R/Q79R/L82R/L99R/E282D/Q299E/V433R/I593E | 42.0 | 25.527 | 0.016 |
| MMLV-II Q68R/Q79R/L82R/L99R/E282D/Q299E/V433R/I593E | 45.2 | 25.504 | 0.065 |
| MMLV-II Q68R/Q79R/L82R/L99R/E282D/Q299E/V433R/I593E | 47.8 | 25.437 | 0.070 |
| MMLV-II Q68R/Q79R/L82R/L99R/E282D/Q299E/V433R/I593E | 49.2 | 25.555 | 0.065 |
| MMLV-II Q68R/Q79R/L82R/L99R/E282D/Q299E/V433R/I593E | 50.0 | 25.571 | 0.028 |
| MMLV-II Q68R/Q79R/L82R/L99R/E282D/Q299E/V433R/I593E | 51.0 | 25.854 | 0.029 |
| MMLV-II Q68R/Q79R/L82R/L99R/E282D/Q299E/V433R/I593E | 51.9 | 26.259 | 0.057 |
| MMLV-II Q68R/Q79R/L82R/L99R/E282D/Q299E/V433R/I593E | 53.8 | 28.329 | 0.053 |
| MMLV-II Q68R/Q79R/L82R/L99R/E282D/Q299E/V433R/I593E | 56.5 | 32.962 | 0.212 |
| MMLV-II Q68R/Q79R/L82R/L99R/E282D/Q299E/V433R/I593E | 59.9 | 34.072 | 0.446 |
| MMLV-II Q68R/Q79R/L82R/L99R/E282D/Q299E/V433R/I593E | 62.6 | 34.931 | 0.205 |
| MMLV-II Q68R/Q79R/L82R/L99R/E282D/Q299E/V433R/I593E | 64.2 | 34.626 | 0.169 |
| MMLV-II Q68R/Q79R/L82R/L99R/E282D/Q299E/V433R/I593E | 65.0 | 35.085 | 0.230 |
| MMLV-II Q68R/Q79R/L82R/L99R/E282D/Q299E/T332E/I593E | 37.0 | 25.940 | 0.130 |
| MMLV-II Q68R/Q79R/L82R/L99R/E282D/Q299E/T332E/I593E | 37.8 | 25.793 | 0.129 |
| MMLV-II Q68R/Q79R/L82R/L99R/E282D/Q299E/T332E/I593E | 39.5 | 25.599 | 0.015 |

TABLE 26-continued

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/I593E | 42.0 | 25.504 | 0.016 |
| MMLV-II Q68R/Q79R/L82R/L99R/E282D/Q299E/T332E/I593E | 45.2 | 25.602 | 0.041 |
| MMLV-II Q68R/Q79R/L82R/L99R/E282D/Q299E/T332E/I593E | 47.8 | 25.604 | 0.058 |
| MMLV-II Q68R/Q79R/L82R/L99R/E282D/Q299E/T332E/I593E | 49.2 | 25.665 | 0.007 |
| MMLV-II Q68R/Q79R/L82R/L99R/E282D/Q299E/T332E/I593E | 50.0 | 25.821 | 0.068 |
| MMLV-II Q68R/Q79R/L82R/L99R/E282D/Q299E/T332E/I593E | 51.0 | 26.315 | 0.047 |
| MMLV-II Q68R/Q79R/L82R/L99R/E282D/Q299E/T332E/I593E | 51.9 | 27.036 | 0.059 |
| MMLV-II Q68R/Q79R/L82R/L99R/E282D/Q299E/T332E/I593E | 53.8 | 31.004 | 0.089 |
| MMLV-II Q68R/Q79R/L82R/L99R/E282D/Q299E/T332E/I593E | 56.5 | 33.765 | 0.274 |
| MMLV-II Q68R/Q79R/L82R/L99R/E282D/Q299E/T332E/I593E | 59.9 | 34.656 | 0.209 |
| MMLV-II Q68R/Q79R/L82R/L99R/E282D/Q299E/T332E/I593E | 62.6 | 35.561 | 0.468 |
| MMLV-II Q68R/Q79R/L82R/L99R/E282D/Q299E/T332E/I593E | 64.2 | 35.877 | 0.154 |
| MMLV-II Q68R/Q79R/L82R/L99R/E282D/Q299E/T332E/I593E | 65.0 | 35.659 | 0.477 |
| MMLV-II Q68R/Q79R/L82R/L99R/E282D/Q299E/T332E/V433R/I593E | 37.0 | 25.780 | 0.046 |
| MMLV-II Q68R/Q79R/L82R/L99R/E282D/Q299E/T332E/V433R/I593E | 37.8 | 25.652 | 0.026 |
| MMLV-II Q68R/Q79R/L82R/L99R/E282D/Q299E/T332E/V433R/I593E | 39.5 | 25.641 | 0.037 |
| MMLV-II Q68R/Q79R/L82R/L99R/E282D/Q299E/T332E/V433R/I593E | 42.0 | 25.507 | 0.005 |
| MMLV-II Q68R/Q79R/L82R/L99R/E282D/Q299E/T332E/V433R/I593E | 45.2 | 25.484 | 0.067 |
| MMLV-II Q68R/Q79R/L82R/L99R/E282D/Q299E/T332E/V433R/I593E | 47.8 | 25.438 | 0.027 |
| MMLV-II Q68R/Q79R/L82R/L99R/E282D/Q299E/T332E/V433R/I593E | 49.2 | 25.534 | 0.022 |
| MMLV-II Q68R/Q79R/L82R/L99R/E282D/Q299E/T332E/V433R/I593E | 50.0 | 25.755 | 0.085 |
| MMLV-II Q68R/Q79R/L82R/L99R/E282D/Q299E/T332E/V433R/I593E | 51.0 | 25.981 | 0.027 |
| MMLV-II Q68R/Q79R/L82R/L99R/E282D/Q299E/T332E/V433R/I593E | 51.9 | 26.242 | 0.052 |
| MMLV-II Q68R/Q79R/L82R/L99R/E282D/Q299E/T332E/V433R/I593E | 53.8 | 29.146 | 0.069 |
| MMLV-II Q68R/Q79R/L82R/L99R/E282D/Q299E/T332E/V433R/I593E | 56.5 | 33.138 | 0.159 |
| MMLV-II Q68R/Q79R/L82R/L99R/E282D/Q299E/T332E/V433R/I593E | 59.9 | 34.551 | 0.152 |
| MMLV-II Q68R/Q79R/L82R/L99R/E282D/Q299E/T332E/V433R/I593E | 62.6 | 35.186 | 0.322 |
| MMLV-II Q68R/Q79R/L82R/L99R/E282D/Q299E/T332E/V433R/I593E | 64.2 | 35.550 | 0.368 |

TABLE 26-continued

Two-Step cDNA synthesis by MMLV RT quadruple and more mutants by Random priming. Data was generated via qPCR human normalizer assay and data is reported by Ct value.

| MMLV RT Mutant | Temperature of Reaction (° C.) | Ct Mean | Ct SD |
|---|---|---|---|
| MMLV-II Q68R/Q79R/L82R/L99R/E282D/Q299E/T332E/V433R/I593E | 65.0 | 35.459 | 0.295 |

Example 9: Extension of Reverse Transcriptase Single Mutants

The amino acid positions that enclosed the MMLV RTase single mutants identified in Examples 6 and 7 were further evaluated to include all possible amino acid substitutions at that position. The single mutants were cloned, overexpressed, and purified as described in Examples 1 and 2, and evaluated as described in Examples 6 and 7. The two-step and one-step reactions for MMLV RTase base construct and MMLV RTase double mutant variants were analyzed and reported by Ct output from the qPCR (Tables 27-29). Numerous single mutant MMLV RTase variants were found to exhibit an increase in the overall activity and thermostability as compared to the MMLV RTase base construct. The most prevalent among these were: L82F, L82K, L82T, L82Y, L2801, T332V, V433K, V433N and I593W.

TABLE 27

Two-Step cDNA Synthesis by MMLV-RT single mutants using Oligo-dT priming. The data was generated via qPCR human normalizer assay and data is reported by Ct value.

| MMLV-RT Variant | Ct Mean | Ct Standard Deviation |
|---|---|---|
| MMLV-II | 40.000 | 0.000 |
| MMLV-II I593A | 40.000 | 0.000 |
| MMLV-II I593C | 37.874 | 0.991 |
| MMLV-II I593D | 40.000 | 0.000 |
| MMLV-II I593E | 40.000 | 0.000 |
| MMLV-II I593F | 40.000 | 0.000 |
| MMLV-II I593G | 39.748 | 0.356 |
| MMLV-II I593H | 39.502 | 0.704 |
| MMLV-II I593K | 40.000 | 0.000 |
| MMLV-II I593L | 38.994 | 1.423 |
| MMLV-II I593M | 39.383 | 0.873 |
| MMLV-II I593N | 40.000 | 0.000 |
| MMLV-II I593P | 40.000 | 0.000 |
| MMLV-II I593Q | 40.000 | 0.000 |
| MMLV-II I593R | 40.000 | 0.000 |
| MMLV-II I593S | 39.614 | 0.545 |
| MMLV-II I593T | 37.709 | 0.520 |
| MMLV-II I593V | 40.000 | 0.000 |
| MMLV-II I593W | 30.504 | 0.073 |
| MMLV-II I593Y | 40.000 | 0.000 |
| MMLV-II L280A | 40.000 | 0.000 |
| MMLV-II L280C | 40.000 | 0.000 |
| MMLV-II L280D | 40.000 | 0.000 |
| MMLV-II L280E | 40.000 | 0.000 |
| MMLV-II L280F | 40.000 | 0.000 |
| MMLV-II L280G | 40.000 | 0.000 |
| MMLV-II L280H | 40.000 | 0.000 |
| MMLV-II L280I | 30.951 | 0.076 |
| MMLV-II L280K | 40.000 | 0.000 |
| MMLV-II L280M | 40.000 | 0.000 |
| MMLV-II L280N | 39.727 | 0.386 |
| MMLV-II L280P | 40.000 | 0.000 |
| MMLV-II L280Q | 40.000 | 0.000 |
| MMLV-II L280R | 39.994 | 0.009 |

TABLE 27-continued

Two-Step cDNA Synthesis by MMLV-RT single mutants using Oligo-dT priming. The data was generated via qPCR human normalizer assay and data is reported by Ct value.

| MMLV-RT Variant | Ct Mean | Ct Standard Deviation |
|---|---|---|
| MMLV-II L280S | 40.000 | 0.000 |
| MMLV-II L280T | 40.000 | 0.000 |
| MMLV-II L280V | 37.749 | 0.142 |
| MMLV-II L280W | 40.000 | 0.000 |
| MMLV-II L280Y | 40.000 | 0.000 |
| MMLV-II L82A | 40.000 | 0.000 |
| MMLV-II L82C | 39.565 | 0.615 |
| MMLV-II L82D | 40.000 | 0.000 |
| MMLV-II L82E | 40.000 | 0.000 |
| MMLV-II L82F | 39.347 | 0.924 |
| MMLV-II L82G | 40.000 | 0.000 |
| MMLV-II L82H | 40.000 | 0.000 |
| MMLV-II L82I | 40.000 | 0.000 |
| MMLV-II L82K | 37.136 | 0.593 |
| MMLV-II L82M | 38.649 | 1.260 |
| MMLV-II L82N | 40.000 | 0.000 |
| MMLV-II L82P | 40.000 | 0.000 |
| MMLV-II L82Q | 39.098 | 1.275 |
| MMLV-II L82R | 40.000 | 0.000 |
| MMLV-II L82S | 39.346 | 0.925 |
| MMLV-II L82T | 38.695 | 1.845 |
| MMLV-II L82V | 38.047 | 1.381 |
| MMLV-II L82W | 37.151 | 0.308 |
| MMLV-II L82Y | 35.014 | 0.421 |
| MMLV-II Q299A | 40.000 | 0.000 |
| MMLV-II Q299C | 40.000 | 0.000 |
| MMLV-II Q299D | 40.000 | 0.000 |
| MMLV-II Q299E | 39.061 | 1.328 |
| MMLV-II Q299F | 40.000 | 0.000 |
| MMLV-II Q299G | 40.000 | 0.000 |
| MMLV-II Q299H | 39.398 | 0.852 |
| MMLV-II Q299I | 39.183 | 1.155 |
| MMLV-II Q299K | 40.000 | 0.000 |
| MMLV-II Q299L | 39.474 | 0.743 |
| MMLV-II Q299M | 40.000 | 0.000 |
| MMLV-II Q299N | 40.000 | 0.000 |
| MMLV-II Q299P | 40.000 | 0.000 |
| MMLV-II Q299R | 40.000 | 0.000 |
| MMLV-II Q299S | 40.000 | 0.000 |
| MMLV-II Q299T | 40.000 | 0.000 |
| MMLV-II Q299V | 40.000 | 0.000 |
| MMLV-II Q299W | 40.000 | 0.000 |
| MMLV-II Q299Y | 40.000 | 0.000 |
| MMLV-II T332A | 39.087 | 1.291 |
| MMLV-II T332C | 38.956 | 1.476 |
| MMLV-II T332D | 40.000 | 0.000 |
| MMLV-II T332E | 39.554 | 0.631 |
| MMLV-II T332F | 40.000 | 0.000 |
| MMLV-II T332G | 37.321 | 2.009 |
| MMLV-II T332H | 39.215 | 1.110 |
| MMLV-II T332I | 39.344 | 0.927 |
| MMLV-II T332K | 40.000 | 0.000 |
| MMLV-II T332L | 40.000 | 0.000 |
| MMLV-II T332M | 37.775 | 1.632 |
| MMLV-II T332N | 37.326 | 0.834 |
| MMLV-II T332P | 40.000 | 0.000 |

TABLE 27-continued

Two-Step cDNA Synthesis by MMLV-RT single mutants using Oligo-dT priming. The data was generated via qPCR human normalizer assay and data is reported by Ct value.

| MMLV-RT Variant | Ct Mean | Ct Standard Deviation |
|---|---|---|
| MMLV-II T332Q | 39.509 | 0.694 |
| MMLV-II T332R | 39.588 | 0.582 |
| MMLV-II T332S | 39.765 | 0.332 |
| MMLV-II T332V | 36.977 | 0.384 |
| MMLV-II T332W | 40.000 | 0.000 |
| MMLV-II T332Y | 40.000 | 0.000 |
| MMLV-II V433A | 40.000 | 0.000 |
| MMLV-II V433C | 37.504 | 0.682 |
| MMLV-II V433D | 40.000 | 0.000 |
| MMLV-II V433E | 35.189 | 0.336 |
| MMLV-II V433F | 39.379 | 0.878 |
| MMLV-II V433G | 39.482 | 0.732 |
| MMLV-II V433H | 40.000 | 0.000 |
| MMLV-II V433I | 39.781 | 0.310 |
| MMLV-II V433K | 35.770 | 0.623 |
| MMLV-II V433L | 39.015 | 0.744 |
| MMLV-II V433M | 39.119 | 1.247 |
| MMLV-II V433N | 33.981 | 0.185 |
| MMLV-II V433P | 40.000 | 0.000 |
| MMLV-II V433Q | 40.000 | 0.000 |
| MMLV-II V433R | 37.230 | 1.247 |
| MMLV-II V433S | 37.850 | 0.846 |
| MMLV-II V433T | 37.564 | 1.895 |
| MMLV-II V433W | 37.770 | 1.622 |
| MMLV-II V433Y | 40.000 | 0.000 |
| MMLV-IV | 26.102 | 0.033 |

TABLE 28

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II | 40.000 | 0.000 |
| MMLV-II I593A | 40.000 | 0.000 |
| MMLV-II I593C | 40.000 | 0.000 |
| MMLV-II I593D | 39.992 | 0.012 |
| MMLV-II I593E | 40.000 | 0.000 |
| MMLV-II I593F | 39.189 | 1.147 |
| MMLV-II I593G | 40.000 | 0.000 |
| MMLV-II I593H | 40.000 | 0.000 |
| MMLV-II I593K | 40.000 | 0.000 |
| MMLV-II I593L | 40.000 | 0.000 |
| MMLV-II I593M | 40.000 | 0.000 |
| MMLV-II I593N | 40.000 | 0.000 |
| MMLV-II I593P | 40.000 | 0.000 |
| MMLV-II I593Q | 39.201 | 0.853 |
| MMLV-II I593R | 38.928 | 1.516 |
| MMLV-II I593S | 39.025 | 1.379 |
| MMLV-II I593T | 38.385 | 1.227 |
| MMLV-II I593V | 39.574 | 0.603 |
| MMLV-II I593W | 32.572 | 0.054 |
| MMLV-II I593Y | 40.000 | 0.000 |
| MMLV-II L280A | 40.000 | 0.000 |
| MMLV-II L280C | 40.000 | 0.000 |
| MMLV-II L280D | 40.000 | 0.000 |
| MMLV-II L280E | 40.000 | 0.000 |
| MMLV-II L280F | 40.000 | 0.000 |
| MMLV-II L280G | 40.000 | 0.000 |
| MMLV-II L280H | 40.000 | 0.000 |
| MMLV-II L280I | 34.152 | 0.276 |
| MMLV-II L280K | 40.000 | 0.000 |
| MMLV-II L280M | 39.973 | 0.038 |
| MMLV-II L280N | 40.000 | 0.000 |
| MMLV-II L280P | 40.000 | 0.000 |
| MMLV-II L280Q | 40.000 | 0.000 |
| MMLV-II L280R | 40.000 | 0.000 |

TABLE 28-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II L280S | 40.000 | 0.000 |
| MMLV-II L280T | 40.000 | 0.000 |
| MMLV-II L280V | 39.260 | 1.046 |
| MMLV-II L280W | 40.000 | 0.000 |
| MMLV-II L280Y | 40.000 | 0.000 |
| MMLV-II L82A | 40.000 | 0.000 |
| MMLV-II L82C | 40.000 | 0.000 |
| MMLV-II L82D | 40.000 | 0.000 |
| MMLV-II L82E | 39.672 | 0.463 |
| MMLV-II L82F | 36.854 | 0.708 |
| MMLV-II L82G | 40.000 | 0.000 |
| MMLV-II L82H | 37.705 | 0.557 |
| MMLV-II L82I | 39.231 | 1.087 |
| MMLV-II L82K | 39.437 | 0.443 |
| MMLV-II L82M | 40.000 | 0.000 |
| MMLV-II L82N | 40.000 | 0.000 |
| MMLV-II L82P | 40.000 | 0.000 |
| MMLV-II L82Q | 40.000 | 0.000 |
| MMLV-II L82R | 38.595 | 1.191 |
| MMLV-II L82S | 40.000 | 0.000 |
| MMLV-II L82T | 38.449 | 1.192 |
| MMLV-II L82V | 39.438 | 0.795 |
| MMLV-II L82W | 39.178 | 1.163 |
| MMLV-II L82Y | 36.758 | 0.962 |
| MMLV-II Q299A | 40.000 | 0.000 |
| MMLV-II Q299C | 40.000 | 0.000 |
| MMLV-II Q299D | 38.003 | 1.414 |
| MMLV-II Q299E | 39.338 | 0.936 |
| MMLV-II Q299F | 40.000 | 0.000 |
| MMLV-II Q299G | 40.000 | 0.000 |
| MMLV-II Q299H | 40.000 | 0.000 |
| MMLV-II Q299I | 39.850 | 0.212 |
| MMLV-II Q299K | 40.000 | 0.000 |
| MMLV-II Q299L | 40.000 | 0.000 |
| MMLV-II Q299M | 40.000 | 0.000 |
| MMLV-II Q299N | 40.000 | 0.000 |
| MMLV-II Q299P | 40.000 | 0.000 |
| MMLV-II Q299R | 40.000 | 0.000 |
| MMLV-II Q299S | 40.000 | 0.000 |
| MMLV-II Q299T | 40.000 | 0.000 |
| MMLV-II Q299V | 40.000 | 0.000 |
| MMLV-II Q299W | 40.000 | 0.000 |
| MMLV-II Q299Y | 40.000 | 0.000 |
| MMLV-II T332A | 39.814 | 0.264 |
| MMLV-II T332C | 40.000 | 0.000 |
| MMLV-II T332D | 40.000 | 0.000 |
| MMLV-II T332E | 40.000 | 0.000 |
| MMLV-II T332F | 40.000 | 0.000 |
| MMLV-II T332G | 38.897 | 1.560 |
| MMLV-II T332H | 40.000 | 0.000 |
| MMLV-II T332I | 40.000 | 0.000 |
| MMLV-II T332K | 40.000 | 0.000 |
| MMLV-II T332L | 38.169 | 2.589 |
| MMLV-II T332M | 37.410 | 1.906 |
| MMLV-II T332N | 38.983 | 1.362 |
| MMLV-II T332P | 39.046 | 1.350 |
| MMLV-II T332Q | 40.000 | 0.000 |
| MMLV-II T332R | 40.000 | 0.000 |
| MMLV-II T332S | 40.000 | 0.000 |
| MMLV-II T332V | 38.650 | 1.326 |
| MMLV-II T332W | 40.000 | 0.000 |
| MMLV-II T332Y | 40.000 | 0.000 |
| MMLV-II V433A | 40.000 | 0.000 |
| MMLV-II V433C | 37.605 | 0.184 |
| MMLV-II V433D | 40.000 | 0.000 |
| MMLV-II V433E | 34.693 | 0.193 |
| MMLV-II V433F | 40.000 | 0.000 |
| MMLV-II V433G | 40.000 | 0.000 |
| MMLV-II V433H | 40.000 | 0.000 |
| MMLV-II V433I | 39.792 | 0.294 |
| MMLV-II V433K | 35.725 | 0.464 |
| MMLV-II V433L | 40.000 | 0.000 |
| MMLV-II V433M | 40.000 | 0.000 |

TABLE 28-continued

Two-Step cDNA Synthesis by MMLV-RT single mutants using random priming. The data was generated via qPCR human normalizer assay and data is reported by Ct value.

| MMLV-RT Variant | Ct Mean | Ct Standard Deviation |
|---|---|---|
| MMLV-II V433N | 34.604 | 0.554 |
| MMLV-II V433P | 40.000 | 0.000 |
| MMLV-II V433Q | 38.844 | 1.001 |
| MMLV-II V433R | 38.817 | 0.839 |
| MMLV-II V433S | 38.202 | 1.372 |
| MMLV-II V433T | 37.573 | 0.623 |
| MMLV-II V433W | 37.611 | 1.690 |
| MMLV-II V433Y | 40.000 | 0.000 |
| MMLV-IV | 26.053 | 0.098 |

TABLE 29

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II | 32.775 | 0.189 |
| MMLV-II I593A | 32.438 | 0.209 |
| MMLV-II I593C | 32.680 | 0.053 |
| MMLV-II I593D | 31.775 | 0.237 |
| MMLV-II I593E | 30.635 | 0.048 |
| MMLV-II I593F | 30.411 | 0.008 |
| MMLV-II I593G | 30.904 | 0.098 |
| MMLV-II I593H | 29.686 | 0.131 |
| MMLV-II I593K | 31.832 | 0.259 |
| MMLV-II I593L | 32.289 | 0.273 |
| MMLV-II I593M | 32.162 | 0.078 |
| MMLV-II I593N | 31.410 | 0.251 |
| MMLV-II I593P | 34.728 | 0.201 |
| MMLV-II I593Q | 31.609 | 0.032 |
| MMLV-II I593R | 31.144 | 0.133 |
| MMLV-II I593S | 30.548 | 0.247 |
| MMLV-II I593T | 29.572 | 0.236 |
| MMLV-II I593V | 30.673 | 0.142 |
| MMLV-II I593W | 28.179 | 0.092 |
| MMLV-II I593Y | 30.858 | 0.067 |
| MMLV-II L280A | 36.160 | 0.729 |
| MMLV-II L280C | 32.097 | 0.261 |
| MMLV-II L280D | 40.000 | 0.000 |
| MMLV-II L280E | 39.115 | 1.251 |
| MMLV-II L280F | 34.573 | 0.371 |
| MMLV-II L280G | 40.000 | 0.000 |
| MMLV-II L280H | 37.255 | 0.322 |
| MMLV-II L280I | 29.267 | 1.032 |
| MMLV-II L280K | 34.274 | 0.095 |
| MMLV-II L280M | 32.746 | 0.223 |
| MMLV-II L280N | 39.677 | 0.457 |
| MMLV-II L280P | 33.045 | 0.095 |
| MMLV-II L280Q | 39.190 | 1.145 |
| MMLV-II L280R | 40.000 | 0.000 |
| MMLV-II L280S | 40.000 | 0.000 |
| MMLV-II L280T | 37.074 | 0.325 |
| MMLV-II L280V | 30.461 | 0.052 |
| MMLV-II L280W | 40.000 | 0.000 |
| MMLV-II L280Y | 40.000 | 0.000 |
| MMLV-II L82A | 31.729 | 0.308 |
| MMLV-II L82C | 31.131 | 0.192 |
| MMLV-II L82D | 34.280 | 0.227 |
| MMLV-II L82E | 32.973 | 0.430 |
| MMLV-II L82F | 29.760 | 0.030 |
| MMLV-II L82G | 33.066 | 0.217 |
| MMLV-II L82H | 30.098 | 0.078 |
| MMLV-II L82I | 31.605 | 0.083 |
| MMLV-II L82K | 29.258 | 0.015 |
| MMLV-II L82M | 30.280 | 0.027 |
| MMLV-II L82N | 33.074 | 0.323 |
| MMLV-II L82P | 38.754 | 1.762 |

TABLE 29-continued

One-Step cDNA Synthesis by MMLV-RT single mutants by gene specific priming. The data was generated via qPCR human normalizer assay and data is reported by Ct value.

| MMLV-RT Variant | Ct Mean | Ct Standard Deviation |
|---|---|---|
| MMLV-II L82Q | 32.001 | 0.164 |
| MMLV-II L82R | 30.208 | 0.128 |
| MMLV-II L82S | 31.841 | 0.231 |
| MMLV-II L82T | 28.908 | 0.044 |
| MMLV-II L82V | 29.533 | 0.057 |
| MMLV-II L82W | 29.580 | 0.056 |
| MMLV-II L82Y | 28.934 | 0.073 |
| MMLV-II Q299A | 31.113 | 0.138 |
| MMLV-II Q299C | 35.953 | 0.542 |
| MMLV-II Q299D | 32.292 | 0.080 |
| MMLV-II Q299E | 31.663 | 0.027 |
| MMLV-II Q299F | 36.143 | 0.317 |
| MMLV-II Q299G | 31.929 | 0.131 |
| MMLV-II Q299H | 32.387 | 0.133 |
| MMLV-II Q299I | 37.763 | 1.582 |
| MMLV-II Q299K | 32.326 | 0.096 |
| MMLV-II Q299L | 34.807 | 0.180 |
| MMLV-II Q299M | 32.514 | 0.375 |
| MMLV-II Q299N | 34.040 | 0.186 |
| MMLV-II Q299P | 39.460 | 0.764 |
| MMLV-II Q299R | 33.044 | 0.354 |
| MMLV-II Q299S | 33.438 | 0.256 |
| MMLV-II Q299T | 35.093 | 0.926 |
| MMLV-II Q299V | 35.114 | 1.045 |
| MMLV-II Q299W | 38.998 | 1.417 |
| MMLV-II Q299Y | 39.055 | 1.336 |
| MMLV-II T332A | 30.528 | 0.084 |
| MMLV-II T332C | 30.785 | 0.135 |
| MMLV-II T332D | 33.310 | 0.348 |
| MMLV-II T332E | 32.711 | 0.106 |
| MMLV-II T332F | 33.201 | 0.179 |
| MMLV-II T332G | 30.424 | 0.054 |
| MMLV-II T332H | 31.913 | 0.306 |
| MMLV-II T332I | 32.072 | 0.115 |
| MMLV-II T332K | 31.591 | 0.082 |
| MMLV-II T332L | 34.011 | 0.133 |
| MMLV-II T332M | 29.039 | 0.164 |
| MMLV-II T332N | 29.500 | 0.135 |
| MMLV-II T332P | 33.976 | 0.272 |
| MMLV-II T332Q | 31.599 | 0.041 |
| MMLV-II T332R | 32.950 | 0.130 |
| MMLV-II T332S | 31.003 | 0.341 |
| MMLV-II T332V | 29.835 | 0.061 |
| MMLV-II T332W | 35.431 | 0.099 |
| MMLV-II T332Y | 33.384 | 0.164 |
| MMLV-II V433A | 30.757 | 0.105 |
| MMLV-II V433C | 29.901 | 0.305 |
| MMLV-II V433D | 34.152 | 0.170 |
| MMLV-II V433E | 28.868 | 0.011 |
| MMLV-II V433F | 31.529 | 0.009 |
| MMLV-II V433G | 33.663 | 0.412 |
| MMLV-II V433H | 31.811 | 0.069 |
| MMLV-II V433I | 30.460 | 0.071 |
| MMLV-II V433K | 30.040 | 0.109 |
| MMLV-II V433L | 31.758 | 0.063 |
| MMLV-II V433M | 30.791 | 0.095 |
| MMLV-II V433N | 28.566 | 0.074 |
| MMLV-II V433P | 37.436 | 1.824 |
| MMLV-II V433Q | 30.586 | 0.104 |
| MMLV-II V433R | 30.773 | 0.080 |
| MMLV-II V433S | 29.768 | 0.074 |
| MMLV-II V433T | 29.096 | 0.107 |
| MMLV-II V433W | 29.130 | 0.064 |
| MMLV-II V433Y | 32.676 | 0.279 |
| MMLV-IV | 25.979 | 0.043 |

TABLE 30

Two-Step cDNA Synthesis by MMLV-RT stacked mutants using oligo dT priming. The data was generated via qPCR human normalizer assay and data is reported by Ct value.

| MMLV-RT Variant | Temperature (° C.) | Ct Mean | Ct Standard Deviation |
|---|---|---|---|
| MMLV-II | 42 | 25.207 | 0.025 |
| MMLV-II | 55 | 28.180 | 0.022 |
| MMLV-II | 42 | 25.287 | 0.068 |
| Q68R/Q79R/L99R/E282D | 55 | 26.442 | 0.044 |
| MMLV-II | 42 | 25.344 | 0.065 |
| Q68R/Q79R/L99R/E282D/V433R | 55 | 26.586 | 0.077 |
| MMLV-II | 42 | 25.266 | 0.112 |
| Q68R/Q79R/L99R/E282D/I593E | 55 | 27.389 | 0.069 |
| MMLV-II | 42 | 25.357 | 0.087 |
| Q68R/Q79R/L99R/E282D/Q299E | 55 | 26.953 | 0.034 |
| MMLV-II | 42 | 25.394 | 0.011 |
| Q68R/Q79R/L82R/L99R/E282D | 55 | 27.171 | 0.028 |
| MMLV-II | 42 | 25.371 | 0.061 |
| Q68R/Q79R/L99R/E282D/Q299E/I593E | 55 | 26.689 | 0.068 |
| MMLV-II | 42 | 25.258 | 0.035 |
| Q68R/Q79R/L82R/L99R/E282D/Q299E/I593E | 55 | 26.979 | 0.034 |
| MMLV-II | 42 | 25.171 | 0.006 |
| Q68R/Q79R/L99R/E282D/Q299E/V433R/I593E | 55 | 26.299 | 0.025 |
| MMLV-II | 42 | 25.146 | 0.052 |
| Q68R/Q79R/L82R/L99R/E282D/Q299E/V433R/I593E | 55 | 26.320 | 0.036 |
| MMLV-II | 42 | 25.176 | 0.044 |
| Q68R/Q79R/L82R/L99R/E282D/Q299E/T332E/I593E | 55 | 26.750 | 0.040 |
| MMLV-II | 42 | 25.110 | 0.046 |
| Q68R/Q79R/L82R/L99R/E282D/Q299E/T332E/V433R/I593E | 55 | 26.587 | 0.049 |
| MMLV-IV | 42 | 25.184 | 0.025 |
| MMLV-IV | 55 | 25.153 | 0.037 |
| SuperScript-IV | 42 | 25.082 | 0.073 |
| SuperScript-IV | 55 | 25.080 | 0.047 |

TABLE 31

Two-Step cDNA Synthesis by MMLV-RT stacked mutants using random priming. The data was generated via qPCR human normalizer assay and data is reported by Ct value.

| MMLV-RT Variant | Temperature (C) | Ct Mean | Ct Standard Deviation |
|---|---|---|---|
| MMLV-II | 42 | 25.264 | 0.019 |
| MMLV-II | 55 | 28.443 | 0.014 |
| MMLV-II Q68R/Q79R/L99R/E282D | 42 | 25.399 | 0.040 |
| | 55 | 26.484 | 0.072 |
| MMLV-II Q68R/Q79R/L99R/E282D/V433R | 42 | 25.324 | 0.063 |
| | 55 | 26.794 | 0.065 |
| MMLV-II Q68R/Q79R/L99R/E282D/I593E | 42 | 25.278 | 0.025 |
| | 55 | 27.616 | 0.058 |
| MMLV-II Q68R/Q79R/L99R/E282D/Q299E | 42 | 25.281 | 0.079 |
| | 55 | 27.148 | 0.025 |
| MMLV-II Q68R/Q79R/L82R/L99R/E282D | 42 | 25.279 | 0.053 |
| | 55 | 27.243 | 0.008 |
| MMLV-II Q68R/Q79R/L99R/E282D/Q299E/I593E | 42 | 25.409 | 0.065 |
| | 55 | 26.704 | 0.066 |
| MMLV-II | 42 | 25.581 | 0.062 |
| Q68R/Q79R/L82R/L99R/E282D/Q299E/I593E | 55 | 26.605 | 0.028 |
| MMLV-II | 42 | 25.355 | 0.158 |
| Q68R/Q79R/L99R/E282D/Q299E/V433R/I593E | 55 | 26.305 | 0.066 |
| MMLV-II | 42 | 25.418 | 0.120 |
| Q68R/Q79R/L82R/L99R/E282D/Q299E/V433R/I593E | 55 | 26.403 | 0.055 |
| MMLV-II | 42 | 25.374 | 0.115 |
| Q68R/Q79R/L82R/L99R/E282D/Q299E/T332E/I593E | 55 | 26.747 | 0.065 |
| MMLV-II | 42 | 25.426 | 0.082 |
| Q68R/Q79R/L82R/L99R/E282D/Q299E/T332E/V433R/I593E | 55 | 26.481 | 0.017 |
| MMLV-IV | 42 | 25.394 | 0.162 |
| MMLV-IV | 55 | 25.185 | 0.022 |
| SuperScript-IV | 42 | 25.299 | 0.132 |
| SuperScript-IV | 55 | 25.214 | 0.021 |

TABLE 32

One-Step cDNA Synthesis by MMLV-RT stacked mutants by gene specific priming. The data was generated via qPCR human normalizer assay and data is reported by Ct value.

| MMLV-RT Variant | Temperature (° C.) | Concentration of RT (nM) | Ct Mean | Ct Standard Deviation |
|---|---|---|---|---|
| MMLV-II | 50 | 0.28 | 26.401 | 0.022 |
| | | 1.4 | 24.701 | 0.061 |
| | | 7.0 | 24.664 | 0.007 |
| | 60 | 0.28 | 31.134 | 0.205 |
| | | 1.4 | 28.109 | 0.042 |
| | | 7.0 | 27.644 | 0.061 |
| MMLV-II Q68R/Q79R/L99R/E282D | 50 | 0.28 | 25.171 | 0.046 |
| | | 1.4 | 24.440 | 0.037 |
| | | 7.0 | 24.406 | 0.010 |
| | 60 | 0.28 | 28.848 | 0.114 |
| | | 1.4 | 25.905 | 0.066 |
| | | 7.0 | 25.618 | 0.057 |
| MMLV-II Q68R/Q79R/L99R/E282D/V433R | 50 | 0.28 | 24.967 | 0.068 |
| | | 1.4 | 24.386 | 0.015 |
| | | 7.0 | 24.433 | 0.079 |
| | 60 | 0.28 | 28.516 | 0.051 |
| | | 1.4 | 25.803 | 0.063 |
| | | 7.0 | 25.620 | 0.035 |
| MMLV-II Q68R/Q79R/L99R/E282D/I593E | 50 | 0.28 | 24.660 | 0.053 |
| | | 1.4 | 24.377 | 0.028 |
| | | 7.0 | 24.355 | 0.021 |
| | 60 | 0.28 | 27.488 | 0.074 |
| | | 1.4 | 25.413 | 0.049 |
| | | 7.0 | 25.209 | 0.136 |
| MMLV-II Q68R/Q79R/L99R/E282D/Q299E | 50 | 0.28 | 25.044 | 0.094 |
| | | 1.4 | 24.422 | 0.023 |
| | | 7.0 | 24.528 | 0.055 |
| | 60 | 0.28 | 28.818 | 0.137 |
| | | 1.4 | 25.953 | 0.082 |
| | | 7.0 | 25.754 | 0.098 |
| MMLV-II Q68R/Q79R/L82R/L99R/E282D | 50 | 0.28 | 25.014 | 0.152 |
| | | 1.4 | 24.467 | 0.020 |
| | | 7.0 | 24.507 | 0.046 |
| | 60 | 0.28 | 28.743 | 0.076 |
| | | 1.4 | 26.662 | 0.012 |
| | | 7.0 | 25.883 | 0.022 |
| MMLV-II Q68R/Q79R/L99R/E282D/Q299E/I593E | 50 | 0.28 | 24.771 | 0.027 |
| | | 1.4 | 24.501 | 0.008 |
| | | 7.0 | 24.485 | 0.087 |
| | 60 | 0.28 | 27.721 | 0.057 |
| | | 1.4 | 25.836 | 0.030 |
| | | 7.0 | 25.199 | 0.016 |
| MMLV-II Q68R/Q79R/L82R/L99R/E282D/Q299E/I593E | 50 | 0.28 | 24.777 | 0.029 |
| | | 1.4 | 24.432 | 0.033 |
| | | 7.0 | 24.435 | 0.024 |
| | 60 | 0.28 | 27.854 | 0.035 |
| | | 1.4 | 25.613 | 0.028 |
| | | 7.0 | 25.072 | 0.030 |
| MMLV-II Q68R/Q79R/L99R/E282D/Q299E/V433R/I593E | 50 | 0.28 | 24.550 | 0.003 |
| | | 1.4 | 24.333 | 0.033 |
| | | 7.0 | 24.345 | 0.030 |
| | 60 | 0.28 | 26.399 | 0.051 |
| | | 1.4 | 25.236 | 0.040 |
| | | 7.0 | 25.105 | 0.050 |
| MMLV-II Q68R/Q79R/L82R/L99R/E282D/Q299E/V433R/I593E | 50 | 0.28 | 24.562 | 0.047 |
| | | 1.4 | 24.350 | 0.039 |
| | | 7.0 | 24.302 | 0.015 |
| | 60 | 0.28 | 26.459 | 0.022 |
| | | 1.4 | 25.247 | 0.069 |
| | | 7.0 | 25.001 | 0.050 |
| MMLV-II Q68R/Q79R/L82R/L99R/E282D/Q299E/T332E/I593E | 50 | 0.28 | 24.614 | 0.047 |
| | | 1.4 | 24.420 | 0.051 |
| | | 7.0 | 24.361 | 0.021 |
| | 60 | 0.28 | 26.769 | 0.089 |
| | | 1.4 | 25.609 | 0.041 |
| | | 7.0 | 25.348 | 0.043 |
| MMLV-II Q68R/Q79R/L82R/L99R/E282D/Q299E/T332E/V433R/I593E | 50 | 0.28 | 24.594 | 0.075 |
| | | 1.4 | 24.402 | 0.045 |
| | | 7.0 | 24.291 | 0.057 |
| | 60 | 0.28 | 26.591 | 0.018 |
| | | 1.4 | 25.517 | 0.048 |
| | | 7.0 | 25.193 | 0.027 |

TABLE 32-continued

One-Step cDNA Synthesis by MMLV-RT stacked mutants by gene specific priming. The data was generated via qPCR human normalizer assay and data is reported by Ct value.

| MMLV-RT Variant | Temperature (° C.) | Concentration of RT (nM) | Ct Mean | Ct Standard Deviation |
|---|---|---|---|---|
| MMLV-IV | 50 | 0.28 | 24.397 | 0.091 |
| | | 1.4 | 24.303 | 0.062 |
| | | 7.0 | 24.189 | 0.039 |
| | 60 | 0.28 | 25.807 | 0.045 |
| | | 1.4 | 25.180 | 0.037 |
| | | 7.0 | 24.625 | 0.011 |
| SuperScript-IV | 50 | 0.28 | 24.743 | 0.049 |
| | | 1.4 | 24.213 | 0.017 |
| | | 7.0 | 24.008 | 0.036 |
| | 60 | 0.28 | 26.124 | 0.103 |
| | | 1.4 | 24.681 | 0.070 |
| | | 7.0 | 24.180 | 0.082 |

TABLE 33

Sequences of quadruple or more mutant MMLV RTase variants.

| SEQ ID NO: | Construct | Construct Sequence (AA) |
|---|---|---|
| 686 | MMLV-II Q68R/Q79R/L99R/ E282D/V433R | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWL<br>TDARKETVMGQPTPKTPRQLREFLGTAGFCRLWIP<br>GFAEMAAPLYPLTKTGTLFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLRILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYTNSRYAFATAHIHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |
| 687 | MMLV-II Q68R/Q79R/L99R/ E282D/I593E | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWL<br>TDARKETVMGQPTPKTPRQLREFLGTAGFCRLWIP<br>GFAEMAAPLYPLTKTGTLFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLVILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYTNSRYAFATAHEHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |
| 688 | MMLV-II Q68R/Q79R/L99R/ E282D/Q299E | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWL<br>TDARKETVMGQPTPKTPRELREFLGTAGFCRLWIP |

TABLE 33-continued

Sequences of quadruple or more mutant MMLV RTase variants.

| SEQ ID NO: | Construct | Construct Sequence (AA) |
|---|---|---|
| | | GFAEMAAPLYPLTKTGTLFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLVILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYTNSRYAFATAHIHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |
| 689 | MMLV-II<br>Q68R/Q79R/L99R/<br>E282D/T332E | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWL<br>TDARKETVMGQPTPKTPRQLREFLGTAGFCRLWIP<br>GFAEMAAPLYPLTKTGELFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLVILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYTNSRYAFATAHIHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |
| 690 | MMLV-II<br>Q68R/Q79R/L99R/<br>L280R | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWR<br>TEARKETVMGQPTPKTPRQLREFLGTAGFCRLWIP<br>GFAEMAAPLYPLTKTGTLFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLVILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYTNSRYAFATAHIHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |
| 691 | MMLV-II<br>Q68R/Q79R/L99R/<br>L280R/E282D | TLNIEDEHRLHETSKEPDVSLGSTWLSDFPQAWAE<br>TGGMGLAVRQAPLIIPLKATSTPVSIKQYPMSREA<br>RLGIKPHIRRLLDQGILVPCQSPWNTPLRPVKKPG<br>TNDYRPVQDLREVNKRVEDIHPTVPNPYNLLSGLP<br>PSHQWYTVLDLKDAFFCLRLHPTSQPLFAFEWRDP<br>EMGISGQLTWTRLPQGFKNSPTLFDEALHRDLADF<br>RIQHPDLILLQYVDDLLLAATSELDCQQGTRALLQ<br>TLGNLGYRASAKKAQICQKQVKYLGYLLKEGQRWR<br>TDARKETVMGQPTPKTPRQLREFLGTAGFCRLWIP<br>GFAEMAAPLYPLTKTGTLFNWGPDQQKAYQEIKQA<br>LLTAPALGLPDLTKPFELFVDEKQGYAKGVLTQKL<br>GPWRRPVAYLSKKLDPVAAGWPPCLRMVAAIAVLT<br>KDAGKLTMGQPLVILAPHAVEALVKQPPDRWLSNA<br>RMTHYQALLLDTDRVQFGPVVALNPATLLPLPEEG<br>LQHNCLDILAEAHGTRPDLTDQPLPDADHTWYTGG<br>SSLLQEGQRKAGAAVTTETEVIWAKALPAGTSAQR<br>AQLIALTQALKMAEGKKLNVYINSRYAFATAHIHG<br>EIYRRRGLLTSEGKEIKNKDEILALLKALFLPKRL<br>SIIHCPGHQKGHSAEARGNRMADQAARKAAITETP<br>DTSTLLIENSSPYTSEHF |

TABLE 33-continued

Sequences of quadruple or more mutant MMLV RTase variants.

| SEQ ID NO: | Construct | Construct Sequence (AA) |
|---|---|---|
| 692 | MMLV-II Q68R/L82R/L99R/ E282D | TLNIEDEHRLHETSKEPDVSLGSTWLSDFPQAWAE TGGMGLAVRQAPLIIPLKATSTPVSIKQYPMSREA RLGIKPHIQRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 693 | MMLV-II Q68R/Q79R/L82R/ L99R/E282D | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRQLREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHIHG EIYRRRGLLTSEGKEIKNKDEILALLKALFLPKRL SIIHCPGHQKGHSAEARGNRMADQAARKAAITETP DTSTLLIENSSPYTSEHF |
| 694 | MMLV-II Q68R/Q79R/L99R/ E282D/Q299E/ I593E | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 695 | MMLV-II Q68R/Q79R/L82R/ L99R/E282D/ Q299E/I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT |

TABLE 33-continued

| SEQ ID NO: | Construct | Construct Sequence (AA) |
|---|---|---|
| Sequences of quadruple or more mutant MMLV RTase variants. | | |
| | | KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 696 | MMLV-II Q68R/Q79R/L99R/ E282D/Q299E/ V433R/I593E | TLNIEDEHRLHETSKEPDVSLGSTWLSDFPQAWAE TGGMGLAVRQAPLIIPLKATSTPVSIKQYPMSREA RLGIKPHIRRLLDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 697 | MMLV-II Q68R/Q79R/L82R/ L99R/E282D/ Q299E/V433R/ I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGTLFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYINSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 698 | MMLV-II Q68R/Q79R/L82R/ L99R/E282D/ Q299E/T332E/ I593E | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGELFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLVILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |
| 699 | MMLV-II Q68R/Q79R/L82R/ L99R/E282D/ Q299E/T332E/ | TLNIEDEHRLHETSKEPDVSLGSTWLSDFPQAWAE TGGMGLAVRQAPLIIPLKATSTPVSIKQYPMSREA RLGIKPHIRRLRDQGILVPCQSPWNTPLRPVKKPG TNDYRPVQDLREVNKRVEDIHPTVPNPYNLLSGLP |

TABLE 33-continued

| Sequences of quadruple or more mutant MMLV RTase variants. | |
|---|---|
| SEQ ID NO: Construct | Construct Sequence (AA) |
| V433R/I593E | PSHQWYTVLDLKDAFFCLRLHPTSQPLFAFEWRDP EMGISGQLTWTRLPQGFKNSPTLFDEALHRDLADF RIQHPDLILLQYVDDLLLAATSELDCQQGTRALLQ TLGNLGYRASAKKAQICQKQVKYLGYLLKEGQRWL TDARKETVMGQPTPKTPRELREFLGTAGFCRLWIP GFAEMAAPLYPLTKTGELFNWGPDQQKAYQEIKQA LLTAPALGLPDLTKPFELFVDEKQGYAKGVLTQKL GPWRRPVAYLSKKLDPVAAGWPPCLRMVAAIAVLT KDAGKLTMGQPLRILAPHAVEALVKQPPDRWLSNA RMTHYQALLLDTDRVQFGPVVALNPATLLPLPEEG LQHNCLDILAEAHGTRPDLTDQPLPDADHTWYTGG SSLLQEGQRKAGAAVTTETEVIWAKALPAGTSAQR AQLIALTQALKMAEGKKLNVYTNSRYAFATAHEHG EIYRRRGLLTSEGKEIKNKDEILALLKALFLPKRL SIIHCPGHQKGHSAEARGNRMADQAARKAAITETP DTSTLLIENSSPYTSEHF |

BIBLIOGRAPHY

1. Coffin et al., "The discovery of reverse transcriptase," *Ann. Rev. Virol.* 3(1): 29-51 (2016).
2. Hogrefe et al., "Mutant reverse transcriptase and methods of use," U.S. Pat. No. 9,783,791.
3. Kotewicz et al., "Cloned genes encoding reverse transcriptase lacking RNase H activity," U.S. Pat. No. 5,405,776.
4. Kotewicz et al., "Isolation of cloned Moloney murine leukemia virus reverse transcriptase lacking ribonuclease H activity," *Nucleic Acids Res.* 16(1): 265-77 (1988).

What is claimed is:

1. An isolated Moloney murine leukemia virus (MMLV) reverse transcriptase (RTase) mutant comprising the amino acid sequence of SEQ ID NO: 699.

2. An isolated MMLV RTase mutant comprising the amino acid sequence of one or more of SEQ ID NOs: 654-657 and 659-667.

3. The MMLV RTase mutant as in either claim 1 or claim 2, wherein the MMLV RTase mutant lacks RNase H activity.

4. The MMLV RTase mutant as in either claim 1 or claim 2, wherein the MMLV RTase mutant possesses at least one of the following characteristics:

enhanced DNA synthesis, increased fidelity, or enhanced thermostability when compared to wild-type MMLV RTase.

5. A composition comprising the isolated MMLV RTase mutant as in either claim 1 or claim 2.

6. The composition of claim 5, wherein the isolated MMLV RTase mutant lacks RNase H activity.

7. The composition of claim 5, wherein the isolated MMLV RTase mutant possesses at least one of the following characteristics: enhanced DNA synthesis, increased fidelity, or enhanced thermostability when compared to wild-type MMLV RTase.

8. A kit comprising the isolated MMLV RTase mutant as in either claim 1 or claim 2.

9. The kit of claim 8, wherein the isolated MMLV RTase mutant lacks RNAse H activity.

10. The kit of claim 8, wherein the isolated MMLV RTase mutant possesses at least one of the following characteristics: enhanced DNA synthesis, increased fidelity, or enhanced thermostability when compared to wild-type MMLV RTase.

11. A method for synthesizing complementary deoxyribonucleic acid (cDNA) comprising:

(a) providing the isolated MMLV RTase mutant as in either claim 1 or claim 2; and (b) contacting the isolated MMLV RTase mutant with a nucleic acid template to permit synthesis of cDNA.

12. A method for performing reverse transcription-polymerase chain reaction (RT-PCR) comprising:

(a) providing the isolated MMLV RTase mutant as in either claim 1 or claim 2; and (b) contacting the isolated MMLV RTase mutant with a nucleic acid template to replicate and amplify the nucleic acid template.

* * * * *

SEQUENCE LISTING

<160> NUMBER OF SEQ ID NOS: 699

<210> SEQ ID NO 1
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 1
ggtatatctc cttcttaaag ttaaacaaaa ttatttctag aggggaatga tccggctgct 60
aacaaagcc 69

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
gatccggctg ctaacaaagc c 21

<210> SEQ ID NO 3
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 3
ttttgtttaa ctttaagaag gagatatacc atgggcagca gccatcatca tc 52

<210> SEQ ID NO 4
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 4
gcagccaact cagcttcctt tcgggctttg ttaaaaatgc tcgctagtgt agggagagc 59

<210> SEQ ID NO 5
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 5
aagcaccgtt gatcatcccg ttagcggcaa cgtctacacc tgtctctatc aaac 54

<210> SEQ ID NO 6
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 6
aagcaccgtt gatcatcccg ttacgtgcaa cgtctacacc tgtctctatc aaac 54

<210> SEQ ID NO 7
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 7
aagcaccgtt gatcatcccg ttagaagcaa cgtctacacc tgtctctatc aaac 54

<210> SEQ ID NO 8
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 8
ccgttgatca tcccgttaaa ggcagcgtct acacctgtct ctatcaaaca gtacccc 57

<210> SEQ ID NO 9
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 9
ccgttgatca tcccgttaaa ggcacgttct acacctgtct ctatcaaaca gtacccc 57

<210> SEQ ID NO 10

<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 10
ccgttgatca tcccgttaaa ggcagaatct acacctgtct ctatcaaaca gtacccc 57

<210> SEQ ID NO 11
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 11
atcatcccgt taaaggcaac gtctgcgcct gtctctatca aacagtaccc catgag 56

<210> SEQ ID NO 12
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 12
atcatcccgt taaaggcaac gtctcgtcct gtctctatca aacagtaccc catgag 56

<210> SEQ ID NO 13
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 13
atcatcccgt taaaggcaac gtctgaacct gtctctatca aacagtaccc catgag 56

<210> SEQ ID NO 14
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 14
ccgttaaagg caacgtctac acctgcgtct atcaaacagt accccatgag tcaagagg 58

<210> SEQ ID NO 15
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 15
ccgttaaagg caacgtctac acctcgttct atcaaacagt accccatgag tcaagagg 58

<210> SEQ ID NO 16
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 16
ccgttaaagg caacgtctac acctgaatct atcaaacagt accccatgag tcaagagg 58

<210> SEQ ID NO 17
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 17
taaaggcaac gtctacacct gtctctgcga aacagtaccc catgagtcaa gagg 54

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 18
taaaggcaac gtctacacct gtctctcgta aacagtaccc catgagtcaa gagg 54

<210> SEQ ID NO 19
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 19
taaaggcaac gtctacacct gtctctgaaa aacagtaccc catgagtcaa gagg 54

<210> SEQ ID NO 20
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 20
ggcaacgtct acacctgtct ctatcgcgca gtaccccatg agtcaagagg c 51

<210> SEQ ID NO 21
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 21
ggcaacgtct acacctgtct ctatccgtca gtaccccatg agtcaagagg c 51

<210> SEQ ID NO 22
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 22
ggcaacgtct acacctgtct ctatcgaaca gtaccccatg agtcaagagg c 51

<210> SEQ ID NO 23
<211> LENGTH: 46
<212> TYPE: DNA

<213> ORGANISM: Artificial Sequence
<220> FEATURE:
<223> OTHER INFORMATION: Synthetic oligonucleotide

<400> SEQUENCE: 23
ctgtctctat caaacagtac cccatgagtg cggaggcccg cctggg 46

<210> SEQ ID NO 24
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 24
ctgtctctat caaacagtac cccatgagtc gtgaggcccg cctggg 46

<210> SEQ ID NO 25
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 25
ctgtctctat caaacagtac cccatgagtg aagaggcccg cctggg 46

<210> SEQ ID NO 26
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 26
ggcccgcctg gggattgcgc cacatattca gcgcttgctg gacca 45

<210> SEQ ID NO 27
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 27
ggcccgcctg gggattcgtc cacatattca gcgcttgctg gacca 45

<210> SEQ ID NO 28
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 28
ggcccgcctg gggattgaac cacatattca gcgcttgctg gacca 45

<210> SEQ ID NO 29
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 29
cgcctgggga ttaagccaca tattgcgcgc ttgctggacc agggg 45

<210> SEQ ID NO 30
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 30
cgcctgggga ttaagccaca tattcgtcgc ttgctggacc agggg 45

<210> SEQ ID NO 31
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 31
cgcctgggga ttaagccaca tattgaacgc ttgctggacc agggg 45

<210> SEQ ID NO 32
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 32
ccgtggaaca cccccettgc gcccgtgaaa aagccaggta caaac 45

<210> SEQ ID NO 33
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 33
ccgtggaaca cccccettcg tcccgtgaaa aagccaggta caaac 45

<210> SEQ ID NO 34
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 34
ccgtggaaca cccccettga acccgtgaaa aagccaggta caaac 45

<210> SEQ ID NO 35
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 35
cacccccctt ctgcccgcga aaaagccagg tacaaacgat tatcgtcc 48

<210> SEQ ID NO 36
<211> LENGTH: 48
<212> TYPE: DNA
<213> ORGANISM: Artificial Sequence
<220> FEATURE:

<223> OTHER INFORMATION: Synthetic oligonucleotide

<400> SEQUENCE: 36 caccccccctt ctgccccgta aaaagccagg tacaaacgat tatcgtcc 48

<210> SEQ ID NO 37
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 37 caccccccctt ctgcccgaaa aaaagccagg tacaaacgat tatcgtcc 48

<210> SEQ ID NO 38
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 38
cccccttctg cccgtggcga agccaggtac aaacgattat cgtcc 45

<210> SEQ ID NO 39
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 39
cccccttctg cccgtgcgta agccaggtac aaacgattat cgtcc 45

<210> SEQ ID NO 40
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 40
cccccttctg cccgtggaaa agccaggtac aaacgattat cgtcc 45

<210> SEQ ID NO 41
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 41
cccccttctg cccgtgaaag cgccaggtac aaacgattat cgtccagtt 49

<210> SEQ ID NO 42
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 42
cccccttctg cccgtgaaac gtccaggtac aaacgattat cgtccagtt 49

<210> SEQ ID NO 43
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 43 ccccttctg cccgtgaaag aaccaggtac aaacgattat cgtccagtt 49

<210> SEQ ID NO 44
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 44
gcccgtgaaa aagccaggtg cgaacgatta tcgtccagtt caagatcttc g 51

<210> SEQ ID NO 45
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 45
gcccgtgaaa aagccaggtc gtaacgatta tcgtccagtt caagatcttc g 51

<210> SEQ ID NO 46
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 46
gcccgtgaaa aagccaggtg aaaacgatta tcgtccagtt caagatcttc g 51

<210> SEQ ID NO 47
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 47
cccgtgaaaa agccaggtac agcggattat cgtccagttc aagatcttcg cg 52

<210> SEQ ID NO 48
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 48
cccgtgaaaa agccaggtac acgtgattat cgtccagttc aagatcttcg cg 52

<210> SEQ ID NO 49
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 49
cccgtgaaaa agccaggtac agaagattat cgtccagttc aagatcttcg cg 52

<210> SEQ ID NO 50
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 50
cgtgaaaaag ccaggtacaa acgatgcgcg tccagttcaa gatcttcgcg 50

<210> SEQ ID NO 51
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 51
cgtgaaaaag ccaggtacaa acgatcgtcg tccagttcaa gatcttcgcg 50

<210> SEQ ID NO 52
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 52
cgtgaaaaag ccaggtacaa acgatgaacg tccagttcaa gatcttcgcg 50

<210> SEQ ID NO 53
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 53
cgtgaaaaag ccaggtacaa acgattatgc gccagttcaa gatcttcgcg agg 53

<210> SEQ ID NO 54
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 54
cgtgaaaaag ccaggtacaa acgattataa accagttcaa gatcttcgcg agg 53

<210> SEQ ID NO 55
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 55
cgtgaaaaag ccaggtacaa acgattatga accagttcaa gatcttcgcg agg 53

<210> SEQ ID NO 56
<211> LENGTH: 53

<212> TYPE: DNA
<213> ORGANISM: Artificial Sequence
<220> FEATURE:
<223> OTHER INFORMATION: Synthetic oligonucleotide

<400> SEQUENCE: 56
gccaggtaca aacgattatc gtccagcgca agatcttcgc gaggtcaaca aac 53

<210> SEQ ID NO 57
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 57
gccaggtaca aacgattatc gtccacgtca agatcttcgc gaggtcaaca aac 53

<210> SEQ ID NO 58
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 58
gccaggtaca aacgattatc gtccagaaca agatcttcgc gaggtcaaca aac 53

<210> SEQ ID NO 59
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 59
agttcaagat cttcgcgagg tcaacgcgcg cgtagaagac atccatccga c 51

<210> SEQ ID NO 60
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 60
agttcaagat cttcgcgagg tcaaccgtcg cgtagaagac atccatccga c 51

<210> SEQ ID NO 61
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 61
agttcaagat cttcgcgagg tcaacgaacg cgtagaagac atccatccga c 51

<210> SEQ ID NO 62
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 62
gcgaggtcaa caaacgcgta gcggacatcc atccgactgt acctaatcc 49

<210> SEQ ID NO 63
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 63
gcgaggtcaa caaacgcgta cgtgacatcc atccgactgt acctaatcc 49

<210> SEQ ID NO 64
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 64
gcgaggtcaa caaacgcgta gatgacatcc atccgactgt acctaatcc 49

<210> SEQ ID NO 65
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 65
acgcgtagaa gacatccatc cggtggtacc taatccttat aatctgttat caggcctgc 59

<210> SEQ ID NO 66
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 66
acgcgtagaa gacatccatc cgcgtgtacc taatccttat aatctgttat caggcctgc 59

<210> SEQ ID NO 67
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 67
acgcgtagaa gacatccatc cggaagtacc taatccttat aatctgttat caggcctgc 59

<210> SEQ ID NO 68
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 68
cgtctgcccc agggctttgc gaacagcccc acattgttcg atgaa 45

<210> SEQ ID NO 69
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 69
cgtctgcccc agggctttcg taacagcccc acattgttcg atgaa 45

<210> SEQ ID NO 70
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 70
cgtctgcccc agggctttga aaacagcccc acattgttcg atgaa 45

<210> SEQ ID NO 71
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 71
agaaggtcaa cgttggctga ctgcggcgcg taaggagacc gtaatg 46

<210> SEQ ID NO 72
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 72
agaaggtcaa cgttggctga ctcgtgcgcg taaggagacc gtaatg 46

<210> SEQ ID NO 73
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 73
agaaggtcaa cgttggctga ctgatgcgcg taaggagacc gtaatg 46

<210> SEQ ID NO 74
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 74
gaaggtcaac gttggctgac tgaagtgcgt aaggagaccg taatggggc 49

<210> SEQ ID NO 75
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 75
gaaggtcaac gttggctgac tgaacgtcgt aaggagaccg taatggggc 49

<210> SEQ ID NO 76
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 76
gaaggtcaac gttggctgac tgaagaacgt aaggagaccg taatggggc 49

<210> SEQ ID NO 77
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 77
gcgtaaggag accgtaatgg gggcgcctac gcctaagacg ccacg 45

<210> SEQ ID NO 78
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 78
gcgtaaggag accgtaatgg ggcgtcctac gcctaagacg ccacg 45

<210> SEQ ID NO 79
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 79
gcgtaaggag accgtaatgg gggaacctac gcctaagacg ccacg 45

<210> SEQ ID NO 80
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 80
gagaccgtaa tggggcagcc tgcgcctaag acgccacgcc agttg 45

<210> SEQ ID NO 81
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 81
gagaccgtaa tggggcagcc tcgtcctaag acgccacgcc agttg 45

<210> SEQ ID NO 82
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 82
gagaccgtaa tggggcagcc tgaacctaag acgccacgcc agttg 45

<210> SEQ ID NO 83
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 83
gtaatggggc agcctacgcc tgcgacgcca cgccagttgc gtgaa 45

<210> SEQ ID NO 84
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 84
gtaatggggc agcctacgcc tcgtacgcca cgccagttgc gtgaa 45

<210> SEQ ID NO 85
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 85
gtaatggggc agcctacgcc tgaaacgcca cgccagttgc gtgaa 45

<210> SEQ ID NO 86
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 86
tggggcagcc tacgcctaag gcgccacgcc agttgcgtga atttt 45

<210> SEQ ID NO 87
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 87
tggggcagcc tacgcctaag cgtccacgcc agttgcgtga atttt 45

<210> SEQ ID NO 88
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 88
tggggcagcc tacgcctaag gaaccacgcc agttgcgtga atttt 45

<210> SEQ ID NO 89

<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 89
gcctacgcct aagacgccag cgcagttgcg tgaatttttg ggcacag 47

<210> SEQ ID NO 90
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 90
gcctacgcct aagacgccaa aacagttgcg tgaatttttg ggcacag 47

<210> SEQ ID NO 91
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 91
gcctacgcct aagacgccag aacagttgcg tgaatttttg ggcacag 47

<210> SEQ ID NO 92
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 92
cctaagacgc cacgccagtt ggcggaattt ttgggcacag cggga 45

<210> SEQ ID NO 93
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 93
cctaagacgc cacgccagtt gaaagaattt ttgggcacag cggga 45

<210> SEQ ID NO 94
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 94
cctaagacgc cacgccagtt ggaagaattt ttgggcacag cggga 45

<210> SEQ ID NO 95
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 95
gcacccctgt accccttaac agcgacaggg acgcttttca actgg 45

<210> SEQ ID NO 96
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 96
gcacccctgt accccttaac acgtacaggg acgcttttca actgg 45

<210> SEQ ID NO 97
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 97
gcacccctgt accccttaac agaaacaggg acgcttttca actgg 45

<210> SEQ ID NO 98
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 98
gtttgataga gacaggtgta gacgttgccg ctaacgggat gatcaacggt gctt 54

<210> SEQ ID NO 99
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 99
gtttgataga gacaggtgta gacgttgcac gtaacgggat gatcaacggt gctt 54

<210> SEQ ID NO 100
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 100
gtttgataga gacaggtgta gacgttgctt ctaacgggat gatcaacggt gctt 54

<210> SEQ ID NO 101
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 101
ggggtactgt ttgatagaga caggtgtaga cgctgccttt aacgggatga tcaacgg 57

<210> SEQ ID NO 102
<211> LENGTH: 57
<212> TYPE: DNA

<213> ORGANISM: Artificial Sequence
<220> FEATURE:
<223> OTHER INFORMATION: Synthetic oligonucleotide

<400> SEQUENCE: 102
ggggtactgt ttgatagaga caggtgtaga acgtgccttt aacgggatga tcaacgg 57

<210> SEQ ID NO 103
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 103
ggggtactgt ttgatagaga caggtgtaga ttctgccttt aacgggatga tcaacgg 57

<210> SEQ ID NO 104
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 104
ctcatggggt actgtttgat agagacaggc gcagacgttg cctttaacgg gatgat 56

<210> SEQ ID NO 105
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 105
ctcatggggt actgtttgat agagacagga cgagacgttg cctttaacgg gatgat 56

<210> SEQ ID NO 106
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 106
ctcatggggt actgtttgat agagacaggt tcagacgttg cctttaacgg gatgat 56

<210> SEQ ID NO 107
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 107
cctcttgact catggggtac tgtttgatag acgcaggtgt agacgttgcc tttaacgg 58

<210> SEQ ID NO 108
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 108
cctcttgact catggggtac tgtttgatag aacgaggtgt agacgttgcc tttaacgg 58

<210> SEQ ID NO 109
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 109
cctcttgact catggggtac tgtttgatag attcaggtgt agacgttgcc tttaacgg 58

<210> SEQ ID NO 110
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 110
cctcttgact catggggtac tgtttcgcag agacaggtgt agacgttgcc ttta 54

<210> SEQ ID NO 111
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 111
cctcttgact catggggtac tgtttacgag agacaggtgt agacgttgcc ttta 54

<210> SEQ ID NO 112
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 112
cctcttgact catggggtac tgtttttcag agacaggtgt agacgttgcc ttta 54

<210> SEQ ID NO 113
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 113
gcctcttgac tcatggggta ctgcgcgata gagacaggtg tagacgttgc c 51

<210> SEQ ID NO 114
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 114
gcctcttgac tcatggggta ctgacggata gagacaggtg tagacgttgc c 51

<210> SEQ ID NO 115
<211> LENGTH: 51
<212> TYPE: DNA
<213> ORGANISM: Artificial Sequence
<220> FEATURE:

<223> OTHER INFORMATION: Synthetic oligonucleotide

<400> SEQUENCE: 115
gcctcttgac tcatggggta ctgttcgata gagacaggtg tagacgttgc c 51

<210> SEQ ID NO 116
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 116
ctgtctctat caaacagtac cccatgagtg cggaggcccg cctggg 46

<210> SEQ ID NO 117
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 117
ctgtctctat caaacagtac cccatgagtc gtgaggcccg cctggg 46

<210> SEQ ID NO 118
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 118
ctgtctctat caaacagtac cccatgagtg aagaggcccg cctggg 46

<210> SEQ ID NO 119
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 119
tggtccagca agcgctgaat atgtggcgca atccccaggc gggcc 45

<210> SEQ ID NO 120
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 120
tggtccagca agcgctgaat atgtggacga atccccaggc gggcc 45

<210> SEQ ID NO 121
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 121
tggtccagca agcgctgaat atgtggttca atccccaggc gggcc 45

<210> SEQ ID NO 122
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 122
cccctggtcc agcaagcgcg caatatgtgg cttaatcccc aggcg 45

<210> SEQ ID NO 123
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 123
cccctggtcc agcaagcgac gaatatgtgg cttaatcccc aggcg 45

<210> SEQ ID NO 124
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 124
cccctggtcc agcaagcgtt caatatgtgg cttaatcccc aggcg 45

<210> SEQ ID NO 125
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 125
gtttgtacct ggctttttca cgggcgcaag gggggtgttc cacgg 45

<210> SEQ ID NO 126
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 126
gtttgtacct ggctttttca cgggacgaag gggggtgttc cacgg 45

<210> SEQ ID NO 127
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 127
gtttgtacct ggctttttca cgggttcaag gggggtgttc cacgg 45

<210> SEQ ID NO 128
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 128
ggacgataat cgtttgtacc tggctttttc gcgggcagaa gggggtg 48

<210> SEQ ID NO 129
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 129
ggacgataat cgtttgtacc tggcttttta cggggcagaa gggggtg 48

<210> SEQ ID NO 130
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 130
ggacgataat cgtttgtacc tggctttttt tcgggcagaa gggggtg 48

<210> SEQ ID NO 131
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 131
ggacgataat cgtttgtacc tggcttcgcc acgggcagaa ggggg 45

<210> SEQ ID NO 132
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 132
ggacgataat cgtttgtacc tggcttacgc acgggcagaa ggggg 45

<210> SEQ ID NO 133
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 133
ggacgataat cgtttgtacc tggcttttcc acgggcagaa ggggg 45

<210> SEQ ID NO 134
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 134
aactggacga taatcgtttg tacctggcgc tttcacgggc agaaggggg 49

<210> SEQ ID NO 135
<211> LENGTH: 49

<212> TYPE: DNA
<213> ORGANISM: Artificial Sequence
<220> FEATURE:
<223> OTHER INFORMATION: Synthetic oligonucleotide

<400> SEQUENCE: 135
aactggacga taatcgtttg tacctggacg tttcacgggc agaaggggg 49

<210> SEQ ID NO 136
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 136
aactggacga taatcgtttg tacctggttc tttcacgggc agaaggggg 49

<210> SEQ ID NO 137
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 137
cgaagatctt gaactggacg ataatcgttc gcacctggct ttttcacggg c 51

<210> SEQ ID NO 138
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 138
cgaagatctt gaactggacg ataatcgtta cgacctggct ttttcacggg c 51

<210> SEQ ID NO 139
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 139
cgaagatctt gaactggacg ataatcgttt tcacctggct ttttcacggg c 51

<210> SEQ ID NO 140
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 140
cgcgaagatc ttgaactgga cgataatccg ctgtacctgg ctttttcacg gg 52

<210> SEQ ID NO 141
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 141
cgcgaagatc ttgaactgga cgataatcac gtgtacctgg ctttttcacg gg 52

<210> SEQ ID NO 142
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 142
cgcgaagatc ttgaactgga cgataatctt ctgtacctgg ctttttcacg gg 52

<210> SEQ ID NO 143
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 143
cgcgaagatc ttgaactgga cgcgcatcgt ttgtacctgg ctttttcacg 50

<210> SEQ ID NO 144
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 144
cgcgaagatc ttgaactgga cgacgatcgt ttgtacctgg ctttttcacg 50

<210> SEQ ID NO 145
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 145
cgcgaagatc ttgaactgga cgttcatcgt ttgtacctgg ctttttcacg 50

<210> SEQ ID NO 146
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 146
cctcgcgaag atcttgaact ggcgcataat cgtttgtacc tggctttttc acg 53

<210> SEQ ID NO 147
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 147
cctcgcgaag atcttgaact ggtttataat cgtttgtacc tggctttttc acg 53

<210> SEQ ID NO 148
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 148
cctcgcgaag atcttgaact ggttcataat cgtttgtacc tggctttttc acg 53

<210> SEQ ID NO 149
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 149
gtttgttgac ctcgcgaaga tcttgcgctg gacgataatc gtttgtacct ggc 53

<210> SEQ ID NO 150
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 150
gtttgttgac ctcgcgaaga tcttgacgtg gacgataatc gtttgtacct ggc 53

<210> SEQ ID NO 151
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 151
gtttgttgac ctcgcgaaga tcttgttctg gacgataatc gtttgtacct ggc 53

<210> SEQ ID NO 152
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 152
gtcggatgga tgtcttctac gcgcgcgttg acctcgcgaa gatcttgaac t 51

<210> SEQ ID NO 153
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 153
gtcggatgga tgtcttctac gcgacggttg acctcgcgaa gatcttgaac t 51

<210> SEQ ID NO 154
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 154
gtcggatgga tgtcttctac gcgttcgttg acctcgcgaa gatcttgaac t 51

<210> SEQ ID NO 155
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 155
ggattaggta cagtcggatg gatgtccgct acgcgtttgt tgacctcgc 49

<210> SEQ ID NO 156
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 156
ggattaggta cagtcggatg gatgtcacgt acgcgtttgt tgacctcgc 49

<210> SEQ ID NO 157
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 157
ggattaggta cagtcggatg gatgtcatct acgcgtttgt tgacctcgc 49

<210> SEQ ID NO 158
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 158
gcaggcctga taacagatta taaggattag gtaccaccgg atggatgtct tctacgcgt 59

<210> SEQ ID NO 159
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 159
gcaggcctga taacagatta taaggattag gtacacgcgg atggatgtct tctacgcgt 59

<210> SEQ ID NO 160
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 160
gcaggcctga taacagatta taaggattag gtacttccgg atggatgtct tctacgcgt 59

<210> SEQ ID NO 161
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 161
ttcatcgaac aatgtggggc tgttcgcaaa gccctggggc agacg 45

<210> SEQ ID NO 162
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 162
ttcatcgaac aatgtggggc tgttacgaaa gccctggggc agacg 45

<210> SEQ ID NO 163
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 163
ttcatcgaac aatgtggggc tgttttcaaa gccctggggc agacg 45

<210> SEQ ID NO 164
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 164
cattacggtc tccttacgcg ccgcagtcag ccaacgttga ccttct 46

<210> SEQ ID NO 165
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 165
cattacggtc tccttacgcg cacgagtcag ccaacgttga ccttct 46

<210> SEQ ID NO 166
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 166
cattacggtc tccttacgcg catcagtcag ccaacgttga ccttct 46

<210> SEQ ID NO 167
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 167
gccccattac ggtctcctta cgcacttcag tcagccaacg ttgaccttc 49

<210> SEQ ID NO 168

<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 168
gccccattac ggtctcctta cgacgttcag tcagccaacg ttgaccttc 49

<210> SEQ ID NO 169
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 169
gccccattac ggtctcctta cgttcttcag tcagccaacg ttgaccttc 49

<210> SEQ ID NO 170
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 170
cgtggcgtct taggcgtagg cgcccccatt acggtctcct tacgc 45

<210> SEQ ID NO 171
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 171
cgtggcgtct taggcgtagg acgccccatt acggtctcct tacgc 45

<210> SEQ ID NO 172
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 172
cgtggcgtct taggcgtagg ttcccccatt acggtctcct tacgc 45

<210> SEQ ID NO 173
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 173
caactggcgt ggcgtcttag gcgcaggctg ccccattacg gtctc 45

<210> SEQ ID NO 174
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 174
caactggcgt ggcgtcttag gacgaggctg ccccattacg gtctc 45

<210> SEQ ID NO 175
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 175
caactggcgt ggcgtcttag gttcaggctg ccccattacg gtctc 45

<210> SEQ ID NO 176
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 176
ttcacgcaac tggcgtggcg tcgcaggcgt aggctgcccc attac 45

<210> SEQ ID NO 177
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 177
ttcacgcaac tggcgtggcg tacgaggcgt aggctgcccc attac 45

<210> SEQ ID NO 178
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 178
ttcacgcaac tggcgtggcg tttcaggcgt aggctgcccc attac 45

<210> SEQ ID NO 179
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 179
aaaattcacg caactggcgt ggcgccttag gcgtaggctg cccca 45

<210> SEQ ID NO 180
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 180
aaaattcacg caactggcgt ggacgcttag gcgtaggctg cccca 45

<210> SEQ ID NO 181
<211> LENGTH: 45
<212> TYPE: DNA

<213> ORGANISM: Artificial Sequence
<220> FEATURE:
<223> OTHER INFORMATION: Synthetic oligonucleotide

<400> SEQUENCE: 181
aaaattcacg caactggcgt ggttccttag gcgtaggctg cccca 45

<210> SEQ ID NO 182
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 182
ctgtgcccaa aaattcacgc aactgcgctg gcgtcttagg cgtaggc 47

<210> SEQ ID NO 183
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 183
ctgtgcccaa aaattcacgc aactgttttg gcgtcttagg cgtaggc 47

<210> SEQ ID NO 184
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 184
ctgtgcccaa aaattcacgc aactgttctg gcgtcttagg cgtaggc 47

<210> SEQ ID NO 185
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 185
tcccgctgtg cccaaaaatt ccgccaactg gcgtggcgtc ttagg 45

<210> SEQ ID NO 186
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 186
tcccgctgtg cccaaaaatt ctttcaactg gcgtggcgtc ttagg 45

<210> SEQ ID NO 187
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 187
tcccgctgtg cccaaaaatt cttccaactg gcgtggcgtc ttagg 45

<210> SEQ ID NO 188
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 188
ccagttgaaa agcgtccctg tcgctgttaa ggggtacagg ggtgc 45

<210> SEQ ID NO 189
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 189
ccagttgaaa agcgtccctg tacgtgttaa ggggtacagg ggtgc 45

<210> SEQ ID NO 190
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 190
ccagttgaaa agcgtccctg tttctgttaa ggggtacagg ggtgc 45

<210> SEQ ID NO 191
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 191
taaaggcaac gtctacacct gtctctggca aacagtaccc catgagtcaa gagg 54

<210> SEQ ID NO 192
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 192
cctcttgact catggggtac tgtttgccag agacaggtgt agacgttgcc ttta 54

<210> SEQ ID NO 193
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 193
taaaggcaac gtctacacct gtctctctga aacagtaccc catgagtcaa gagg 54

<210> SEQ ID NO 194
<211> LENGTH: 54
<212> TYPE: DNA
<213> ORGANISM: Artificial Sequence
<220> FEATURE:

<223> OTHER INFORMATION: Synthetic oligonucleotide

<400> SEQUENCE: 194
cctcttgact catggggtac tgtttcagag agacaggtgt agacgttgcc ttta 54

<210> SEQ ID NO 195
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 195
taaaggcaac gtctacacct gtctctgtga aacagtaccc catgagtcaa gagg 54

<210> SEQ ID NO 196
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 196
cctcttgact catggggtac tgtttcacag agacaggtgt agacgttgcc ttta 54

<210> SEQ ID NO 197
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 197
taaaggcaac gtctacacct gtctctccga aacagtaccc catgagtcaa gagg 54

<210> SEQ ID NO 198
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 198
cctcttgact catggggtac tgtttcggag agacaggtgt agacgttgcc ttta 54

<210> SEQ ID NO 199
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 199
taaaggcaac gtctacacct gtctctatga aacagtaccc catgagtcaa gagg 54

<210> SEQ ID NO 200
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 200
cctcttgact catggggtac tgtttcatag agacaggtgt agacgttgcc ttta 54

<210> SEQ ID NO 201
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 201
taaaggcaac gtctacacct gtctctagca aacagtaccc catgagtcaa gagg 54

<210> SEQ ID NO 202
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 202
cctcttgact catggggtac tgtttgctag agacaggtgt agacgttgcc ttta 54

<210> SEQ ID NO 203
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 203
taaaggcaac gtctacacct gtctctacca aacagtaccc catgagtcaa gagg 54

<210> SEQ ID NO 204
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 204
cctcttgact catggggtac tgtttggtag agacaggtgt agacgttgcc ttta 54

<210> SEQ ID NO 205
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 205
taaaggcaac gtctacacct gtctcttgca aacagtaccc catgagtcaa gagg 54

<210> SEQ ID NO 206
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 206
cctcttgact catggggtac tgtttgcaag agacaggtgt agacgttgcc ttta 54

<210> SEQ ID NO 207
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 207
taaaggcaac gtctacacct gtctctttta aacagtaccc catgagtcaa gagg 54

<210> SEQ ID NO 208
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 208
cctcttgact catggggtac tgtttaaaag agacaggtgt agacgttgcc ttta 54

<210> SEQ ID NO 209
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 209
taaaggcaac gtctacacct gtctcttata aacagtaccc catgagtcaa gagg 54

<210> SEQ ID NO 210
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 210
cctcttgact catggggtac tgtttataag agacaggtgt agacgttgcc ttta 54

<210> SEQ ID NO 211
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 211
taaaggcaac gtctacacct gtctctcata aacagtaccc catgagtcaa gagg 54

<210> SEQ ID NO 212
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 212
cctcttgact catggggtac tgtttatgag agacaggtgt agacgttgcc ttta 54

<210> SEQ ID NO 213
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 213
taaaggcaac gtctacacct gtctcttgga aacagtaccc catgagtcaa gagg 54

<210> SEQ ID NO 214
<211> LENGTH: 54

<212> TYPE: DNA
<213> ORGANISM: Artificial Sequence
<220> FEATURE:
<223> OTHER INFORMATION: Synthetic oligonucleotide

<400> SEQUENCE: 214
cctcttgact catggggtac tgtttccaag agacaggtgt agacgttgcc ttta 54

<210> SEQ ID NO 215
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 215
taaaggcaac gtctacacct gtctctgata aacagtaccc catgagtcaa gagg 54

<210> SEQ ID NO 216
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 216
cctcttgact catggggtac tgtttatcag agacaggtgt agacgttgcc ttta 54

<210> SEQ ID NO 217
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 217
taaaggcaac gtctacacct gtctctaaca aacagtaccc catgagtcaa gagg 54

<210> SEQ ID NO 218
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 218
cctcttgact catggggtac tgtttgttag agacaggtgt agacgttgcc ttta 54

<210> SEQ ID NO 219
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 219
taaaggcaac gtctacacct gtctctcaga aacagtaccc catgagtcaa gagg 54

<210> SEQ ID NO 220
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 220
cctcttgact catggggtac tgtttctgag agacaggtgt agacgttgcc ttta 54

<210> SEQ ID NO 221
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 221
taaaggcaac gtctacacct gtctctaaaa aacagtaccc catgagtcaa gagg 54

<210> SEQ ID NO 222
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 222
cctcttgact catggggtac tgtttttttag agacaggtgt agacgttgcc ttta 54

<210> SEQ ID NO 223
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 223
ctgtctctat caaacagtac cccatgagtg gcgaggcccg cctggg 46

<210> SEQ ID NO 224
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 224
cccaggcggg cctcgccact catggggtac tgtttgatag agacag 46

<210> SEQ ID NO 225
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 225
ctgtctctat caaacagtac cccatgagtc tggaggcccg cctggg 46

<210> SEQ ID NO 226
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 226
cccaggcggg cctccagact catggggtac tgtttgatag agacag 46

<210> SEQ ID NO 227
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 227
ctgtctctat caaacagtac cccatgagta ttgaggcccg cctggg 46

<210> SEQ ID NO 228
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 228
cccaggcggg cctcaatact catggggtac tgtttgatag agacag 46

<210> SEQ ID NO 229
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 229
ctgtctctat caaacagtac cccatgagtg tggaggcccg cctggg 46

<210> SEQ ID NO 230
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 230
cccaggcggg cctccacact catggggtac tgtttgatag agacag 46

<210> SEQ ID NO 231
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 231
ctgtctctat caaacagtac cccatgagtc cggaggcccg cctggg 46

<210> SEQ ID NO 232
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 232
cccaggcggg cctccggact catggggtac tgtttgatag agacag 46

<210> SEQ ID NO 233
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 233
ctgtctctat caaacagtac cccatgagta tggaggcccg cctggg 46

<210> SEQ ID NO 234
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 234
cccaggcggg cctccatact catggggtac tgtttgatag agacag 46

<210> SEQ ID NO 235
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 235
ctgtctctat caaacagtac cccatgagta gcgaggcccg cctggg 46

<210> SEQ ID NO 236
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 236
cccaggcggg cctcgctact catggggtac tgtttgatag agacag 46

<210> SEQ ID NO 237
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 237
ctgtctctat caaacagtac cccatgagta ccgaggcccg cctggg 46

<210> SEQ ID NO 238
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 238
cccaggcggg cctcggtact catggggtac tgtttgatag agacag 46

<210> SEQ ID NO 239
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 239
ctgtctctat caaacagtac cccatgagtt gcgaggcccg cctggg 46

<210> SEQ ID NO 240
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 240
cccaggcggg cctcgcaact catggggtac tgtttgatag agacag 46

<210> SEQ ID NO 241
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 241
ctgtctctat caaacagtac cccatgagtt ttgaggcccg cctggg 46

<210> SEQ ID NO 242
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 242
cccaggcggg cctcaaaact catggggtac tgtttgatag agacag 46

<210> SEQ ID NO 243
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 243
ctgtctctat caaacagtac cccatgagtt atgaggcccg cctggg 46

<210> SEQ ID NO 244
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 244
cccaggcggg cctcataact catggggtac tgtttgatag agacag 46

<210> SEQ ID NO 245
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 245
ctgtctctat caaacagtac cccatgagtc atgaggcccg cctggg 46

<210> SEQ ID NO 246
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 246
cccaggcggg cctcatgact catggggtac tgtttgatag agacag 46

<210> SEQ ID NO 247

<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 247
ctgtctctat caaacagtac cccatgagtt gggaggcccg cctggg 46

<210> SEQ ID NO 248
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 248
cccaggcggg cctcccaact catggggtac tgtttgatag agacag 46

<210> SEQ ID NO 249
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 249
ctgtctctat caaacagtac cccatgagtg atgaggcccg cctggg 46

<210> SEQ ID NO 250
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 250
cccaggcggg cctcatcact catggggtac tgtttgatag agacag 46

<210> SEQ ID NO 251
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 251
ctgtctctat caaacagtac cccatgagta acgaggcccg cctggg 46

<210> SEQ ID NO 252
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 252
cccaggcggg cctcgttact catggggtac tgtttgatag agacag 46

<210> SEQ ID NO 253
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 253
ctgtctctat caaacagtac cccatgagta aagaggcccg cctggg 46

<210> SEQ ID NO 254
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 254
cccaggcggg cctctttact catggggtac tgtttgatag agacag 46

<210> SEQ ID NO 255
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 255
cgcctgggga ttaagccaca tattggccgc ttgctggacc agggg 45

<210> SEQ ID NO 256
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 256
cccctggtcc agcaagcggc caatatgtgg cttaatcccc aggcg 45

<210> SEQ ID NO 257
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 257
cgcctgggga ttaagccaca tattctgcgc ttgctggacc agggg 45

<210> SEQ ID NO 258
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 258
cccctggtcc agcaagcgca gaatatgtgg cttaatcccc aggcg 45

<210> SEQ ID NO 259
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 259
cgcctgggga ttaagccaca tattattcgc ttgctggacc agggg 45

<210> SEQ ID NO 260
<211> LENGTH: 45
<212> TYPE: DNA

<213> ORGANISM: Artificial Sequence
<220> FEATURE:
<223> OTHER INFORMATION: Synthetic oligonucleotide

<400> SEQUENCE: 260
cccctggtcc agcaagcgaa taatatgtgg cttaatcccc aggcg 45

<210> SEQ ID NO 261
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 261
cgcctgggga ttaagccaca tattgtgcgc ttgctggacc agggg 45

<210> SEQ ID NO 262
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 262
cccctggtcc agcaagcgca caatatgtgg cttaatcccc aggcg 45

<210> SEQ ID NO 263
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 263
cgcctgggga ttaagccaca tattccgcgc ttgctggacc agggg 45

<210> SEQ ID NO 264
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 264
cccctggtcc agcaagcgcg gaatatgtgg cttaatcccc aggcg 45

<210> SEQ ID NO 265
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 265
cgcctgggga ttaagccaca tattatgcgc ttgctggacc agggg 45

<210> SEQ ID NO 266
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 266
cccctggtcc agcaagcgca taatatgtgg cttaatcccc aggcg 45

<210> SEQ ID NO 267
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 267
cgcctgggga ttaagccaca tattagccgc ttgctggacc agggg 45

<210> SEQ ID NO 268
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 268
cccctggtcc agcaagcggc taatatgtgg cttaatcccc aggcg 45

<210> SEQ ID NO 269
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 269
cgcctgggga ttaagccaca tattacccgc ttgctggacc agggg 45

<210> SEQ ID NO 270
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 270
cccctggtcc agcaagcggg taatatgtgg cttaatcccc aggcg 45

<210> SEQ ID NO 271
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 271
cgcctgggga ttaagccaca tatttgccgc ttgctggacc agggg 45

<210> SEQ ID NO 272
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 272
cccctggtcc agcaagcggc aaatatgtgg cttaatcccc aggcg 45

<210> SEQ ID NO 273
<211> LENGTH: 45
<212> TYPE: DNA
<213> ORGANISM: Artificial Sequence
<220> FEATURE:

<223> OTHER INFORMATION: Synthetic oligonucleotide

<400> SEQUENCE: 273
cgcctgggga ttaagccaca tatttttcgc ttgctggacc agggg 45

<210> SEQ ID NO 274
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 274
cccctggtcc agcaagcgaa aaatatgtgg cttaatcccc aggcg 45

<210> SEQ ID NO 275
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 275
cgcctgggga ttaagccaca tatttatcgc ttgctggacc agggg 45

<210> SEQ ID NO 276
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 276
cccctggtcc agcaagcgat aaatatgtgg cttaatcccc aggcg 45

<210> SEQ ID NO 277
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 277
cgcctgggga ttaagccaca tattcatcgc ttgctggacc agggg 45

<210> SEQ ID NO 278
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 278
cccctggtcc agcaagcgat gaatatgtgg cttaatcccc aggcg 45

<210> SEQ ID NO 279
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 279
cgcctgggga ttaagccaca tatttggcgc ttgctggacc agggg 45

<210> SEQ ID NO 280
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 280
cccctggtcc agcaagcgcc aaatatgtgg cttaatcccc aggcg 45

<210> SEQ ID NO 281
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 281
cgcctgggga ttaagccaca tattgatcgc ttgctggacc agggg 45

<210> SEQ ID NO 282
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 282
cccctggtcc agcaagcgat caatatgtgg cttaatcccc aggcg 45

<210> SEQ ID NO 283
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 283
cgcctgggga ttaagccaca tattaaccgc ttgctggacc agggg 45

<210> SEQ ID NO 284
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 284
cccctggtcc agcaagcggt taatatgtgg cttaatcccc aggcg 45

<210> SEQ ID NO 285
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 285
cgcctgggga ttaagccaca tattaaacgc ttgctggacc agggg 45

<210> SEQ ID NO 286
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 286
cccctggtcc agcaagcgtt taatatgtgg cttaatcccc aggcg 45

<210> SEQ ID NO 287
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 287
ccgtggaaca cccccttgg ccccgtgaaa aagccaggta caaac 45

<210> SEQ ID NO 288
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 288
gtttgtacct ggctttttca cggggccaag gggggtgttc cacgg 45

<210> SEQ ID NO 289
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 289
ccgtggaaca cccccttat tcccgtgaaa aagccaggta caaac 45

<210> SEQ ID NO 290
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 290
gtttgtacct ggctttttca cgggaataag gggggtgttc cacgg 45

<210> SEQ ID NO 291
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 291
ccgtggaaca cccccttgt gcccgtgaaa aagccaggta caaac 45

<210> SEQ ID NO 292
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 292
gtttgtacct ggctttttca cgggcacaag gggggtgttc cacgg 45

<210> SEQ ID NO 293
<211> LENGTH: 45

<212> TYPE: DNA
<213> ORGANISM: Artificial Sequence
<220> FEATURE:
<223> OTHER INFORMATION: Synthetic oligonucleotide

<400> SEQUENCE: 293
ccgtggaaca cccccctcc gcccgtgaaa aagccaggta caaac 45

<210> SEQ ID NO 294
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 294
gtttgtacct ggctttttca cgggcggaag gggggtgttc cacgg 45

<210> SEQ ID NO 295
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 295
ccgtggaaca cccccttat gcccgtgaaa aagccaggta caaac 45

<210> SEQ ID NO 296
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 296
gtttgtacct ggctttttca cgggcataag gggggtgttc cacgg 45

<210> SEQ ID NO 297
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 297
ccgtggaaca cccccttag ccccgtgaaa aagccaggta caaac 45

<210> SEQ ID NO 298
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 298
gtttgtacct ggctttttca cggggctaag gggggtgttc cacgg 45

<210> SEQ ID NO 299
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 299
ccgtggaaca cccccccttac ccccgtgaaa aagccaggta caaac 45

<210> SEQ ID NO 300
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 300
gtttgtacct ggctttttca cggggtaag gggggtgttc cacgg 45

<210> SEQ ID NO 301
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 301
ccgtggaaca cccccctttg ccccgtgaaa aagccaggta caaac 45

<210> SEQ ID NO 302
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 302
gtttgtacct ggctttttca cggggcaaag gggggtgttc cacgg 45

<210> SEQ ID NO 303
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 303
ccgtggaaca cccccctttt tcccgtgaaa aagccaggta caaac 45

<210> SEQ ID NO 304
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 304
gtttgtacct ggctttttca cgggaaaaag gggggtgttc cacgg 45

<210> SEQ ID NO 305
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 305
ccgtggaaca cccccccttta tcccgtgaaa aagccaggta caaac 45

<210> SEQ ID NO 306
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 306
gtttgtacct ggctttttca cgggataaag gggggtgttc cacgg 45

<210> SEQ ID NO 307
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 307
ccgtggaaca cccccccttca tcccgtgaaa aagccaggta caaac 45

<210> SEQ ID NO 308
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 308
gtttgtacct ggctttttca cgggatgaag gggggtgttc cacgg 45

<210> SEQ ID NO 309
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 309
ccgtggaaca cccccctttg gcccgtgaaa aagccaggta caaac 45

<210> SEQ ID NO 310
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 310
gtttgtacct ggctttttca cgggccaaag gggggtgttc cacgg 45

<210> SEQ ID NO 311
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 311
ccgtggaaca cccccttga tcccgtgaaa aagccaggta caaac 45

<210> SEQ ID NO 312
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 312
gtttgtacct ggctttttca cgggatcaag gggggtgttc cacgg 45

<210> SEQ ID NO 313
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 313
ccgtggaaca ccccccttaa ccccgtgaaa aagccaggta caaac 45

<210> SEQ ID NO 314
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 314
gtttgtacct ggctttttca cggggttaag ggggtgttc cacgg 45

<210> SEQ ID NO 315
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 315
ccgtggaaca ccccccttca gcccgtgaaa aagccaggta caaac 45

<210> SEQ ID NO 316
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 316
gtttgtacct ggctttttca cgggctgaag ggggtgttc cacgg 45

<210> SEQ ID NO 317
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 317
ccgtggaaca ccccccttaa acccgtgaaa aagccaggta caaac 45

<210> SEQ ID NO 318
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 318
gtttgtacct ggctttttca cgggtttaag ggggtgttc cacgg 45

<210> SEQ ID NO 319
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 319
agaaggtcaa cgttggctga ctggcgcgcg taaggagacc gtaatg 46

<210> SEQ ID NO 320
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 320
cattacggtc tccttacgcg cgccagtcag ccaacgttga ccttct 46

<210> SEQ ID NO 321
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 321
agaaggtcaa cgttggctga ctctggcgcg taaggagacc gtaatg 46

<210> SEQ ID NO 322
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 322
cattacggtc tccttacgcg ccagagtcag ccaacgttga ccttct 46

<210> SEQ ID NO 323
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 323
agaaggtcaa cgttggctga ctattgcgcg taaggagacc gtaatg 46

<210> SEQ ID NO 324
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 324
cattacggtc tccttacgcg caatagtcag ccaacgttga ccttct 46

<210> SEQ ID NO 325
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 325
agaaggtcaa cgttggctga ctgtggcgcg taaggagacc gtaatg 46

<210> SEQ ID NO 326

<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 326
cattacggtc tccttacgcg ccacagtcag ccaacgttga ccttct 46

<210> SEQ ID NO 327
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 327
agaaggtcaa cgttggctga ctccggcgcg taaggagacc gtaatg 46

<210> SEQ ID NO 328
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 328
cattacggtc tccttacgcg ccggagtcag ccaacgttga ccttct 46

<210> SEQ ID NO 329
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 329
agaaggtcaa cgttggctga ctatggcgcg taaggagacc gtaatg 46

<210> SEQ ID NO 330
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 330
cattacggtc tccttacgcg ccatagtcag ccaacgttga ccttct 46

<210> SEQ ID NO 331
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 331
agaaggtcaa cgttggctga ctagcgcgcg taaggagacc gtaatg 46

<210> SEQ ID NO 332
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 332
cattacggtc tccttacgcg cgctagtcag ccaacgttga ccttct 46

<210> SEQ ID NO 333
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 333
agaaggtcaa cgttggctga ctaccgcgcg taaggagacc gtaatg 46

<210> SEQ ID NO 334
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 334
cattacggtc tccttacgcg cggtagtcag ccaacgttga ccttct 46

<210> SEQ ID NO 335
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 335
agaaggtcaa cgttggctga cttgcgcgcg taaggagacc gtaatg 46

<210> SEQ ID NO 336
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 336
cattacggtc tccttacgcg cgcaagtcag ccaacgttga ccttct 46

<210> SEQ ID NO 337
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 337
agaaggtcaa cgttggctga cttttgcgcg taaggagacc gtaatg 46

<210> SEQ ID NO 338
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 338
cattacggtc tccttacgcg caaaagtcag ccaacgttga ccttct 46

<210> SEQ ID NO 339
<211> LENGTH: 46
<212> TYPE: DNA

<213> ORGANISM: Artificial Sequence
<220> FEATURE:
<223> OTHER INFORMATION: Synthetic oligonucleotide

<400> SEQUENCE: 339
agaaggtcaa cgttggctga cttatgcgcg taaggagacc gtaatg 46

<210> SEQ ID NO 340
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 340
cattacggtc tccttacgcg cataagtcag ccaacgttga ccttct 46

<210> SEQ ID NO 341
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 341
agaaggtcaa cgttggctga ctcatgcgcg taaggagacc gtaatg 46

<210> SEQ ID NO 342
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 342
cattacggtc tccttacgcg catgagtcag ccaacgttga ccttct 46

<210> SEQ ID NO 343
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 343
agaaggtcaa cgttggctga cttgggcgcg taaggagacc gtaatg 46

<210> SEQ ID NO 344
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 344
cattacggtc tccttacgcg cccaagtcag ccaacgttga ccttct 46

<210> SEQ ID NO 345
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 345
agaaggtcaa cgttggctga ctaacgcgcg taaggagacc gtaatg 46

<210> SEQ ID NO 346
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 346
cattacggtc tccttacgcg cgttagtcag ccaacgttga ccttct 46

<210> SEQ ID NO 347
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 347
agaaggtcaa cgttggctga ctcaggcgcg taaggagacc gtaatg 46

<210> SEQ ID NO 348
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 348
cattacggtc tccttacgcg cctgagtcag ccaacgttga ccttct 46

<210> SEQ ID NO 349
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 349
agaaggtcaa cgttggctga ctaaagcgcg taaggagacc gtaatg 46

<210> SEQ ID NO 350
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 350
cattacggtc tccttacgcg ctttagtcag ccaacgttga ccttct 46

<210> SEQ ID NO 351
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 351
gcctacgcct aagacgccag gccagttgcg tgaatttttg ggcacag 47

<210> SEQ ID NO 352
<211> LENGTH: 47
<212> TYPE: DNA
<213> ORGANISM: Artificial Sequence
<220> FEATURE:

<223> OTHER INFORMATION: Synthetic oligonucleotide

<400> SEQUENCE: 352
ctgtgcccaa aaattcacgc aactggcctg gcgtcttagg cgtaggc 47

<210> SEQ ID NO 353
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 353
gcctacgcct aagacgccac tgcagttgcg tgaatttttg ggcacag 47

<210> SEQ ID NO 354
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 354
ctgtgcccaa aaattcacgc aactgcagtg gcgtcttagg cgtaggc 47

<210> SEQ ID NO 355
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 355
gcctacgcct aagacgccaa ttcagttgcg tgaatttttg ggcacag 47

<210> SEQ ID NO 356
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 356
ctgtgcccaa aaattcacgc aactgaattg gcgtcttagg cgtaggc 47

<210> SEQ ID NO 357
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 357
gcctacgcct aagacgccag tgcagttgcg tgaatttttg ggcacag 47

<210> SEQ ID NO 358
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 358
ctgtgcccaa aaattcacgc aactgcactg gcgtcttagg cgtaggc 47

<210> SEQ ID NO 359
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 359
gcctacgcct aagacgccac cgcagttgcg tgaatttttg ggcacag 47

<210> SEQ ID NO 360
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 360
ctgtgcccaa aaattcacgc aactgcggtg gcgtcttagg cgtaggc 47

<210> SEQ ID NO 361
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 361
gcctacgcct aagacgccaa tgcagttgcg tgaatttttg ggcacag 47

<210> SEQ ID NO 362
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 362
ctgtgcccaa aaattcacgc aactgcattg gcgtcttagg cgtaggc 47

<210> SEQ ID NO 363
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 363
gcctacgcct aagacgccaa gccagttgcg tgaatttttg ggcacag 47

<210> SEQ ID NO 364
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 364
ctgtgcccaa aaattcacgc aactggcttg gcgtcttagg cgtaggc 47

<210> SEQ ID NO 365
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 365
gcctacgcct aagacgccaa cccagttgcg tgaatttttg ggcacag 47

<210> SEQ ID NO 366
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 366
ctgtgcccaa aaattcacgc aactgggttg gcgtcttagg cgtaggc 47

<210> SEQ ID NO 367
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 367
gcctacgcct aagacgccat gccagttgcg tgaatttttg ggcacag 47

<210> SEQ ID NO 368
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 368
ctgtgcccaa aaattcacgc aactggcatg gcgtcttagg cgtaggc 47

<210> SEQ ID NO 369
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 369
gcctacgcct aagacgccat ttcagttgcg tgaatttttg ggcacag 47

<210> SEQ ID NO 370
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 370
ctgtgcccaa aaattcacgc aactgaaatg gcgtcttagg cgtaggc 47

<210> SEQ ID NO 371
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 371
gcctacgcct aagacgccat atcagttgcg tgaatttttg ggcacag 47

<210> SEQ ID NO 372
<211> LENGTH: 47

<212> TYPE: DNA
<213> ORGANISM: Artificial Sequence
<220> FEATURE:
<223> OTHER INFORMATION: Synthetic oligonucleotide

<400> SEQUENCE: 372
ctgtgcccaa aaattcacgc aactgatatg gcgtcttagg cgtaggc 47

<210> SEQ ID NO 373
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 373
gcctacgcct aagacgccac atcagttgcg tgaatttttg ggcacag 47

<210> SEQ ID NO 374
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 374
ctgtgcccaa aaattcacgc aactgatgtg gcgtcttagg cgtaggc 47

<210> SEQ ID NO 375
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 375
gcctacgcct aagacgccat ggcagttgcg tgaatttttg ggcacag 47

<210> SEQ ID NO 376
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 376
ctgtgcccaa aaattcacgc aactgccatg gcgtcttagg cgtaggc 47

<210> SEQ ID NO 377
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 377
gcctacgcct aagacgccag atcagttgcg tgaatttttg ggcacag 47

<210> SEQ ID NO 378
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 378
ctgtgcccaa aaattcacgc aactgatctg gcgtcttagg cgtaggc 47

<210> SEQ ID NO 379
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 379
gcctacgcct aagacgccaa accagttgcg tgaatttttg ggcacag 47

<210> SEQ ID NO 380
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 380
ctgtgcccaa aaattcacgc aactggtttg gcgtcttagg cgtaggc 47

<210> SEQ ID NO 381
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 381
gcctacgcct aagacgccac agcagttgcg tgaatttttg ggcacag 47

<210> SEQ ID NO 382
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 382
ctgtgcccaa aaattcacgc aactgctgtg gcgtcttagg cgtaggc 47

<210> SEQ ID NO 383
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 383
aggcaacgtc tacacctgtc tctcgtaaac agtaccccat gagtcgtgag gcccgcctgg 60
gg 62

<210> SEQ ID NO 384
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 384
ccccaggcgg gcctcacgac tcatggggta ctgtttacga gagacaggtg tagacgttgc 60
ct 62

<210> SEQ ID NO 385
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 385
aggcaacgtc tacacctgtc tctaaaaaac agtaccccat gagtcgtgag g 51

<210> SEQ ID NO 386
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 386
cctcacgact catggggtac tgttttttag agacaggtgt agacgttgcc t 51

<210> SEQ ID NO 387
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 387
aggcaacgtc tacacctgtc tctatgaaac agtaccccat gagtcgtgag g 51

<210> SEQ ID NO 388
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 388
cctcacgact catggggtac tgtttcatag agacaggtgt agacgttgcc t 51

<210> SEQ ID NO 389
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 389
aggcaacgtc tacacctgtc tctatgaaac agtaccccat gagtattgag gcc 53

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 393
gtctctatca aacagtaccc catggcgcaa gaggcccgcc tggg 44

<210> SEQ ID NO 394
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 394
gtctctatca aacagtaccc catgcgtcaa gaggcccgcc tggg 44

<210> SEQ ID NO 395
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 395
catgagtcaa gaggcccgcg aggggattaa gccacatatt cagcg 45

<210> SEQ ID NO 396
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 396
gagtcaagag gcccgcctgg cgattaagcc acatattcag cgcttgc 47

<210> SEQ ID NO 397
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 397
gagtcaagag gcccgcctgc gtattaagcc acatattcag cgcttgc 47

<210> SEQ ID NO 398
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 398
gagtcaagag gcccgcctgg agattaagcc acatattcag cgcttgc 47

<210> SEQ ID NO 399
<211> LENGTH: 44
<212> TYPE: DNA
<213> ORGANISM: Artificial Sequence
<220> FEATURE:

<223> OTHER INFORMATION: Synthetic oligonucleotide

<400> SEQUENCE: 399
ggcccgcctg gggattaagg cgcatattca gcgcttgctg gacc 44

<210> SEQ ID NO 400
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 400
ggcccgcctg gggattaagc gtcatattca gcgcttgctg gacc 44

<210> SEQ ID NO 401
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 401
ggcccgcctg gggattaagg agcatattca gcgcttgctg gacc 44

<210> SEQ ID NO 402
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 402
ccgcctgggg attaagccag cgattcagcg cttgctggac cag 43

<210> SEQ ID NO 403
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 403
ccgcctgggg attaagccac gtattcagcg cttgctggac cag 43

<210> SEQ ID NO 404
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 404
ccgcctgggg attaagccag agattcagcg cttgctggac cag 43

<210> SEQ ID NO 405
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 405
gattaagcca catattcagc gcttggcgga ccaggggatc ttggtcc 47

<210> SEQ ID NO 406
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 406
gattaagcca catattcagc gcttgcgtga ccaggggatc ttggtcc 47

<210> SEQ ID NO 407
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 407
gattaagcca catattcagc gcttggagga ccaggggatc ttggtcc 47

<210> SEQ ID NO 408
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 408
gccacatatt cagcgcttgc tggcgcaggg gatcttggtc ccatg 45

<210> SEQ ID NO 409
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 409
gccacatatt cagcgcttgc tgcgtcaggg gatcttggtc ccatg 45

<210> SEQ ID NO 410
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 410
gccacatatt cagcgcttgc tggagcaggg gatcttggtc ccatg 45

<210> SEQ ID NO 411
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 411
aggtcaacaa acgcgtagaa gacgcgcatc cgactgtacc taatccttat aat 53

<210> SEQ ID NO 412
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 412
aggtcaacaa acgcgtagaa gaccgtcatc cgactgtacc taatccttat aat 53

<210> SEQ ID NO 413
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 413
aggtcaacaa acgcgtagaa gacgagcatc cgactgtacc taatccttat aat 53

<210> SEQ ID NO 414
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 414
gcgtagaaga catccatccg actgcgccta atccttataa tctgttatca ggc 53

<210> SEQ ID NO 415
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 415
gcgtagaaga catccatccg actcgtccta atccttataa tctgttatca ggc 53

<210> SEQ ID NO 416
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 416
gcgtagaaga catccatccg actgagccta atccttataa tctgttatca ggc 53

<210> SEQ ID NO 417
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 417
agggctttaa aaacagcccc acagcgttcg atgaagcact tcaccgtga 49

<210> SEQ ID NO 418
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 418
agggctttaa aaacagcccc acacgtttcg atgaagcact tcaccgtga 49

<210> SEQ ID NO 419
<211> LENGTH: 49

<212> TYPE: DNA
<213> ORGANISM: Artificial Sequence
<220> FEATURE:
<223> OTHER INFORMATION: Synthetic oligonucleotide

<400> SEQUENCE: 419
agggctttaa aaacagcccc acagagttcg atgaagcact tcaccgtga 49

<210> SEQ ID NO 420
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 420
tttaaaaaca gccccacatt gttcgatgcg gcacttcacc gtgacttagc ag 52

<210> SEQ ID NO 421
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 421
tttaaaaaca gccccacatt gttcgatcgt gcacttcacc gtgacttagc ag 52

<210> SEQ ID NO 422
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 422
tttaaaaaca gccccacatt gttcgatgat gcacttcacc gtgacttagc ag 52

<210> SEQ ID NO 423
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 423
cacattgttc gatgaagcac ttcacgcgga cttagcagac ttccgtatcc a 51

<210> SEQ ID NO 424
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 424
cacattgttc gatgaagcac ttcacaaaga cttagcagac ttccgtatcc a 51

<210> SEQ ID NO 425
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 425
gatgaagcac ttcaccgtga cttagaggac ttccgtatcc aacacccag 49

<210> SEQ ID NO 426
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 426
aagcacttca ccgtgactta gcagcgttcc gtatccaaca cccagactt 49

<210> SEQ ID NO 427
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 427
aagcacttca ccgtgactta gcacgtttcc gtatccaaca cccagactt 49

<210> SEQ ID NO 428
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 428
aagcacttca ccgtgactta gcagagttcc gtatccaaca cccagactt 49

<210> SEQ ID NO 429
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 429
cacttcaccg tgacttagca gacgcgcgta tccaacaccc agacttaatt c 51

<210> SEQ ID NO 430
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 430
cacttcaccg tgacttagca gaccgtcgta tccaacaccc agacttaatt c 51

<210> SEQ ID NO 431
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 431
cacttcaccg tgacttagca gacgagcgta tccaacaccc agacttaatt c 51

<210> SEQ ID NO 432
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 432
ttcaccgtga cttagcagac ttcgcgatcc aacacccaga cttaattctg tta 53

<210> SEQ ID NO 433
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 433
ttcaccgtga cttagcagac ttcaaaatcc aacacccaga cttaattctg tta 53

<210> SEQ ID NO 434
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 434
ttcaccgtga cttagcagac ttcgagatcc aacacccaga cttaattctg tta 53

<210> SEQ ID NO 435
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 435
ccgtgactta gcagacttcc gtgcgcaaca cccagactta attctgttac ag 52

<210> SEQ ID NO 436
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 436
ccgtgactta gcagacttcc gtcgtcaaca cccagactta attctgttac ag 52

<210> SEQ ID NO 437
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 437
ccgtgactta gcagacttcc gtgagcaaca cccagactta attctgttac ag 52

<210> SEQ ID NO 438
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 438
gtgacttagc agacttccgt atcgcgcacc cagacttaat tctgttacag tat 53

<210> SEQ ID NO 439
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 439
gtgacttagc agacttccgt atccgtcacc cagacttaat tctgttacag tat 53

<210> SEQ ID NO 440
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 440
gtgacttagc agacttccgt atcgagcacc cagacttaat tctgttacag tat 53

<210> SEQ ID NO 441
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 441
agcaaaaggc gtatcaggag atcgcgcaag ctttgttgac cgcaccc 47

<210> SEQ ID NO 442
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 442
agcaaaaggc gtatcaggag atccgtcaag ctttgttgac cgcaccc 47

<210> SEQ ID NO 443
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 443
agcaaaaggc gtatcaggag atcgagcaag ctttgttgac cgcaccc 47

<210> SEQ ID NO 444
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 444
cgtatcagga gatcaaacaa gctttggcga ccgcacccgc gttggg 46

<210> SEQ ID NO 445
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 445
cgtatcagga gatcaaacaa gctttgcgta ccgcacccgc gttggg 46

<210> SEQ ID NO 446
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 446
cgtatcagga gatcaaacaa gctttggaga ccgcacccgc gttggg 46

<210> SEQ ID NO 447
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 447
gttggctgac tgaagcgcgt gcggagaccg taatggggca gc 42

<210> SEQ ID NO 448
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 448
gttggctgac tgaagcgcgt cgtgagaccg taatggggca gc 42

<210> SEQ ID NO 449
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 449
gttggctgac tgaagcgcgt gaggagaccg taatggggca gc 42

<210> SEQ ID NO 450
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 450
tacgcctaag acgccacgcg cgttgcgtga atttttgggc acagc 45

<210> SEQ ID NO 451
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 451
tacgcctaag acgccacgcc gtttgcgtga atttttgggc acagc 45

<210> SEQ ID NO 452

<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 452
tacgcctaag acgccacgcg agttgcgtga atttttgggc acagc 45

<210> SEQ ID NO 453
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 453
gcgtgaattt ttgggcacag cggcgttctg tcgtttatgg attcctggg 49

<210> SEQ ID NO 454
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 454
gcgtgaattt ttgggcacag cgcgtttctg tcgtttatgg attcctggg 49

<210> SEQ ID NO 455
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 455
gcgtgaattt ttgggcacag cggagttctg tcgtttatgg attcctggg 49

<210> SEQ ID NO 456
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 456
gggcacagcg ggattctgtg cgttatggat tcctgggttc gctga 45

<210> SEQ ID NO 457
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 457
gggcacagcg ggattctgta aattatggat tcctgggttc gctga 45

<210> SEQ ID NO 458
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 458
gggcacagcg ggattctgtg agttatggat tcctgggttc gctga 45

<210> SEQ ID NO 459
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 459
gtcaaaaaca ggtaaagtac cttggggcgt tgctgaaaga aggtcaacgt tgg 53

<210> SEQ ID NO 460
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 460
gtcaaaaaca ggtaaagtac cttgggcgtt tgctgaaaga aggtcaacgt tgg 53

<210> SEQ ID NO 461
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 461
gtcaaaaaca ggtaaagtac cttggggagt tgctgaaaga aggtcaacgt tgg 53

<210> SEQ ID NO 462
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 462
tgctgaaaga aggtcaacgt tgggcgactg aagcgcgtaa ggagacc 47

<210> SEQ ID NO 463
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 463
tgctgaaaga aggtcaacgt tggcgtactg aagcgcgtaa ggagacc 47

<210> SEQ ID NO 464
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 464
tgctgaaaga aggtcaacgt tgggagactg aagcgcgtaa ggagacc 47

<210> SEQ ID NO 465
<211> LENGTH: 45
<212> TYPE: DNA

<213> ORGANISM: Artificial Sequence
<220> FEATURE:
<223> OTHER INFORMATION: Synthetic oligonucleotide

<400> SEQUENCE: 465
tttgttgacc gcacccgcgg cgggtcttcc ggatttaacc aagcc 45

<210> SEQ ID NO 466
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 466
tttgttgacc gcacccgcgc gtggtcttcc ggatttaacc aagcc 45

<210> SEQ ID NO 467
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 467
tttgttgacc gcacccgcgg agggtcttcc ggatttaacc aagcc 45

<210> SEQ ID NO 468
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 468
ctgcacccct gtacccctta gcgaaaacag ggacgctttt caactgg 47

<210> SEQ ID NO 469
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 469
ctgcacccct gtacccctta cgtaaaacag ggacgctttt caactgg 47

<210> SEQ ID NO 470
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 470
ctgcacccct gtacccctta gagaaaacag ggacgctttt caactgg 47

<210> SEQ ID NO 471
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 471
cccctgtacc ccttaacaaa aacagcgacg cttttcaact gggggcc 47

<210> SEQ ID NO 472
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 472
cccctgtacc ccttaacaaa aacacgtacg cttttcaact gggggcc 47

<210> SEQ ID NO 473
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 473
cccctgtacc ccttaacaaa aacagagacg cttttcaact gggggcc 47

<210> SEQ ID NO 474
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 474
ctgtacccct taacaaaaac aggggcgctt ttcaactggg ggccagac 48

<210> SEQ ID NO 475
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 475
ctgtacccct taacaaaaac agggcgtctt ttcaactggg ggccagac 48

<210> SEQ ID NO 476
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 476
ctgtacccct taacaaaaac aggggagctt ttcaactggg ggccagac 48

<210> SEQ ID NO 477
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 477
ccttaacaaa aacagggacg cttttcgcgt gggggccaga ccagcaaa 48

<210> SEQ ID NO 478
<211> LENGTH: 48
<212> TYPE: DNA
<213> ORGANISM: Artificial Sequence
<220> FEATURE:

<223> OTHER INFORMATION: Synthetic oligonucleotide

<400> SEQUENCE: 478
ccttaacaaa aacagggacg cttttccgtt gggggccaga ccagcaaa 48

<210> SEQ ID NO 479
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 479
cttccggatt taaccaagcc ctttgcgctg ttcgttgatg aaaaacaggg atat 54

<210> SEQ ID NO 480
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 480
cttccggatt taaccaagcc ctttcgtctg ttcgttgatg aaaaacaggg atat 54

<210> SEQ ID NO 481
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 481
cttccggatt taaccaagcc ctttgatctg ttcgttgatg aaaaacaggg atat 54

<210> SEQ ID NO 482
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 482
gatttaacca agccctttga gctggcggtt gatgaaaaac agggatatgc aaaag 55

<210> SEQ ID NO 483
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 483
gatttaacca agccctttga gctgcgtgtt gatgaaaaac agggatatgc aaaag 55

<210> SEQ ID NO 484
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 484
gatttaacca agccctttga gctggaggtt gatgaaaaac agggatatgc aaaag 55

<210> SEQ ID NO 485
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 485
cccaaaagtt aggcccgtgg gcgcgccctg ttgcttactt gagtaa 46

<210> SEQ ID NO 486
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 486
cccaaaagtt aggcccgtgg aaacgccctg ttgcttactt gagtaa 46

<210> SEQ ID NO 487
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 487
cccaaaagtt aggcccgtgg gagcgccctg ttgcttactt gagtaa 46

<210> SEQ ID NO 488
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 488
agttgacgat gggtcaaccc ttagcgatct tggctccaca tgctgtaga 49

<210> SEQ ID NO 489
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 489
agttgacgat gggtcaaccc ttacgtatct tggctccaca tgctgtaga 49

<210> SEQ ID NO 490
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 490
agttgacgat gggtcaaccc ttagagatct tggctccaca tgctgtaga 49

<210> SEQ ID NO 491
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 491
ggatcgtgta caatttggac cagttgcggc tttgaatcca gctactttgc ttc 53

<210> SEQ ID NO 492
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 492
ggatcgtgta caatttggac cagttcgtgc tttgaatcca gctactttgc ttc 53

<210> SEQ ID NO 493
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 493
ggatcgtgta caatttggac cagttgaggc tttgaatcca gctactttgc ttc 53

<210> SEQ ID NO 494
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 494
cgttatgctt ttgcaacagc gcatgcgcat ggcgaaattt accgccgc 48

<210> SEQ ID NO 495
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 495
cgttatgctt ttgcaacagc gcatcgtcat ggcgaaattt accgccgc 48

<210> SEQ ID NO 496
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 496
cgttatgctt ttgcaacagc gcatgagcat ggcgaaattt accgccgc 48

<210> SEQ ID NO 497
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 497
gcaacagcgc atatccatgg cgcgatttac cgccgccgtg gtc 43

<210> SEQ ID NO 498
<211> LENGTH: 43

<212> TYPE: DNA
<213> ORGANISM: Artificial Sequence
<220> FEATURE:
<223> OTHER INFORMATION: Synthetic oligonucleotide

<400> SEQUENCE: 498
gcaacagcgc atatccatgg ccgtatttac cgccgccgtg gtc 43

<210> SEQ ID NO 499
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 499
gcaacagcgc atatccatgg cgatatttac cgccgccgtg gtc 43

<210> SEQ ID NO 500
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 500
caacagcgca tatccatggc gaagcgtacc gccgccgtgg tctg 44

<210> SEQ ID NO 501
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 501
caacagcgca tatccatggc gaacgttacc gccgccgtgg tctg 44

<210> SEQ ID NO 502
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 502
caacagcgca tatccatggc gaagagtacc gccgccgtgg tctg 44

<210> SEQ ID NO 503
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 503
agcggaggct cgtggaaacg cgatggcgga ccaagctgcc c 41

<210> SEQ ID NO 504
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 504

-continued agcggaggct cgtggaaaca aaatggcgga ccaagctgcc c 41

<210> SEQ ID NO 505
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 505
agcggaggct cgtggaaacg agatggcgga ccaagctgcc c 41

<210> SEQ ID NO 506
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 506
gtggaaaccg tatggcggac gcggctgccc gtaaggcggc 40

<210> SEQ ID NO 507
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 507
gtggaaaccg tatggcggac cgtgctgccc gtaaggcggc 40

<210> SEQ ID NO 508
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 508
gtggaaaccg tatggcggac gaggctgccc gtaaggcggc 40

<210> SEQ ID NO 509
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 509
tatggcggac caagctgccg cgaaggcggc gatcacagag ac 42

<210> SEQ ID NO 510
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 510
tatggcggac caagctgcca aaaaggcggc gatcacagag ac 42

<210> SEQ ID NO 511
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 511
tatggcggac caagctgccg agaaggcggc gatcacagag ac 42

<210> SEQ ID NO 512
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 512
gcaagcgctg aatatgtggc ttaatcgcca ggcgggcctc ttgactc 47

<210> SEQ ID NO 513
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 513
gcaagcgctg aatatgtggc ttaatacgca ggcgggcctc ttgactc 47

<210> SEQ ID NO 514
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 514
gcaagcgctg aatatgtggc ttaatctcca ggcgggcctc ttgactc 47

<210> SEQ ID NO 515
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 515
ggtccagcaa gcgctgaata tgcgccttaa tccccaggcg ggcc 44

<210> SEQ ID NO 516
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 516
ggtccagcaa gcgctgaata tgacgcttaa tccccaggcg ggcc 44

<210> SEQ ID NO 517
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 517
ggtccagcaa gcgctgaata tgctccttaa tccccaggcg ggcc 44

<210> SEQ ID NO 518
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 518
ctggtccagc aagcgctgaa tcgctggctt aatccccagg cgg 43

<210> SEQ ID NO 519
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 519
ctggtccagc aagcgctgaa tacgtggctt aatccccagg cgg 43

<210> SEQ ID NO 520
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 520
ctggtccagc aagcgctgaa tctctggctt aatccccagg cgg 43

<210> SEQ ID NO 521
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 521
ggaccaagat cccctggtcc gccaagcgct gaatatgtgg cttaatc 47

<210> SEQ ID NO 522
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 522
ggaccaagat cccctggtca cgcaagcgct gaatatgtgg cttaatc 47

<210> SEQ ID NO 523
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 523
ggaccaagat cccctggtcc tccaagcgct gaatatgtgg cttaatc 47

<210> SEQ ID NO 524
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 524
catgggacca agatcccctg cgccagcaag cgctgaatat gtggc 45

<210> SEQ ID NO 525
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 525
catgggacca agatcccctg acgcagcaag cgctgaatat gtggc 45

<210> SEQ ID NO 526
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 526
catgggacca agatcccctg ctccagcaag cgctgaatat gtggc 45

<210> SEQ ID NO 527
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 527
attataagga ttaggtacag tcggatgcgc gtcttctacg cgtttgttga cct 53

<210> SEQ ID NO 528
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 528
attataagga ttaggtacag tcggatgacg gtcttctacg cgtttgttga cct 53

<210> SEQ ID NO 529
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 529
attataagga ttaggtacag tcggatgctc gtcttctacg cgtttgttga cct 53

<210> SEQ ID NO 530
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 530
gcctgataac agattataag gattaggcgc agtcggatgg atgtcttcta cgc 53

<210> SEQ ID NO 531

<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 531
gcctgataac agattataag gattaggacg agtcggatgg atgtcttcta cgc 53

<210> SEQ ID NO 532
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 532
gcctgataac agattataag gattaggctc agtcggatgg atgtcttcta cgc 53

<210> SEQ ID NO 533
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 533
tcacggtgaa gtgcttcatc gaacgctgtg gggctgtttt taaagccct 49

<210> SEQ ID NO 534
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 534
tcacggtgaa gtgcttcatc gaaacgtgtg gggctgtttt taaagccct 49

<210> SEQ ID NO 535
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 535
tcacggtgaa gtgcttcatc gaactctgtg gggctgtttt taaagccct 49

<210> SEQ ID NO 536
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 536
ctgctaagtc acggtgaagt gccgcatcga acaatgtggg gctgttttta aa 52

<210> SEQ ID NO 537
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 537
ctgctaagtc acggtgaagt gcacgatcga acaatgtggg gctgttttta aa 52

<210> SEQ ID NO 538
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 538
ctgctaagtc acggtgaagt gcatcatcga acaatgtggg gctgttttta aa 52

<210> SEQ ID NO 539
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 539
tggatacgga agtctgctaa gtccgcgtga agtgcttcat cgaacaatgt g 51

<210> SEQ ID NO 540
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 540
tggatacgga agtctgctaa gtctttgtga agtgcttcat cgaacaatgt g 51

<210> SEQ ID NO 541
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 541
tggatacgga agtctgctaa gtcctcgtga agtgcttcat cgaacaatgt g 51

<210> SEQ ID NO 542
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 542
aagtctgggt gttggatacg gaacgctgct aagtcacggt gaagtgctt 49

<210> SEQ ID NO 543
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 543
aagtctgggt gttggatacg gaaacgtgct aagtcacggt gaagtgctt 49

<210> SEQ ID NO 544
<211> LENGTH: 49
<212> TYPE: DNA

<213> ORGANISM: Artificial Sequence
<220> FEATURE:
<223> OTHER INFORMATION: Synthetic oligonucleotide

<400> SEQUENCE: 544
aagtctgggt gttggatacg gaactctgct aagtcacggt gaagtgctt 49

<210> SEQ ID NO 545
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 545
gaattaagtc tgggtgttgg atacgcgcgt ctgctaagtc acggtgaagt g 51

<210> SEQ ID NO 546
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 546
gaattaagtc tgggtgttgg atacgacggt ctgctaagtc acggtgaagt g 51

<210> SEQ ID NO 547
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 547
gaattaagtc tgggtgttgg atacgctcgt ctgctaagtc acggtgaagt g 51

<210> SEQ ID NO 548
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 548
taacagaatt aagtctgggt gttggatcgc gaagtctgct aagtcacggt gaa 53

<210> SEQ ID NO 549
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 549
taacagaatt aagtctgggt gttggatttt gaagtctgct aagtcacggt gaa 53

<210> SEQ ID NO 550
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 550
taacagaatt aagtctgggt gttggatctc gaagtctgct aagtcacggt gaa 53

<210> SEQ ID NO 551
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 551
ctgtaacaga attaagtctg ggtgttgcgc acggaagtct gctaagtcac gg 52

<210> SEQ ID NO 552
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 552
ctgtaacaga attaagtctg ggtgttgacg acggaagtct gctaagtcac gg 52

<210> SEQ ID NO 553
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 553
ctgtaacaga attaagtctg ggtgttgctc acggaagtct gctaagtcac gg 52

<210> SEQ ID NO 554
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 554
atactgtaac agaattaagt ctgggtgcgc gatacggaag tctgctaagt cac 53

<210> SEQ ID NO 555
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 555
atactgtaac agaattaagt ctgggtgacg gatacggaag tctgctaagt cac 53

<210> SEQ ID NO 556
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 556
atactgtaac agaattaagt ctgggtgctc gatacggaag tctgctaagt cac 53

<210> SEQ ID NO 557
<211> LENGTH: 47
<212> TYPE: DNA
<213> ORGANISM: Artificial Sequence
<220> FEATURE:

<223> OTHER INFORMATION: Synthetic oligonucleotide

<400> SEQUENCE: 557
gggtgcggtc aacaaagctt gcgcgatctc ctgatacgcc ttttgct 47

<210> SEQ ID NO 558
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 558
gggtgcggtc aacaaagctt gacggatctc ctgatacgcc ttttgct 47

<210> SEQ ID NO 559
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 559
gggtgcggtc aacaaagctt gctcgatctc ctgatacgcc ttttgct 47

<210> SEQ ID NO 560
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 560
cccaacgcgg gtgcggtcgc caaagcttgt ttgatctcct gatacg 46

<210> SEQ ID NO 561
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 561
cccaacgcgg gtgcggtacg caaagcttgt ttgatctcct gatacg 46

<210> SEQ ID NO 562
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 562
cccaacgcgg gtgcggtctc caaagcttgt ttgatctcct gatacg 46

<210> SEQ ID NO 563
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 563
gctgccccat tacggtctcc gcacgcgctt cagtcagcca ac 42

<210> SEQ ID NO 564
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 564
gctgccccat tacggtctca cgacgcgctt cagtcagcca ac 42

<210> SEQ ID NO 565
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 565
gctgccccat tacggtctcc tcacgcgctt cagtcagcca ac 42

<210> SEQ ID NO 566
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 566
gctgtgccca aaaattcacg caacgcgcgt ggcgtcttag gcgta 45

<210> SEQ ID NO 567
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 567
gctgtgccca aaaattcacg caaacggcgt ggcgtcttag gcgta 45

<210> SEQ ID NO 568
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 568
gctgtgccca aaaattcacg caactcgcgt ggcgtcttag gcgta 45

<210> SEQ ID NO 569
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 569
cccaggaatc cataaacgac agaacgccgc tgtgcccaaa aattcacgc 49

<210> SEQ ID NO 570
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 570
cccaggaatc cataaacgac agaaacgcgc tgtgcccaaa aattcacgc 49

<210> SEQ ID NO 571
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 571
cccaggaatc cataaacgac agaactccgc tgtgcccaaa aattcacgc 49

<210> SEQ ID NO 572
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 572
tcagcgaacc caggaatcca taacgcacag aatcccgctg tgccc 45

<210> SEQ ID NO 573
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 573
tcagcgaacc caggaatcca taatttacag aatcccgctg tgccc 45

<210> SEQ ID NO 574
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 574
tcagcgaacc caggaatcca taactcacag aatcccgctg tgccc 45

<210> SEQ ID NO 575
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 575
ccaacgttga ccttctttca gcaacgcccc aaggtacttt acctgttttt gac 53

<210> SEQ ID NO 576
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 576
ccaacgttga ccttctttca gcaaacgccc aaggtacttt acctgttttt gac 53

<210> SEQ ID NO 577
<211> LENGTH: 53

<212> TYPE: DNA
<213> ORGANISM: Artificial Sequence
<220> FEATURE:
<223> OTHER INFORMATION: Synthetic oligonucleotide

<400> SEQUENCE: 577
ccaacgttga ccttctttca gcaactcccc aaggtacttt acctgttttt gac 53

<210> SEQ ID NO 578
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 578
ggtctcctta cgcgcttcag tcgcccaacg ttgaccttct ttcagca 47

<210> SEQ ID NO 579
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 579
ggtctcctta cgcgcttcag tacgccaacg ttgaccttct ttcagca 47

<210> SEQ ID NO 580
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 580
ggtctcctta cgcgcttcag tctcccaacg ttgaccttct ttcagca 47

<210> SEQ ID NO 581
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 581
ggcttggtta aatccggaag acccgccgcg ggtgcggtca acaaa 45

<210> SEQ ID NO 582
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 582
ggcttggtta aatccggaag accacgcgcg ggtgcggtca acaaa 45

<210> SEQ ID NO 583
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 583
ggcttggtta aatccggaag accctccgcg ggtgcggtca acaaa 45

<210> SEQ ID NO 584
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 584
ccagttgaaa agcgtccctg ttttcgctaa ggggtacagg ggtgcag 47

<210> SEQ ID NO 585
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 585
ccagttgaaa agcgtccctg ttttacgtaa ggggtacagg ggtgcag 47

<210> SEQ ID NO 586
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 586
ccagttgaaa agcgtccctg ttttctctaa ggggtacagg ggtgcag 47

<210> SEQ ID NO 587
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 587
ggcccccagt tgaaaagcgt cgctgttttt gttaaggggt acagggg 47

<210> SEQ ID NO 588
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 588
ggcccccagt tgaaaagcgt acgtgttttt gttaaggggt acagggg 47

<210> SEQ ID NO 589
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 589
ggcccccagt tgaaaagcgt ctctgttttt gttaaggggt acagggg 47

<210> SEQ ID NO 590
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 590
gtctggcccc cagttgaaaa gcgcccctgt ttttgttaag gggtacag 48

<210> SEQ ID NO 591
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 591
gtctggcccc cagttgaaaa gacgccctgt ttttgttaag gggtacag 48

<210> SEQ ID NO 592
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 592
gtctggcccc cagttgaaaa gctcccctgt ttttgttaag gggtacag 48

<210> SEQ ID NO 593
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 593
tttgctggtc tggcccccac gcgaaaagcg tccctgtttt tgttaagg 48

<210> SEQ ID NO 594
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 594
tttgctggtc tggcccccaa cggaaaagcg tccctgtttt tgttaagg 48

<210> SEQ ID NO 595
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 595
tttgctggtc tggcccccac tcgaaaagcg tccctgtttt tgttaagg 48

<210> SEQ ID NO 596
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 596
atatccctgt ttttcatcaa cgaacagcgc aaagggcttg gttaaatccg gaag 54

<210> SEQ ID NO 597
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 597
atatccctgt ttttcatcaa cgaacagacg aaagggcttg gttaaatccg gaag 54

<210> SEQ ID NO 598
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 598
atatccctgt ttttcatcaa cgaacagatc aaagggcttg gttaaatccg gaag 54

<210> SEQ ID NO 599
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 599
cttttgcata tccctgtttt tcatcaaccg ccagctcaaa gggcttggtt aaatc 55

<210> SEQ ID NO 600
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 600
cttttgcata tccctgtttt tcatcaacac gcagctcaaa gggcttggtt aaatc 55

<210> SEQ ID NO 601
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 601
cttttgcata tccctgtttt tcatcaacct ccagctcaaa gggcttggtt aaatc 55

<210> SEQ ID NO 602
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 602
ttactcaagt aagcaacagg gcgcgcccac gggcctaact tttggg 46

<210> SEQ ID NO 603
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 603
ttactcaagt aagcaacagg gcgtttccac gggcctaact tttggg 46

<210> SEQ ID NO 604
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 604
ttactcaagt aagcaacagg gcgctcccac gggcctaact tttggg 46

<210> SEQ ID NO 605
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 605
tctacagcat gtggagccaa gatcgctaag ggttgaccca tcgtcaact 49

<210> SEQ ID NO 606
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 606
tctacagcat gtggagccaa gatacgtaag ggttgaccca tcgtcaact 49

<210> SEQ ID NO 607
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 607
tctacagcat gtggagccaa gatctctaag ggttgaccca tcgtcaact 49

<210> SEQ ID NO 608
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 608
gaagcaaagt agctggattc aaagccgcaa ctggtccaaa ttgtacacga tcc 53

<210> SEQ ID NO 609
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 609
gaagcaaagt agctggattc aaagcacgaa ctggtccaaa ttgtacacga tcc 53

<210> SEQ ID NO 610

<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 610
gaagcaaagt agctggattc aaagcctcaa ctggtccaaa ttgtacacga tcc 53

<210> SEQ ID NO 611
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 611
gcggcggtaa atttcgccat gcgcatgcgc tgttgcaaaa gcataacg 48

<210> SEQ ID NO 612
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 612
gcggcggtaa atttcgccat gacgatgcgc tgttgcaaaa gcataacg 48

<210> SEQ ID NO 613
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 613
gcggcggtaa atttcgccat gctcatgcgc tgttgcaaaa gcataacg 48

<210> SEQ ID NO 614
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 614
gaccacggcg gcggtaaatc gcgccatgga tatgcgctgt tgc 43

<210> SEQ ID NO 615
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 615
gaccacggcg gcggtaaata cggccatgga tatgcgctgt tgc 43

<210> SEQ ID NO 616
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 616
gaccacggcg gcggtaaata tcgccatgga tatgcgctgt tgc 43

<210> SEQ ID NO 617
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 617
cagaccacgg cggcggtacg cttcgccatg gatatgcgct gttg 44

<210> SEQ ID NO 618
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 618
cagaccacgg cggcggtaac gttcgccatg gatatgcgct gttg 44

<210> SEQ ID NO 619
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 619
cagaccacgg cggcggtact cttcgccatg gatatgcgct gttg 44

<210> SEQ ID NO 620
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 620
gggcagcttg gtccgccatc gcgtttccac gagcctccgc t 41

<210> SEQ ID NO 621
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 621
gggcagcttg gtccgccatt ttgtttccac gagcctccgc t 41

<210> SEQ ID NO 622
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 622
gggcagcttg gtccgccatc tcgtttccac gagcctccgc t 41

<210> SEQ ID NO 623
<211> LENGTH: 40
<212> TYPE: DNA

<213> ORGANISM: Artificial Sequence
<220> FEATURE:
<223> OTHER INFORMATION: Synthetic oligonucleotide

<400> SEQUENCE: 623
gccgccttac gggcagccgc gtccgccata cggtttccac 40

<210> SEQ ID NO 624
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 624
gccgccttac gggcagcacg gtccgccata cggtttccac 40

<210> SEQ ID NO 625
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 625
gccgccttac gggcagcctc gtccgccata cggtttccac 40

<210> SEQ ID NO 626
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 626
gtctctgtga tcgccgcctt cgcggcagct tggtccgcca ta 42

<210> SEQ ID NO 627
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 627
gtctctgtga tcgccgcctt tttggcagct tggtccgcca ta 42

<210> SEQ ID NO 628
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 628
gtctctgtga tcgccgcctt ctcggcagct tggtccgcca ta 42

<210> SEQ ID NO 629
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 629
atttgctgaa agaaggtcaa cgttggcgta ctgatgcgcg taaggagacc 50

<210> SEQ ID NO 630
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 630
ggtctcctta cgcgcatcag tacgccaacg ttgaccttct ttcagcaaat 50

<210> SEQ ID NO 631
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 631
gggattaagc cacatattcg tcgcttgcgt gaccagggga tcttggtccc 50

<210> SEQ ID NO 632
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 632
gggaccaaga tcccctggtc acgcaagcga cgaatatgtg gcttaatccc 50

<210> SEQ ID NO 633
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 633
gtcgagtatc tcagaaaaga agaca 25

<210> SEQ ID NO 634
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 634
ctcggatgta ggaagtttca cc 22

<210> SEQ ID NO 635
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' SUN
<220> FEATURE:
<221> NAME/KEY: misc_feature
<222> LOCATION: (10)..(11)
<223> OTHER INFORMATION: ZEN molecule
<220> FEATURE:
<221> NAME/KEY: misc_feature
<222> LOCATION: (24)..(24)

<223> OTHER INFORMATION: 3' IABkFQ

<400> SEQUENCE: 635
atgccctgcg taaactggat gaca 24

<210> SEQ ID NO 636
<211> LENGTH: 2055
<212> TYPE: DNA
<213> ORGANISM: Artificial Sequence
<220> FEATURE:
<223> OTHER INFORMATION: Synthetic oligonucleotide

<400> SEQUENCE: 636
atgactttaa atattgagga tgagcatcgt ttacatgaga catcaaaaga acccgacgtg 60
agcttagggt caacgtggct ttctgacttc ccccaggcgt gggcggagac tggcggaatg 120
gggttagctg tccgccaagc accgttgatc atcccgttaa aggcaacgtc tacacctgtc 180
tctatcaaac agtaccccat gagtcaagag gcccgcctgg ggattaagcc acatattcag 240
cgcttgctgg accaggggat cttggtccca tgtcaatctc cgtggaacac ccccctt ctg 300 cccgtgaaaa agccaggtac aaacgattat cgtccagttc aagatcttcg cgaggtcaac 360
aaacgcgtag aagacatcca tccgactgta cctaatcctt ataatctgtt atcaggcctg 420
cccccatcgc accaatggta tacagtatta gacttgaaag acgcgttctt ttgcctgcgt 480
ctgcacccaa cgtctcagcc gctgtttgcg ttcgaatggc gtgatcctga aatgggaatt 540
tcgggtcagt taacctggac tcgtctgccc cagggcttta aaaacagccc cacattgttc 600
gatgaagcac ttcaccgtga cttagcagac ttccgtatcc aacacccaga cttaattctg 660
ttacagtatg ttgacgacct tttgttggcg gcaacgtctg aacttgactg tcagcaaggc 720
acacgcgcgt tattacaaac gttaggtaac ttaggatatc gtgcgtccgc gaaaaaggcg 780
caaatttgtc aaaaacaggt aaagtacctt gggtatttgc tgaaagaagg tcaacgttgg 840
ctgactgaag cgcgtaagga gaccgtaatg gggcagccta cgcctaagac gccacgccag 900
ttgcgtgaat ttttgggcac agcgggattc tgtcgtttat ggattcctgg gttcgctgaa 960
atggctgcac ccctgtaccc cttaacaaaa acagggacgc ttttcaactg gggggccagac 1020 cagcaaaagg cgtatcagga gatcaaacaa gctttgttga ccgcacccgc gttgggtctt 1080
ccggatttaa ccaagccctt tgagctgttc gttgatgaaa aacagggata tgcaaaagga 1140
gtattaaccc aaaagttagg cccgtggcgt cgccctgttg cttacttgag taaaaaattg 1200
gatcctgtcg cagcaggatg gccaccgtgc ttgcgtatgg tcgcggcaat tgccgttttg 1260
acaaaggatg caggtaagtt gacgatgggt caacccttag taatcttggc tccacatgct 1320
gtagaagcgt tagtaaagca gcccccagac cgctggcttt ctaatgcgcg catgacccac 1380
tatcaggcgc ttctgcttga tacggatcgt gtacaatttg gaccagttgt agctttgaat 1440
ccagctactt tgcttcccct tccagaagaa ggacttcagc acaattgttt agatattctg 1500
gccgaggcac atgggacgcg ccctgatttg acggatcagc cactgcctga tgccgaccat 1560
acatggtata ctggcggcag tagtcttctt caagaggggc aacgcaaggc gggagcagcc 1620
gtcactacgg agaccgaagt tatctgggcc aaagcgttac ccgcgggaac atccgcgcaa 1680
cgtgcacagt taatcgctct gacacaggcc ctgaagatgg cagagggcaa aaagttgaat 1740
gtctacacca actcacgtta tgcttttgca acagcgcata tccatggcga aatttaccgc 1800
cgccgtggtc tgctgactag tgagggtaag gaaattaaaa ataaagatga gattcttgcg 1860
ttgttaaaag ctttattctt accaaaacgc ctttcgatca ttcattgccc ggggcatcaa 1920

```
aagggtcact cagcggaggc tcgtggaaac cgtatggcgg accaagctgc ccgtaaggcg   1980

gcgatcacag agaccccgga tacatcaacg ctgttgatcg aaaacagctc tccctacact   2040

agcgagcatt tttaa                                                    2055


<210> SEQ ID NO 637
<211> LENGTH: 684
<212> TYPE: PRT
<213> ORGANISM: Artificial Sequence
<220> FEATURE:
<223> OTHER INFORMATION: RTase mutant

<400> SEQUENCE: 637

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335
```

Trp Gly Pro Asp Gln Gln Lys Ala Tyr Gln Glu Ile Lys Gln Ala Leu
340 345 350

Leu Thr Ala Pro Ala Leu Gly Leu Pro Asp Leu Thr Lys Pro Phe Glu
355 360 365

Leu Phe Val Asp Glu Lys Gln Gly Tyr Ala Lys Gly Val Leu Thr Gln
370 375 380

Lys Leu Gly Pro Trp Arg Arg Pro Val Ala Tyr Leu Ser Lys Lys Leu
385 390 395 400

Asp Pro Val Ala Ala Gly Trp Pro Pro Cys Leu Arg Met Val Ala Ala
405 410 415

Ile Ala Val Leu Thr Lys Asp Ala Gly Lys Leu Thr Met Gly Gln Pro
420 425 430

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 638
<211> LENGTH: 684
<212> TYPE: PRT
<213> ORGANISM: Artificial Sequence
<220> FEATURE:
<223> OTHER INFORMATION: RTase mutant

<400> SEQUENCE: 638

Met Thr Leu Asn Ile Glu Asp Glu His Arg Leu His Glu Thr Ser Lys
1 5 10 15

```
Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430
```

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 639
<211> LENGTH: 684
<212> TYPE: PRT
<213> ORGANISM: Artificial Sequence
<220> FEATURE:
<223> OTHER INFORMATION: RTase mutant

<400> SEQUENCE: 639

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Arg Glu Ala Arg Leu Gly Ile Lys Pro His Ile Gln
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

```
Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
```

```
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 640
<211> LENGTH: 684
<212> TYPE: PRT
<213> ORGANISM: Artificial Sequence
<220> FEATURE:
<223> OTHER INFORMATION: RTase mutant

<400> SEQUENCE: 640

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
```

```
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640
```

```
Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 641
<211> LENGTH: 684
<212> TYPE: PRT
<213> ORGANISM: Artificial Sequence
<220> FEATURE:
<223> OTHER INFORMATION: RTase mutant

<400> SEQUENCE: 641

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Arg Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320
```

Met Ala Ala Pro Leu Tyr Pro Leu Thr Lys Thr Gly Thr Leu Phe Asn
325 330 335

Trp Gly Pro Asp Gln Gln Lys Ala Tyr Gln Glu Ile Lys Gln Ala Leu
340 345 350

Leu Thr Ala Pro Ala Leu Gly Leu Pro Asp Leu Thr Lys Pro Phe Glu
355 360 365

Leu Phe Val Asp Glu Lys Gln Gly Tyr Ala Lys Gly Val Leu Thr Gln
370 375 380

Lys Leu Gly Pro Trp Arg Arg Pro Val Ala Tyr Leu Ser Lys Lys Leu
385 390 395 400

Asp Pro Val Ala Ala Gly Trp Pro Pro Cys Leu Arg Met Val Ala Ala
405 410 415

Ile Ala Val Leu Thr Lys Asp Ala Gly Lys Leu Thr Met Gly Gln Pro
420 425 430

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 642
<211> LENGTH: 684
<212> TYPE: PRT
<213> ORGANISM: Artificial Sequence
<220> FEATURE:
<223> OTHER INFORMATION: RTase mutant

<400> SEQUENCE: 642

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415
```

```
Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

```
<210> SEQ ID NO 643
<211> LENGTH: 684
<212> TYPE: PRT
<213> ORGANISM: Artificial Sequence
<220> FEATURE:
<223> OTHER INFORMATION: RTase mutant

<400> SEQUENCE: 643

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95
```

```
Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
```

```
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 644
<211> LENGTH: 684
<212> TYPE: PRT
<213> ORGANISM: Artificial Sequence
<220> FEATURE:
<223> OTHER INFORMATION: RTase mutant

<400> SEQUENCE: 644

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Lys Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
```

```
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620
```

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 645
<211> LENGTH: 684
<212> TYPE: PRT
<213> ORGANISM: Artificial Sequence
<220> FEATURE:
<223> OTHER INFORMATION: RTase mutant

<400> SEQUENCE: 645

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Met Lys Gln
50 55 60

Tyr Pro Met Ser Gln Glu Ala Arg Leu Gly Ile Lys Pro His Ile Gln
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

Leu Leu Lys Glu Gly Gln Arg Trp Leu Thr Glu Ala Arg Lys Glu Thr
275 280 285

Val Met Gly Gln Pro Thr Pro Lys Thr Pro Arg Gln Leu Arg Glu Phe
290 295 300

```
Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 646
<211> LENGTH: 684
<212> TYPE: PRT
<213> ORGANISM: Artificial Sequence
<220> FEATURE:

<223> OTHER INFORMATION: RTase mutant

<400> SEQUENCE: 646

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Ile Glu Ala Arg Leu Gly Ile Lys Pro His Ile Gln
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

Leu Leu Lys Glu Gly Gln Arg Trp Leu Thr Glu Ala Arg Lys Glu Thr
275 280 285

Val Met Gly Gln Pro Thr Pro Lys Thr Pro Arg Gln Leu Arg Glu Phe
290 295 300

Leu Gly Thr Ala Gly Phe Cys Arg Leu Trp Ile Pro Gly Phe Ala Glu
305 310 315 320

Met Ala Ala Pro Leu Tyr Pro Leu Thr Lys Thr Gly Thr Leu Phe Asn
325 330 335

Trp Gly Pro Asp Gln Gln Lys Ala Tyr Gln Glu Ile Lys Gln Ala Leu
340 345 350

Leu Thr Ala Pro Ala Leu Gly Leu Pro Asp Leu Thr Lys Pro Phe Glu
355 360 365

Leu Phe Val Asp Glu Lys Gln Gly Tyr Ala Lys Gly Val Leu Thr Gln
370 375 380

Lys Leu Gly Pro Trp Arg Arg Pro Val Ala Tyr Leu Ser Lys Lys Leu
385 390 395 400

```
Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 647
<211> LENGTH: 684
<212> TYPE: PRT
<213> ORGANISM: Artificial Sequence
<220> FEATURE:
<223> OTHER INFORMATION: RTase mutant

<400> SEQUENCE: 647

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Lys Glu Ala Arg Leu Gly Ile Lys Pro His Ile Gln
65                  70                  75                  80
```

```
Arg Leu Leu Asp Gln Gly Ile Leu Val Pro Cys Gln Ser Pro Trp Asn
            85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
```

500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 648
<211> LENGTH: 684
<212> TYPE: PRT
<213> ORGANISM: Artificial Sequence
<220> FEATURE:
<223> OTHER INFORMATION: RTase mutant

<400> SEQUENCE: 648

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Gln Glu Ala Arg Leu Gly Ile Lys Pro His Ile His
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly

```
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605
```

```
Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 649
<211> LENGTH: 684
<212> TYPE: PRT
<213> ORGANISM: Artificial Sequence
<220> FEATURE:
<223> OTHER INFORMATION: RTase mutant

<400> SEQUENCE: 649

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Ile
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285
```

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680

<210> SEQ ID NO 650
<211> LENGTH: 684

```
<212> TYPE: PRT
<213> ORGANISM: Artificial Sequence
<220> FEATURE:
<223> OTHER INFORMATION: RTase mutant

<400> SEQUENCE: 650

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Lys Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380
```

```
Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 651
<211> LENGTH: 684
<212> TYPE: PRT
<213> ORGANISM: Artificial Sequence
<220> FEATURE:
<223> OTHER INFORMATION: RTase mutant

<400> SEQUENCE: 651

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60
```

```
Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Asn Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
```

```
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 652
<211> LENGTH: 684
<212> TYPE: PRT
<213> ORGANISM: Artificial Sequence
<220> FEATURE:
<223> OTHER INFORMATION: RTase mutant

<400> SEQUENCE: 652

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
```

```
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590
```

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 653
<211> LENGTH: 684
<212> TYPE: PRT
<213> ORGANISM: Artificial Sequence
<220> FEATURE:
<223> OTHER INFORMATION: RTase mutant

<400> SEQUENCE: 653

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Gln Glu Ala Arg Leu Gly Ile Lys Pro His Ile Gln
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

```
Leu Leu Lys Glu Gly Gln Arg Trp Leu Thr Trp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 654
<211> LENGTH: 684
<212> TYPE: PRT
<213> ORGANISM: Artificial Sequence
<220> FEATURE:
<223> OTHER INFORMATION: RTase mutant

<400> SEQUENCE: 654

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

```
Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 655
<211> LENGTH: 684
<212> TYPE: PRT
<213> ORGANISM: Artificial Sequence
<220> FEATURE:
<223> OTHER INFORMATION: RTase mutant

<400> SEQUENCE: 655

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45
```

-continued

```
Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Arg Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
```

```
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 656
<211> LENGTH: 684
<212> TYPE: PRT
<213> ORGANISM: Artificial Sequence
<220> FEATURE:
<223> OTHER INFORMATION: RTase mutant

<400> SEQUENCE: 656

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
```

```
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575
```

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 657
<211> LENGTH: 684
<212> TYPE: PRT
<213> ORGANISM: Artificial Sequence
<220> FEATURE:
<223> OTHER INFORMATION: RTase mutant

<400> SEQUENCE: 657

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Gln Glu Ala Arg Leu Gly Ile Lys Pro His Ile Arg
65 70 75 80

Arg Leu Leu Asp Gln Gly Ile Leu Val Pro Cys Gln Ser Pro Trp Asn
85 90 95

Thr Pro Leu Leu Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

```
Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670
```

```
Ile Glu Asn Ser Ser Pro Tyr Thr Ser Glu His Phe
        675                 680


<210> SEQ ID NO 658
<211> LENGTH: 684
<212> TYPE: PRT
<213> ORGANISM: Artificial Sequence
<220> FEATURE:
<223> OTHER INFORMATION: RTase mutant

<400> SEQUENCE: 658

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350
```

Leu Thr Ala Pro Ala Leu Gly Leu Pro Asp Leu Thr Lys Pro Phe Glu
355 360 365

Leu Phe Val Asp Glu Lys Gln Gly Tyr Ala Lys Gly Val Leu Thr Gln
370 375 380

Lys Leu Gly Pro Trp Arg Arg Pro Val Ala Tyr Leu Ser Lys Lys Leu
385 390 395 400

Asp Pro Val Ala Ala Gly Trp Pro Pro Cys Leu Arg Met Val Ala Ala
405 410 415

Ile Ala Val Leu Thr Lys Asp Ala Gly Lys Leu Thr Met Gly Gln Pro
420 425 430

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 659
<211> LENGTH: 684
<212> TYPE: PRT
<213> ORGANISM: Artificial Sequence
<220> FEATURE:
<223> OTHER INFORMATION: RTase mutant

<400> SEQUENCE: 659

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

-continued

```
Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
```

```
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 660
<211> LENGTH: 683
<212> TYPE: PRT
<213> ORGANISM: Artificial Sequence
<220> FEATURE:
<223> OTHER INFORMATION: RTase mutant

<400> SEQUENCE: 660

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
```

```
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560
```

```
Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His
        675                 680
```

<210> SEQ ID NO 661
<211> LENGTH: 684
<212> TYPE: PRT
<213> ORGANISM: Artificial Sequence
<220> FEATURE:
<223> OTHER INFORMATION: RTase mutant

<400> SEQUENCE: 661

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240
```

```
Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655
```

```
Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 662
<211> LENGTH: 684
<212> TYPE: PRT
<213> ORGANISM: Artificial Sequence
<220> FEATURE:
<223> OTHER INFORMATION: RTase mutant

<400> SEQUENCE: 662

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Arg Lys Gln
    50                  55                  60

Tyr Pro Met Ser Gln Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335
```

```
Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 663
<211> LENGTH: 684
<212> TYPE: PRT
<213> ORGANISM: Artificial Sequence
<220> FEATURE:
<223> OTHER INFORMATION: RTase mutant

<400> SEQUENCE: 663

```
Met Thr Leu Asn Ile Glu Asp Glu His Arg Leu His Glu Thr Ser Lys
1               5                   10                  15
```

```
Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
```

```
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 664
<211> LENGTH: 684
<212> TYPE: PRT
<213> ORGANISM: Artificial Sequence
<220> FEATURE:
<223> OTHER INFORMATION: RTase mutant

<400> SEQUENCE: 664

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
```

```
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540
```

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 665
<211> LENGTH: 684
<212> TYPE: PRT
<213> ORGANISM: Artificial Sequence
<220> FEATURE:
<223> OTHER INFORMATION: RTase mutant

<400> SEQUENCE: 665

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Gln Glu Ala Arg Leu Gly Ile Lys Pro His Ile Gln
65 70 75 80

Arg Leu Leu Asp Gln Gly Ile Leu Val Pro Cys Gln Ser Pro Trp Asn
85 90 95

Thr Pro Leu Arg Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

```
Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640
```

```
Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 666
<211> LENGTH: 684
<212> TYPE: PRT
<213> ORGANISM: Artificial Sequence
<220> FEATURE:
<223> OTHER INFORMATION: RTase mutant

<400> SEQUENCE: 666

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320
```

```
Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 667
<211> LENGTH: 684
<212> TYPE: PRT
<213> ORGANISM: Artificial Sequence
<220> FEATURE:
<223> OTHER INFORMATION: RTase mutant

<400> SEQUENCE: 667

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
```

```
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 668
<211> LENGTH: 684
<212> TYPE: PRT
<213> ORGANISM: Artificial Sequence
<220> FEATURE:
<223> OTHER INFORMATION: RTase mutant

<400> SEQUENCE: 668

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Gln Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
```

```
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Ala Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525
```

```
Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 669
<211> LENGTH: 684
<212> TYPE: PRT
<213> ORGANISM: Artificial Sequence
<220> FEATURE:
<223> OTHER INFORMATION: RTase mutant

<400> SEQUENCE: 669

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Gln
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205
```

```
Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620
```

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 670
<211> LENGTH: 684
<212> TYPE: PRT
<213> ORGANISM: Artificial Sequence
<220> FEATURE:
<223> OTHER INFORMATION: RTase mutant

<400> SEQUENCE: 670

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Gln Glu Ala Arg Leu Gly Ile Lys Pro His Ile Arg
65 70 75 80

Arg Leu Leu Asp Gln Gly Ile Leu Val Pro Cys Gln Ser Pro Trp Asn
85 90 95

Thr Pro Leu Arg Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

Leu Leu Lys Glu Gly Gln Arg Trp Leu Thr Asp Ala Arg Lys Glu Thr
275 280 285

Val Met Gly Gln Pro Thr Pro Lys Thr Pro Arg Gln Leu Arg Glu Phe
290 295 300

```
Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 671
<211> LENGTH: 684
<212> TYPE: PRT
<213> ORGANISM: Artificial Sequence
<220> FEATURE:
<223> OTHER INFORMATION: RTase mutant

<400> SEQUENCE: 671

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Leu Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala

```
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 672
<211> LENGTH: 684
<212> TYPE: PRT
<213> ORGANISM: Artificial Sequence
<220> FEATURE:
<223> OTHER INFORMATION: RTase mutant

<400> SEQUENCE: 672

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
```

```
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Glu Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510
```

```
Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 673
<211> LENGTH: 684
<212> TYPE: PRT
<213> ORGANISM: Artificial Sequence
<220> FEATURE:
<223> OTHER INFORMATION: RTase mutant

<400> SEQUENCE: 673

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190
```

```
Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605
```

```
Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 674
<211> LENGTH: 684
<212> TYPE: PRT
<213> ORGANISM: Artificial Sequence
<220> FEATURE:
<223> OTHER INFORMATION: RTase mutant

<400> SEQUENCE: 674

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Lys Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285
```

```
Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 675
<211> LENGTH: 684
<212> TYPE: PRT

<213> ORGANISM: Artificial Sequence
<220> FEATURE:
<223> OTHER INFORMATION: RTase mutant

<400> SEQUENCE: 675

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Arg Glu Ala Arg Leu Gly Ile Lys Pro His Ile Arg
65 70 75 80

Arg Leu Leu Asp Gln Gly Ile Leu Val Pro Cys Gln Ser Pro Trp Asn
85 90 95

Thr Pro Leu Asn Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

Leu Leu Lys Glu Gly Gln Arg Trp Leu Thr Asp Ala Arg Lys Glu Thr
275 280 285

Val Met Gly Gln Pro Thr Pro Lys Thr Pro Arg Gln Leu Arg Glu Phe
290 295 300

Leu Gly Thr Ala Gly Phe Cys Arg Leu Trp Ile Pro Gly Phe Ala Glu
305 310 315 320

Met Ala Ala Pro Leu Tyr Pro Leu Thr Lys Thr Gly Thr Leu Phe Asn
325 330 335

Trp Gly Pro Asp Gln Gln Lys Ala Tyr Gln Glu Ile Lys Gln Ala Leu
340 345 350

Leu Thr Ala Pro Ala Leu Gly Leu Pro Asp Leu Thr Lys Pro Phe Glu
355 360 365

Leu Phe Val Asp Glu Lys Gln Gly Tyr Ala Lys Gly Val Leu Thr Gln
370 375 380

Lys Leu Gly Pro Trp Arg Arg Pro Val Ala Tyr Leu Ser Lys Lys Leu 385 390 395 400

Asp Pro Val Ala Ala Gly Trp Pro Pro Cys Leu Arg Met Val Ala Ala
405 410 415

Ile Ala Val Leu Thr Lys Asp Ala Gly Lys Leu Thr Met Gly Gln Pro
420 425 430

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 676
<211> LENGTH: 684
<212> TYPE: PRT
<213> ORGANISM: Artificial Sequence
<220> FEATURE:
<223> OTHER INFORMATION: RTase mutant

<400> SEQUENCE: 676

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Ile Glu Ala Arg Leu Gly Ile Lys Pro His Ile Arg

```
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495
```

```
Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 677
<211> LENGTH: 684
<212> TYPE: PRT
<213> ORGANISM: Artificial Sequence
<220> FEATURE:
<223> OTHER INFORMATION: RTase mutant

<400> SEQUENCE: 677

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Lys Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175
```

```
Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590
```

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 678
<211> LENGTH: 684
<212> TYPE: PRT
<213> ORGANISM: Artificial Sequence
<220> FEATURE:
<223> OTHER INFORMATION: RTase mutant

<400> SEQUENCE: 678

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Arg Glu Ala Arg Leu Gly Ile Lys Pro His Ile His
65 70 75 80

Arg Leu Leu Asp Gln Gly Ile Leu Val Pro Cys Gln Ser Pro Trp Asn
85 90 95

Thr Pro Leu Arg Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

```
Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 679
<211> LENGTH: 684
<212> TYPE: PRT
<213> ORGANISM: Artificial Sequence
<220> FEATURE:
<223> OTHER INFORMATION: RTase mutant

<400> SEQUENCE: 679

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Ile Lys Gln
    50                  55                  60

Tyr Pro Met Ser Arg Glu Ala Arg Leu Gly Ile Lys Pro His Ile Ile
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
```

370 375 380

Lys Leu Gly Pro Trp Arg Arg Pro Val Ala Tyr Leu Ser Lys Lys Leu
385 390 395 400

Asp Pro Val Ala Ala Gly Trp Pro Pro Cys Leu Arg Met Val Ala Ala
405 410 415

Ile Ala Val Leu Thr Lys Asp Ala Gly Lys Leu Thr Met Gly Gln Pro
420 425 430

Leu Val Ile Leu Ala Pro His Ala Val Glu Ala Leu Val Lys Gln Pro
435 440 445

Pro Asp Arg Trp Leu Ser Asn Ala Arg Met Thr His Tyr Gln Ala Leu
450 455 460

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 680
<211> LENGTH: 684
<212> TYPE: PRT
<213> ORGANISM: Artificial Sequence
<220> FEATURE:
<223> OTHER INFORMATION: RTase mutant

<400> SEQUENCE: 680

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln

```
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480
```

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 681
<211> LENGTH: 684
<212> TYPE: PRT
<213> ORGANISM: Artificial Sequence
<220> FEATURE:
<223> OTHER INFORMATION: RTase mutant

<400> SEQUENCE: 681

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Ile Lys Gln
50 55 60

Tyr Pro Met Ser Arg Glu Ala Arg Leu Gly Ile Lys Pro His Ile Arg
65 70 75 80

Arg Leu Leu Asp Gln Gly Ile Leu Val Pro Cys Gln Ser Pro Trp Asn
85 90 95

Thr Pro Leu Arg Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

```
Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Trp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575
```

```
Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 682
<211> LENGTH: 684
<212> TYPE: PRT
<213> ORGANISM: Artificial Sequence
<220> FEATURE:
<223> OTHER INFORMATION: RTase mutant

<400> SEQUENCE: 682

Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
        35                  40                  45

Leu Ile Ile Pro Leu Lys Ala Thr Ser Thr Pro Val Ser Lys Lys Gln
    50                  55                  60

Tyr Pro Met Ser Arg Glu Ala Arg Leu Gly Ile Lys Pro His Ile Arg
65                  70                  75                  80

Arg Leu Leu Asp Gln Gly Ile Leu Val Pro Cys Gln Ser Pro Trp Asn
                85                  90                  95

Thr Pro Leu Arg Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255
```

```
Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Asp Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
```

675 680

<210> SEQ ID NO 683
<211> LENGTH: 684
<212> TYPE: PRT
<213> ORGANISM: Artificial Sequence
<220> FEATURE:
<223> OTHER INFORMATION: RTase mutant

<400> SEQUENCE: 683

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Met Lys Gln
50 55 60

Tyr Pro Met Ser Arg Glu Ala Arg Leu Gly Ile Lys Pro His Ile Arg
65 70 75 80

Arg Leu Leu Asp Gln Gly Ile Leu Val Pro Cys Gln Ser Pro Trp Asn
85 90 95

Thr Pro Leu Arg Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

Gln Trp Tyr Thr Val Leu Asp Leu Lys Asp Ala Phe Phe Cys Leu Arg
145 150 155 160

Leu His Pro Thr Ser Gln Pro Leu Phe Ala Phe Glu Trp Arg Asp Pro
165 170 175

Glu Met Gly Ile Ser Gly Gln Leu Thr Trp Thr Arg Leu Pro Gln Gly
180 185 190

Phe Lys Asn Ser Pro Thr Leu Phe Asp Glu Ala Leu His Arg Asp Leu
195 200 205

Ala Asp Phe Arg Ile Gln His Pro Asp Leu Ile Leu Leu Gln Tyr Val
210 215 220

Asp Asp Leu Leu Leu Ala Ala Thr Ser Glu Leu Asp Cys Gln Gln Gly
225 230 235 240

Thr Arg Ala Leu Leu Gln Thr Leu Gly Asn Leu Gly Tyr Arg Ala Ser
245 250 255

Ala Lys Lys Ala Gln Ile Cys Gln Lys Gln Val Lys Tyr Leu Gly Tyr
260 265 270

Leu Leu Lys Glu Gly Gln Arg Trp Leu Thr Asp Ala Arg Lys Glu Thr
275 280 285

Val Met Gly Gln Pro Thr Pro Lys Thr Pro Arg Gln Leu Arg Glu Phe
290 295 300

Leu Gly Thr Ala Gly Phe Cys Arg Leu Trp Ile Pro Gly Phe Ala Glu
305 310 315 320

Met Ala Ala Pro Leu Tyr Pro Leu Thr Lys Thr Gly Thr Leu Phe Asn
325 330 335

Trp Gly Pro Asp Gln Gln Lys Ala Tyr Gln Glu Ile Lys Gln Ala Leu
340 345 350

Leu Thr Ala Pro Ala Leu Gly Leu Pro Asp Leu Thr Lys Pro Phe Glu

```
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560

Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680
```

<210> SEQ ID NO 684
<211> LENGTH: 684
<212> TYPE: PRT
<213> ORGANISM: Artificial Sequence
<220> FEATURE:
<223> OTHER INFORMATION: RTase mutant

<400> SEQUENCE: 684

```
Met Thr Leu Asn Ile Glu Asp Glu His Arg Leu His Glu Thr Ser Lys
1               5                   10                  15

Glu Pro Asp Val Ser Leu Gly Ser Thr Trp Leu Ser Asp Phe Pro Gln
            20                  25                  30

Ala Trp Ala Glu Thr Gly Gly Met Gly Leu Ala Val Arg Gln Ala Pro
```

```
        35                  40                  45

Leu Ile Ile Pro Leu Lys Ala Thr Ser Thr Pro Val Ser Ile Lys Gln
    50                  55                  60

Tyr Pro Met Ser Ile Glu Ala Arg Leu Gly Ile Lys Pro His Ile His
65                  70                  75                  80

Arg Leu Leu Asp Gln Gly Ile Leu Val Pro Cys Gln Ser Pro Trp Asn
                85                  90                  95

Thr Pro Leu Lys Pro Val Lys Lys Pro Gly Thr Asn Asp Tyr Arg Pro
            100                 105                 110

Val Gln Asp Leu Arg Glu Val Asn Lys Arg Val Glu Asp Ile His Pro
        115                 120                 125

Thr Val Pro Asn Pro Tyr Asn Leu Leu Ser Gly Leu Pro Pro Ser His
    130                 135                 140

Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460
```

Leu Leu Asp Thr Asp Arg Val Gln Phe Gly Pro Val Val Ala Leu Asn
465 470 475 480

Pro Ala Thr Leu Leu Pro Leu Pro Glu Glu Gly Leu Gln His Asn Cys
485 490 495

Leu Asp Ile Leu Ala Glu Ala His Gly Thr Arg Pro Asp Leu Thr Asp
500 505 510

Gln Pro Leu Pro Asp Ala Asp His Thr Trp Tyr Thr Gly Gly Ser Ser
515 520 525

Leu Leu Gln Glu Gly Gln Arg Lys Ala Gly Ala Ala Val Thr Thr Glu
530 535 540

Thr Glu Val Ile Trp Ala Lys Ala Leu Pro Ala Gly Thr Ser Ala Gln
545 550 555 560

Arg Ala Gln Leu Ile Ala Leu Thr Gln Ala Leu Lys Met Ala Glu Gly
565 570 575

Lys Lys Leu Asn Val Tyr Thr Asn Ser Arg Tyr Ala Phe Ala Thr Ala
580 585 590

His Ile His Gly Glu Ile Tyr Arg Arg Arg Gly Leu Leu Thr Ser Glu
595 600 605

Gly Lys Glu Ile Lys Asn Lys Asp Glu Ile Leu Ala Leu Leu Lys Ala
610 615 620

Leu Phe Leu Pro Lys Arg Leu Ser Ile Ile His Cys Pro Gly His Gln
625 630 635 640

Lys Gly His Ser Ala Glu Ala Arg Gly Asn Arg Met Ala Asp Gln Ala
645 650 655

Ala Arg Lys Ala Ala Ile Thr Glu Thr Pro Asp Thr Ser Thr Leu Leu
660 665 670

Ile Glu Asn Ser Ser Pro Tyr Thr Ser Glu His Phe
675 680

<210> SEQ ID NO 685
<211> LENGTH: 684
<212> TYPE: PRT
<213> ORGANISM: Artificial Sequence
<220> FEATURE:
<223> OTHER INFORMATION: RTase mutant

<400> SEQUENCE: 685

Met Thr Leu Asn Ile Glu Asp Glu His Arg Leu His Glu Thr Ser Lys
1 5 10 15

Glu Pro Asp Val Ser Leu Gly Ser Thr Trp Leu Ser Asp Phe Pro Gln
20 25 30

Ala Trp Ala Glu Thr Gly Gly Met Gly Leu Ala Val Arg Gln Ala Pro
35 40 45

Leu Ile Ile Pro Leu Lys Ala Thr Ser Thr Pro Val Ser Met Lys Gln
50 55 60

Tyr Pro Met Ser Ile Glu Ala Arg Leu Gly Ile Lys Pro His Ile His
65 70 75 80

Arg Leu Leu Asp Gln Gly Ile Leu Val Pro Cys Gln Ser Pro Trp Asn
85 90 95

Thr Pro Leu Lys Pro Val Lys Lys Pro Gly Thr Asn Asp Tyr Arg Pro
100 105 110

Val Gln Asp Leu Arg Glu Val Asn Lys Arg Val Glu Asp Ile His Pro
115 120 125

Thr Val Pro Asn Pro Tyr Asn Leu Leu Ser Gly Leu Pro Pro Ser His
130 135 140

```
Gln Trp Tyr Thr Val Leu Asp Leu Lys Asp Ala Phe Phe Cys Leu Arg
145                 150                 155                 160

Leu His Pro Thr Ser Gln Pro Leu Phe Ala Phe Glu Trp Arg Asp Pro
                165                 170                 175

Glu Met Gly Ile Ser Gly Gln Leu Thr Trp Thr Arg Leu Pro Gln Gly
            180                 185                 190

Phe Lys Asn Ser Pro Thr Leu Phe Asp Glu Ala Leu His Arg Asp Leu
        195                 200                 205

Ala Asp Phe Arg Ile Gln His Pro Asp Leu Ile Leu Leu Gln Tyr Val
    210                 215                 220

Asp Asp Leu Leu Leu Ala Ala Thr Ser Glu Leu Asp Cys Gln Gln Gly
225                 230                 235                 240

Thr Arg Ala Leu Leu Gln Thr Leu Gly Asn Leu Gly Tyr Arg Ala Ser
                245                 250                 255

Ala Lys Lys Ala Gln Ile Cys Gln Lys Gln Val Lys Tyr Leu Gly Tyr
            260                 265                 270

Leu Leu Lys Glu Gly Gln Arg Trp Leu Thr Met Ala Arg Lys Glu Thr
        275                 280                 285

Val Met Gly Gln Pro Thr Pro Lys Thr Pro Arg Gln Leu Arg Glu Phe
    290                 295                 300

Leu Gly Thr Ala Gly Phe Cys Arg Leu Trp Ile Pro Gly Phe Ala Glu
305                 310                 315                 320

Met Ala Ala Pro Leu Tyr Pro Leu Thr Lys Thr Gly Thr Leu Phe Asn
                325                 330                 335

Trp Gly Pro Asp Gln Gln Lys Ala Tyr Gln Glu Ile Lys Gln Ala Leu
            340                 345                 350

Leu Thr Ala Pro Ala Leu Gly Leu Pro Asp Leu Thr Lys Pro Phe Glu
        355                 360                 365

Leu Phe Val Asp Glu Lys Gln Gly Tyr Ala Lys Gly Val Leu Thr Gln
    370                 375                 380

Lys Leu Gly Pro Trp Arg Arg Pro Val Ala Tyr Leu Ser Lys Lys Leu
385                 390                 395                 400

Asp Pro Val Ala Ala Gly Trp Pro Pro Cys Leu Arg Met Val Ala Ala
                405                 410                 415

Ile Ala Val Leu Thr Lys Asp Ala Gly Lys Leu Thr Met Gly Gln Pro
            420                 425                 430

Leu Val Ile Leu Ala Pro His Ala Val Glu Ala Leu Val Lys Gln Pro
        435                 440                 445

Pro Asp Arg Trp Leu Ser Asn Ala Arg Met Thr His Tyr Gln Ala Leu
    450                 455                 460

Leu Leu Asp Thr Asp Arg Val Gln Phe Gly Pro Val Val Ala Leu Asn
465                 470                 475                 480

Pro Ala Thr Leu Leu Pro Leu Pro Glu Glu Gly Leu Gln His Asn Cys
                485                 490                 495

Leu Asp Ile Leu Ala Glu Ala His Gly Thr Arg Pro Asp Leu Thr Asp
            500                 505                 510

Gln Pro Leu Pro Asp Ala Asp His Thr Trp Tyr Thr Gly Gly Ser Ser
        515                 520                 525

Leu Leu Gln Glu Gly Gln Arg Lys Ala Gly Ala Ala Val Thr Thr Glu
    530                 535                 540

Thr Glu Val Ile Trp Ala Lys Ala Leu Pro Ala Gly Thr Ser Ala Gln
545                 550                 555                 560
```

```
Arg Ala Gln Leu Ile Ala Leu Thr Gln Ala Leu Lys Met Ala Glu Gly
                565                 570                 575

Lys Lys Leu Asn Val Tyr Thr Asn Ser Arg Tyr Ala Phe Ala Thr Ala
            580                 585                 590

His Ile His Gly Glu Ile Tyr Arg Arg Arg Gly Leu Leu Thr Ser Glu
        595                 600                 605

Gly Lys Glu Ile Lys Asn Lys Asp Glu Ile Leu Ala Leu Leu Lys Ala
    610                 615                 620

Leu Phe Leu Pro Lys Arg Leu Ser Ile Ile His Cys Pro Gly His Gln
625                 630                 635                 640

Lys Gly His Ser Ala Glu Ala Arg Gly Asn Arg Met Ala Asp Gln Ala
                645                 650                 655

Ala Arg Lys Ala Ala Ile Thr Glu Thr Pro Asp Thr Ser Thr Leu Leu
            660                 665                 670

Ile Glu Asn Ser Ser Pro Tyr Thr Ser Glu His Phe
        675                 680


<210> SEQ ID NO 686
<211> LENGTH: 683
<212> TYPE: PRT
<213> ORGANISM: Artificial Sequence
<220> FEATURE:
<223> OTHER INFORMATION: RTase mutant

<400> SEQUENCE: 686

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240
```

```
Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Arg Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
```

660 665 670

Glu Asn Ser Ser Pro Tyr Thr Ser Glu His Phe
675 680

<210> SEQ ID NO 687
<211> LENGTH: 683
<212> TYPE: PRT
<213> ORGANISM: Artificial Sequence
<220> FEATURE:
<223> OTHER INFORMATION: RTase mutant

<400> SEQUENCE: 687

Thr Leu Asn Ile Glu Asp Glu His Arg Leu His Glu Thr Ser Lys Glu
1 5 10 15

Pro Asp Val Ser Leu Gly Ser Thr Trp Leu Ser Asp Phe Pro Gln Ala
20 25 30

Trp Ala Glu Thr Gly Gly Met Gly Leu Ala Val Arg Gln Ala Pro Leu
35 40 45

Ile Ile Pro Leu Lys Ala Thr Ser Thr Pro Val Ser Ile Lys Gln Tyr
50 55 60

Pro Met Ser Arg Glu Ala Arg Leu Gly Ile Lys Pro His Ile Arg Arg
65 70 75 80

Leu Leu Asp Gln Gly Ile Leu Val Pro Cys Gln Ser Pro Trp Asn Thr
85 90 95

Pro Leu Arg Pro Val Lys Lys Pro Gly Thr Asn Asp Tyr Arg Pro Val
100 105 110

Gln Asp Leu Arg Glu Val Asn Lys Arg Val Glu Asp Ile His Pro Thr
115 120 125

Val Pro Asn Pro Tyr Asn Leu Leu Ser Gly Leu Pro Pro Ser His Gln
130 135 140

Trp Tyr Thr Val Leu Asp Leu Lys Asp Ala Phe Phe Cys Leu Arg Leu
145 150 155 160

His Pro Thr Ser Gln Pro Leu Phe Ala Phe Glu Trp Arg Asp Pro Glu
165 170 175

Met Gly Ile Ser Gly Gln Leu Thr Trp Thr Arg Leu Pro Gln Gly Phe
180 185 190

Lys Asn Ser Pro Thr Leu Phe Asp Glu Ala Leu His Arg Asp Leu Ala
195 200 205

Asp Phe Arg Ile Gln His Pro Asp Leu Ile Leu Leu Gln Tyr Val Asp
210 215 220

Asp Leu Leu Leu Ala Ala Thr Ser Glu Leu Asp Cys Gln Gln Gly Thr
225 230 235 240

Arg Ala Leu Leu Gln Thr Leu Gly Asn Leu Gly Tyr Arg Ala Ser Ala
245 250 255

Lys Lys Ala Gln Ile Cys Gln Lys Gln Val Lys Tyr Leu Gly Tyr Leu
260 265 270

Leu Lys Glu Gly Gln Arg Trp Leu Thr Asp Ala Arg Lys Glu Thr Val
275 280 285

Met Gly Gln Pro Thr Pro Lys Thr Pro Arg Gln Leu Arg Glu Phe Leu
290 295 300

Gly Thr Ala Gly Phe Cys Arg Leu Trp Ile Pro Gly Phe Ala Glu Met
305 310 315 320

Ala Ala Pro Leu Tyr Pro Leu Thr Lys Thr Gly Thr Leu Phe Asn Trp
325 330 335

Gly Pro Asp Gln Gln Lys Ala Tyr Gln Glu Ile Lys Gln Ala Leu Leu

```
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 688
<211> LENGTH: 683
<212> TYPE: PRT
<213> ORGANISM: Artificial Sequence
<220> FEATURE:
<223> OTHER INFORMATION: RTase mutant

<400> SEQUENCE: 688

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
```

-continued

```
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445
```

```
Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 689
<211> LENGTH: 683
<212> TYPE: PRT
<213> ORGANISM: Artificial Sequence
<220> FEATURE:
<223> OTHER INFORMATION: RTase mutant

<400> SEQUENCE: 689

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125
```

-continued

```
Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Glu Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540
```

Glu Val Ile Trp Ala Lys Ala Leu Pro Ala Gly Thr Ser Ala Gln Arg
545 550 555 560

Ala Gln Leu Ile Ala Leu Thr Gln Ala Leu Lys Met Ala Glu Gly Lys
565 570 575

Lys Leu Asn Val Tyr Thr Asn Ser Arg Tyr Ala Phe Ala Thr Ala His
580 585 590

Ile His Gly Glu Ile Tyr Arg Arg Arg Gly Leu Leu Thr Ser Glu Gly
595 600 605

Lys Glu Ile Lys Asn Lys Asp Glu Ile Leu Ala Leu Leu Lys Ala Leu
610 615 620

Phe Leu Pro Lys Arg Leu Ser Ile Ile His Cys Pro Gly His Gln Lys
625 630 635 640

Gly His Ser Ala Glu Ala Arg Gly Asn Arg Met Ala Asp Gln Ala Ala
645 650 655

Arg Lys Ala Ala Ile Thr Glu Thr Pro Asp Thr Ser Thr Leu Leu Ile
660 665 670

Glu Asn Ser Ser Pro Tyr Thr Ser Glu His Phe
675 680

<210> SEQ ID NO 690
<211> LENGTH: 683
<212> TYPE: PRT
<213> ORGANISM: Artificial Sequence
<220> FEATURE:
<223> OTHER INFORMATION: RTase mutant

<400> SEQUENCE: 690

Thr Leu Asn Ile Glu Asp Glu His Arg Leu His Glu Thr Ser Lys Glu
1 5 10 15

Pro Asp Val Ser Leu Gly Ser Thr Trp Leu Ser Asp Phe Pro Gln Ala
20 25 30

Trp Ala Glu Thr Gly Gly Met Gly Leu Ala Val Arg Gln Ala Pro Leu
35 40 45

Ile Ile Pro Leu Lys Ala Thr Ser Thr Pro Val Ser Ile Lys Gln Tyr
50 55 60

Pro Met Ser Arg Glu Ala Arg Leu Gly Ile Lys Pro His Ile Arg Arg
65 70 75 80

Leu Leu Asp Gln Gly Ile Leu Val Pro Cys Gln Ser Pro Trp Asn Thr
85 90 95

Pro Leu Arg Pro Val Lys Lys Pro Gly Thr Asn Asp Tyr Arg Pro Val
100 105 110

Gln Asp Leu Arg Glu Val Asn Lys Arg Val Glu Asp Ile His Pro Thr
115 120 125

Val Pro Asn Pro Tyr Asn Leu Leu Ser Gly Leu Pro Pro Ser His Gln
130 135 140

Trp Tyr Thr Val Leu Asp Leu Lys Asp Ala Phe Phe Cys Leu Arg Leu
145 150 155 160

His Pro Thr Ser Gln Pro Leu Phe Ala Phe Glu Trp Arg Asp Pro Glu
165 170 175

Met Gly Ile Ser Gly Gln Leu Thr Trp Thr Arg Leu Pro Gln Gly Phe
180 185 190

Lys Asn Ser Pro Thr Leu Phe Asp Glu Ala Leu His Arg Asp Leu Ala
195 200 205

Asp Phe Arg Ile Gln His Pro Asp Leu Ile Leu Leu Gln Tyr Val Asp
210 215 220

```
Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Arg Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
```

```
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 691
<211> LENGTH: 683
<212> TYPE: PRT
<213> ORGANISM: Artificial Sequence
<220> FEATURE:
<223> OTHER INFORMATION: RTase mutant

<400> SEQUENCE: 691

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Arg Thr Asp Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
```

```
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 692
<211> LENGTH: 683
<212> TYPE: PRT
<213> ORGANISM: Artificial Sequence
<220> FEATURE:
<223> OTHER INFORMATION: RTase mutant

<400> SEQUENCE: 692

Thr Leu Asn Ile Glu Asp Glu His Arg Leu His Glu Thr Ser Lys Glu
```

-continued

```
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Gln Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430
```

```
Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 693
<211> LENGTH: 683
<212> TYPE: PRT
<213> ORGANISM: Artificial Sequence
<220> FEATURE:
<223> OTHER INFORMATION: RTase mutant

<400> SEQUENCE: 693

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110
```

```
Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525
```

```
Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Ile His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 694
<211> LENGTH: 683
<212> TYPE: PRT
<213> ORGANISM: Artificial Sequence
<220> FEATURE:
<223> OTHER INFORMATION: RTase mutant

<400> SEQUENCE: 694

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205
```

```
Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
```

625 630 635 640

Gly His Ser Ala Glu Ala Arg Gly Asn Arg Met Ala Asp Gln Ala Ala
645 650 655

Arg Lys Ala Ala Ile Thr Glu Thr Pro Asp Thr Ser Thr Leu Leu Ile
660 665 670

Glu Asn Ser Ser Pro Tyr Thr Ser Glu His Phe
675 680

<210> SEQ ID NO 695
<211> LENGTH: 683
<212> TYPE: PRT
<213> ORGANISM: Artificial Sequence
<220> FEATURE:
<223> OTHER INFORMATION: RTase mutant

<400> SEQUENCE: 695

Thr Leu Asn Ile Glu Asp Glu His Arg Leu His Glu Thr Ser Lys Glu
1 5 10 15

Pro Asp Val Ser Leu Gly Ser Thr Trp Leu Ser Asp Phe Pro Gln Ala
20 25 30

Trp Ala Glu Thr Gly Gly Met Gly Leu Ala Val Arg Gln Ala Pro Leu
35 40 45

Ile Ile Pro Leu Lys Ala Thr Ser Thr Pro Val Ser Ile Lys Gln Tyr
50 55 60

Pro Met Ser Arg Glu Ala Arg Leu Gly Ile Lys Pro His Ile Arg Arg
65 70 75 80

Leu Arg Asp Gln Gly Ile Leu Val Pro Cys Gln Ser Pro Trp Asn Thr
85 90 95

Pro Leu Arg Pro Val Lys Lys Pro Gly Thr Asn Asp Tyr Arg Pro Val
100 105 110

Gln Asp Leu Arg Glu Val Asn Lys Arg Val Glu Asp Ile His Pro Thr
115 120 125

Val Pro Asn Pro Tyr Asn Leu Leu Ser Gly Leu Pro Pro Ser His Gln
130 135 140

Trp Tyr Thr Val Leu Asp Leu Lys Asp Ala Phe Phe Cys Leu Arg Leu
145 150 155 160

His Pro Thr Ser Gln Pro Leu Phe Ala Phe Glu Trp Arg Asp Pro Glu
165 170 175

Met Gly Ile Ser Gly Gln Leu Thr Trp Thr Arg Leu Pro Gln Gly Phe
180 185 190

Lys Asn Ser Pro Thr Leu Phe Asp Glu Ala Leu His Arg Asp Leu Ala
195 200 205

Asp Phe Arg Ile Gln His Pro Asp Leu Ile Leu Leu Gln Tyr Val Asp
210 215 220

Asp Leu Leu Leu Ala Ala Thr Ser Glu Leu Asp Cys Gln Gln Gly Thr
225 230 235 240

Arg Ala Leu Leu Gln Thr Leu Gly Asn Leu Gly Tyr Arg Ala Ser Ala
245 250 255

Lys Lys Ala Gln Ile Cys Gln Lys Gln Val Lys Tyr Leu Gly Tyr Leu
260 265 270

Leu Lys Glu Gly Gln Arg Trp Leu Thr Asp Ala Arg Lys Glu Thr Val
275 280 285

Met Gly Gln Pro Thr Pro Lys Thr Pro Arg Glu Leu Arg Glu Phe Leu
290 295 300

Gly Thr Ala Gly Phe Cys Arg Leu Trp Ile Pro Gly Phe Ala Glu Met

```
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680
```

<210> SEQ ID NO 696
<211> LENGTH: 683
<212> TYPE: PRT
<213> ORGANISM: Artificial Sequence
<220> FEATURE:
<223> OTHER INFORMATION: RTase mutant

<400> SEQUENCE: 696

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Leu Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

```
Ala Val Leu Thr Lys Asp Ala Gly Lys Leu Thr Met Gly Gln Pro Leu
            420                 425                 430

Arg Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 697
<211> LENGTH: 683
<212> TYPE: PRT
<213> ORGANISM: Artificial Sequence
<220> FEATURE:
<223> OTHER INFORMATION: RTase mutant

<400> SEQUENCE: 697

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95
```

```
Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Arg Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510
```

```
Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 698
<211> LENGTH: 683
<212> TYPE: PRT
<213> ORGANISM: Artificial Sequence
<220> FEATURE:
<223> OTHER INFORMATION: RTase mutant

<400> SEQUENCE: 698

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190
```

```
Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Glu Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
```

```
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680


<210> SEQ ID NO 699
<211> LENGTH: 683
<212> TYPE: PRT
<213> ORGANISM: Artificial Sequence
<220> FEATURE:
<223> OTHER INFORMATION: RTase mutant

<400> SEQUENCE: 699

Thr Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Arg Glu Ala Arg Leu Gly Ile Lys Pro His Ile Arg Arg
65                  70                  75                  80

Leu Arg Asp Gln Gly Ile Leu Val Pro Cys Gln Ser Pro Trp Asn Thr
                85                  90                  95

Pro Leu Arg Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125

Val Pro Asn Pro Tyr Asn Leu Leu Ser Gly Leu Pro Pro Ser His Gln
    130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Asp Ala Arg Lys Glu Thr Val
        275                 280                 285

Met Gly Gln Pro Thr Pro Lys Thr Pro Arg Glu Leu Arg Glu Phe Leu
```

```
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Glu Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Arg Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Gly Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
545                 550                 555                 560

Ala Gln Leu Ile Ala Leu Thr Gln Ala Leu Lys Met Ala Glu Gly Lys
                565                 570                 575

Lys Leu Asn Val Tyr Thr Asn Ser Arg Tyr Ala Phe Ala Thr Ala His
            580                 585                 590

Glu His Gly Glu Ile Tyr Arg Arg Arg Gly Leu Leu Thr Ser Glu Gly
        595                 600                 605

Lys Glu Ile Lys Asn Lys Asp Glu Ile Leu Ala Leu Leu Lys Ala Leu
    610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
            660                 665                 670

Glu Asn Ser Ser Pro Tyr Thr Ser Glu His Phe
        675                 680
```